(12) United States Patent
Bleich et al.

(10) Patent No.: US 9,463,041 B2
(45) Date of Patent: *Oct. 11, 2016

(54) DEVICES AND METHODS FOR TISSUE ACCESS

(71) Applicant: Amendia, Inc., Marietta, GA (US)

(72) Inventors: Jeffery L. Bleich, Palo Alto, CA (US); Edwin J. Hlavka, Minneapolis, MN (US); Vahid Saadat, Saratoga, CA (US); David J. Miller, Austin, TX (US); James R. Yurchenco, Palo Alto, CA (US)

(73) Assignee: Amendia, Inc., Marietta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/969,691

(22) Filed: Dec. 15, 2015

(65) Prior Publication Data

US 2016/0135834 A1 May 19, 2016

Related U.S. Application Data

(60) Division of application No. 12/984,162, filed on Jan. 4, 2011, now Pat. No. 9,247,952, which is a continuation-in-part of application No. 11/251,205, filed on Oct. 15, 2005, now Pat. No. 7,918,849, and
(Continued)

(51) Int. Cl.
*A61B 17/00* (2006.01)
*A61B 17/32* (2006.01)
(Continued)

(52) U.S. Cl.
CPC ... *A61B 17/320016* (2013.01); *A61B 17/1671* (2013.01); *A61B 17/29* (2013.01);
(Continued)

(58) Field of Classification Search
CPC .......... A61B 17/1659; A61B 17/1671; A61B 17/14; A61B 17/141; A61B 17/148; A61B 2017/143; A61B 2017/145; A61B 2017/146; A61B 2017/320028

USPC ................ 606/79, 82, 84, 85, 167, 176, 177
See application file for complete search history.

(56) References Cited

U.S. PATENT DOCUMENTS 184,804 A * 11/1876 Stohlmann ............ A61B 17/14
125/21
289,194 A 11/1883 How
(Continued)

FOREIGN PATENT DOCUMENTS

| CN | 1338911 | 3/2002 |
|---|---|---|
| CN | 101291633 | 10/2008 |

(Continued)

OTHER PUBLICATIONS

Kawahara et al., Recapping T-Saw Limoplasty for Spinal Cord Tumors, Spine, 1999, vol. 24 No. 13, pp. 1363-1370. Jan. 1, 1999.
(Continued)

*Primary Examiner* — Kevin T Truong
*Assistant Examiner* — Si Ming Ku
(74) *Attorney, Agent, or Firm* — David L. King

(57) ABSTRACT

Methods and apparatus are provided for selective surgical removal of tissue, e.g., for enlargement of diseased spinal structures, such as impinged lateral recesses and pathologically narrowed neural foramen. In some embodiments, a surgical tissue removal device includes a flexible elongate body that is adapted to conform with the target anatomy and a guidewire connector at the distal end region of the flexible elongate body configured to removably connect to the end of a guidewire so that the guidewire and flexible elongate body can be pulled distally. The body may have at least one blade edge, and the flexible elongate body may be a thin, flat, ribbon shaped flexible body that comprises a profile having a width that is substantially greater than a height.

15 Claims, 87 Drawing Sheets

Related U.S. Application Data a continuation-in-part of application No. 12/917,253, filed on Nov. 1, 2010, now Pat. No. 8,551,097, which is a continuation-in-part of application No. 11/468, 247, filed on Aug. 29, 2006, now Pat. No. 7,857,813, said application No. 12/984,162 is a continuation-in-part of application No. 12/127,535, filed on May 27, 2008, now Pat. No. 8,257,356, which is a continuation-in-part of application No. 11/468,247, filed on Aug. 29, 2006, now Pat. No. 7,857,813, and a continuation-in-part of application No. 11/251,199, filed on Oct. 15, 2005, now Pat. No. 8,192,435.

(60) Provisional application No. 60/619,306, filed on Oct. 15, 2004, provisional application No. 60/622,865, filed on Oct. 28, 2004, provisional application No. 60/681,719, filed on May 16, 2005, provisional application No. 60/681,864, filed on May 16, 2005, provisional application No. 60/685,190, filed on May 27, 2005.

(51) Int. Cl.

| | | |
|---|---|---|
| *A61B 17/16* | (2006.01) | |
| *A61B 17/29* | (2006.01) | |
| *A61B 17/3205* | (2006.01) | |
| *A61B 17/3207* | (2006.01) | |
| *A61B 17/34* | (2006.01) | |
| *A61F 2/00* | (2006.01) | |
| *A61B 5/00* | (2006.01) | |
| *A61B 17/295* | (2006.01) | |
| *A61B 18/02* | (2006.01) | |
| *A61B 18/08* | (2006.01) | |
| *A61B 18/14* | (2006.01) | |
| *A61B 18/18* | (2006.01) | |
| *A61B 18/20* | (2006.01) | |
| *A61B 17/14* | (2006.01) | |
| *A61B 18/00* | (2006.01) | |
| *A61N 1/36* | (2006.01) | |
| *A61N 7/02* | (2006.01) | |

(52) U.S. Cl.
CPC ... *A61B17/32002* (2013.01); *A61B 17/32053* (2013.01); *A61B 17/320758* (2013.01); *A61B 17/3401* (2013.01); *A61B 17/3403* (2013.01); *A61B 17/3421* (2013.01); *A61B 17/3496* (2013.01); *A61B 18/1487* (2013.01); *A61B 90/04* (2016.02); *A61F 2/0045* (2013.01); *A61B 5/4893* (2013.01); *A61B 17/295* (2013.01); *A61B 18/02* (2013.01); *A61B 18/082* (2013.01); *A61B 18/1477* (2013.01); *A61B 18/1815* (2013.01); *A61B 18/20* (2013.01); *A61B 2017/003* (2013.01); *A61B 2017/00261* (2013.01); *A61B 2017/00287* (2013.01); *A61B 2017/00867* (2013.01); *A61B 2017/143* (2013.01); *A61B 2017/145* (2013.01); *A61B 2017/320004* (2013.01); *A61B 2017/32006* (2013.01); *A61B 2017/320044* (2013.01); *A61B 2017/3445* (2013.01); *A61B 2017/3447* (2013.01); *A61B 2018/00577* (2013.01); *A61B 2018/00595* (2013.01); *A61B 2018/1407* (2013.01); *A61B 2018/1425* (2013.01); *A61B 2034/2063* (2016.02); *A61B 2090/061* (2016.02); *A61B 2090/08021* (2016.02); *A61B 2090/374* (2016.02); *A61B 2090/376* (2016.02); *A61B 2090/3762* (2016.02); *A61N 1/36017* (2013.01); *A61N 7/02* (2013.01)

(56) References Cited

U.S. PATENT DOCUMENTS

| | | |
|---|---|---|
| 863,389 A | 8/1907 | Harkin |
| 1,039,487 A | 9/1912 | Casebolt |
| 1,201,467 A | 10/1916 | Hoglund |
| 1,374,638 A | 4/1921 | De Cew et al. |
| 1,543,195 A | 6/1925 | Thygesen |
| 1,690,812 A | 11/1928 | Bertels |
| 1,938,200 A | 12/1933 | Wells |
| 2,243,757 A | 5/1941 | Kohls et al. |
| 2,269,749 A | 1/1942 | Wilkie |
| 2,372,553 A | 3/1945 | Coddington |
| 2,437,697 A | 3/1948 | Kalom |
| 2,516,882 A | 8/1950 | Kalom |
| 2,704,064 A | 3/1955 | Fizell |
| 2,820,281 A | 1/1958 | Amsen |
| 2,843,128 A | 7/1958 | Storz |
| 2,982,005 A | 5/1961 | Booth |
| RE25,582 E | 5/1964 | Davies |
| 3,150,470 A | 9/1964 | Barron |
| 3,200,814 A | 8/1965 | Taylor et al. |
| 3,214,824 A | 11/1965 | Brown |
| 3,389,447 A | 6/1968 | Theobald et al. |
| 3,491,776 A | 1/1970 | Fleming |
| 3,495,590 A | 2/1970 | Zeiller |
| 3,528,152 A | 9/1970 | Funakubo et al. |
| 3,651,844 A | 3/1972 | Barnes |
| 3,664,329 A | 5/1972 | Naylor |
| 3,682,162 A | 8/1972 | Coyler |
| 3,699,729 A | 10/1972 | Garvey et al. |
| 3,752,166 A | 8/1973 | Lyon et al. |
| 3,774,355 A | 11/1973 | Dawson et al. |
| 3,830,226 A | 8/1974 | Staub et al. |
| 3,835,859 A | 9/1974 | Roberts et al. |
| 3,956,858 A | 5/1976 | Catlin et al. |
| 3,957,036 A | 5/1976 | Normann |
| 3,978,862 A | 9/1976 | Morrison |
| 3,999,294 A | 12/1976 | Shoben |
| 4,015,931 A | 4/1977 | Thakur |
| 4,108,182 A | 8/1978 | Hartman et al. |
| 4,160,320 A | 7/1979 | Wikoff |
| 4,172,440 A | 10/1979 | Schneider et al. |
| 4,203,444 A | 5/1980 | Bonnell et al. |
| 4,207,897 A | 6/1980 | Lloyd et al. |
| 4,259,276 A | 3/1981 | Rawlings |
| 4,405,061 A | 9/1983 | Bergandy |
| D273,806 S | 5/1984 | Bolesky et al. |
| 4,464,836 A | 8/1984 | Hissa |
| 4,502,184 A | 3/1985 | Karubian |
| 4,515,168 A | 5/1985 | Chester et al. |
| 4,518,022 A | 5/1985 | Valdes et al. |
| 4,545,374 A | 10/1985 | Jacobson |
| 4,573,448 A | 3/1986 | Kambin |
| 4,580,545 A | 4/1986 | Dorsten |
| 4,590,949 A | 5/1986 | Pohndorf |
| 4,616,660 A | 10/1986 | Johns |
| 4,621,636 A | 11/1986 | Fogarty |
| 4,625,725 A | 12/1986 | Davison et al. |
| 4,660,571 A | 4/1987 | Hess et al. |
| 4,678,459 A | 7/1987 | Onik et al. |
| 4,690,642 A | 9/1987 | Kyotani |
| 4,700,702 A | 10/1987 | Nilsson |
| 4,709,699 A | 12/1987 | Michael et al. |
| 4,741,343 A | 5/1988 | Bowman |
| 4,750,249 A | 6/1988 | Richardson |
| 4,794,931 A | 1/1989 | Yock |
| 4,808,157 A | 2/1989 | Coombs |
| 4,817,628 A | 4/1989 | Zealear et al. |
| 4,856,193 A | 8/1989 | Grachan |
| 4,867,155 A | 9/1989 | Isaacson |
| 4,872,452 A | 10/1989 | Alexsn |
| 4,873,978 A | 10/1989 | Ginsburg |
| 4,883,460 A | 11/1989 | Zanetti |
| 4,894,063 A | 1/1990 | Nashe |

(56) References Cited

U.S. PATENT DOCUMENTS

| | | |
|---|---|---|
| 4,912,799 A | 4/1990 | Coleman, Jr. |
| RE33,258 E | 7/1990 | Onik et al. |
| 4,943,295 A | 7/1990 | Hartlaub et al. |
| 4,946,462 A | 8/1990 | Watanabe |
| 4,957,117 A | 9/1990 | Wysham |
| 4,962,766 A | 10/1990 | Herzon |
| 4,973,329 A | 11/1990 | Park et al. |
| 4,990,148 A | 2/1991 | Worrick, III et al. |
| 4,994,036 A | 2/1991 | Biscoping et al. |
| 4,994,072 A | 2/1991 | Bhate et al. |
| 4,995,200 A | 2/1991 | Eberhart |
| 5,019,082 A | 5/1991 | Frey et al. |
| 5,025,787 A | 6/1991 | Sutherland et al. |
| 5,026,379 A | 6/1991 | Yoon |
| 5,026,386 A | 6/1991 | Michelson |
| 5,078,137 A | 1/1992 | Edell et al. |
| 5,089,003 A | 2/1992 | Fallin et al. |
| 5,100,424 A | 3/1992 | Jang et al. |
| 5,108,403 A | 4/1992 | Stern |
| 5,123,400 A | 6/1992 | Edgerton |
| 5,125,928 A | 6/1992 | Parins et al. |
| 5,147,364 A | 9/1992 | Comparetto |
| 5,152,749 A | 10/1992 | Giesy et al. |
| 5,161,534 A | 11/1992 | Berthiaume |
| 5,163,939 A | 11/1992 | Winston |
| 5,176,649 A | 1/1993 | Wakabayashi |
| 5,178,145 A | 1/1993 | Rea |
| 5,178,161 A | 1/1993 | Kovacs |
| 5,191,888 A | 3/1993 | Palmer et al. |
| 5,195,507 A | 3/1993 | Bilweis |
| 5,201,704 A | 4/1993 | Ray |
| 5,215,105 A | 6/1993 | Kizelshteyn et al. |
| 5,219,358 A | 6/1993 | Bendel et al. |
| 5,234,435 A | 8/1993 | Seagrave, Jr. |
| 5,242,418 A | 9/1993 | Weinstein |
| 5,250,035 A | 10/1993 | Smith et al. |
| 5,255,691 A | 10/1993 | Otten |
| 5,271,415 A | 12/1993 | Foerster et al. |
| 5,281,218 A | 1/1994 | Imran |
| 5,284,153 A | 2/1994 | Raymond et al. |
| 5,284,154 A | 2/1994 | Raymond et al. |
| 5,300,077 A | 4/1994 | Howell |
| 5,325,868 A | 7/1994 | Kimmelstiel |
| 5,341,807 A | 8/1994 | Nardella |
| 5,351,679 A | 10/1994 | Mayzels et al. |
| 5,353,784 A | 10/1994 | Nady-Mohamed |
| 5,353,789 A | 10/1994 | Schlobohm |
| 5,353,802 A | 10/1994 | Ollmar |
| 5,360,441 A | 11/1994 | Otten |
| 5,365,928 A | 11/1994 | Rhinehart et al. |
| 5,374,261 A | 12/1994 | Yoon |
| 5,383,879 A | 1/1995 | Philips |
| 5,385,146 A | 1/1995 | Goldreyer |
| 5,387,218 A | 2/1995 | Meswania |
| 5,396,880 A | 3/1995 | Kagan et al. |
| 5,421,348 A | 6/1995 | Larnard |
| 5,423,331 A | 6/1995 | Wysham |
| 5,437,661 A | 8/1995 | Reiser |
| 5,439,464 A | 8/1995 | Shapiro |
| 5,441,044 A | 8/1995 | Tovey et al. |
| 5,441,510 A | 8/1995 | Simpson et al. |
| 5,454,815 A | 10/1995 | Geisser et al. |
| 5,456,254 A | 10/1995 | Pietroski et al. |
| 5,496,325 A | 3/1996 | Mclees |
| 5,512,037 A | 4/1996 | Russell et al. |
| 5,515,848 A | 5/1996 | Corbett, III et al. |
| 5,531,749 A | 7/1996 | Michelson |
| 5,534,009 A | 7/1996 | Lander |
| 5,546,958 A | 8/1996 | Thorud et al. |
| 5,554,110 A | 9/1996 | Edwards et al. |
| 5,555,892 A | 9/1996 | Tipton |
| 5,560,372 A | 10/1996 | Cory |
| 5,562,695 A | 10/1996 | Obenchain |
| 5,571,181 A | 11/1996 | Li |
| 5,582,618 A | 12/1996 | Chine et al. |
| 5,591,170 A | 1/1997 | Spievack et al. |
| 5,598,848 A | 2/1997 | Swanson et al. |
| 5,620,447 A | 4/1997 | Smith et al. |
| 5,630,426 A | 5/1997 | Eggers et al. |
| 5,634,475 A | 6/1997 | Wolvek |
| 5,643,304 A | 7/1997 | Schechter et al. |
| 5,651,373 A | 7/1997 | Mah |
| 5,656,012 A | 8/1997 | Sienkiewicz |
| 5,680,860 A | 10/1997 | Imran |
| 5,681,324 A | 10/1997 | Kammerer et al. |
| 5,697,889 A | 12/1997 | Slotman et al. |
| 5,709,697 A | 1/1998 | Ratcliff et al. |
| 5,725,530 A | 3/1998 | Popken |
| 5,735,792 A | 4/1998 | Vanden Hoek et al. |
| 5,755,732 A | 5/1998 | Green et al. |
| 5,759,159 A | 6/1998 | Masreliez |
| 5,762,629 A | 6/1998 | Kambin |
| 5,766,168 A | 6/1998 | Mantell |
| 5,769,865 A | 6/1998 | Kermode et al. |
| 5,775,331 A | 7/1998 | Raymond et al. |
| 5,779,642 A | 7/1998 | Nightengale |
| 5,788,653 A | 8/1998 | Lorenzo |
| 5,792,044 A | 8/1998 | Foley et al. |
| 5,795,308 A | 8/1998 | Russin |
| 5,800,350 A | 9/1998 | Coppesn et al. |
| 5,803,902 A | 9/1998 | Sienkiewicz et al. |
| 5,803,904 A | 9/1998 | Mehdizadeh |
| 5,807,263 A | 9/1998 | Chance |
| 5,810,744 A | 9/1998 | Chu et al. |
| 5,813,405 A | 9/1998 | Montano, Jr. et al. |
| 5,824,040 A | 10/1998 | Cox et al. |
| 5,830,151 A | 11/1998 | Hadzic et al. |
| 5,830,157 A | 11/1998 | Foote |
| 5,830,188 A | 11/1998 | Abouleish |
| 5,833,692 A | 11/1998 | Cesarini et al. |
| 5,836,810 A | 11/1998 | Asum |
| 5,836,948 A | 11/1998 | Zucherman et al. |
| 5,843,110 A | 12/1998 | Dross et al. |
| 5,846,196 A | 12/1998 | Siekmeyer et al. |
| 5,846,244 A | 12/1998 | Cripe |
| 5,851,191 A | 12/1998 | Gozani |
| 5,851,209 A | 12/1998 | Kummer et al. |
| 5,851,214 A | 12/1998 | Larsen et al. |
| 5,853,373 A | 12/1998 | Griffith et al. |
| 5,865,844 A | 2/1999 | Plaia et al. |
| 5,868,767 A | 2/1999 | Farley et al. |
| 5,879,353 A | 3/1999 | Terry |
| 5,885,219 A | 3/1999 | Nightengale |
| 5,895,417 A | 4/1999 | Pomeranz et al. |
| 5,897,583 A | 4/1999 | Meyer et al. |
| 5,899,909 A | 5/1999 | Claren et al. |
| 5,904,657 A | 5/1999 | Unsworth et al. |
| 5,916,173 A | 6/1999 | Kirsner |
| 5,918,604 A | 7/1999 | Whelan |
| 5,919,190 A | 7/1999 | VanDusseldorp |
| 5,928,158 A | 7/1999 | Aristides |
| 5,928,159 A | 7/1999 | Eggers et al. |
| 5,941,822 A | 8/1999 | Sjladnev et al. |
| 5,961,522 A | 10/1999 | Mehdizadeh |
| 5,972,013 A | 10/1999 | Schmidt |
| 5,976,110 A | 11/1999 | Greengrass et al. |
| 5,976,146 A | 11/1999 | Ogawa et al. |
| 6,002,964 A | 12/1999 | Feler et al. |
| 6,004,326 A | 12/1999 | Castro et al. |
| 6,004,330 A | 12/1999 | Middleman et al. |
| 6,010,493 A | 1/2000 | Snoke |
| 6,015,406 A | 1/2000 | Goble et al. |
| 6,022,362 A | 2/2000 | Lee et al. |
| 6,030,383 A | 2/2000 | Benderev |
| 6,030,401 A | 2/2000 | Marino |
| 6,038,480 A | 3/2000 | Hrdlicka et al. |
| 6,048,345 A | 4/2000 | Berke et al. |
| 6,068,642 A | 5/2000 | Johnson et al. |
| 6,073,051 A | 6/2000 | Sharkey et al. |
| 6,099,514 A | 8/2000 | Sharkey et al. |
| 6,102,930 A | 8/2000 | Simmons, Jr. |
| 6,106,558 A | 8/2000 | Picha |
| 6,113,534 A | 9/2000 | Koros et al. |
| D432,384 S | 10/2000 | Simons |

(56) References Cited

U.S. PATENT DOCUMENTS

| | | |
|---|---|---|
| 6,132,387 A | 10/2000 | Gozani et al. |
| 6,136,014 A | 10/2000 | Sirimanne et al. |
| 6,142,993 A | 11/2000 | Whayne et al. |
| 6,142,994 A | 11/2000 | Swanson et al. |
| 6,146,380 A | 11/2000 | Racz et al. |
| 6,152,894 A | 11/2000 | Kubler |
| 6,169,916 B1 | 1/2001 | West |
| 6,205,360 B1 | 3/2001 | Carter |
| 6,214,001 B1 | 4/2001 | Casscells et al. |
| 6,214,016 B1 | 4/2001 | Williams et al. |
| 6,236,892 B1 | 5/2001 | Feler |
| 6,251,115 B1 | 6/2001 | Williams et al. |
| 6,256,540 B1 | 7/2001 | Panescu et al. |
| 6,259,945 B1 | 7/2001 | Epstein et al. |
| 6,261,582 B1 | 7/2001 | Needham et al. |
| 6,266,551 B1 | 7/2001 | Osadchy et al. |
| 6,266,558 B1 | 7/2001 | Gozani et al. |
| 6,267,760 B1 | 7/2001 | Swanson |
| 6,272,367 B1 | 8/2001 | Chance |
| 6,277,094 B1 | 8/2001 | Schendel |
| 6,280,447 B1 | 8/2001 | Marino et al. |
| 6,292,702 B1 | 9/2001 | King et al. |
| 6,298,256 B1 | 10/2001 | Meyer |
| 6,312,392 B1 | 11/2001 | Herzon |
| 6,324,418 B1 | 11/2001 | Crowley et al. |
| 6,324,432 B1 | 11/2001 | Rigaux et al. |
| 6,325,764 B1 | 12/2001 | Griffith et al. |
| 6,334,068 B1 | 12/2001 | Hacker |
| 6,343,226 B1 | 1/2002 | Sunde et al. |
| 6,358,254 B1 | 3/2002 | Anderson |
| 6,360,750 B1 | 3/2002 | Gerber et al. |
| 6,364,886 B1 | 4/2002 | Sklar |
| 6,368,324 B1 | 4/2002 | Dinger et al. |
| 6,370,411 B1 | 4/2002 | Osadchy et al. |
| 6,370,435 B2 | 4/2002 | Panescu et al. |
| 6,383,509 B1 | 5/2002 | Donovan et al. |
| 6,390,906 B1 | 5/2002 | Subramanian |
| 6,391,028 B1 | 5/2002 | Fanton et al. |
| 6,416,505 B1 | 7/2002 | Fleischman et al. |
| 6,423,071 B1 | 7/2002 | Lawson |
| 6,423,080 B1 | 7/2002 | Gellman et al. |
| 6,425,859 B1 | 7/2002 | Foley et al. |
| 6,425,887 B1 | 7/2002 | McGuckin et al. |
| 6,428,486 B2 | 8/2002 | Ritchart et al. |
| 6,436,101 B1 | 8/2002 | Hamada |
| 6,442,848 B1 | 9/2002 | Dean |
| 6,446,621 B1 | 9/2002 | Svensson |
| 6,451,335 B1 | 9/2002 | Goldenheim et al. |
| 6,454,767 B2 | 9/2002 | Alleyne |
| 6,464,682 B1 | 10/2002 | Snoke |
| 6,466,817 B1 | 10/2002 | Kaula et al. |
| 6,468,289 B1 | 10/2002 | Bonutti |
| 6,470,209 B2 | 10/2002 | Snoke |
| 6,478,805 B1 | 11/2002 | Marino et al. |
| 6,487,439 B1 | 11/2002 | skladnev et al. |
| 6,488,636 B2 | 12/2002 | Bryan et al. |
| 6,491,646 B1 | 12/2002 | Blackledge |
| 6,500,128 B2 | 12/2002 | Marino |
| 6,500,189 B1 | 12/2002 | Lang et al. |
| 6,512,958 B1 | 1/2003 | Swoyer et al. |
| 6,516,223 B2 | 2/2003 | Hofmann |
| 6,520,907 B1 | 2/2003 | Foley et al. |
| 6,527,786 B1 | 3/2003 | Davis et al. |
| 6,533,749 B1 | 3/2003 | Mitusina et al. |
| 6,535,759 B1 | 3/2003 | Epstein et al. |
| 6,540,742 B1 | 4/2003 | Thomas et al. |
| 6,540,761 B2 | 4/2003 | Houser |
| 6,546,270 B1 | 4/2003 | Goldin et al. |
| 6,558,353 B2 | 5/2003 | Zohmann |
| 6,558,390 B2 | 5/2003 | Cragg |
| 6,562,033 B2 | 5/2003 | Shah et al. |
| 6,564,078 B1 | 5/2003 | Marino et al. |
| 6,564,079 B1 | 5/2003 | Cory et al. |
| 6,564,088 B1 | 5/2003 | Soller et al. |
| 6,569,160 B1 | 5/2003 | Goldin et al. |
| 6,575,979 B1 | 6/2003 | Cragg |
| 6,579,291 B1 | 6/2003 | Keith et al. |
| 6,584,345 B2 | 6/2003 | Govari |
| 6,592,559 B1 | 7/2003 | Pakter et al. |
| 6,595,932 B2 | 7/2003 | Ferrera |
| 6,597,955 B2 | 7/2003 | Panescu et al. |
| 6,606,523 B1 | 8/2003 | Jenkins |
| 6,607,530 B1 | 8/2003 | Carl et al. |
| 6,609,018 B2 | 8/2003 | Cory et al. |
| 6,610,066 B2 | 8/2003 | Dinger et al. |
| 6,620,129 B2 | 9/2003 | Stecker et al. |
| 6,622,731 B2 | 9/2003 | Daniel et al. |
| 6,624,510 B1 | 9/2003 | Chan et al. |
| 6,626,916 B1 | 9/2003 | Yeung et al. |
| 6,632,184 B1 | 10/2003 | Truwit |
| 6,638,233 B2 | 10/2003 | Corvi et al. |
| RE38,335 E | 11/2003 | Aust et al. |
| 6,648,883 B2 | 11/2003 | Francischelli et al. |
| 6,666,874 B2 | 12/2003 | Heitzmann et al. |
| 6,673,063 B2 | 1/2004 | Brett |
| 6,673,068 B1 | 1/2004 | Berube |
| 6,678,552 B2 | 1/2004 | Pearlman |
| 6,682,535 B2 | 1/2004 | Hoogland |
| 6,682,536 B2 | 1/2004 | Vardi et al. |
| 6,685,709 B2 | 2/2004 | Sklar |
| 6,699,246 B2 | 3/2004 | Zucherman et al. |
| 6,723,049 B2 | 4/2004 | Skladnev et al. |
| 6,726,531 B1 | 4/2004 | Harrel |
| 6,726,685 B2 | 4/2004 | To et al. |
| 6,733,496 B2 | 5/2004 | Sharkey et al. |
| 6,736,815 B2 | 5/2004 | Ginn |
| 6,736,835 B2 | 5/2004 | Pellegrino et al. |
| 6,746,451 B2 | 6/2004 | Middleton et al. |
| 6,752,814 B2 | 6/2004 | Gellman et al. |
| 6,760,616 B2 | 7/2004 | Hoey et al. |
| 6,764,491 B2 | 7/2004 | Frey et al. |
| 6,772,012 B2 | 8/2004 | Ricart et al. |
| 6,776,765 B2 | 8/2004 | Soukup et al. |
| 6,786,876 B2 | 9/2004 | Cox |
| 6,788,966 B2 | 9/2004 | Kenan et al. |
| 6,790,210 B1 | 9/2004 | Cragg et al. |
| 6,795,737 B2 | 9/2004 | Gielen et al. |
| 6,805,695 B2 | 10/2004 | keith et al. |
| 6,805,697 B1 | 10/2004 | Helm et al. |
| 6,807,444 B2 | 10/2004 | Tu et al. |
| 6,830,561 B2 | 12/2004 | Jansen et al. |
| 6,830,570 B1 | 12/2004 | Frey et al. |
| 6,832,111 B2 | 12/2004 | Tu et al. |
| 6,845,264 B1 | 1/2005 | Skladnev et al. |
| 6,847,849 B2 | 1/2005 | Mamo et al. |
| 6,851,430 B2 | 2/2005 | Tsou |
| 6,865,409 B2 | 3/2005 | Getsla et al. |
| 6,872,204 B2 | 3/2005 | Houser |
| 6,875,221 B2 | 4/2005 | Cull |
| 6,882,879 B2 | 4/2005 | Rock |
| 6,884,220 B2 | 4/2005 | Aviv et al. |
| 6,890,353 B2 | 5/2005 | Cohn et al. |
| 6,895,283 B2 | 5/2005 | Erickson et al. |
| 6,899,716 B2 | 5/2005 | Cragg |
| 6,907,884 B2 | 6/2005 | Pellegrino et al. |
| 6,911,003 B2 | 6/2005 | Anderson et al. |
| 6,911,016 B2 | 6/2005 | Balzum et al. |
| 6,916,328 B2 | 7/2005 | Brett |
| 6,923,813 B2 | 8/2005 | Phillips et al. |
| 6,929,647 B2 | 8/2005 | Cohen |
| 6,949,104 B2 | 9/2005 | Griffis et al. |
| 6,953,461 B2 | 10/2005 | McClurken et al. |
| 6,962,587 B2 | 11/2005 | Johnson et al. |
| 6,969,392 B2 | 11/2005 | Gitis et al. |
| 6,971,986 B2 | 12/2005 | Staskin et al. |
| 6,972,199 B2 | 12/2005 | Lebouitz et al. |
| 6,973,342 B1 | 12/2005 | Swanson |
| 6,976,986 B2 | 12/2005 | Berube |
| 6,991,643 B2 | 1/2006 | Saadat |
| 6,994,693 B2 | 2/2006 | Tal |
| 6,997,934 B2 | 2/2006 | Snaow et al. |
| 6,999,820 B2 | 2/2006 | Jordan |
| 7,001,333 B2 | 2/2006 | Hamel et al. |
| 7,008,431 B2 | 3/2006 | Simonson |

(56) References Cited

U.S. PATENT DOCUMENTS

| | | |
|---|---|---|
| 7,010,352 B2 | 3/2006 | Hogan |
| 7,011,635 B1 | 3/2006 | Delay |
| 7,011,663 B2 | 3/2006 | Michelson |
| 7,014,616 B2 | 3/2006 | Ferrera |
| 7,033,373 B2 | 4/2006 | de la Torre et al. |
| 7,041,099 B2 | 5/2006 | Thomas et al. |
| 7,047,084 B2 | 5/2006 | Erickson et al. |
| 7,048,682 B2 | 5/2006 | Neisz et al. |
| 7,050,848 B2 | 5/2006 | Hoey et al. |
| 7,063,682 B1 | 6/2006 | Whayne et al. |
| 7,069,083 B2 | 6/2006 | Finch et al. |
| 7,070,556 B2 | 7/2006 | Anderson et al. |
| 7,070,596 B1 | 7/2006 | Woloszko et al. |
| 7,079,883 B2 | 7/2006 | Marino et al. |
| 7,081,122 B1 | 7/2006 | Reiley et al. |
| 7,087,053 B2 | 8/2006 | Vanney |
| 7,087,058 B2 | 8/2006 | Cragg |
| 7,107,104 B2 | 9/2006 | Keravel et al. |
| 7,118,576 B2 | 10/2006 | Gitis et al. |
| 7,141,019 B2 | 11/2006 | Pearlman |
| 7,166,073 B2 | 1/2007 | Ritland |
| 7,166,081 B2 | 1/2007 | Mckinley |
| 7,166,107 B2 | 1/2007 | Anderson |
| 7,169,107 B2 | 1/2007 | jersey-Willuhn et al. |
| 7,169,147 B2 | 1/2007 | Nosel |
| 7,172,562 B2 | 2/2007 | Mckinley |
| 7,177,677 B2 | 2/2007 | Kaula et al. |
| 7,181,289 B2 | 2/2007 | Pffluenger et al. |
| 7,189,240 B1 | 3/2007 | Dekel |
| 7,192,430 B2 | 3/2007 | Truckai et al. |
| 7,198,598 B2 | 4/2007 | Smith et al. |
| 7,198,626 B2 | 4/2007 | Lee et al. |
| 7,207,949 B2 | 4/2007 | Miles et al. |
| 7,211,082 B2 | 5/2007 | Hall et al. |
| 7,214,186 B2 | 5/2007 | Ritland |
| 7,214,197 B2 | 5/2007 | Prass |
| 7,216,001 B2 | 5/2007 | Hacker et al. |
| 7,223,278 B2 | 5/2007 | Davison et al. |
| 7,236,832 B2 | 6/2007 | Hemmeling et al. |
| 7,238,189 B2 | 7/2007 | Schmieding et al. |
| 7,239,911 B2 | 7/2007 | Scholz |
| 7,245,789 B2 | 7/2007 | Bates et al. |
| 7,270,658 B2 | 9/2007 | Woloszko et al. |
| 7,270,659 B2 | 9/2007 | Ricart et al. |
| 7,282,033 B2 | 10/2007 | Urmey |
| 7,282,061 B2 | 10/2007 | Sharkey et al. |
| 7,295,881 B2 | 11/2007 | Cohen et al. |
| 7,318,823 B2 | 1/2008 | Sharps et al. |
| 7,337,005 B2 | 2/2008 | Kim et al. |
| 7,337,006 B2 | 2/2008 | Kim et al. |
| 7,367,972 B2 | 5/2008 | Francischelli et al. |
| 7,383,639 B2 | 6/2008 | Malandain |
| 7,390,330 B2 | 6/2008 | Harp |
| 7,419,487 B2 | 9/2008 | Johnson et al. |
| 7,449,019 B2 | 11/2008 | Uchida et al. |
| 7,452,351 B2 | 11/2008 | Miller et al. |
| 7,470,236 B1 | 12/2008 | Kelleher et al. |
| 7,476,226 B2 | 1/2009 | Weikel et al. |
| 7,494,473 B2 | 2/2009 | Eggers et al. |
| 7,500,977 B2 | 3/2009 | Assell et al. |
| 7,503,920 B2 | 3/2009 | Siegal |
| 7,507,218 B2 | 3/2009 | Aliski et al. |
| 7,522,953 B2 | 4/2009 | Gharib et al. |
| 7,553,307 B2 | 6/2009 | Bleich et al. |
| 7,555,343 B2 | 6/2009 | Bleich |
| 7,578,819 B2 | 8/2009 | Bleich et al. |
| 7,617,006 B2 | 11/2009 | Metzler et al. |
| 7,641,658 B2 | 1/2010 | Shaolian et al. |
| 7,648,521 B2 | 1/2010 | Hestad |
| 7,655,026 B2 | 2/2010 | Justis et al. |
| 7,666,186 B2 | 2/2010 | Harp |
| 7,666,209 B2 | 2/2010 | Zucherman et al. |
| 7,738,968 B2 | 6/2010 | Bleich |
| 7,738,969 B2 | 6/2010 | Bleich |
| 7,740,631 B2 | 6/2010 | Bleich et al. |
| 7,857,813 B2 | 12/2010 | Schmitz et al. |
| 8,303,516 B2 | 11/2012 | Schmitz et al. |
| 8,366,712 B2 | 2/2013 | Bleich et al. |
| 8,398,641 B2 | 3/2013 | Wallace et al. |
| 2001/0014806 A1 | 8/2001 | Ellman et al. |
| 2001/0025192 A1 | 9/2001 | Gerber et al. |
| 2001/0039419 A1 | 11/2001 | Francischelli et al. |
| 2002/0022788 A1 | 2/2002 | Corvi et al. |
| 2002/0029060 A1 | 3/2002 | Hogendijk |
| 2002/0106681 A1 | 8/2002 | Wexler et al. |
| 2002/0128700 A1 | 9/2002 | Cross |
| 2002/0138091 A1 | 9/2002 | Pflueger |
| 2002/0165590 A1 | 11/2002 | Cowe et al. |
| 2002/0183647 A1 | 12/2002 | Gozani et al. |
| 2003/0015203 A1 | 1/2003 | Makower et al. |
| 2003/0074037 A1 | 4/2003 | Moore et al. |
| 2003/0105503 A1 | 6/2003 | Marino |
| 2003/0113906 A1 | 6/2003 | Sangha et al. |
| 2003/0130655 A1 | 7/2003 | Woloszko et al. |
| 2003/0130738 A1 | 7/2003 | Hovda et al. |
| 2003/0167021 A1 | 9/2003 | Shimm |
| 2003/0187368 A1 | 10/2003 | Sata et al. |
| 2003/0188749 A1 | 10/2003 | Nichols et al. |
| 2003/0212400 A1 | 11/2003 | Bloemer et al. |
| 2003/0225412 A1* | 12/2003 | Shiraishi ............ A61B 17/1659 606/85 |
| 2003/0225415 A1 | 12/2003 | Richard |
| 2004/0006379 A1 | 1/2004 | Brett |
| 2004/0006391 A1 | 1/2004 | Reiley |
| 2004/0019359 A1 | 1/2004 | Worley et al. |
| 2004/0030330 A1 | 2/2004 | Brasell et al. |
| 2004/0049208 A1 | 3/2004 | Hill et al. |
| 2004/0059260 A1 | 3/2004 | Truwit |
| 2004/0064058 A1 | 4/2004 | McKay |
| 2004/0097927 A1 | 5/2004 | Yeung et al. |
| 2004/0106940 A1 | 6/2004 | Shailian et al. |
| 2004/0111084 A1 | 6/2004 | Brett |
| 2004/0122433 A1 | 6/2004 | Loubens et al. |
| 2004/0122482 A1 | 6/2004 | Tung et al. |
| 2004/0127893 A1 | 7/2004 | Hovda |
| 2004/0143165 A1 | 7/2004 | Alleyne |
| 2004/0143280 A1 | 7/2004 | Suddaby |
| 2004/0162609 A1 | 8/2004 | Hossainey et al. |
| 2004/0167444 A1 | 8/2004 | Laroya et al. |
| 2004/0167553 A1 | 8/2004 | Simpson et al. |
| 2004/0181150 A1 | 9/2004 | Evans et al. |
| 2004/0199084 A1 | 10/2004 | Kelleher et al. |
| 2004/0199159 A1 | 10/2004 | Lee et al. |
| 2004/0199167 A1* | 10/2004 | Fletcher ................ A61B 17/14 606/79 |
| 2004/0220576 A1 | 11/2004 | Sklar |
| 2004/0260358 A1 | 12/2004 | Vaughan et al. |
| 2005/0027199 A1 | 2/2005 | Clarke |
| 2005/0033393 A1 | 2/2005 | Daglow |
| 2005/0049592 A1 | 3/2005 | keith et al. |
| 2005/0149035 A1 | 7/2005 | Pimenta et al. |
| 2005/0171587 A1 | 8/2005 | Daglow et al. |
| 2005/0182454 A1 | 8/2005 | Gharib et al. |
| 2005/0187537 A1 | 8/2005 | Loeb et al. |
| 2005/0197661 A1 | 9/2005 | Carrison et al. |
| 2005/0203599 A1 | 9/2005 | Garabedian et al. |
| 2005/0209610 A1 | 9/2005 | Carrison |
| 2005/0209617 A1 | 9/2005 | Koven et al. |
| 2005/0209622 A1 | 9/2005 | Carrison |
| 2005/0216023 A1 | 9/2005 | Aram et al. |
| 2005/0222598 A1 | 10/2005 | Ho et al. |
| 2005/0222647 A1 | 10/2005 | Washistrand et al. |
| 2005/0256423 A1 | 11/2005 | Kirsner |
| 2005/0261692 A1 | 11/2005 | Carrison et al. |
| 2005/0267529 A1 | 12/2005 | Crockett et al. |
| 2005/0277942 A1 | 12/2005 | Kullas et al. |
| 2005/0283148 A1 | 12/2005 | Janssen et al. |
| 2006/0004369 A1 | 1/2006 | Patel et al. |
| 2006/0015035 A1 | 1/2006 | Rock |
| 2006/0025702 A1 | 2/2006 | Sterratino et al. |
| 2006/0025703 A1 | 2/2006 | Miles et al. |
| 2006/0025797 A1 | 2/2006 | Lock et al. |
| 2006/0030854 A1 | 2/2006 | Haines |
| 2006/0036211 A1 | 2/2006 | Solsberg et al. |

(56) References Cited

U.S. PATENT DOCUMENTS

| | | |
|---|---|---|
| 2006/0036271 A1 | 2/2006 | schomer et al. |
| 2006/0036272 A1 | 2/2006 | Solsberg et al. |
| 2006/0058732 A1 | 3/2006 | Harp |
| 2006/0064101 A1 | 3/2006 | Arramon |
| 2006/0079919 A1 | 4/2006 | Harp |
| 2006/0085048 A1 | 4/2006 | Cory et al. |
| 2006/0085049 A1 | 4/2006 | Cory et al. |
| 2006/0089633 A1 | 4/2006 | Bleich et al. |
| 2006/0089650 A1 | 4/2006 | Nolde |
| 2006/0089688 A1 | 4/2006 | Panescu |
| 2006/0095028 A1 | 5/2006 | Bleich |
| 2006/0095059 A1 | 5/2006 | Bleich et al. |
| 2006/0100651 A1 | 5/2006 | Bleich |
| 2006/0122458 A1 | 6/2006 | Bleich |
| 2006/0122620 A1 | 6/2006 | Kim |
| 2006/0122653 A1 | 6/2006 | bradley et al. |
| 2006/0122654 A1 | 6/2006 | Bradley et al. |
| 2006/0129201 A1 | 6/2006 | Lee et al. |
| 2006/0142753 A1 | 6/2006 | Francischelli et al. |
| 2006/0149278 A1 | 7/2006 | Abdou |
| 2006/0161189 A1 | 7/2006 | Harp |
| 2006/0173374 A1 | 8/2006 | Neubardt et al. |
| 2006/0184175 A1 | 8/2006 | Schomer et al. |
| 2006/0195107 A1 | 8/2006 | Jones et al. |
| 2006/0200153 A1 | 9/2006 | Harp |
| 2006/0200154 A1 | 9/2006 | Harp |
| 2006/0200155 A1 | 9/2006 | Harp |
| 2006/0200219 A1 | 9/2006 | Thrope et al. |
| 2006/0206115 A1 | 9/2006 | Schomer et al. |
| 2006/0206117 A1 | 9/2006 | Harp |
| 2006/0206118 A1 | 9/2006 | Kim et al. |
| 2006/0206178 A1 | 9/2006 | Kim |
| 2006/0224060 A1 | 10/2006 | Garell et al. |
| 2006/0224078 A1 | 10/2006 | Hoey et al. |
| 2006/0235451 A1 | 10/2006 | Schomer et al. |
| 2006/0235452 A1 | 10/2006 | Schomer et al. |
| 2006/0241648 A1 | 10/2006 | Bleich et al. |
| 2006/0264952 A1 | 11/2006 | Nelson et al. |
| 2006/0264994 A1 | 11/2006 | Schomer et al. |
| 2006/0271080 A1 | 11/2006 | Suddaby |
| 2006/0276720 A1 | 12/2006 | McGinnis et al. |
| 2006/0276802 A1 | 12/2006 | vresilovic et al. |
| 2006/0276836 A1 | 12/2006 | Bergin et al. |
| 2007/0010717 A1 | 1/2007 | Cragg |
| 2007/0016097 A1 | 1/2007 | Farquhar et al. |
| 2007/0016185 A1 | 1/2007 | Tullis et al. |
| 2007/0027464 A1 | 2/2007 | Way et al. |
| 2007/0027514 A1 | 2/2007 | Gerber |
| 2007/0049962 A1 | 3/2007 | Marino et al. |
| 2007/0055215 A1 | 3/2007 | Tran et al. |
| 2007/0055262 A1 | 3/2007 | Tomita et al. |
| 2007/0055263 A1 | 3/2007 | Way et al. |
| 2007/0073356 A1 | 3/2007 | Rooney et al. |
| 2007/0106219 A1 | 5/2007 | Grabinsky |
| 2007/0123766 A1 | 5/2007 | Whalen, III et al. |
| 2007/0123888 A1 | 5/2007 | Bleich et al. |
| 2007/0123890 A1 | 5/2007 | Way et al. |
| 2007/0162044 A1 | 7/2007 | Marino |
| 2007/0162061 A1 | 7/2007 | Way et al. |
| 2007/0162062 A1 | 7/2007 | Norton et al. |
| 2007/0166345 A1 | 7/2007 | Pavcnik et al. |
| 2007/0168007 A1 | 7/2007 | Kuzma et al. |
| 2007/0198019 A1 | 8/2007 | Schomer et al. |
| 2007/0213583 A1 | 9/2007 | Kim et al. |
| 2007/0213733 A1 | 9/2007 | Bleich et al. |
| 2007/0213734 A1 | 9/2007 | Bleich et al. |
| 2007/0213735 A1 | 9/2007 | Saadat et al. |
| 2007/0213795 A1 | 9/2007 | Bradley et al. |
| 2007/0225703 A1 | 9/2007 | Schmitz et al. |
| 2007/0255162 A1 | 11/2007 | Abboud et al. |
| 2007/0255369 A1 | 11/2007 | Bonde et al. |
| 2007/0260252 A1 | 11/2007 | Schmitz et al. |
| 2007/0270795 A1 | 11/2007 | Francischelli et al. |
| 2007/0270865 A1 | 11/2007 | Arnin et al. |
| 2007/0276286 A1 | 11/2007 | Miller |
| 2007/0276390 A1 | 11/2007 | Solsberg et al. |
| 2007/0282217 A1 | 12/2007 | McGinnis et al. |
| 2007/0293782 A1 | 12/2007 | Marino |
| 2007/0299403 A1 | 12/2007 | Crowe et al. |
| 2007/0299459 A1 | 12/2007 | Way et al. |
| 2008/0015582 A1 | 1/2008 | Dipoto et al. |
| 2008/0033465 A1 | 2/2008 | Schmitz et al. |
| 2008/0051812 A1 | 2/2008 | Schmitz et al. |
| 2008/0058820 A1 | 3/2008 | Harp |
| 2008/0058874 A1 | 3/2008 | Westlund et al. |
| 2008/0064945 A1 | 3/2008 | Marino et al. |
| 2008/0064976 A1 | 3/2008 | Kelleher et al. |
| 2008/0064977 A1 | 3/2008 | Kelleher et al. |
| 2008/0065178 A1 | 3/2008 | kelleher et al. |
| 2008/0071191 A1 | 3/2008 | Kelleher et al. |
| 2008/0086034 A1 | 4/2008 | Schmitz et al. |
| 2008/0091227 A1 | 4/2008 | Schmitz et al. |
| 2008/0097465 A1 | 4/2008 | Rollins et al. |
| 2008/0103504 A1 | 5/2008 | Schmitz et al. |
| 2008/0119711 A1 | 5/2008 | Nikumb et al. |
| 2008/0125621 A1 | 5/2008 | Gellman et al. |
| 2008/0125709 A1 | 5/2008 | Chang et al. |
| 2008/0140153 A1 | 6/2008 | Burdulis |
| 2008/0140169 A1 | 6/2008 | Imran |
| 2008/0146867 A1 | 6/2008 | Gellman et al. |
| 2008/0147084 A1 | 6/2008 | Bleich et al. |
| 2008/0161809 A1 | 7/2008 | Schmitz et al. |
| 2008/0161810 A1 | 7/2008 | Melkent |
| 2008/0188850 A1 | 8/2008 | Mody et al. |
| 2008/0197024 A1 | 8/2008 | Simpson et al. |
| 2008/0200912 A1 | 8/2008 | Long et al. |
| 2008/0221383 A1 | 9/2008 | Way et al. |
| 2008/0221586 A1 | 9/2008 | Garcia-Bengochea et al. |
| 2008/0255439 A1 | 10/2008 | Tang et al. |
| 2008/0275458 A1 | 11/2008 | Bleich et al. |
| 2008/0288005 A1 | 11/2008 | jackson |
| 2008/0312660 A1 | 12/2008 | bleich et al. |
| 2008/0319459 A1 | 12/2008 | Al-najjar |
| 2009/0018507 A1 | 1/2009 | Schmitz et al. |
| 2009/0018610 A1 | 1/2009 | Gharib et al. |
| 2009/0036936 A1 | 2/2009 | Solsberg et al. |
| 2009/0054804 A1 | 2/2009 | Gharib et al. |
| 2009/0054936 A1 | 2/2009 | Eggen et al. |
| 2009/0054941 A1 | 2/2009 | Eggen et al. |
| 2009/0062871 A1 | 3/2009 | Chin et al. |
| 2009/0062872 A1 | 3/2009 | Chin et al. |
| 2009/0069709 A1 | 3/2009 | Schmitz et al. |
| 2009/0082763 A1 | 3/2009 | Quick et al. |
| 2009/0105604 A1 | 4/2009 | Bertagnoli et al. |
| 2009/0105788 A1 | 4/2009 | Bartol et al. |
| 2009/0118709 A1 | 5/2009 | Sand et al. |
| 2009/0124934 A1 | 5/2009 | Rabbitte et al. |
| 2009/0138056 A1 | 5/2009 | Anderson et al. |
| 2009/0143807 A1 | 6/2009 | Sand |
| 2009/0143829 A1 | 6/2009 | Shluzas |
| 2009/0149865 A1 | 6/2009 | Schmitz et al. |
| 2009/0171381 A1 | 7/2009 | Schmitz et al. |
| 2009/0177112 A1 | 7/2009 | Gharib et al. |
| 2009/0177144 A1 | 7/2009 | Masmanidis et al. |
| 2009/0177241 A1 | 7/2009 | Bleich et al. |
| 2009/0182382 A1 | 7/2009 | Justis et al. |
| 2009/0192403 A1 | 7/2009 | Gharib et al. |
| 2009/0204016 A1 | 8/2009 | Gharib et al. |
| 2009/0204119 A1 | 8/2009 | Bleich et al. |
| 2009/0204192 A1 | 8/2009 | Carlton et al. |
| 2009/0209879 A1 | 8/2009 | Kaula et al. |
| 2009/0216284 A1 | 8/2009 | Chin et al. |
| 2009/0299166 A1 | 12/2009 | Nishida |
| 2010/0004654 A1 | 1/2010 | Schmitz et al. |
| 2010/0010334 A1 | 1/2010 | Bleich et al. |
| 2010/0057087 A1 | 3/2010 | Cha |
| 2010/0094231 A1 | 4/2010 | Bleich et al. |
| 2010/0274250 A1 | 10/2010 | Wallace et al. |
| 2010/0331883 A1 | 12/2010 | Schmitz et al. |
| 2010/0331900 A1 | 12/2010 | Garabedian et al. |
| 2011/0004207 A1 | 1/2011 | Wallace et al. |
| 2011/0190772 A1 | 8/2011 | Saadat et al. |
| 2011/0224709 A1 | 9/2011 | Bleich |
| 2011/0224710 A1 | 9/2011 | Bleich |

(56) References Cited

U.S. PATENT DOCUMENTS

| | | |
|---|---|---|
| 2012/0016368 A1 | 1/2012 | Bleich et al. |
| 2012/0022538 A1 | 1/2012 | Schmitz et al. |
| 2012/0065639 A1 | 3/2012 | Schmitz et al. |
| 2012/0123294 A1 | 5/2012 | Sun et al. |
| 2012/0143206 A1 | 6/2012 | Wallace et al. |
| 2012/0184809 A1 | 7/2012 | Bleich et al. |
| 2012/0191003 A1 | 7/2012 | Garabedian et al. |
| 2012/0239041 A1 | 9/2012 | Bleich et al. |
| 2013/0012831 A1 | 1/2013 | Schmitz et al. |
| 2013/0053851 A1 | 2/2013 | Schmitz et al. |
| 2013/0053853 A1 | 2/2013 | Schmitz et al. |
| 2013/0172895 A1 | 7/2013 | Wallace et al. |
| 2013/0310837 A1 | 11/2013 | Saadat et al. |
| 2014/0012239 A1 | 1/2014 | Schmitz et al. |

FOREIGN PATENT DOCUMENTS

| | | |
|---|---|---|
| DE | 3209403 A1 | 9/1983 |
| DE | 4036804 A1 | 5/1992 |
| EP | 359883 A1 | 3/1990 |
| EP | 1304080 A2 | 4/2003 |
| EP | 1340467 A2 | 11/2003 |
| EP | 1207794 B1 | 5/2004 |
| EP | 1315463 B1 | 5/2005 |
| EP | 1611851 A1 | 1/2006 |
| EP | 1006885 B1 | 9/2006 |
| FR | 2706309 | 12/1994 |
| GB | 1460837 A | 1/1977 |
| JP | 04141159 A | 5/1992 |
| JP | 2960140 B2 | 10/1999 |
| JP | 23116868 | 4/2003 |
| JP | 24065380 A2 | 3/2004 |
| RU | 2107459 | 3/1998 |
| WO | 9222259 A2 | 12/1992 |
| WO | 9622057 | 7/1996 |
| WO | 9714362 A1 | 4/1997 |
| WO | 9734536 A2 | 9/1997 |
| WO | 9918866 A1 | 4/1999 |
| WO | 9921500 A1 | 5/1999 |
| WO | 0067651 A1 | 11/2000 |
| WO | 0108571 A1 | 2/2001 |
| WO | 0162168 A2 | 8/2001 |
| WO | 0207901 A1 | 1/2002 |
| WO | 0234120 A2 | 5/2002 |
| WO | 02076311 A2 | 10/2002 |
| WO | 03026482 A2 | 4/2003 |
| WO | 03066147 A1 | 8/2003 |
| WO | 2004002331 A1 | 1/2004 |
| WO | 2004028351 A2 | 4/2004 |
| WO | 2004043272 A1 | 5/2004 |
| WO | 2004056267 A1 | 7/2004 |
| WO | 2004078066 A2 | 9/2004 |
| WO | 2004080316 A1 | 9/2004 |
| WO | 2004096080 A2 | 11/2004 |
| WO | 2005057467 A2 | 2/2005 |
| WO | 2005057467 | 6/2005 |
| WO | 2005077282 A1 | 8/2005 |
| WO | 2005089433 A2 | 9/2005 |
| WO | 2006009705 A2 | 1/2006 |
| WO | 2006015302 A1 | 2/2006 |
| WO | 2006017507 A2 | 2/2006 |
| WO | 2006039279 A2 | 4/2006 |
| WO | 2006042206 A2 | 4/2006 |
| WO | 2006044727 A2 | 4/2006 |
| WO | 2006047598 A1 | 5/2006 |
| WO | 2006058079 A3 | 6/2006 |
| WO | 2006058195 A2 | 6/2006 |
| WO | 2006062555 A2 | 6/2006 |
| WO | 2006086241 A2 | 8/2006 |
| WO | 2006099285 A2 | 9/2006 |
| WO | 2006102085 A2 | 9/2006 |
| WO | 2007008709 A2 | 1/2007 |
| WO | 2007021588 A1 | 2/2007 |
| WO | 2007022194 A2 | 2/2007 |
| WO | 2007059343 A2 | 2/2007 |
| WO | 2007067632 A2 | 6/2007 |
| WO | 2008008898 A2 | 1/2008 |
| WO | 2008157513 A1 | 12/2008 |
| WO | 2009012265 A2 | 1/2009 |
| WO | 200921116 A2 | 2/2009 |
| WO | 2009018220 A1 | 2/2009 |
| WO | 2009036156 A1 | 3/2009 |
| WO | 2009046046 A1 | 4/2009 |
| WO | 2009058566 A1 | 5/2009 |
| WO | 2009151926 A2 | 12/2009 |
| WO | 2010014538 | 4/2010 |

OTHER PUBLICATIONS

Peavy er al., "Comparison of Cortical Bone Abiations by using Infrared Laser Wavelengths 2.9 to 9.2, Lasers in Surgery and Medicine," 1999, vol. 26, 421-434. Jan. 1, 1999.

Zeppelin Laminectomy Rongeur K901372[online] Retrieved from the internet: ,URL: http://www.zeppelinn-medical.com/download/instruments. pdf> Oct. 24, 2006.

Reckling Frederick, "Modified Stethoscope Earpiece Makes Excellent Gigli Saw Guide," J Bone and Joint Surgery Am, Dec. 1972, 54-A(8), 1787-1788. Dec. 1, 1972.

Schwieger et al., "Abrasive Water Jet Cutting as a New Procedure for Cutting Cancellous Bone-In Vitro Testing in comparison with the Oscillating Saw," Wiley Interscience, www.interscience, wiley. Com, Sep. 20, 2004, 223-228. Sep. 20, 2004.

Leguideleguid et al, U.S. Appl. No. 14/061,641 Entitled Tissue Modification Devices, filled Oct. 23, 2013.

Schmitz et al., U.S. Appl. No. 14/064,085 entitled "Access and Tissue Modification Systems and Methods," filed Oct. 25, 2013.

Schmitz et al, U.S. Appl. No. 14/082,052 entitled flexible tissue Removal Devices and Methods, filed Nov. 15, 2013.

Bleich et al., U.S. Appl. No. 14/180,221 enitled "Flexible tissue rasp," filed Feb. 13, 2014.

Tomita and Kawahara, The Threaded Saw: a New Device for Cutting Bone, The journal of Bone and Joint Surgery, 1996, vol. 78, 1915-1917.

Herkowitz, "The Cervical Spine Surgery Atlas", 2004, Lippincott Williams & Wilkins; 2nd Edition; pp. 203-206,& 208; Dec. 2003.

Ohta et al., "Superimposed Mechanomyographic Response at Different Contraction Intensirt in Medical Gastocnemius and Soleus Muscles," International Journl of Sport and Health Science: vol. 5, 63-70, Nov. 2007.

Bleich et al.; U.S. Appl. No. 13/757,599 entitled "Multiple pathways for spinal nerve root decompression from a single access point," filed Feb. 1, 2013.

Mimran et al.; U.S. Appl. No. 13/757,661 entitled "Tissue modification devices and methods,"filed Feb. 1, 2013.

Arcenio et al.; U.S. Appl. No. 12/980,165 entitled "Systems and Methods for Performing Spinal Fusion", filed Dec. 28, 2010.

Bleich et al.; U.S. Appl. No. 12/984,162 entitled "Devices and Methods for Tissue Access", filed Jan. 4, 2011.

Wallace et al.; U.S. Appl. No. 12/911,537 entitled "Devices and Methods for treating Tissue", filed Oct. 25, 2010.

Wallace et al.; U.S. Appl. No. 13/007,381 entitled "Tissue Modification Devices," filed Jan. 14, 2011.

Mopec Bone-Cutting tool, Product brochure, Total pages 4. First accessed Dec. 15, 2005.

Edwards et al; "T-Saw Laminoplasty for the Management of Cervical Spondylotic Myelopthy,"Spine, Lippincott Williams & Wilkins, Inc. 200, vol. 25(14): 1788-1794. Jan. 1, 2000.

Honl et al, "The Use of Water-Jetting Technology in Prostheses Revision Surgery—First Results of Parameter Studios on Bone and Bone Cemnt," Biomed Mater Res(Applied Biomaterials), John Wiley & Sons, Inc, 200, 53, 6; 781-790. Jan. 1, 2000.

Jun, Byung-Yoon, "Posterior Lumbar Interbody Fusion With Restoration of Lamina and Facet Fusion,"Spine, Lippincott Williams& Wilkins, Inc., 2000, vol. 25 No. 8, 917-922. Jan. 1, 2000.

Abdel-Wanis et al., Tumor Growth potential after tumoral and instrumental contamination: an in-vivo comparative study of T-saw, Gigli saw, and scalpel, Journal of orthopaedic science, 2001, vol. 6, 424-429. Jan. 1, 2001.

(56) References Cited

OTHER PUBLICATIONS

Codman Laminectomy Shaver (a Johnson & Johnson company ww.codman.com) catalogue, pp. 416-431, (online) Retrieved from the internet:<URL; http://ww.codman.com/PDFs/Catalog_04_R.pdf>. Jan. 1, 2001.
Ellman Int. Disc-FX System Accessories K052241[online] Retrieved from the internet: <URL: http://www.ellman.com/medical/>. Jan. 1, 2001.
Hara et al., "En Bloc Laminoplasty Performed with Threadwire Saw: Technical Note,"Neurosurgery, Jan. 2001, vol. 48, No. 1, pp. 235-239. Jan. 1, 2001.
Hata et al.,A less invasive surgery for rotator cuff tear: Mini-open repair, Journal of Shoulder and Elbow Surgery, 2001, vol. 10 No. 11-16. Jan. 1, 2001.
Integra Ruggles TM Kerrison {online] Retrieved from the internet: <URL: hhtp:// www.integra-ls.com/products!?product=22>. Jan. 1, 2001.
US Surgical Kerrison Spinal Rongeur K943116 [online] Retrieved from the internet <URL: http://www.ussurg.com/uss/index.html>. Jan. 1, 2001.
Sen, Cengiz, Tibia proksimalinde Gigli testeresi ile yapilanperkutan osteotominin guvenilirligi: Kadavra calismasi, Acta orthopaedica et traumatologica turcica, 2002, vol. 36, 136-140: (in Russian w/ Eng Summary). Jan. 1, 2002.
Shiraishi T., "A new technique for exposure of the cervical spine laminae," Journal of neurosurgery. Spin, 2002, vol. 96 (1), 122-126. Jan. 1, 2002.
Shiraishi T., Skip laminectomy—a new treatment for cervical spondylotic myelopathy, preserving bilateral musclar attachments to the spinous processess: a preliminary report, Spin, 2002, vol. 2(2), 108-115. Jan. 1, 2002.
Tomita et al., "The Use of the T-saw for Expansive Midline laminoplasty in the Treatment of Cervical Myelopathy," Orthopedics and Traumatology, No. 3, pp. 169-178, 2002 Jan. 1, 2002.
Martin-Benlloch et al., Expansice Laminoplasty as a Method for Managing Cervical Multilevel Spondylotic Myelopathy,Spine, Lippincott Williams& Wilkins, Inc., 2003, vol. 28 No. 7, 680-684. Jan. 1, 2003.
Miyamoto et al., "Kyphectomy Using a Surgical Threadwire (T-Saw) for Kyphotic Defomity in a Child with Myelomeningocele,"Spine, Lippincott Williams &Wilkins, Inc., 2003, vol. 28 No. 10, E187-E190. Jan. 1, 2003.
Shiraishi et al. "Results of Skip Laminectomy—Minmum 2-Year Follow-up Study Compared with Open-Door Laminoplasty,"Spine, Lippincott Williams& Wilkins, Inc., 2003, vol. 28 No. 24, 2667-2672. Jan. 1, 2003.
Takada et al., Unusual Metastasis to the Cauda Equina From Renal Cell Carcinoma, Spine, Lippincott Williams& Wilkins, Inc., 2003, vol. 28 No. 6, E114-E117. Jan. 1, 2003.
Eralp et al., "A comparison of two osteotomy techniques for tibial lengthening," Archives of orthopaedic and trauma surgery, 2004, vol. 124:298-300. Jan. 1, 2004.
Skippen et al., "The Chain Saw—A Scottish Invention," Scottish Medical Journal, 2004, vol. 49(2), 72-75. Jan. 1, 2004.
Bohinski et al. "Novel use of a threadwire saw for high sacral amputation," Journal of neurosurgery: Spine, 2005, vol. 3, 71-78. Jan. 1, 2005.
Nakagiri et al., "Thoracoscopic Rib Resection Using a Gigli Saw," The Annals of Thoracic Surgery, 2005, vol. 80, 755-756. Jan. 1, 2005.
Osaka et al., "Clincical significance of a wide excision policy for sacrococcygeal chordoma,"J Cancer Res Clin Oncol, 2005, Total pp. 6. Jan. 1, 2005.
Fessler Richard G, "Minimally Invasive Microendoscopic Decompressive Laminotomy for Lumbar Stenosis," American Association of Neurological Surgeons, 2006, Online CME course, [Retrieved on Jun. 29, 2006 from the internet http://www.aans.emedtrain.com/lumbar_ste Jan. 1, 2006.
Park et; "Cases of the Excision of Carious Joints," John Scrymgeour, Glasgow, 1806, Total pp. 6. Jan. 1, 1806.
Pancoast, Joseph, "A treatise on Operative Sugery,"Carey and Hart, Philadelphia, 1844, Total pp. 11. Jan. 1, 1844.
Truax, Charles, "The Mechanics of Surgery,"Chicago, IL; 1899, Total pp. 3. Jan. 1, 1899.
Burrows, Harold, "Surgical instruments and appliances used in operations,"Faber and Faber, London, 1937, total pp. 4. Jan. 1, 1937.
Nilkins, Robert H, "Neurosurgical Classics,"Johnson Reprint Corporation, New York, 1965, 377-382. Jan. 1, 1965.
Dammann, Gordon, Pictorial Encyclopedia of Civil War Medical Instruments and Equipment, Pictorial Histories Publishing Company, Missoula, Montana, 1983, Total pp. 2. Jan. 1, 1983.
Barer Malvin, "Instrument to Enhance Passage of the Gigli Saw," Journal of Pediatric Orthopedics, Raven Press, New York, 1984, 4:762-763. Jan. 1, 1984.
Paley et al., "Percutaneous Osteotomies," Orthopedic Clinics of North America, 1991, vol. 22 No. 613-624. Jan. 1, 1991.
Paktiss et al., "Afghan Percutaneous Osteotomy," Journal of Pediatric Orthopaedics, Raven Press Ltd, New York, 1993, vol. 13 No. 4, 531-533. Jan. 1, 1993.
Peltier, Leonard Orthopedics: A History and Iconography, Norman Publishing, San Francisco, 1993, Total pp. 3. Jan. 1, 1993.
Rutkow, Ira, "Surgery An illustrated History," Mosby Year book, Inc., St. Louis, 1993, Total pp. 4. 1/193.
Goel, Atul, "Neurosurgical forum, Supraorbital Craniotomy," Journal of Neurosurgery, 1994, vol. 81, 642-643. Jan. 1, 1994.
Tomita et al., "Total en bloc spondylectomy and circumspinal decompression for solitary spinal metastasis," Paraplegia, 194, 32:36-46. Jan. 1, 1994.
Tomita K. et al., Total en bloc spondylectomy for solitary spinal metastases, International Orthopaedics (SICOT), 1994, 18: 291-298. Jan. 1, 1994.
Brunori et al., "Celebrating the centennial (1894-1994): Leonardo Gigli and his wire saw,"J. Neurosurg, 1995, 82: 1086-1090. Jan. 1, 1995.
Tomita et al., "The Threadwire Saw: a New Device for Cutting Bon," The Journal of Bone and Joint Surgery, 1996, vol. 78, 1915-1917. Jan. 1, 1996.
Stevens et al., "Calvarial Bone Graft Harvest Ussing the gigli Saw," Journal of Oral and Maxillofacial Surgery, 1998, vol. 56, 798-799. Jan. 1, 1998.
Baumgart et al., Indikation and Technik der Knochedndurchtrennung, Der Chirurg, 1998, vol. 69; 1188-1196. (in German with Eng Summary). Jan. 1, 1998.
Tomita et al. Expansive Midline T-Saw Laminoplasty (Modified Spinour Process-Splitting) for the management of Cevical Myelopathy,Spine, Lippincott Williams& Wilkins, Inc, 1998, 23(1), 32-37 Jan. 1, 1998.
Fujit et al., "Chordoma in the Cervica Spine Managed with En BLoc Excision," Spine, Lippincott Williams & Wilkins, Inc. , 1999, 24(17), 1848-1851. Jan. 1, 1999.
Gore Smoother User Manual, W. L. Gore & Associates, Inc. Flagstaff, AZ, Dec. 1999, Total pp. 3. Jan. 1, 1999.

\* cited by examiner

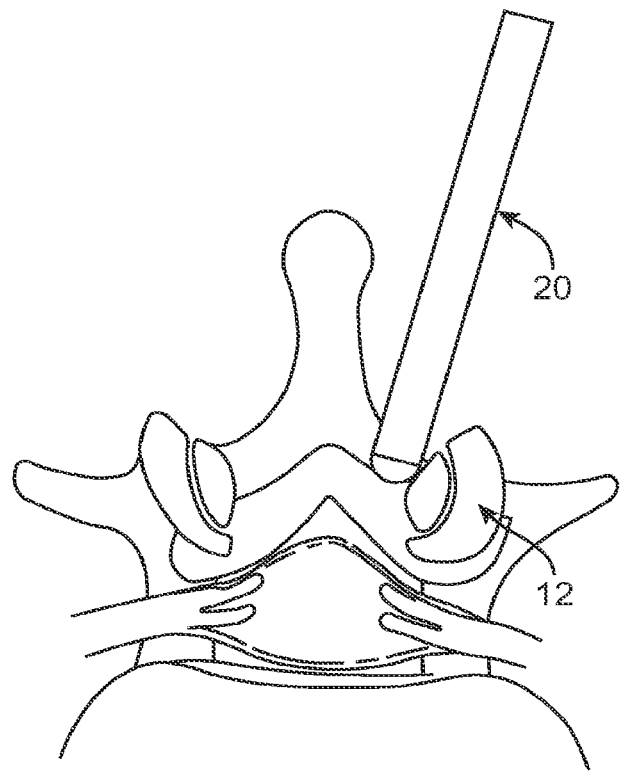
FIG. 40a
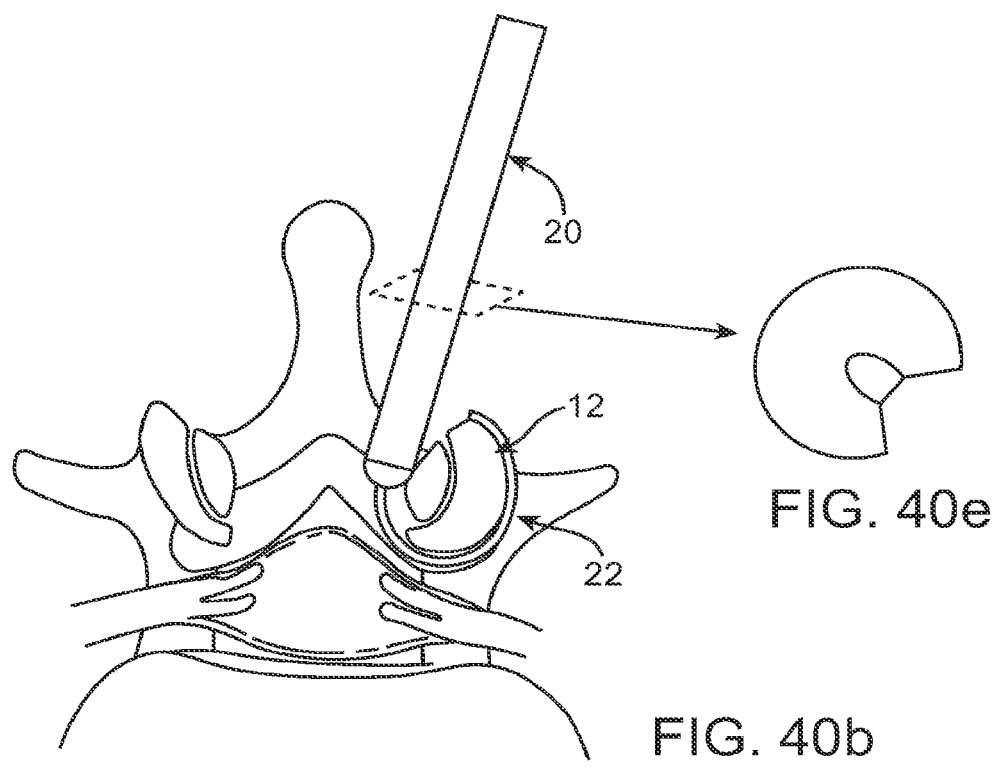
FIG. 40e
FIG. 40b

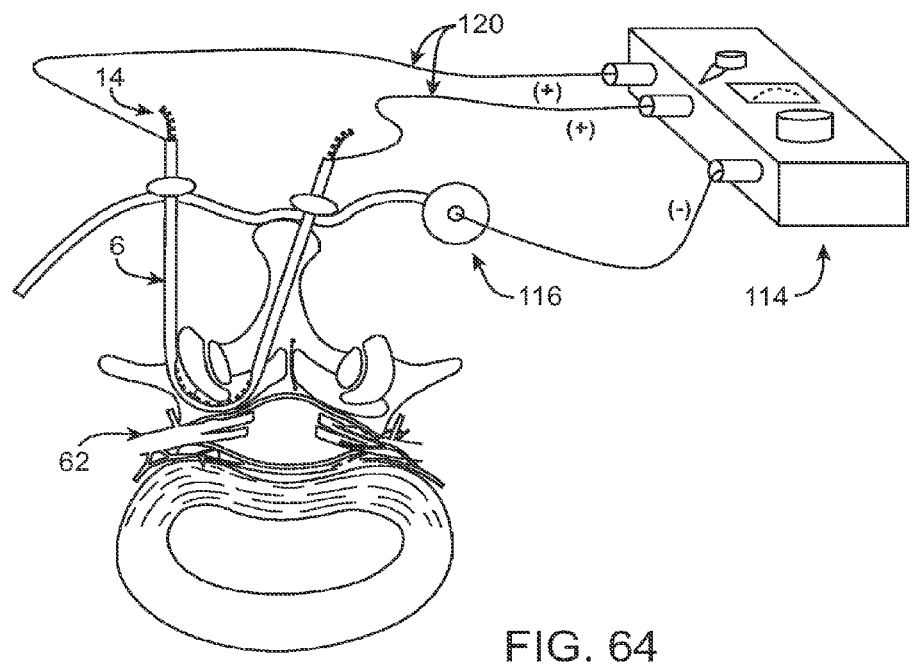
FIG. 64
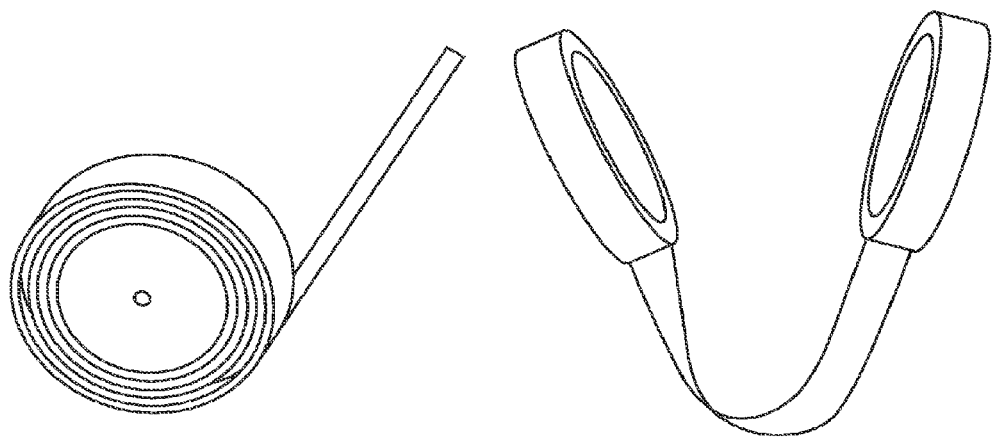
FIG. 65a
FIG. 65b

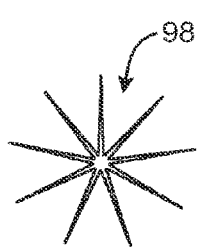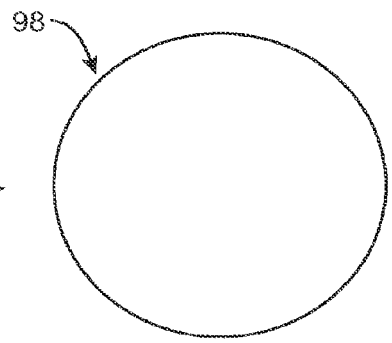
FIG. 85a  FIG. 85b  FIG. 85c
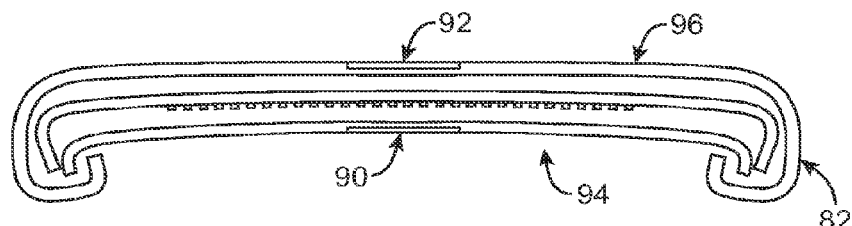
FIG. 86a
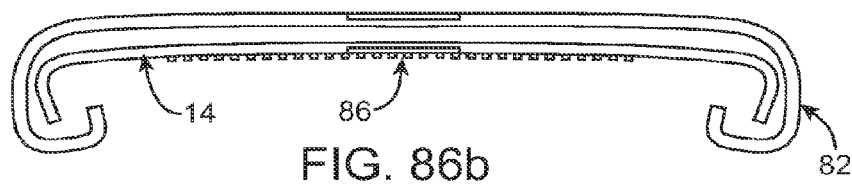
FIG. 86b
FIG. 86c

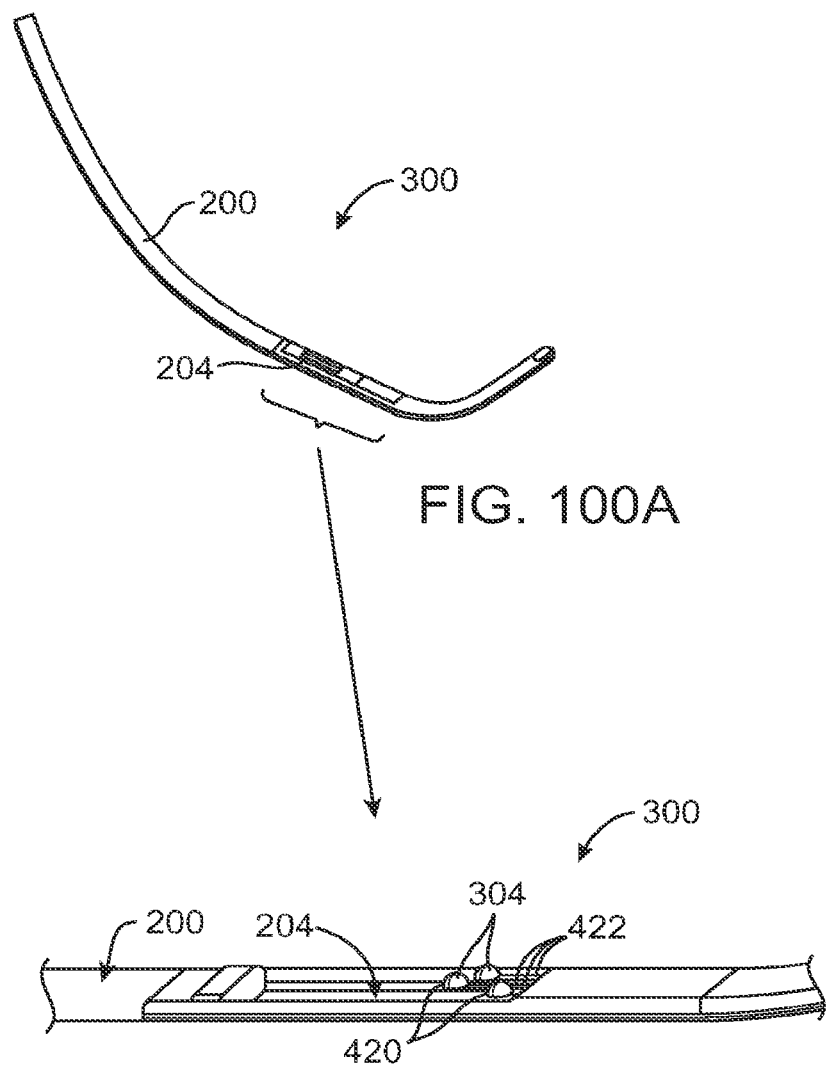

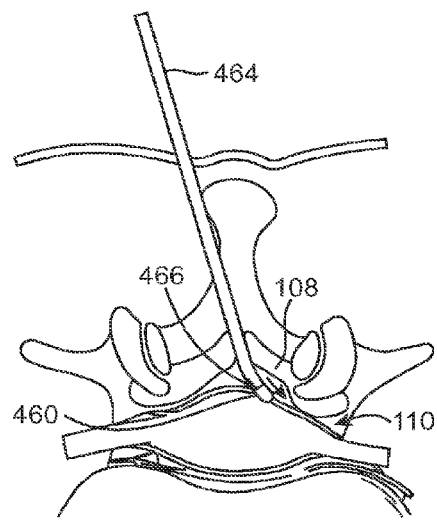
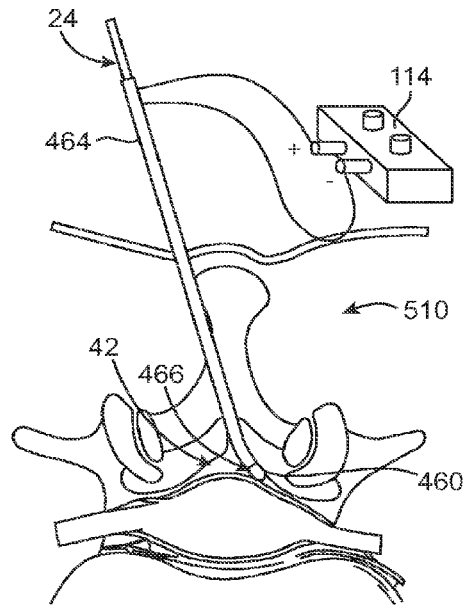
FIG. 119    FIG. 120
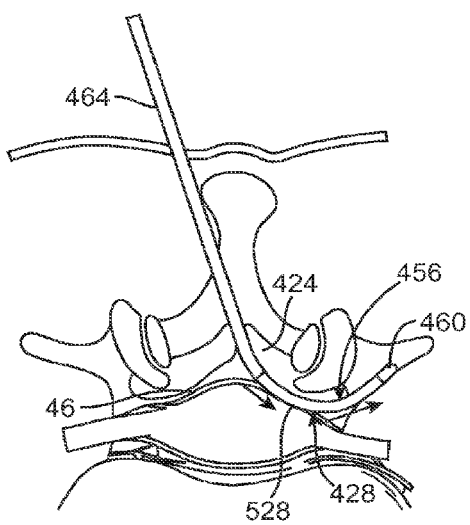
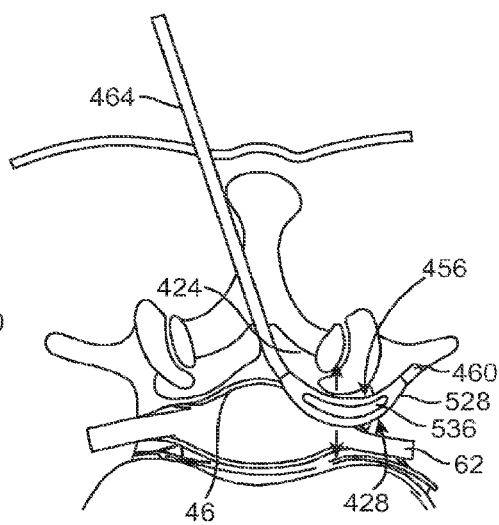
FIG. 121    FIG. 122

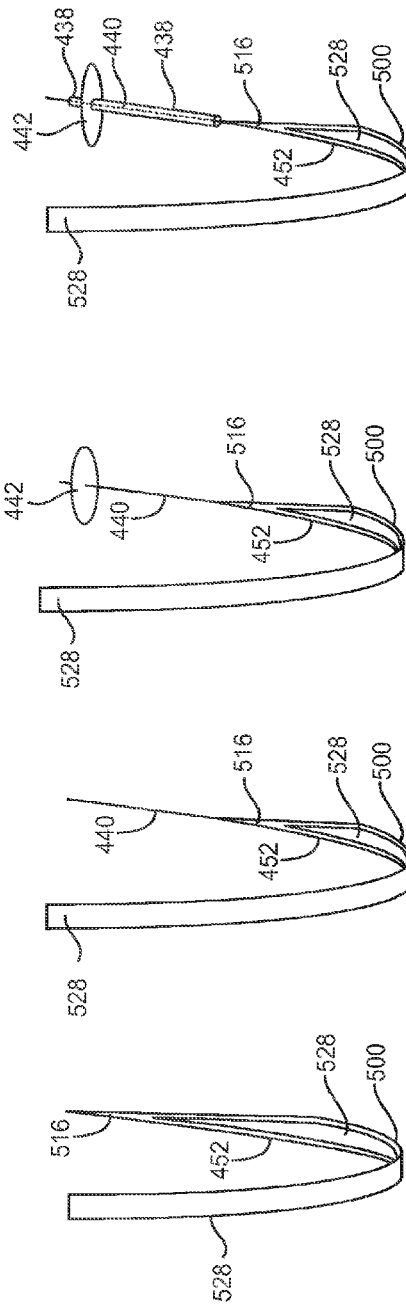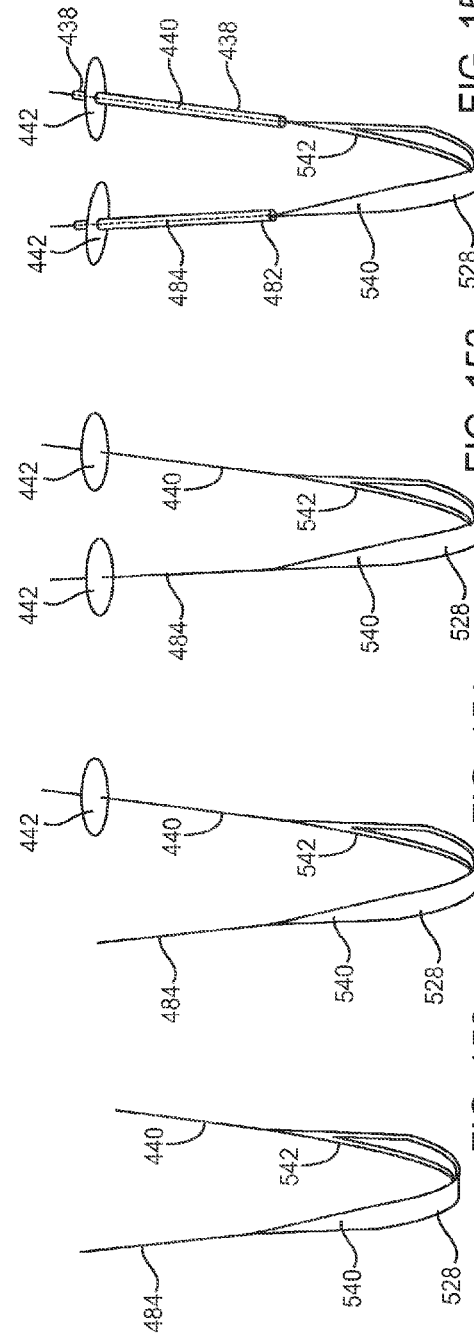

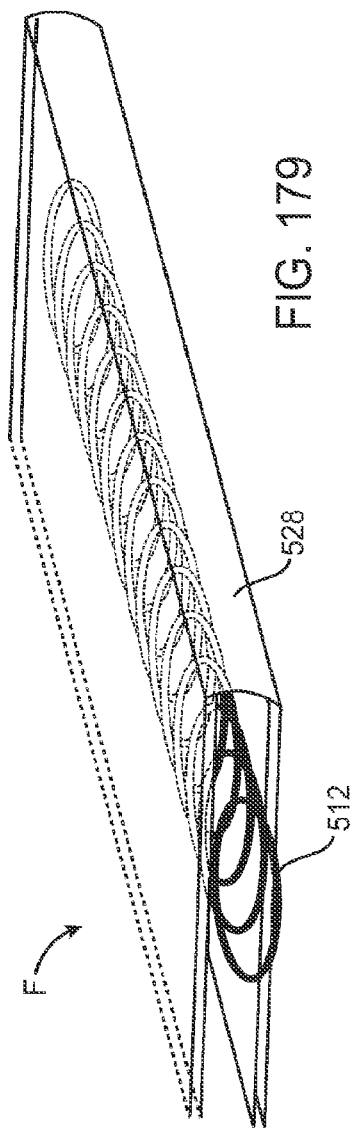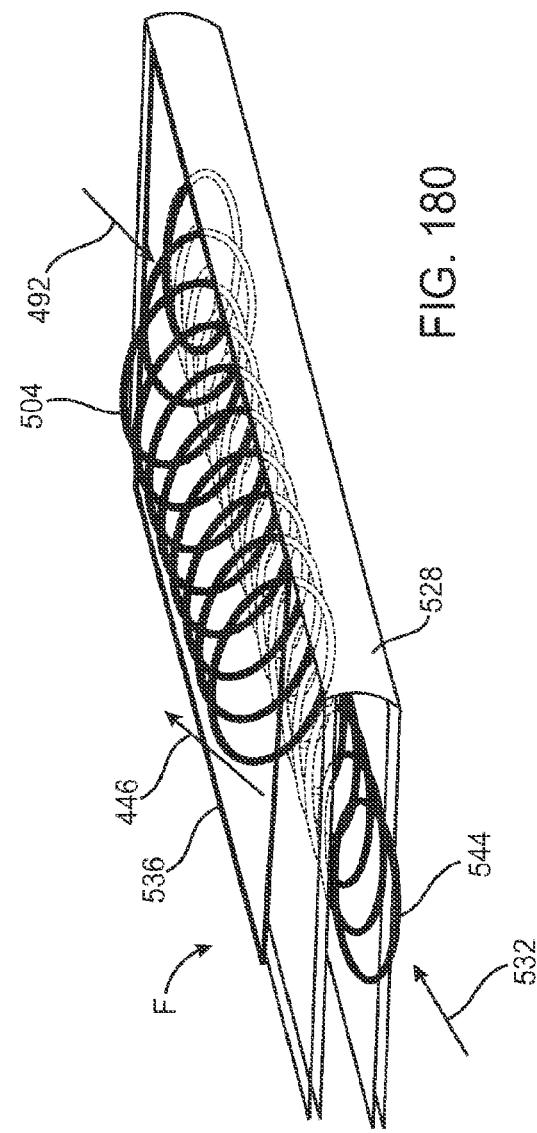

DEVICES AND METHODS FOR TISSUE ACCESS

CROSS-REFERENCE TO RELATED APPLICATIONS

This patent application is a division of U.S. patent application Ser. No. 12/984,162 which is a continuation-in-part of U.S. patent application Ser. No. 11/251,205, now U.S. Pat. No. 7,918,849 titled "DEVICES AND METHODS FOR TISSUE ACCESS", filed Oct. 15, 2005; which claims the benefit of U.S. Provisional Application Nos.: 60/619,306, filed Oct. 15, 2004; 60/622,865, filed Oct. 28, 2004; 60/681,719, filed May 16, 2005; 60/681,864, filed May 16, 2005; and 60/685,190, filed May 27, 2005, each of which is incorporated by reference herein in its entirety.

U.S. patent application Ser. No. 12/984,162 is also a continuation-in-part of U.S. patent application Ser. No. 12/917,253, now U.S. Pat. No. 8,551,097 titled "TISSUE ACCESS GUIDEWIRE SYSTEM AND METHOD", filed Nov. 1, 2010, which is a continuation of U.S. patent application Ser. No. 11/468,247 titled "TISSUE ACCESS GUIDEWIRE SYSTEM AND METHOD", filed Aug. 29, 2006, now U.S. Pat. No. 7,857,813, each of which is incorporated by reference herein in its entirety.

U.S. patent application Ser. No. 12/984,162 is also a continuation-in-part of U.S. patent application Ser. No. 12/127,535, now U.S. Pat. No. 8,257,356 titled "GUIDEWIRE EXCHANGE SYSTEMS TO TREAT SPINAL STENOSIS", filed May 27, 2008; which claims the benefit as a continuation-in-part of U.S. patent application Ser. No. 11/468,247, now U.S. Pat. No. 7,857,813 titled "TISSUE ACCESS GUIDEWIRE SYSTEM AND METHOD", filed Aug. 29, 2006. U.S. patent application Ser. No. 12/127,535 also claims the benefit as a continuation-in-part of U.S. patent application Ser. No. 11/251,199, now U.S. Pat. No. 8,192,435 titled "Devices and Methods for Tissue Modification", filed Oct. 15, 2005, which claims the benefit of U.S. Provisional Patent Application Nos.: 60/685,190, filed May 27, 2005; 60/681,719, filed May 16, 2005; 60/681,864, filed May 16, 2005; 60/622,865, filed Oct. 28, 2004; and 60/619,306, filed Oct. 15, 2004; each of which is incorporated by reference herein in its entirety.

FIELD OF THE INVENTION

The present invention relates to methods and apparatus for selective surgical removal of tissue, such as for the treatment of spinal neural and neurovascular impingement, through selective resection, ablation, and remodeling of tissue in the lateral recess, neural foramina and central spinal canal, more particularly, for safely performing lateral recess and neuroforaminal enlargement of the spine.

More particularly, the present invention relates to treating neural and neurovascular impingement in the spine through the creation of a safe working space adjacent to neural and neurovascular structures, followed by selective surgical removal of tissue. Both percutaneous and open surgical variations of the invention are disclosed.

BACKGROUND OF THE INVENTION

Pathological compression of spinal neural and neurovascular structures most commonly results from a degenerative, age-related process, increasing in prevalence and severity in elderly populations, with potential congenital anatomic components, that result in back, radicular extremity pain and both neurological (e.g., sensory) and mechanical (e.g., motor) dysfunction. Prevalence is also influenced by congenital spinal anatomy. Disease progression leads to increased neural irritation, neural and neurovascular impingement, and ischemia, and is frequently accompanied by progressively increased pain, often in conjunction with reflex, sensory and motor neurological deficits.

In the United States, Spinal Stenosis occurs with an incidence of between 4 percent and 6 percent of adults 50 years of age or older, and is the most frequent reason cited for back surgery in patients 60 years of age and older.

Spinal Stenosis often includes neural and/or neurovascular impingement, which may occur in the central spinal canal, the lateral recesses of the spinal canal, or in the spinal neural foramina. The most common causes of neural compression within the spine are spinal disc disease (collapse, bulging, herniation); ligamentum flavum buckling, thickening and/or hypertrophy; zygapophysial (facet) joint hypertrophy; osteophyte formation; and spondylolisthesis.

Disease progression increases neural irritation, impingement, and ischemia, and is frequently accompanied by progressively increased pain, often in conjunction with reflex, sensory and motor neurological changes (e.g., deficits).

Current surgical treatments for Spinal Stenosis include laminectomy (usually partial, but sometimes complete), laminotomy and/or facetectomy (usually partial, but sometimes complete), with or without fusion. While standard surgical procedures (e.g., spinal decompressions) lead to improvements in symptoms for 6 months or more in approximately 60% of cases, there is an unacceptable incidence of long-term complications and morbidity: approximately 40% of patients do not obtain sustained improvement with current surgical decompressions.

Several companies offer tools that facilitate surgical access to the areas of the spine where neural impingement is likely to occur, in order to allow the surgeon to decompress the impinged neural structures through the removal of vertebral lamina, ligamentum flavum, facet complex, bone spurs, and/or intervertebral disc material. These surgical resections are frequently (i.e., occurs in 15% to 20% of cases) accompanied by fusion (arthrodesis). Spinal arthrodesis is performed to fuse adjacent vertebrae and prevent movement of these structures in relation to each other. The fusion is commonly a treatment for pain of presumed disc or facet joint origin; for severe spondylolisthesis; for presumed spinal instability; and for spines that have been rendered "unstable" by the surgical decompression procedures, as described above. The definition of "spinal instability" remains controversial in current literature.

Spinal arthrodesis may be achieved through various surgical techniques. Biocompatible metallic hardware and/or autograft or allograft bone is commonly placed (e.g., secured) anteriorly and/or posteriorly in the vertebral column in order to achieve surgical fusion. These materials are secured along and between the vertebral bodies (to restore vertebral height and replace disk material) and/or within the posterior elements, typically with pedicle screw fixation. Autograft bone is often harvested from the patient's iliac crest. Cadaveric allograft is frequently cut in disc shaped sections of long bones for replacement of the intervertebral discs in the fusion procedure.

Critics have frequently stated that, while discectomy and fusion procedures frequently improve symptoms of neural impingement in the short term, both are highly destructive procedures that diminish spinal function, drastically disrupt normal anatomy, and increase long-term morbidity above levels seen in untreated patients.

The high morbidity associated with discectomy may be due to several factors. First, discectomy reduces disc height, causing increased pressure on facet joints. This stress leads to facet arthritis and facet joint hypertrophy, which then causes further neural compression. The surgically-imposed reduction in disc height also may lead to neuroforaminal stenosis, as the vertebral pedicles, which form the superior and inferior borders of the neural foramina, become closer to one another. The loss of disc height also creates ligament laxity, which may lead to spondylolisthesis, spinal instability or osteophyte or "bone spur" formation, as it has been hypothesized that ligaments may calcify in their attempt to become more "bone-like".

In addition, discectomy frequently leads to an incised and further compromised disc annulus. This frequently leads to recurrent herniation of nuclear material through the surgically created or expanded annular opening It may also cause further buckling of the ligamentum flavum.

The high morbidity associated with fusion is related to several factors. First, extensive hardware implantation may lead to complications due to breakage, loosening, nerve injury, infection, rejection, or scar tissue formation. In addition, autograft bone donor sites (typically the patient's iliac crest) are a frequent source of complaints, such as infection, deformity, and protracted pain. Perhaps the most important reason for the long-term morbidity caused by spinal fusion is the loss of mobility in the fused segment of the spine. Not only do immobile vertebral segments lead to functional limitations, but they also cause increased stress on adjacent vertebral structures, thereby frequently accelerating the degeneration of other discs, joints, bone and other soft tissue structures within the spine.

Recently, less invasive, percutaneous approaches to spinal discectomy and fusion have been tried with some success. While these less invasive techniques offer advantages, such as a quicker recovery and less tissue destruction during the procedure, the new procedures do not diminish the fact that even less invasive spinal discectomy or fusion techniques are inherently destructive procedures that accelerate the onset of acquired spinal stenosis and result in severe long-term consequences.

Additional less invasive treatments of neural impingement within the spine include percutaneous removal of nuclear disc material and procedures that decrease the size and volume of the disc through the creation of thermal disc injury. While these percutaneous procedures may produce less tissue injury, their efficacy remains unproven.

Even more recently, attempts have been made to replace pathological discs with prosthetic materials. While prosthetic disc replacement is a restorative procedure, it is a highly invasive and complex surgery. Any synthetic lumbar disc will be required to withstand tremendous mechanical stresses and will require several years of development. Current synthetic disc designs can not achieve the longevity desired. Further, synthetic discs may not be an appropriate therapeutic approach to a severely degenerative spine, where profound facet arthropathy and other changes are likely to increase the complexity of disc replacement. Like most prosthetic joints, it is likely that synthetic discs will have a limited lifespan and that there will be continued need for minimally invasive techniques that delay the need for disc replacement.

Even if prosthetic discs become a viable solution, the prosthetic discs will be very difficult to revise for patients. The prosthesis will, therefore, be best avoided in many cases. A simpler, less invasive approach to restoration of functional spinal anatomy would play an important role in the treatment of neural impingent in the spine. The artificial discs in U.S. clinical trials, as with any first generation prosthesis, are bound to fail in many cases, and will be very difficult to revise for patients. The prostheses will, therefore, be best avoided, in many cases. Lumbar prosthetic discs are available in several countries worldwide.

In view of the aforementioned limitations of prior art techniques for treating neural and neurovascular impingement in the spine, it would be desirable to provide methods and apparatus for selective surgical removal of tissue that reduce or overcome these limitations.

SUMMARY OF THE INVENTION

In view of the foregoing, the present invention provides apparatus and methods for selective removal of tissue, e.g., soft tissue and bone, preferably in a minimally invasive fashion. The present invention provides apparatus and methods for safe and selective delivery of surgical tools into to the epidural space; and for apparatus and methods that enable safe and selective surgical removal, ablation, and remodeling of soft tissue and bone, preferably in a minimally invasive fashion, with the apparatus delivered into the epidural space. An important preferred variation of the methods and apparatus are used to treat neural and neurovascular impingement in the spine, through a novel approach to safe and selective enlargement of the pathologically narrow spinal neural foramen, the impinged lateral recess, and central canal.

The present invention eliminates much or all of the need to resect non-impinging tissues in order to gain surgical access. In a preferred embodiment, the methods and apparatus are used for the treatment of neural and neurovascular impingement in the spine through a novel approach to safe enlargement of the pathologically narrow spinal neural foramen and the impinged lateral recess. Tissue removal may be performed in a partially or completely open surgical fashion, or in a less invasive or minimally invasive percutaneous fashion. In some embodiments, the invention provides neural stimulation, localization, and/or protection in order to provide a protected working space and to facilitate safe tissue remodeling or removal.

The apparatus and methods have been designed to avoid removal of non-target tissue and to minimize and/or completely prevent trauma to adjacent neural and vascular structures. The methods and apparatus can be used for the treatment of neural and neurovascular impingement in the spine, for example, safe enlargement of the pathologically impinged lateral recess and narrowed spinal neural foramen. Perineural tissue can be removed safely and selectively in a partially or completely open surgical fashion, or in a less invasive or minimally invasive percutaneous fashion. The apparatus and methods described herein can be utilized for lateral recess and neuroforaminal enlargement to provide adequate bone and soft tissue resection. The apparatus and methods described herein can reduce unnecessary destruction of functional bone, ligament or muscle in order to gain access to tissues to be resected.

The present invention encompasses both open and percutaneous approaches to spinal neurovascular decompression, for example, through passage of an atraumatic, thin tissue removal device from the epidural space laterally through the neural foramen. Variations of the present invention preferably provide for access, neural protection and/or decompression.

Methods and apparatus for spinal lateral recess, neuroforaminal, and/or central canal enlargement, through selective and safe alteration of the tissues that pathologically impinge neural and neurovascular structures in the spine are disclosed. Impinging tissues to be removed from, or remodeled in, the spine's central canal, lateral recess, and neural foramen, with the herein described methods and apparatus, can include ligamentum flavum; bone spurs or ligamentous calcifications; localized disc extrusions; enlarged facet joint complex; bone; scar tissue or adhesions; and osteophytes.

In an open variation, access may be achieved via an access element comprising a cannulated probe, which optionally may be similar in shape to currently used neuroforaminal instruments, such as the Ball-tipped, Woodson Elevator, or "Hockey Stick" Probes. The probe may be placed through the surgical incision into the epidural space. A curved atraumatic needle then may be advanced through the cannula of the probe and driven laterally to cannulate the neural foramen. A preferably straight, flexible guide wire or needle then may be advanced through the curved needle and driven posteriorly through the skin of the patient's back. Alternatively, surgical incisions may be made on either side of the foramen, and the guide wire may be pulled through the second incision.

Another preferred open surgical approach utilizes a cannulated probe, as described above, the tip of which is placed into the lateral recess, adjacent to or into the neural foramina. Next, a curved and atraumatic guide wire is advanced out of the distal lumen of the cannulated probe, through the neural foramina laterally, and around the lateral then posterior aspect of the facet capsule, until the distal tip of the wire is driven back into the surgical opening. At that point, the surgeon has access to both ends of the guide wire, and the tissue removal device may be pulled or advanced into position via the guide wire. The guide wire may be attached to the tissue removal device by any of several possible means. One simple method for using a guide wire to pull a tissue removal device would be to have an eyelet present in the proximal guide wire, through which the tissue removal device may be thread. Open access optionally may be aided by the use of image guidance, an epidural endoscope, an endoscopic channel added to the cannulated probes described above, or any other visualization technique.

In a percutaneous variation, access may be achieved via an access element comprising an epidural needle or probe, or via an epidural endoscope having a working channel. The access element may be positioned in the epidural space, and a curved atraumatic needle then may be advanced through the needle, probe or working channel and driven laterally to cannulate the neural foramen. As with the open variation, a preferably straight, flexible guide wire or needle may be advanced through the curved needle and driven posteriorly through the skin of the patient's back. Percutaneous access optionally may be aided by the use of image guidance, an epidural endoscope or any other visualization technique.

In a preferred embodiment, the methods and apparatus include the placement of a working backstop or barrier into the epidural space or neural foramina, to a location between the tool positioned for tissue alteration, and adjacent vulnerable neural or vascular structures, to help prevent neural or vascular injury during surgery. In a further preferred embodiment, the methods and apparatus utilize neural stimulation techniques, to enable neural localization, as a means of improving the safety of the procedure.

In one variation of the present invention, an epidural needle may be converted to a working tool in order to resect or remodel spinal tissue, which is enabled by the use of methods and apparatuses described herein.

After placement of an epidural needle into the epidural space, a special epidural catheter is threaded through the needle into the epidural space. This catheter apparatus contains a needle tip cover in its distal end, which, after it is converted to an open position in the epidural space, is pulled back over the needle tip, by pulling on the proximal portion of the catheter. The catheter based cover blunts and thereby protects the vulnerable structures of the spine, such as the dura, from the sharp epidural needle tip. With the epidural needle tip covered, the needle may be more safely advanced into the epidural space, in a direction somewhat parallel to the dura, towards the contralateral or ipsilateral lateral recess and neural foramen. The needle may be advanced blindly; with image guidance; or with endoscopic guidance.

The epidural catheter, with the cap or cover for the epidural needle, may or may not contain a rigid or flexible fiberoptic cable. With a fiberoptic element and a clear tip to the catheter, the epidural needle may be converted to an epidural endoscope or "needlescope".

One preferred embodiment of the epidural needle apparatus contains two adjacent lumens ("double barreled"), with a working channel adjacent to the epidural needle. The working channel may be fixed and permanent, or removable, as in with a rail and track connection. A removable working channel, in one embodiment, may be inserted or removed while the tip of the epidural needle remains in the epidural space. The distal beveled opening of the working channel, in a preferred variation, is located proximal to and on the same side of the needle as the epidural needle tip beveled opening faces, facilitating visualization of the working channel tools when a fiberoptic element has been placed in through the epidural needle lumen.

The epidural needle or the working channel of the epidural needle may be a vehicle for insertion of a working backstop or barrier, another apparatus that facilitates safe tissue resection and remodeling in the epidural space. The barrier is a thin flat device that may be delivered into or adjacent to the epidural space or neural foramina, through the needle or working channel, or through an endoscope or open incision. Such a backstop may consist of a flexible, curved, thin and flat piece of material. This barrier will serve to protect neural and neurovascular structures from being damaged during tissue manipulation and resection, because it will be placed between the tissue to be ablated, resected, irritated, manipulated or remodeled, and the vulnerable neural and vascular structures or dura. The tools for tissue resection and ablation will be used on the side of the barrier opposite from the vulnerable neural and vascular structures, which will be safely protected from inadvertent injury.

With access, as well as optional neural protection and/or neural localization, established, decompression or selective tissue removal or remodeling may proceed. A tissue removal device with a tissue removal surface is advanced into position, for example, through, along, over or with the neural protection element, e.g. via rail(s) or channel(s) of the neural protection element, or along the guide wire(s); or is pulled into position via the guide wire or the neural protection element, etc. When properly positioned, the tissue removal surface contacts the impinging tissue slated for removal.

The abrasion device may, for example, include a thin belt or ribbon, with an abrasive, shaving, and/or cutting surface, that is placed through the neural foramina and is held firmly against the tissue to be removed. The belt optionally may be placed, at least partially, within a protective sheath or covering, with the area exposed to the abrasive surface of the device somewhat limited to the area where tissue abrasion and removal is desired. The abrasive element may be provided in one or more of a variety of potentially interchangeable shapes, ranging from flat to curved; narrow to wide; or solid to perforated. The abrasive surface may also have various enabling designs, or surface patterns, or coarseness of abrasive material. The apparatus is placed with both free ends of the abrasive element, as well as the ends of the optional protective sleeve or covering, external to the patient for manipulation by a medical practitioner.

When the optional protective sleeve or sheath is provided, both ends of the sleeve may be held under tension, external to the patient, such that the abrasive belt or ribbon may be pulled back and forth through the sleeve without causing significant friction against and/or trauma to adjacent tissues. Initially, both ends of the abrasive ribbon are pulled simultaneously, pulling the device in a posterior and/or lateral direction, thereby bringing impinging spinal tissue in contact with the abrasive and/or cutting surface of the ribbon. When one end of the ribbon is pulled with more force than the other, the ribbon moves in the direction of the stronger pull, while the lesser pull on the opposite end maintains force and creates friction with movement between the abrasive surface and the tissue to be resected.

In an open surgical variation, the ribbon or belt and/or the protective covering or sleeve may be placed through the surgical incision. In a percutaneous variation, the device may be inserted through a needle over a wire. As with the percutaneous approaches, placement may be aided by the use of image guidance and/or the use of an epidural endoscope.

Once the surgical apparatus has been placed, the medical practitioner may enlarge the lateral recess and neural foramina via frictional abrasion, i.e., by sliding the abrasive surface across the tissue to be resected. Impinging tissue to be targeted for abrasion may include, but is not limited to, lateral ligamentum flavum, anterior and medial facet, and osteophytes. The medical practitioner controls the force and speed of the abrasive surface against the tissue to be removed, while optional covers define the tissue exposed to the abrasive element.

One variation of the abrasive element cover envelopes the abrasive surface and the backside of the belt or ribbon in areas where tissue abrasion is not intended. A nerve stimulator may be incorporated into the abrasive surface and/or the protective cover or sleeve in order to verify correct placement and enhance safety by allowing the medical practitioner to ensure that neural tissue is not subject to inadvertent abrasion.

In one variation, the methods and apparatus include placement of a compression dressing following the surgical procedure. Following neuroforaminal and lateral recess enlargement, it may be advantageous to leave, as a surgical dressing, a belt or ribbon pulled tightly against the abraded tissue surface. It is expected that a compression dressing will enhance hemostasis, promote healing and promote subsequent tissue remodeling with the neural foramen more widely open. Furthermore, the surgical dressing would provide a barrier to trap tissue debris away from neural or neurovascular structures, while providing an optional technique for delivering medication, possibly as a depot, to the operative site. Finally, the dressing would also present a smooth surface towards the nerve root during the immediate post-operative period.

The present invention also describes methods and apparatus that may be used as a compression dressing, after tissue resection or ablation. One variation of the compression dressing is placed in a position where it is firmly wrapped around the facet and ligamentum flavum through the neural foramina, as illustrated in FIG. 49. By tightly pressing against treated tissue surfaces, such a device serves to promote desired tissue remodeling; to prevent edema from leading to impingement on neural or vascular tissue during early healing, to contain debris; to promote postoperative hemostasis; to block scar formation between the raw tissue surfaces and the adjacent neural and vascular structures; to avoid inflammation or irritation to neural and vascular structures from contact with adjacent resected tissue surfaces; and as a mechanism for sustained drug delivery post-operatively (e.g. steroids, procoagulants, adhesion barriers).

This neuroforaminal compression dressing may, for example, comprise the optional protective sheath, percutaneously held tightly in place against the abraded surface. Alternatively or additionally, a separate percutaneously removable compression dressing may be placed following tissue abrasion, with or without a biodegradable component. In a further alternative embodiment, an entirely biodegradable compression dressing may be placed tightly against the abraded surface, with the compression dressing remaining completely implanted following the procedure.

In order to reduce a risk of neurological damage during selective tissue removal, variations of the present invention optionally may provide neural protection during tissue removal. In one variation, a neural protection element, e.g., a sheath, shield or backstop, is positioned (e.g., advanced over, or is pulled into place via the guide wire) such that the neural protection element separates impinging tissue in the neural foramen from the underlying dura, adjacent nerve root, dorsal root ganglion, and/or neural vasculature. Tissue removal then may proceed by advancing a tissue removal device into position between impinging tissue and the neural protection element. The neural protection element preferably comprises an atraumatic profile, to reduce tissue injury. For example, the element may comprise rounded edges. Further, low friction materials, coatings, or hydrophilic coatings on the tissue removal element or on the shield may be helpful in atraumatic introduction of these devices through the epidural space and neural foramen.

The neural protection element may comprise a window or local opening that limits exposure of the tissue removal device to the patient's tissue only to the localized area of the opening. The opening may be positioned such that it directly underlies the area of desired tissue removal, e.g., such that it directly underlies the neural foramen and impinging tissue. Irrigation and/or aspiration optionally may be performed through the window, e.g., for debris removal. Suction also may be drawn through the window to engage the impinging tissue and/or to provide a seal against the target tissue. Optionally, the sheath window may comprise a cutting element that coacts with the tissue removal device. Furthermore, the tissue removal device may present its cutting elements at the window. The window optionally may be opened, closed or resized by a medical practitioner as desired. For example, the window may be closed during delivery, opened during tissue removal, then closed during retrieval of the sheath. When the neural protection element comprises a backside shield, the tissue removal device may be delivered through rails within the edges of the shield, or in conjunction with the shield.

Neural protection can be provided during tissue removal, for example, to reduce the risk of neurological damage during selective tissue removal. The neural protection element can be positioned after the needle tip has been placed adjacent to, or within the neural foramina. The neural protection element can be a sheath, shield, backstop, or combinations thereof.

As an added safety precaution, variations of the present invention optionally may comprise neural localization elements to ensure proper positioning of the neural protection element and/or the tissue removal device. The neural localization elements may comprise separate elements or may be integrated with the neural protection element and/or the tissue removal device. In one variation, the neural protection element may comprise a sheath with integrated neural localization elements. In another variation, the neural protection element may comprise a shield with integrated neural localization elements. In yet another variation, the neural protection element may comprise a portion of the tissue removal apparatus that is intended to remain stationary during tissue removal, located adjacent to the moving tissue removal elements. The conductive neural localization elements may be used to ensure that the neural structures and their adjacent vascular structures are on the non-working or backside of the neural protection element.

Neural localization elements on the backside of the neural protection element (i.e., the side of the neural protection element that contacts or is in proximity to the nerve root when properly positioned) may be activated with a stimulation waveform to stimulate the nerve root, thereby providing a positive control that confirms placement of the backside in proximity to the nerve root. Appropriate low intensity electrical stimulation on the backside surface should result in the stimulation of sensory and/or motor nerves in the patient's extremity. Likewise, neural localization elements on the working side of the neural protection element, or on the tissue removal element, (i.e., the side of the neural protection element or tissue removal element that faces impinging tissue slated for removal) may be activated with a stimulation waveform in anticipation of a negative response or no neural stimulation that confirms that the working side is not in contact with the nerve root and that tissue removal may safely proceed. Neural localization elements may be provided on any side or surface of the neural protection element and/or tissue removal element.

Safe tissue removal, ablation and remodeling with these methods and devices is further enabled by complementary methods and apparatuses that assist with accurate neural localization. Neural localization will be performed by neural stimulation through electrically conductive materials located within the capped epidural needle tip; within the epidural tools that will be in contact with tissue to be modified; or one or both sides of the working barrier. Neural stimulation will be performed in conjunction with monitoring of the patient for sensory and/or motor response to the electrical impulses.

Said backstop may also contain neural localization capabilities, including a conductive element on the working side and/or the non-working side. The conductive element may be used to ensure that the neural and their adjacent vascular structures are on the non-working side of the barrier. In the instance that the barrier is placed through the lateral recess or neural foramina, appropriate low intensity electrical stimulation on the non-working surface should result in the stimulation of sensory or motor nerves in the patient's extremity, while appropriate electrical conduction on the working surface should result in no neural stimulation.

Neural stimulation may be monitored by monitoring somatosensory-evoked potentials (SSEPs), motor-evoked potentials (MEPs), and/or by looking for visual signs of muscular contraction within the extremities. (Somatosensory evoked potentials (SSEPs) are non-invasive studies performed by repetitive, sub-maximal, electrical stimulation of a sensory or mixed sensory and motor nerve. In response to the nerve stimulation the brain generates cerebral action potentials (electrical waves), that can be measured and recorded over the scalp and spine with surface electrodes. Typically, needle electrodes are used for intraoperative SSEP monitoring, as they require less current, and reduce artifact. The recorded response is a series of waves that reflect activation of neural structures.) SSEP, SEP, MEP or EMG feedback may be monitored and/or recorded visually, or may be monitored audibly, potentially conveying quantitative feedback related to the volume or frequency of the auditory signal (e.g., a Geiger counter type of quantitative auditory feedback). Intensity of signal or stimulation may be monitored and used to localize the nerve during placement, as well.

For example, the surgeon may use the neural stimulator to ensure that there is not stimulation of vulnerable neurons on the working side of the barrier, prior to initiating tissue manipulation with the working tools. For example, with the barrier in position in the lateral recess or neural foramina, the surgeon may send electrical current first along the working side of the barrier, then along the backside of the barrier. Low level stimulation of the working side would be expected to result in no neural stimulation, while the same stimulation on the backside of the barrier would be expected to stimulate dorsal roots, nerve roots, or ganglia.

Neural localization may be further enabled by the addition of surgical instruments (e.g. cautery devices, graspers, shavers, burrs, probes, etc.). The surgical instruments can be used that selectively deliver electrical current while the patient is monitored for nerve stimulation, for example to further enable neural localization, that selectively deliver electrical current (e.g., stimulate electrically) while the patient is monitored for nerve stimulation in similar fashions, for example to further neural localization. Quantification of stimulation can enable neural localization. For example, the user can use a calibrated sensor input that recognizes stronger stimulation as the device is moved closer to neural structures, or is able to differentiate between stimulators that are closer to or further from neural structures. For added safety, a surgical device can be designed to automatically stimulate before or during tissue removal (e.g., resection), and can be designed to automatically stop tissue removal (e.g., resection) when nerve stimulation has been sensed.

The tissue removal device (e.g., a tissue abrasion device) can be placed, either percutaneously or through an open surgical approach, through the neural foramina of the spine, and at least partially around the anterior border of the facet joint, anterior to the ligamentum flavum. The removal device (e.g., the abrasion device) alternatively or additionally can be placed through the neural foramen anterior to the facet joint, but into and through the body of, or posterior to the ligamentum flavum. After spinal neuroforaminal placement, the device can be used to remove or selectively remove tissues that impinge on the neurovascular structures within the lateral recess and neural foramen, anterior to the facet joint, thereby enlarging the lateral recess and neural foramina via selective tissue removal. Impinging tissue to be targeted for removal can include, but is not limited to, lateral ligamentum flavum, anterior and medial facet capsule, facet bone, and/or osteophytes. In another variation the tissue removal device can be positioned for removal of central stenosis.

The tissue removal surface of the tissue removal device may comprise various tissue removal elements for selectively removing all or a portion of the impinging tissue. In one variation, the tissue removal surface comprises one or more non-powered mechanical tissue removal elements that are drawn or pulled, e.g., under tension, across the impinging tissue to remove the tissue by cutting, shaving, etc.

During tissue removal, the tissue removal device may be drawn across impinging tissue in a single direction or may be reciprocated. The mechanical elements may comprise cutting elements, such as blades, band saws, or wire saws. The blades may comprise various shapes (e.g. serrated), sizes, and configurations, as desired. Alternatively, the mechanical elements may comprise abrasives, such as a diamond or oxide coating. Furthermore, coacting blades may be provided to achieve a guillotine-type or scissor-type cutting action. Blades may be attached to the tissue removal device or may be formed by punching, grinding, or stamping through the device with optional subsequent grinding of the punched edge. Alternatively, the blades may be formed by a chemical etching process. The blades may comprise a 3-dimensional profile to facilitate cutting, for example, a bow or a corrugation or a 'cheese grater' profile. Furthermore, the blades may be placed at one or more angles relative to the direction of tissue removal. Cutting surfaces of the blades may be oriented in a single direction or may be oriented in multiple directions. Additionally, the blades may be serrated. As another alternative, the mechanical elements may comprise cutting wires or wire saws, for example, one or more Gigli saws. A plurality or cutting wires or Gigli saws may be joined or woven together or flattened to form a substantially planar cutting surface. Further, a wire saw(s) or Gigli saw(s) may be attached to a ribbon backing, said ribbon thereby limiting the depth of penetration of the tissue removal device ("depth-stop ribbon").

In another variation, the tissue removal surface comprises one or more powered mechanical tissue removal elements. The powered mechanical tissue removal elements may comprise, for example, band saws, belt shavers, rotary burrs or blades, reciprocating burrs or blades, etc.

The tissue removal surface can have an energy delivery system that ablates, vaporizes, breaks up, or changes the modulus of the tissue, for example, aiding tissue removal. The tissue removal system can deliver one or more of various energies to facilitate removal of tissue. The energies can be electrical, ultrasound, thermal, microwave, laser, cryo, or combinations thereof. In another variation, the tissue removal surface comprises one or more electrosurgery elements for tissue removal/ablation. The electrosurgery elements additionally or alternatively can be utilized to achieve hemostasis and/or to facilitate neural localization. Monopolar or bipolar RF elements can, for example, be utilized and activated with a thermal or substantially non-thermal waveform.

Any other known tissue removal elements may be utilized with the tissue removal device including, for example, lasers, high-pressure fluid, thermal elements, radioactive elements, etc. It should be understood that various tissue removal elements may be used in any combination, as desired.

In order to reduce friction during placement, diagnosis, treatment and/or removal, the access elements, the neural protection element and/or the tissue removal device can have or comprise a lubricious coating, for example, a hydrophilic coating, a poly(tetrafluoroethylene) coating, etc. The coating can reduce friction during placement, diagnosis, treatment and/or removal. Furthermore, the tissue removal device, the access elements and/or the neural protection element may by biocompatible and/or non-friable. Debris removal elements also may be provided.

The method can be performed through an epidural needle that has been inserted into the epidural space. The epidural needle may be inserted percutaneously, or via an open incision, via a standard posterior paramedian (interlaminar) or midline (interspinous) approach, for example, using a loss of resistance technique known to those having an ordinary level of skill in the art.

A catheter can then be threaded through the needle and into the epidural space. The catheter distal tip can have a protective hood, cover, or needle cap, for example, which can be designed to be placed over the needle tip. When the catheter distal tip has been placed in the epidural space, the user can open the protective hood covering. After the protective covering is opened, the catheter can be slidably retracted through the needle until the protective hood cover firmly encloses the sharp edges or points in the area of the epidural needle tip. When the protective hood cover firmly protects the needle tip, the catheter can be fixed to the needle. The needle with the protective hood covering on the needle tip can be configured as a blunt instrument.

The needle can then be advanced until the needle distal end is in a lateral recess, adjacent to the neural foramina. The user can use tactile feedback from the needle, image guidance (e.g., fluoroscopy), or combinations thereof, to position the needle distal end to the lateral recess.

A tissue removal device can be positioned between the impinging tissue to be removed and the neural protection element. A curved flexible stylet can be inserted into the catheter. The catheter can then be advanced through the needle. The tip of the catheter can be driven, for example, along the inferior border of the facet, cephalad to the neural and neurovascular structures, and through the neural foramina laterally.

An atraumatic curved needle can be advanced through the epidural catheter and driven through the neural foramina, also between the tissue to be removed and the neural structures to be protected.

A curved thin shield can be advanced through the epidural needle and driven through the neural foramina, also positioned between the tissues to be removed and tissues to be protected.

The catheter, curved needle, or shield can serve as a barrier, for example, between the tissue to be removed and the neural and neurovascular structures. The catheter, curved needle, or shield can serve can assist in the delivery of a barrier, for example, between the tissue to be removed and the neural and neurovascular structures. The catheter, curved needle, or shield can be expanded within the neural foramina to serve as a barrier, for example, between the tissue to be removed and the neural and neurovascular structures. The neural protection element can have an atraumatic profile, for example, to reduce tissue injury. The neural protection element can have rounded edges.

The user can visualize the epidural space, for example, via a fiber optic element that can be covered by a distal clear tip. The fiber optic element can be delivered within the epidural catheter. The fiber optic element can be delivered via a working channel within or adjacent to the epidural needle.

In an open surgery variation, access can be achieved via an access element comprising a cannulated probe, such as a cannulated ball-tipped probe, Woodson elevator, or Hockey Stick hybrid. The probe can be placed through the surgical incision into the epidural space. A curved element, such as an atraumatic needle, then can be advanced through the cannula of the probe and driven laterally to cannulate the neural foramen. In addition to direct visualization and tactile feedback, open access can be aided by the use of image guidance, an epidural endoscope or any other visualization technique.

When the neural protection element comprises a sheath, the tissue removal device can be delivered through or along the sheath, or in conjunction with the sheath. The sheath can have a window or local opening that limits exposure of the tissue removal device to the patient's tissue only to the localized area of the opening. The opening can be positioned directly underlying the area of desired tissue removal, e.g., directly underlying the neural foramen and impinging tissue in the central canal, the lateral recess, and/or within the neural foramen.

Irrigation and/or aspiration can be performed through the window, e.g., for debris removal. Suction also can be drawn through the window to engage the impinging tissue and/or to provide a seal against the target tissue and/or to remove tissue debris and/or to remove fluid. The sheath window can have a cutting or ablation element that coacts with the tissue removal device. The tissue removal device can present the tissue removal elements at the window. The window optionally can be opened, closed or resized by a medical practitioner as desired. For example, the window can be closed during delivery, opened during tissue removal, then closed during retrieval of the sheath.

Neural localization elements can be used to improve positioning of the neural protection element and/or the tissue removal device. The neural localization elements can have separate elements or can be integrated with the neural protection element and/or the tissue removal device. In one variation, the neural protection element can have a sheath or other element with integrated neural localization elements. Electrically conductive neural localization elements can be used to ensure that the neural structures are on the nonworking or backside of the barrier. Neural localization elements on the back side of the neural protection element (i.e., the side of the neural protection element that contacts the nerve root when properly positioned) can be activated with a back side electrical current (e.g., delivered as a waveform). The back side electrical current can stimulate the nerve root or other neural structures, for example, providing a signal to the user that the back side has been placed adjacent to the nerve root. Low intensity electrical current on the back side surface can result in the stimulation of sensory or motor nerves in the patient's extremity. Neural localization elements on the working side of the neural protection element (i.e., the side of the neural protection element that faces impinging tissue slated for removal) can be activated with a front side electrical current (e.g., delivered as a waveform, for example with distinct characteristics than the waveform of the back side electrical current). The electrical current can stimulate a negative response or no neural stimulation, for example, providing a signal to the user that the working side is not in contact with the nerve root and that tissue removal may safely proceed. Neural localization elements can be provided on any or all sides of the neural protection element.

After access is established, optionally including neural protection and/or neural localization, and the tissue removal device can be positioned such that the tissue removal surface contacts the impinging tissue slated for removal, then the user can selectively remove tissue. Tissue removal can result in neural and/or neurovascular decompression.

The elastic modulus of impinging tissue can be altered, for example, to facilitate removal of the tissue. For example, the modulus of soft tissue can be increased to gain purchase on the soft tissue with the tissue removal elements. Such modulus alteration can be achieved, for example, through compression, denaturation, electrosurgical exposure, thermal remodeling (hot or cold), chemical alteration, epoxy or glues or hydrogels, or any combination thereof. Remodeling of the tissue during or after modulus alteration can alleviate impingement and obviate or reduce a need for tissue removal.

In combination with the energy delivery system, or as a stand alone tissue removal option, one or more non-powered mechanical tissue removal elements (e.g. abrasives or cutting elements such as blades or saws) can be drawn across the impinging tissue to remove the tissue by cutting, shaving, slicing, scissoring, guillotining, scraping, tearing, abrading, or combinations thereof. The blade can be drawn across impinging tissue in a single direction and/or can be reciprocated. The mechanical tissue removal elements can have abrasives, such as a diamond or oxide coating.

The blades can have various shapes, sizes and configurations. The blades can coact, for example, in a guillotine-type or scissor-type cutting action. The blades can be attached to or integral with the tissue removal device. The blades can be formed by grinding, punching or stamping through the tissue removal device. The blades can be formed by grinding of a punched or stamped edge of the tissue removal device. The blades can be formed by a chemical etching process. The blades can have a 3-dimensional profile to facilitate cutting, for example, a bow or a corrugation or a 'cheese grater' profile. The blades can be placed at one or more angles relative to the direction of tissue removal. The blades can be configured with the blade cutting across the tissue (i.e., similar to a band saw). The blades can have cutting surfaces. The cutting surfaces can be oriented in a single or multiple directions. The blades can be serrated.

The saw can be a wire saw or saws. The wire saw can be a Gigli saw. Multiple wire saws or Gigli saws can be joined or woven together or flattened to form a substantially planar cutting surface. The wire saw can be mounted on a flat ribbon. The ribbon can be a depth stop, for example, limiting for saw penetration.

The tissue removal surface can have one or more powered mechanical tissue removal elements. The powered mechanical tissue removal elements can have, for example, band saws, belt shavers, rotary burrs or blades, reciprocating burrs or blades, or combinations thereof.

The apparatus and methods can facilitate selective elimination of pathological spinal tissue, thereby enabling symptomatic relief in patients suffering from spinal stenosis.

A method for modifying spinal anatomy is disclosed. The method includes delivering a surgical apparatus to an epidural space and surgically altering tissues that impinge neural or vascular structures in the lateral recess, neural foramina or central canal of the spine with the apparatus. Surgically altering tissues can include ablating tissue, resecting tissue, removing tissue, abrading tissue, retracting tissue, stenting tissue, retaining tissue, or thermally shrinking tissue. Surgically altering tissues can additionally include enlarging the lateral recess, neural foramina or central canal of the spine.

Delivering the surgical apparatus to an epidural space can include delivering an epidural needle to the epidural space, and enlarging the lateral recess, neural foramina or central canal of the spine can include focally altering tissue with tools delivered through the epidural needle. Delivering the surgical apparatus to an epidural space also can include delivering an epidural needle to the epidural space, and enlarging the lateral recess, neural foramina or central canal of the spine also can include focally altering tissue with tools delivered through a working channel disposed adjacent to the epidural needle.

Delivering the surgical apparatus can include converting the epidural needle to an endoscope within the epidural space. Delivering the surgical apparatus to an epidural space also can include delivering a working endoscope to the epidural space, and enlarging the lateral recess, neural foramina or central canal of the spine can also include focally altering tissue with tools delivered through the working endoscope. Delivering the surgical apparatus can also include converting the epidural needle into a blunt tipped instrument after placement of the needle's tip within the epidural space. Converting the epidural needle can also include threading an epidural catheter through the epidural needle into the epidural space, and covering the needle's tip with an epidural needle cover delivered via the catheter.

Delivering the surgical apparatus can also include converting the epidural needle into an endoscope via a visualization element disposed within the epidural catheter. Delivering the surgical apparatus can include infusing fluid into the epidural space to improve visualization. Delivering the surgical apparatus can include inserting a removable working channel alongside the surgical apparatus. Delivering the surgical apparatus can include inserting a distal tip of a dual lumened epidural needle into the epidural space and using at least one of the dual lumens as a working channel for the delivery of instruments into the epidural space. Delivering the surgical apparatus can include inserting an instrument chosen from the group consisting of a tissue cauterization tool, a tissue laser device, a radiofrequency delivery device, a ronguer, a tissue grasper, a tissue rasp, a probe, a bone drill, a tissue shaver, a burr, a tissue sander and combinations thereof through the surgical apparatus.

Delivering the epidural needle can include inserting the epidural needle to a position with a tip of the needle in proximity to where treatment will be directed. Delivering the epidural needle can include inserting the epidural needle at an interspace below the level of the spine where the treatment will be directed.

Delivering surgical apparatus can include delivering the apparatus via an open surgical route. Delivering the epidural needle can include delivering the needle via a posterior, interlaminar percutaneous route. Delivering the epidural needle can include delivering the needle via a posterior, translaminar, percutaneous route. Delivering the epidural needle can include delivering the needle via a posterior, midline, interspinous , percutaneous route. Delivering the epidural needle can include delivering the needle via a percutaneous route through the neural foramen from its lateral aspect. Enlarging can include placing a mechanical barrier or backstop between tissue to be resected and adjacent neural or vascular structures. The barrier can be steerable.

The method of modifying the spinal anatomy can include confirming proper placement of the surgical apparatus. Confirming proper placement can include confirming proper placement with a nerve stimulator. Confirming proper placement with a nerve stimulator further comprises confirming proper placement with stimulation leads placed on a tissue remodeling side of the surgical apparatus. The method of modifying the spinal anatomy can include confirming proper placement of the surgical apparatus or barrier with a nerve stimulator having stimulation leads placed on a tissue remodeling side of the barrier or on a back side of the barrier.

The method of modifying the spinal anatomy can include monitoring nerve stimulation with the nerve stimulator via somatosensory evoked potentials (SSEPs). The method of modifying the spinal anatomy can include monitoring nerve stimulation with the nerve stimulator via motor evoked potentials (MEPs). The method of modifying the spinal anatomy can include monitoring nerve stimulation with the nerve stimulator via motor evoked patient movement. The method of modifying the spinal anatomy can include monitoring nerve stimulation via verbal patient sensory response to the nerve stimulator.

The method of modifying the spinal anatomy can include monitoring enlargement via imaging. The method of modifying the spinal anatomy can include surgically altering the tissues under fluoroscopic imaging, MRI imaging, CT imaging., ultrasound imaging., radiological imaging, surgical triangulation, infrared or RF surgical triangulation.

The method of modifying the spinal anatomy can include placing an element that provides tissue compression of surgically remodeled tissue or bone surface in order to enlarge the neural pathway or foramina post-surgical enlargement. The method of modifying the spinal anatomy can include placing an element that provides tissue compression and retention in order to remodel tissue or bone surface in order to enlarge the neural pathway or foramina de novo. Placing the element can include placing the element using a percutaneous technique via the epidural space, through a neural foramen at a level to be treated for spinal stenosis, and around a facet complex or a lamina adjacent to the facet complex. The method of modifying the spinal anatomy can include tightening the element to a determined tension. Placing the element can include placing an element having a posterior anchor that is a cord or tie looped through a hole that has been drilled in the cephalad lamina of the immediately adjacent vertebrae. The method of modifying the spinal anatomy can include tensioning the element to a determined level via a tension gauge or other measurement device element holding tension against the tissue to be remodeled.

The method of modifying the spinal anatomy can include releasing a biologically active material for the purposes of decreasing inflammation, or promoting remodeling of soft tissue or bone growth from the element.

Apparatus for focal tissue alteration are disclosed herein. The apparatus have an element configured for placement into an epidural space, and surgical tools configured for delivery through the element into the epidural space to remodel spinal anatomy that impinges upon neural, neurovascular or tendon structures. The element can include an epidural needle, and wherein the surgical tools further comprise a tissue remodeling device configured for placement via the epidural needle.

The epidural needle can be configured for placement into the epidural space via an approach chosen from the group consisting of a posterior interspinal midline approach, a posterior paramedian interlaminar approach, a posterior translaminar paramedian approach through a hole in the lamina, a neural foramina approach around an anterior border of a facet joint, and combinations thereof. The epidural needle can include two adjacent lumens, the second lumen configured to act as a working channel for the delivery of the surgical tools into the epidural space.

The apparatus can have an epidural catheter configured to convert the epidural needle into a blunt tipped instrument via an epidural needle tip cover that may be opened and then pulled back to cover the needle's tip. The epidural catheter can have a fiberoptic cable for visualization. The apparatus can have an insertable and removable working channel for tool access configured for placement alongside the needle.

The tissue remodeling device can be chosen from the group consisting of a tissue cauterization tool, a tissue laser device, a radiofrequency delivery device, a ronguer, a tissue grasper, a tissue rasp, a probe, a bone drill, a tissue shaver, a burr, a tissue sander, and combinations thereof.

The surgical tools can produce nerve stimulation. The apparatus can have a device for monitoring neural stimulation to identify when a working surface of the surgical tools is in close proximity to vulnerable neural tissue during tissue remodeling.

An apparatus for protecting adjacent structures during remodeling of spinal anatomy that impinges upon neural, neurovascular or tendon structures is disclosed. The apparatus has a mechanical barrier configured for placement between tissue to be resected and the adjacent structures. The mechanical barrier can be configured for insertion through an open incision. The mechanical barrier can be configured for insertion through a working channel of an endoscope.

The apparatus can be configured for use with a visualization element. The visualization element can be chosen from the group consisting of an epidural endoscope, a fluoroscope, ultrasound, XRay, MRI and combinations thereof. The apparatus can have a nerve stimulator to facilitate proper placement of the barrier. A conductive element can be included on a tissue modification side of the barrier or on a backside of the barrier to facilitate nerve localization. A working surface of the tissue remodeling device can have neurostimulation capabilities, thereby allowing for a positive and negative control in localizing neural tissue prior to tissue removal.

The apparatus can include a monitoring technique for monitoring electrical nerve stimulation. The monitoring technique can be chosen from the group consisting of SSEPs (somatosensory evoked potentials); MEPs (motor evoked potentials); EMG; verbal inquiries of the patient's sensory experience to the electrical stimulation; visual techniques, mechanical techniques, tactile techniques monitoring neuro muscular stimulation and movement, and combinations thereof.

The apparatus can include an element configured to provide tissue compression against surgically remodeled tissue or bone surface in a neural pathway or foramina post-enlargement. The element is configured for percutaneous placement via the epidural space, through the neuroforamen at the level to be treated for spinal stenosis, and around the facet complex or the lamina adjacent to the facet complex. The element is configured to release a biologically active material for the purposes of decreasing inflammation, or promoting remodeling of soft tissue or bone growth.

The apparatus can be configured for tightening to a determined tension for purposes of relieving spinal stenosis. The element can include a posterior anchor having a cord or tie looped through a hole that has been drilled in the cephalad lamina of the immediately adjacent vertebrae. Tension of the element is configured to be set at a determined level by a tension gauge, or other measurement device element holding tension against tissue to be remodeled.

The apparatus can have a neuro foraminal compression element configured to retract and hold pressure on spinal tissue when placed under tension, in order to relieve pressure on impinged neural and vascular structures and promote tissue remodeling. The apparatus can have a tensioning device for the neuro foraminal compression element configured to secure two ends of the element together at a posterior aspect of the vertebral lamina at a desired tension by pulling the element to the desired level of tension prior to locking the opposite ends of the element together at said tension.

The apparatus can have a tensioning device configured to tighten a loop formed by the neuro foraminal compression element around the facet joint complex, within the lateral aspect of the lamina, and configured to tighten the compression element across a locking or crimping element to a specified tension, pulling the ligamentum flavum posteriorly in the spinal canal, in the lateral recess and in the neural foramen.

The apparatus can have a tensioning device configured to tighten a loop formed by the neural foraminal compression element around the lamina, close to a facet joint complex, within a lateral aspect of the lamina, and configured to tighten the compression element across a locking or crimping element to a specified tension, pulling the ligamentum flavum posteriorly in the spinal canal, in the lateral recess and in the neural foramen.

At least one free end of the neural foraminal compression element can be configured for subcutaneous placement to facilitate future removal of the element. The compression element can be biodegradable.

The compression element can contain a therapeutic agent chosen from the group consisting of medications, bioactive compounds, steroids, depot steroids, anti-inflammatories, and combinations thereof. The agent can be configured for immediate release. The agent can be configured for sustained local delivery.

A method of altering bone or soft tissue in a patient is disclosed. The method includes placing a tissue abrasion device through tissue to be altered, holding the tissue abrasion device under tension to bring an abrasive surface of the device firmly against the tissue to be altered, and sliding the abrasive surface of the abrasive element against the tissue to be altered, thereby altering bone or soft tissue immediately adjacent to the abrasive surface. Altering can include abrading, removing, or remodeling.

Placing the tissue abrasion device through tissue to be altered can include placing the device through spinal tissue that impinges on neural, neurovascular or ligamentous structures in the patient's spine. Placing the tissue abrasion device can include placing the tissue abrasion device through a neural, neurovascular, or ligamentous pathway within the patient's spine, holding the tissue abrasion device under tension to bring the abrasive surface against tissue within the pathway, and where sliding includes enlarging the pathway via frictional abrasion of the tissue. Placing a tissue abrasion device through the pathway can include placing the tissue abrasion device through neural foramina of the patient's spine and around the anterior border of a facet joint. Placing the tissue abrasion device through neural foramina of the patient's spine and around the anterior border of a facet joint can include placing the device via a route chosen from the group consisting of an open surgical approach, a percutaneous approach, a posterior percutaneous approach, an interlaminar percutaneous approach, a translaminar percutaneous approach, an interspinous percutaneous approach, through the neural foramen from a lateral direction, and combinations thereof. Placing the tissue abrasion device can include placing the device within a protective sheath or cover.

The method can include altering spinal tissues that impinge on neural, neurovascular, or ligamentous structures in the patient's spine.

Enlarging the pathway can include enlarging a diseased pathway within the patient's spine.

Holding the tissue abrasion device under tension against tissue within the pathway can include placing an abrasive surface of the tissue abrasion device against tissue chosen from the group consisting of an anterior surface of facet joint capsule, a medial surface of facet joint capsule, a superior articular process of the facet joint, ligamentum flavum, tissues attached to ligamentum flavum, extruded spinal disc material, scar tissue, and combinations thereof.

Sliding the tissue abrasion device against the tissue can include sliding the abrasive surface of the tissue abrasion device against the tissue. Sliding the abrasive surface can include enlarging the lateral recess, neural foramina or central spinal canal via frictional abrasion. Sliding the abrasive surface can include preferentially abrading tissue chosen from the group consisting of ligamentum flavum, bone spurs, facet capsule, superior articular process, extruded spinal disc material, scar tissue and combinations thereof that impinge on neural or vascular structures.

The method can include confirming proper placement of the tissue abrasion device. Confirming proper placement of the device can include confirming proper placement with a nerve stimulator. Confirming proper placement with a nerve stimulator can include confirming proper placement with a nerve stimulator having stimulation leads placed at a location chosen from the group consisting of a non-abrasive side of the tissue abrasion device, a back side of a protective sleeve or cover placed over the tissue abrasion device, an abrasive side of the tissue abrasion device, a working side of the tissue abrasion device, and combinations thereof. Confirming proper placement can include confirming placement via a modality chosen from the group consisting of fluoroscopic, MRI, CT, infrared, ultrasound imaging, surgical triangulation, and combinations thereof.

The method can include monitoring nerve stimulation via somatosensory-evoked potentials (SSEPs) with the nerve stimulator. The method can include monitoring nerve stimulation via motor-evoked potentials (MEPs) with the nerve stimulator. The method can include monitoring nerve stimulation via verbal patient sensory response to the nerve stimulator.

The method can include replacing the tissue abrasion device with a compression element that is held against altered tissue or bone.

Apparatus for the removal of impinging soft tissue or bone within a patient are disclosed. The apparatus can have a tissue abrasion device configured for placement through impinged tissue pathways. The tissue abrasion device can have an abrasive surface configured for placement adjacent to the impinging tissue. The impinged tissue pathways can have pathways chosen from the group consisting of neural pathways, neurovascular pathways, ligamentous pathways, and combinations thereof. The tissue abrasion device can be configured for the removal of spinal structures that impinge neural or neurovascular tissues within the patient, and wherein the tissue abrasion device is configured for placement through neural foramina of the patient's spine and around the anterior border of a facet joint.

The apparatus can have a protective cover disposed about the tissue abrasion device, where the protective cover is configured to limit exposure of an abrasive surface of the device to areas where tissue removal is desired. The apparatus can have a nerve stimulator in communication with the tissue abrasion device to facilitate proper placement of the device.

The apparatus can have a conductive element disposed on an abrasive surface of the device to enable nerve localization by sending a small electrical current through the conductive element.

The apparatus can have an epidural needle, where the tissue abrasion device is configured for placement through the epidural needle.

The apparatus can have a visualization element for direct visualization of the neural foramina. The apparatus can have a neural foramina compression element.

The compression element can be configured to promote hemostasis and desired tissue remodeling during healing. The element can be configured to be left in place after being secured with adequate tension against tissue abraded with the tissue abrasion device. The compression element can be configured to protect a tissue surface abraded with the device. The compression element can be configured to prevent adhesions during healing. The compression element can be configured to protect vulnerable structures adjacent to tissue abraded with the tissue abrasion device from an inflammatory response triggered by tissue abrasion.

The tissue abrasion device can be configured for placement in front of, across, and then behind tissue to be abraded, such as through a naturally occurring or artificially created anatomical foramen or tissue pathway. The abrasive surface can be disposed on all or part of one side of the tissue abrasion device. The abrasive surface can be disposed on an element chosen from the group consisting of a length of ribbon, strap, cable, belt, cord, string, suture, wire and combinations thereof. The ends of the device can be configured for manual grasping. The apparatus can have a handle to which ends of the device are attached for manual grasping. The device can be configured for attachment to an electromechanical power-driven device.

The device can be configured to be placed under tension in order to bring the abrasive surface into contact with tissue to be removed. The abrasive surface can be configured to be pulled against tissue to be removed. The abrasive device can have multiple abrasive elements with different abrasive surfaces, configured for interchangeable use. The multiple abrasive elements can have varying grades of abrasive material. The multiple abrasive elements can have different grooves, patterns of grooves, or material patterns on the abrasive surface to facilitate preferential abrasion of tissue at desired locations. The patterns of grooves can have diagonal parallel grooves that preferentially move the abrasive element towards one direction on the surface being abraded as the abrasive element is pulled in one direction, and towards an opposing direction as the abrasive element is pulled in a second direction. The multiple abrasive elements can have different shapes that guide the extent and location of tissue removal.

The apparatus can be configured to carry debris away from the site of tissue removal.

The tissue abrasion device can vary in profile along its length. The tissue abrasion device can have openings that facilitate passage of debris behind the device for storage or removal.

The apparatus can have a monitor for monitoring electrical nerve stimulation with the nerve stimulator. The monitor can be configured to monitor a feedback chosen from the group consisting of SSEPs, MEPs, EMG, verbal communication of patient sensation, visual monitoring, mechanical monitoring, tactile means, monitoring of neuromuscular stimulation and movement, and combinations thereof.

The compression element can be biodegradable. The compression element can contain a therapeutic agent configured for delivery to abraded tissue or adjacent neural and neurovascular structures. The therapeutic agent can be a medication, bioactive compound, steroid, depot steroid, anti-inflammatory, adhesion barrier, procoagulant compound, or combination thereof.

The protective cover can be attached, external to the patient, to a suspension system that includes elements to firmly and individually grasp each end of the cover and hold it in position under tension against the tissue surface to be abraded, with an open portion of the cover exposing the abrasive element directly over tissue to be abraded. The protective cover can be configured to protect a non-abrasive side of the tissue abrasion device. The protective cover can have channels along its lateral aspects for the insertion and sliding of the tissue abrasion device. The protective cover can include channels along its lateral aspects for the insertion and sliding of a second protective cover configured for placement between an abrasive surface of the tissue abrasion device, and tissue adjacent to tissue to be abraded with the abrasive surface.

Apparatus for selective surgical removal of tissue is disclosed. The apparatus can have an access element, a neural protection element, and a tissue removal device. The apparatus can have a neural localization element. The neural localization element can be integrated into the neural protection element. The apparatus can have debris removal elements. The apparatus can have hemostasis elements.

The access element can be a cannulated probe, ball-tip probe, elevator, epidural needle, epidural probe, epidural endoscope, curved tube, curved cannula, guide wire, straight guide wire, curved guide wire, or combination thereof.

The neural protection element can be an element configured for delivery via the access element. The neural protection element can be configured for transforaminal placement between impinging tissue and a nerve root. The access element can be configured for transforaminal placement. The neural protection element can have a sheath having a window. The tissue removal device can be configured for placement within the sheath such that tissue removal elements disposed on a tissue removal surface of the device are locally exposed within the window. The window can be configured for transforaminal placement.

The tissue removal device can be configured for transforaminal placement between the neural protection element and the impinging tissue. The tissue removal device can be a tissue removal surface having tissue removal element configured to remove the impinging tissue. The tissue removal elements can be powered tissue removal elements, non-powered tissue removal elements, mechanical tissue removal elements, cutting tissue removal elements, abrasive tissue removal elements, electrosurgical tissue removal elements, blades, punched features, stamped features, etched features, ground features, sharpened features, electrodes, monopolar electrodes, bipolar electrodes, or combinations thereof.

A method for selective surgical removal of tissue is disclosed. The method can include accessing a spinal neural foramen having impinging tissue, placing a neural protection element transforaminally between the impinging tissue and an underlying nerve root, placing a tissue removal device transforaminally between the impinging tissue and the neural protection element; and selectively removing the impinging tissue with the tissue removal device.

Accessing the spinal neural foramen can include accessing the neural foramen via an open surgical approach. Accessing the spinal neural foramen can include accessing the neural foramen via a percutaneous approach. Accessing the spinal neural foramen can include placing a guide wire transforaminally.

Placing the neural protection element transforaminally can include placing the neural protection element via the guide wire. Placing the tissue removal device transforaminally can include placing the tissue removal device via the neural protection element.

Selectively removing the impinging tissue can include mechanically cutting the tissue. Selectively removing the impinging tissue can include mechanically abrading the tissue. Selectively removing the impinging tissue can include electrosurgically removing the tissue.

The method can include, prior to selective removal of the impinging tissue, confirming proper placement of the neural protection element and the tissue removal device. Confirming proper placement can include localizing the nerve root with a stimulation waveform.

The method can include removing debris generated during selective tissue removal. The method can include stanching bleeding from the site of selective tissue removal. The method can include removing the neural protection element and the tissue removal device from the neural foramen.

A method for selective surgical removal of tissue is disclosed. The method can include accessing impinging tissue, placing a neural protection element transforaminally between the impinging tissue and an underlying nerve root, placing a tissue removal device between the impinging tissue and the neural protection element, and selectively removing the impinging tissue with the tissue removal device.

An apparatus for selectively removing a first tissue adjacent to a second tissue is disclosed. The apparatus can have a tissue removal device and a tissue protection device, where the tissue protection device can have a first side and a second side, where the first side is configured to deliver a first electrical stimulation, and the second side is configured to deliver a second electrical stimulation. The apparatus can have an atraumatic access device.

The tissue protection device can be configured to prevent the removal of the second tissue. The tissue removal device can have an RF device. The tissue removal device can have an electrical textile conductor. The tissue removal device can have an ablation needle. The tissue removal device can have a conductive wire loop. The tissue removal device can have a mechanical tissue removal device. The tissue removal device can be slidably attached to the tissue protection device. The tissue removal device can be attached by a rail to the tissue protection device. The mechanical tissue removal device can be configured to reciprocate to remove tissue.

An apparatus for selectively removing a first tissue adjacent to a second tissue is disclosed. The apparatus can have a tissue removal device comprising a first tissue removal element and a second tissue removal element, where the first tissue removal element is configured to remove tissue in a first direction, the second tissue removal element is configured to remove tissue in a second direction, and the first direction is substantially opposite the second direction. The first tissue removal element can have a first leading edge and a first scoop, the first leading edge can be adjacent or integral with the first scoop, and the first leading edge can be configured to deliver energy. The energy can have RF. The first leading edge can have a beveled configuration.

An apparatus for selectively removing a first tissue adjacent to a second tissue is disclosed. The apparatus can have a tissue removal device comprising a first tissue removal element, the first tissue removal element ca have a first leading edge and a first scoop, the first leading edge can be adjacent or integral with the first scoop, and the first leading edge can be configured to emit energy. The first leading edge can have a dull edge.

The energy can have RF. The energy can have mechanical vibrations. The energy can have acoustic energy. The energy can have ultrasound energy. The first tissue and the second tissue can be spinal tissue.

The apparatus can have a tissue protection device comprising a first side and a second side, the first side can be configured to deliver a first electrical stimulation, and the second side can be configured to deliver a second electrical stimulation.

The tissue removal device can be slidably attached to the tissue protection device.

An apparatus for damaging a first spinal tissue and preserving a second spinal tissue adjacent to the first spinal tissue is disclosed. The apparatus can have a tissue removal device comprising a first tip and a body, the tip can be configured to transmit an energy to the first spinal tissue, and the body can be configured to not transmit energy. The energy can have RF.

A method for damaging a first spinal tissue and preserving a second spinal tissue adjacent to the first spinal tissue is disclosed. The method can include inserting a needle through the first spinal tissue where the needle can have a body and a tip, placing the tip into the second spinal tissue where the body is in the second spinal tissue, and emitting an energy through the tip.

The method can include suctioning through the tip. The body can emit no energy. The second tissue can have a tissue surface. The energy can have an electrical energy. The energy can have RF energy. The energy can have acoustic energy. The energy can have ultrasound energy.

A method for damaging a target spinal tissue is disclosed. The method can include deploying a tissue protection barrier adjacent to the target spinal tissue, where the tissue protection barrier can have a first side and a second side. The method can include monitoring electrical signals against the first side, delivering an electrical signal through the back side, and reciprocating a tissue removal device against the spinal tissue.

The tissue protection barrier can have a window, and the method can include positioning the window adjacent to the target spinal tissue. The window can be on the first side. The tissue protection barrier can have a lubricious coating.

The tissue removal device can be in the tissue protection barrier. The tissue removal device can be slidably attached to the tissue protection barrier. The tissue removal device comprises a lubricious coating. The tissue removal device can emit an energy. The energy can have RF. The tissue removal device can have a scoop. The tissue removal device can have a spring. The method can include deploying energy to the target tissue through the spring.

Finally, the present invention also describes methods and apparatus that promote tissue remodeling, separate from the tissue resection or ablation. These devices tightly wrap, retract, or hold in position, under tension, impinging tissues within the spinous posterior elements.

It is expected that the apparatus and methods of the present invention will facilitate a minimally invasive approach to the selective elimination of pathological spinal tissue, thereby enabling symptomatic relief in patients suffering from spinal stenosis.

In some embodiments, a surgical tissue removal device includes a flexible elongate body that is adapted to conform with the target anatomy, the body has at least one blade edge, where the flexible elongate body is a thin, flat, ribbon shaped flexible body that comprises a profile having a width that is substantially greater than a height. In some embodiments, the device further includes a guidewire connector at the distal end region of the flexible elongate body configured to removably connect to the end of a guidewire so that the guidewire and flexible elongate body can be pulled distally. In some embodiments, a portion of the flexible elongate body includes a lubricious layer.

In some embodiments, the device further includes a distal handle configured to couple to the distal end of the flexible elongate body and a proximal handle configured to couple to the proximal end region of the flexible elongate body, wherein the distal handle and the proximal handle are configured to allow the body to be reciprocated proximally and distally to cut tissue. In some embodiments, the distal handle is configured to connect to a guidewire while the proximal end of the guidewire is connected to the distal end of the flexible elongate body.

In some embodiments, the guidewire connector region is configured to hook the flexible elongate body to the end region of the guidewire. In some embodiments, the blade edge is a v-shaped blade edge. In some embodiments, the at least one blade edge comprises a plurality of discrete sharpened blade edges for cutting through tissue and bone. In some embodiments, the blade edge is flush with a surface of the elongate body.

In some embodiments, a surgical tissue removal device includes a flexible elongate body that is adapted to conform with the target anatomy, the body has at least one blade edge extending from one surface of the flexible elongate body, where the flexible elongate body is a thin, flat, ribbon shaped flexible body that further comprises a profile having a width that is substantially greater than a height. In some embodiments, the device further includes a guidewire connector on the flexible elongate body configured to connect to the end of a guidewire so that the end of the guidewire connects into the guidewire connector at the distal end region of the flexible elongate body so that the guidewire and flexible elongate body can be pulled distally to draw the blade edge distally across the target anatomy.

In some embodiments, the flexible elongate body is configured to pass through a subject's spinal foramen. In some embodiments, the at least one blade edge comprises a plurality of blade edges located on the surface of the flexible elongate body near the end of the flexible elongate body comprising the guidewire connector so that the end of the flexible elongate body opposite of the guidewire connector does not include a blade edge.

In some embodiments, the at least one blade edge comprises a plurality of blade edges and where the plurality of blade edges comprise a plurality of blade edges located on the surface of the flexible elongate body near the center of the flexible elongate body so that the ends of the flexible elongate body do not include any blade edges.

In some embodiments, at least a portion of the flexible elongate body includes a lubricious layer.

In some embodiments, the device further includes a distal handle configured to couple to the distal end of the flexible elongate body and a proximal handle configured to couple to the proximal end region of the flexible elongate body, wherein the distal handle and the proximal handle are configured to allow the body to be reciprocated proximally and distally to cut tissue. In some embodiments, the distal handle is configured to connect to a guidewire while the proximal end of the guidewire is connected to the distal end of the flexible elongate body. In some embodiments, the guidewire connector region is configured to hook the flexible elongate body to the end region of the guidewire.

In some embodiments, the blade edge is a v-shaped blade edge. In some embodiments, the at least one blade edge comprises a plurality of discrete sharpened blade edges for cutting through tissue and bone. In some embodiments, the body has an axial length and a plurality of blade edges arranged in rows extending from one surface of the flexible elongate body, wherein the rows are disposed transverse to the axial length of the elongate body and the rows are separated by gaps that extend transverse to the axial length of the elongate body.

BRIEF DESCRIPTION OF THE DRAWINGS

The above and other objects and advantages of the present invention will be apparent upon consideration of the following detailed description, taken in conjunction with the accompanying drawings, in which like reference characters refer to like parts throughout, and in which:

FIG. 3a illustrates a needle inserted to an interspinal ligament.

FIG. 2a is a view of a working backstop or barrier apparatus, including an optional rail for controlled tool placement in relation to the barrier, and an optional conductive element for neural stimulation and localization.

FIGS. 40*a*-40*e* are cross-sectional views through a patient's spine, illustrating another variation of the method and apparatus of FIGS. 28-35;

FIG. 64 is a schematic cross-sectional view through a patient's spine, illustrating a method and apparatus for achieving neural localization during use of the tissue abrasion apparatus;

FIG. 65 are schematic views of additional apparatus, showing a spool or reel to reel configuration of a portion of the device that may be utilized for selective surgical removal of tissue;

FIG. 85 are cross-sectional views through a protective sleeve or sheath, compact during insertion (b), and expanded (c) by passing the apparatus through its lumen;

FIG. 86 are schematic views of additional apparatus that may be utilized for selective surgical removal of tissue;

FIGS. 100A and 100B are a schematic view and a detail view of another variation of the tissue removal device.

FIGS. 103-108 are schematic lateral views of additional apparatus that may be utilized for visualization in the epidural space, enabling the selective surgical removal of tissue;

FIG. 103 illustrate an embodiment of an endoscope in a clear tipped cannula;

FIG. 104 illustrate an embodiment of a 0-degree endoscope rotated in unison with a curved, clear tipped cannula;

FIG. 105 illustrate an embodiment of a 30-degree endoscope rotated separately inside of a clear tipped cannula;

FIG. 107 illustrate an embodiment of a clear tipped cannula with a flexible neck;

FIG. 108 illustrates an embodiment of an endoscope with a built-in clear cover (e.g., a combination device embodiment);

FIGS. 109-114 are schematic lateral views of similar apparatus for visualization in the epidural space, along with additional method and apparatus that enable the safe placement and use of tools for selective surgical ablation, resection, abrasion and remodeling of tissue;

FIG. 109 illustrate various embodiments of a clear tipped cannula with a free adjacent tool;

FIG. 110 illustrate various embodiments of a clear tipped cannula with an attached adjacent tool;

FIG. 112 illustrate various embodiments of cannulas with a nerve stimulator at the tip (e.g., EMG sensors peripherally placed);

FIG. 113 illustrate various embodiments of a clear tipped cannula with a nerve stimulator at a tip of the free tool; and FIG. 114 illustrate various embodiments of a clear tipped cannula with a nerve stimulator at a tip of the free or attached tool.

FIG. 119 is a cross-sectional view through a patient's spine, illustrating advancement of the instrument into the lateral recess of the spine, adjacent or into the neural foramina;

FIG. 120 is a cross-sectional view through a patient's spine, illustrating attachment of a neural stimulation and localization device to the apparatus (The neural monitoring apparatus is not shown);

FIGS. 121-122 are cross-sectional views through a patient's spine, illustrating advancement and in-situ enlargement of the tissue protection barrier through the lateral recess and neural foramina, between the tissue to be removed and the neural structures to be protected;

FIGS. 146-153 illustrate embodiments of fixed rail shields, demonstrating dilating tips, distal wire anchor systems for added ability to pull tension across the impinging tissue, and combined proximal and distal wire anchoring systems.

FIGS. 179-180 illustrate an embodiment of section F of FIG. 175.

DETAILED DESCRIPTION

Figure 1:
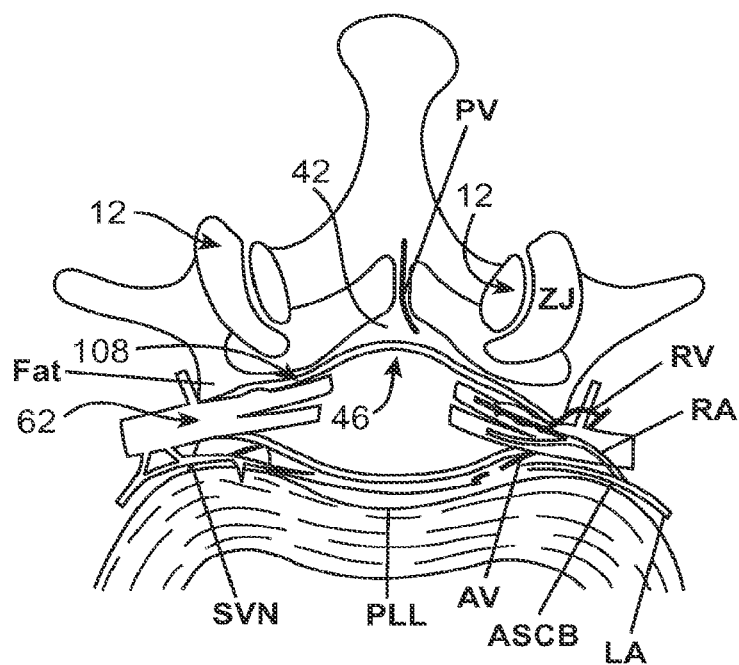
FIG. 1 is a cross section through the posterior aspect of the lumbar spine.

The present invention relates to methods and apparatus for the selective surgical alteration (e.g., removal and remodeling) of tissue that impinges upon spinal neural or vascular structures, with particular attention towards avoiding injury and/or trauma to the affected or adjacent neural, vascular and neurovascular structures. More particularly, the present invention relates to methods and apparatus for spinal lateral recess 108 and neural foraminal 110 enlargement, and central canal enlargement of the spine, in cases of neurovascular impingement, through a novel approach to selective and safe enlargement of the pathologically narrow spinal neural foramen, impinged lateral recess 108 and/or compromised central spinal canal. The approach includes alteration of the tissues that pathologically impinge neural and neurovascular structures in the spine. Impinging tissues to be removed from or remodeled in the spine's central canal, lateral recess 108, and neural foramen 110 may include, but are not limited to, ligamentum flavum 10; bone spurs or ligamentous calcifications; localized disc extrusions; enlarged facet joint complex 12, facet capsule, superior articular processes; osteophytes, and scar tissue or adhesions.

The variations of the invention designed to treat spinal stenosis are summarized in this paragraph, and described in greater detail in the paragraphs that follow. The methods begin with insertion of an epidural needle apparatus 2, which is converted, after placement in the epidural space, from a sharp tipped instrument, into a blunt tipped tool. The blunt tool is manipulated within the epidural space 42, either under image guidance; under direct vision with an accompanying epidural endoscope; or under direct vision when the instrument itself is given endoscopic function. The same blunt tipped epidural instrument may have an attached fixed or removable working channel. An additional apparatus of the current invention, a working backstop or barrier 134 that serves to protect adjacent vulnerable structures during the procedure, may subsequently be inserted into the epidural space 42, as well as through the neural foramina 110, through the needle or endoscope or an adjacent working channel. Safe resection, ablation, and remodeling may be further ensured through the integration into the invention of electrical neural stimulation and monitoring for localization, optionally available through nerve stimulation functionality in the epidural instrument; the working tools used through the needle or working channel; and/or the working backstop. Finally, further variations of the device and method enable the surgeon to remodel stenotic spinal anatomy, either after tissue resection or as a stand-alone procedure, through the placement of devices for holding, retracting or retaining anatomic structures away from vulnerable neural and neurovascular structures within the posterior elements of the spine.

FIG. 1 shows the posterior elements of the spine in axial cross section. The epidural space 42 in the spine is consistently more accessible in its posterior most aspect, a fat filled zone most popular for safe epidural needle 2 placement, posterior to the dura mater 46. The dura 46 covers and contains the central neural elements of the spine, including the spinal cord, nerve roots, and spinal fluid.

Figure 2:
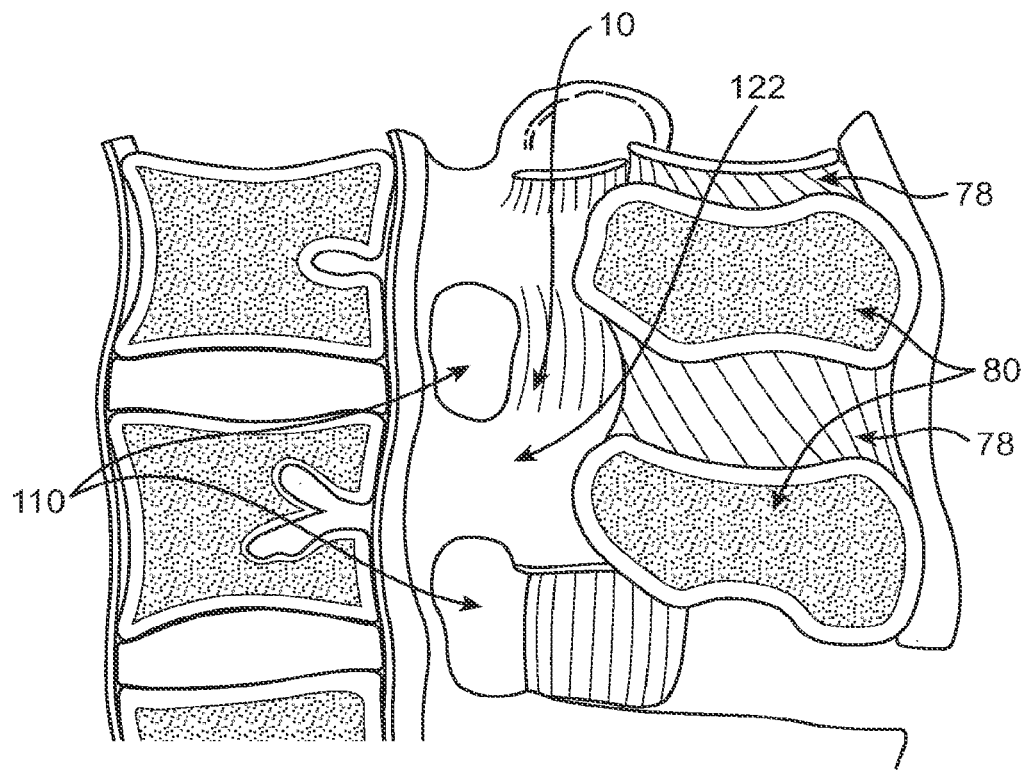
FIG. 2 is a sagittal section through the lumbar spine.

FIG. 2 illustrates the spine in sagittal section. The spine comprises multiple vertebrae each having spinous process 80, transverse processes, facet joint complex 12, and neural foramen 110. Pedicles form inferior and superior boundaries of the neural formen 110 and are connected to the spinous process by lamina. Interspinal ligaments 78 extend between adjacent spinous processes 80, while ligamentum flavum 10 connect adjacent lamina 122 and are separated from dura mater 46 and spinal cord (not shown) by epidural space 42. Dura mater 46 encapsulates the spinal cord as it runs down the spinal canal, as well as nerve roots 62 as they exit through the lateral recesses 108 and neural foramen 110. Vertebral bodies and spinal discs are disposed anterior of the spinal cord.

FIGS. 1 and 2 show two of the most important anatomic structures involved in the impingement of neural and neurovascular tissue in spinal stenosis—the ligamentum flavum 10 and the facet joint complex 12.

Figure 3A:
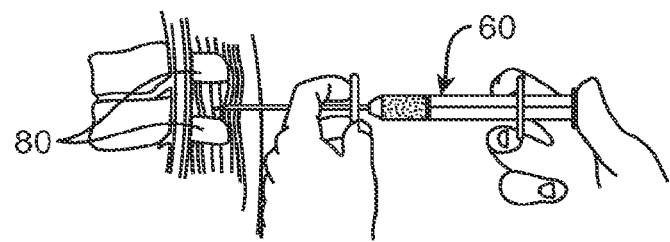
FIGS. 3a, b, c are sagittal views through a patient's spine, illustrating a prior art method for epidural needle insertion, a loss of resistance method.
Figure 3B:
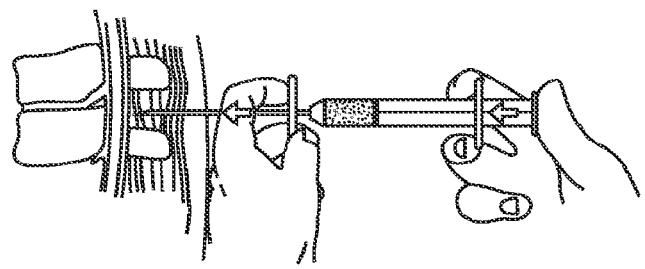
FIG. 3b illustrates constant pressure applied on the syringe plunger.
Figure 3C:
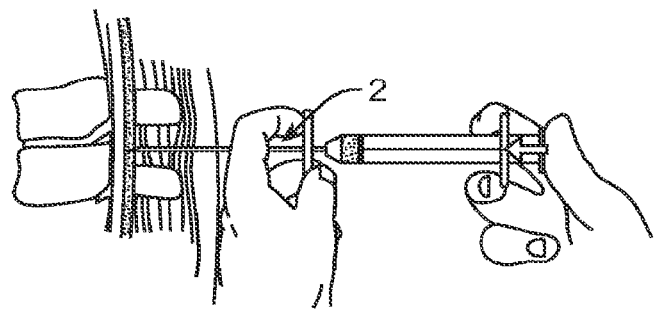
FIG. 3c illustrates saline injected into the epidural space.
Figure 4:
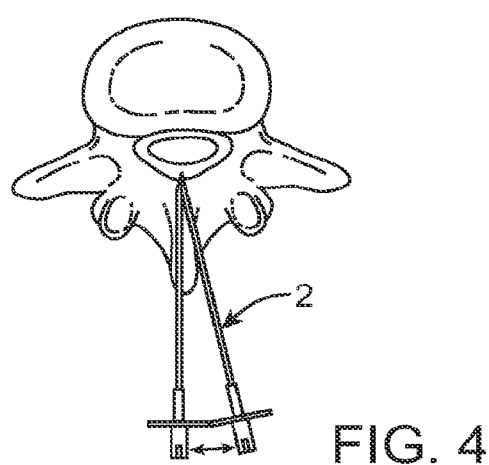
FIG. 4 is a cross-sectional view through a patient's spine, illustrating two prior art variations of the method of FIGS. 3a, b, c.
Figure 74A:
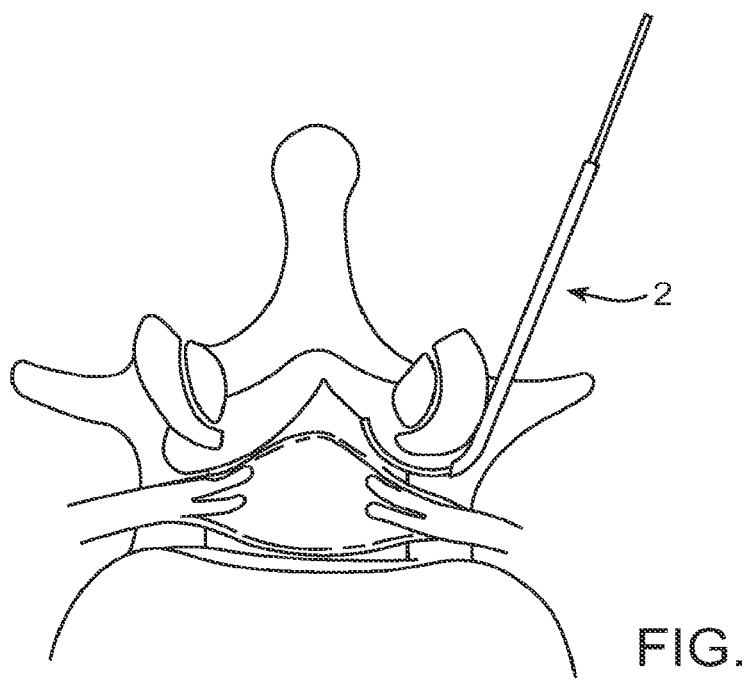
FIG. 74 are schematic cross-sectional views through a patient's spine illustrating a posterior lateral approach to placement of the spinal compression, retraction or retention apparatuses.
Figure 74B:
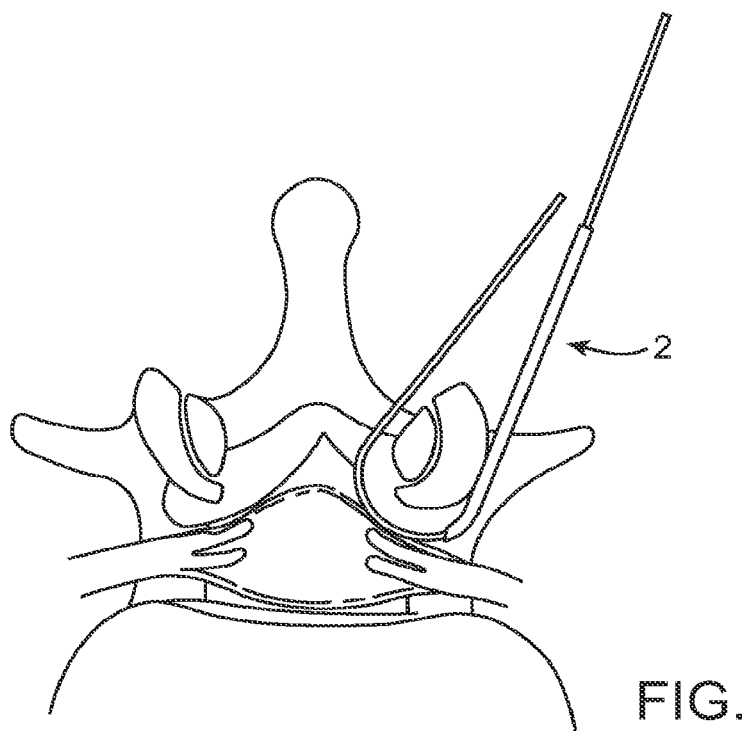

For posterior approaches to the lateral recess 108 and neural foramen 110, the needle 2 is inserted at or one level below the spinal interspace where tissue abrasion and removal is desired. The epidural needle 2 may be inserted into the epidural space 42, midline, ipsilateral, or contralateral to the area where the spinal canal, lateral recess 108 and/or neuroforaminal stenosis or impingement is to be treated. Referring now to FIG. 3, a prior art method for epidural needle 2 insertion is shown, comprising a standard loss-of-resistance technique. Needle based device placement may be approached from either the medial or the lateral side of the neural foramen 110. FIG. 3 illustrate a midline interspinous approach to the posterior epidural space 42. Using this technique, a large bore (e.g. 12 to 18 gauge) epidural needle 2 is inserted into interspinal ligaments, and is directed towards the posterior epidural space 42, while fluid (e.g. sterile saline) or air is compressed within the syringe 60, meeting resistance to injection. Upon entry of the needle tip into the epidural space 42, perhaps through the ligamentum flavum 10, there is a manually perceptible "loss of resistance" to the continued pressure on the plunger of the syringe, as the compressed fluid or air easily enters the epidural space 42, without resistance, signifying correct needle tip position (i.e., placement). The epidural space 42 has a slight negative pressure. Alternative posterior epidural needle 2 entry approaches into the epidural space 42 are illustrated in FIG. 4, including interlaminar paramedian and midline interspinous techniques, a preferred approach to the medial side of the neural foramen 110 for epidural placement of the epidural needle 2. An alternative posterior translaminar approach, where the needle is placed through a hole in the lamina 122, is not shown. The epidural space 42 may also be entered via a more lateral, neuroforaminal approach to needle placement, as shown in FIG. 74. When interlaminar access is not possible (e.g. unusual cases when laminae 6 are too tightly approximated, even with flexion of the back), the epidural space 42 may be entered via a translaminar burr hole using a drill designed for safe epidural entry. Each of these approaches allows placement of the tip of epidural needle in the posterior epidural space 42. As discussed, percutaneous access to the lateral recess 108 and neural foramen 110 may be achieved from the epidural space.

With any percutaneous epidural approach, after a sterile prep and drape, the epidural needle's 2 sharp tip is inserted through the skin to perform a loss-of-resistance technique.

The epidural needle's 2 sharp tip is inserted through the skin until it begins to engage the interspinous ligaments 78. Subsequently, a fluid or air filled (loss of resistance) syringe 60 is depressed and will meet resistance to injection, until the needle tip is advanced, through the ligamentum flavum 10, entering the epidural space 42, which actually has a slight negative pressure. There is a clear "loss of resistance" to the pressurized contents of the syringe 60, which occurs upon entering the epidural space 42, signifying correct needle tip placement.

When interlaminar access is not possible (e.g. unusual cases when laminae are too tightly approximated, even with flexion of the back), the epidural space 42 may be entered via a translaminar burr hole, using a drill designed for safe epidural entry. Each of these approaches allows placement of the epidural needle 2 tip in the posterior epidural space 42, poised for access to the lateral recess 108 and neural foramen 110.

Figure 5:
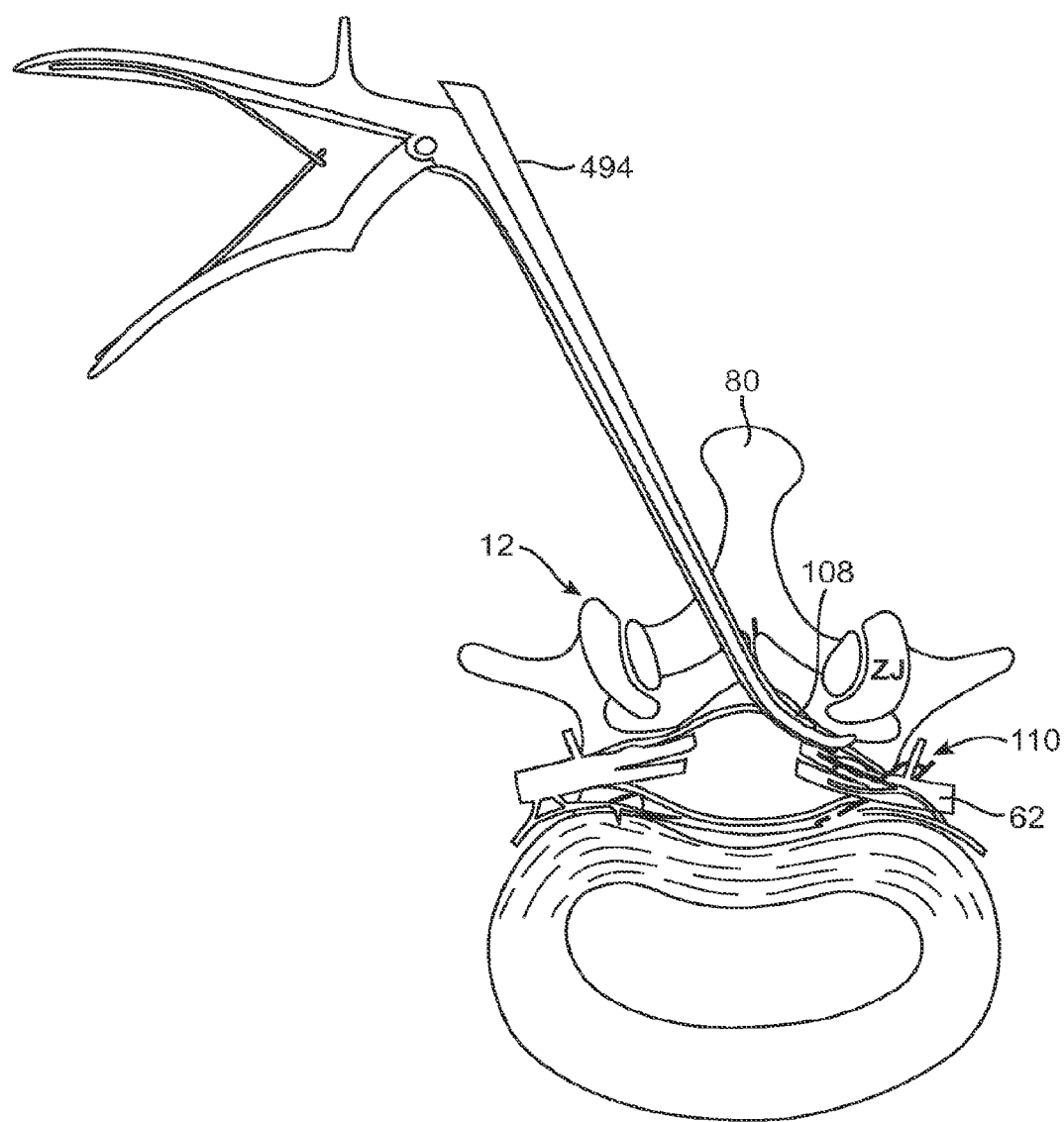
FIG. 5 is a cross-sectional view through a patient's spine, illustrating a prior art open surgical technique for neuroforaminal decompression.

As seen in FIG. 5, the current surgical standard of care for treating neuroforaminal stenosis comprises performing an open decompression via a surgical cut-down to access the stenosed lateral recess 108 and neural foramen 110. All or a portion of the spinous process 80 or facet joint complex 12 may be removed in order to obtain access. Bone and/or ligament from the recess 108 and the neural foramen 110 then may be removed with Rongeur 494. A Woodson elevator or ball-tip probe may be used to determine the adequacy of decompression.

This prior art surgical procedure is imprecise and may not provide for an adequate decompression due to an inability to access all of the foramen 110. Furthermore, a risk of injuring nerve root 62 exists due to a lack of neural protection. Furtherstill, instability caused by the procedure often necessitates spinal fusion.

Figure 6:
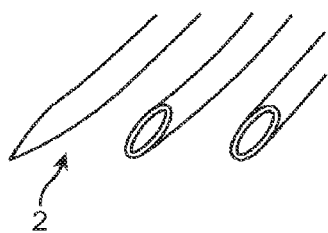
FIG. 6 is an illustration of standard Touhy epidural needle tips.
Figure 10A:
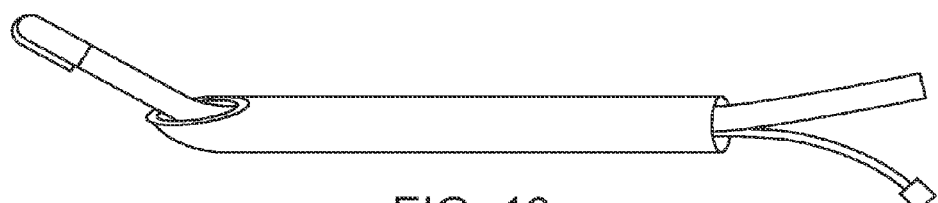
FIG. 10 are also a schematic side view of variations of the apparatus of FIG. 9.
Figure 10B:
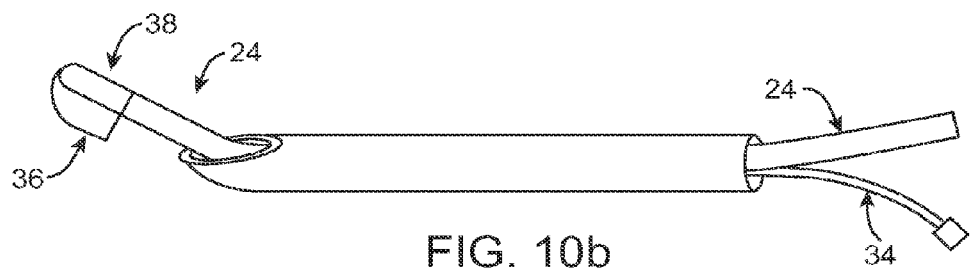
Figure 10C:
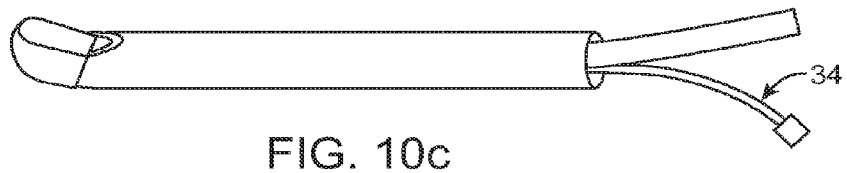
Figure 11A:
FIG. 11 are also a schematic side view of variations of the apparatus of FIG. 7.
Figure 11B:
Figure 11C:
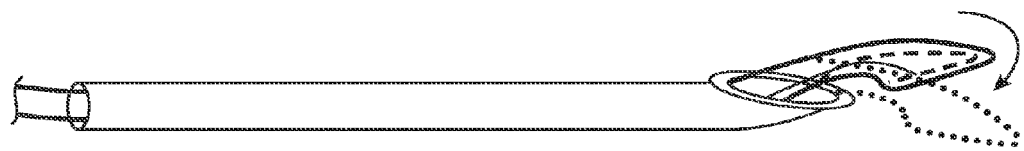
Figure 11D:
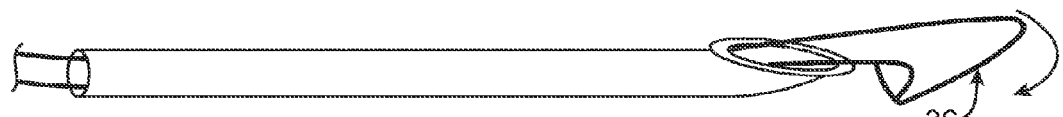
Figure 11E:
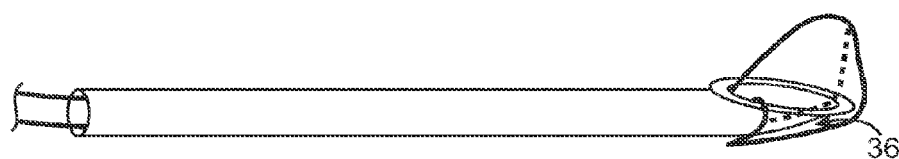
Figure 12A:
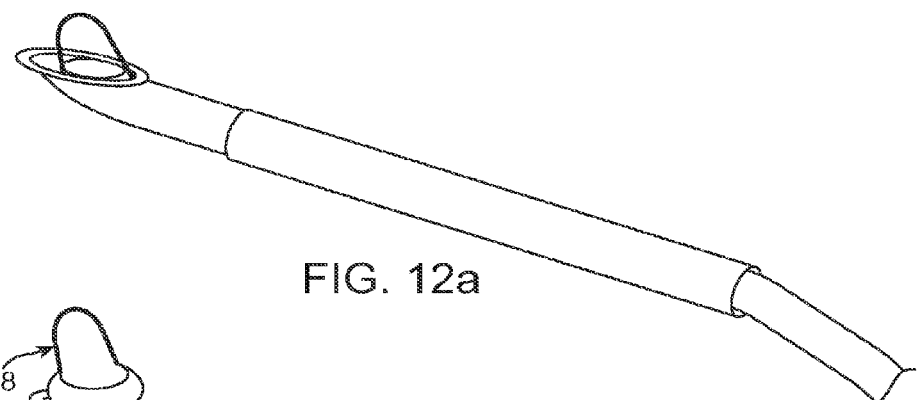
FIG. 12 are also a schematic side view of variations of the apparatus of FIG. 9.
Figure 12B:
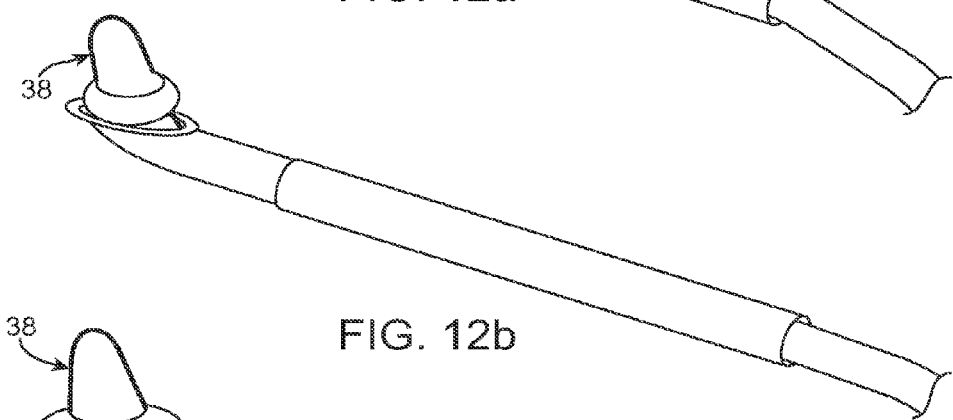
Figure 12C:
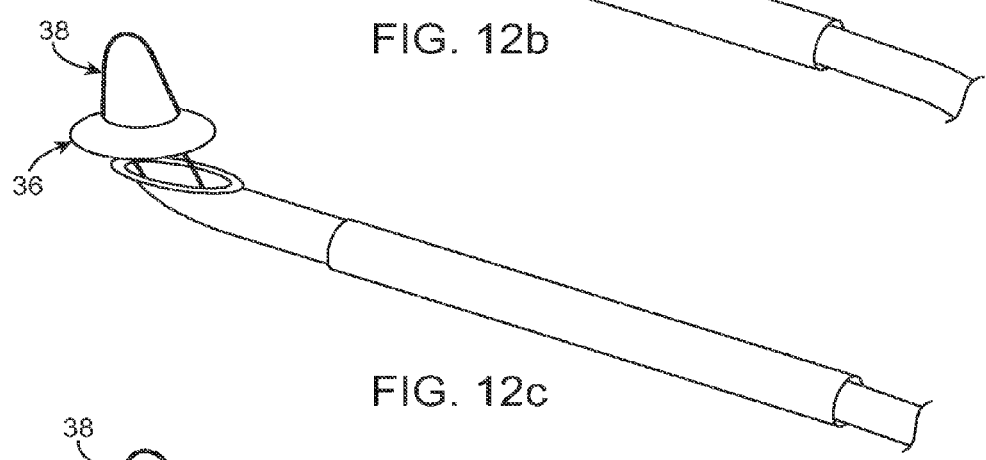
Figure 12D:
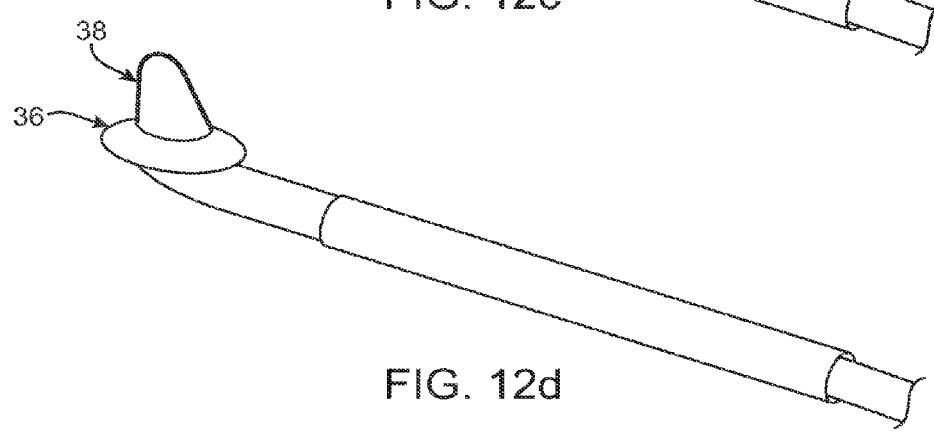

After the epidural needle's 2 distal tip has been placed in the posterior epidural space 42, a specially designed epidural catheter 24 is threaded through the needle 2. Once threaded into the epidural space 42, the epidural catheter's unique epidural needle tip cover 36, located in the distal end of the epidural catheter 24 (with needle tip covering capabilities), is opened and pulled back to cover the sharp epidural needle 2 tip, locked in place, and thereby converts the needle to a non-sharp instrument. The needle, thus converted, may be manipulated and advanced more safely in the epidural space. The blunted needle is subsequently advanced in a direction parallel to the dura 46, in a gentle manner, taking care to avoid inadvertent dural, neural or vascular trauma. With reference to FIGS. 7, 9, 10, 11, 12, 13, and 14, methods and apparatus for protecting, covering and blunting the sharp tip of the epidural needle 2 post-insertion, and optionally converting the epidural needle 2 to an epidural endoscope 38, are described. The catheter apparatus 24 is inserted through the needle 2, and into the epidural space 42, as in FIGS. 7b, 9b, 10a, 11b, 12b, 13a, and 14c. The catheter tip may be converted to the open position by one of several mechanisms, for example, the catheter illustrated in FIG. 6 has a port 34 for injection of air or liquid, which drives (e.g., opens) the actuator for the catheter's (needle) tip (cover). By forcing air or fluid into port 34 in the epidural catheter 24, a portion of the catheter's tip 36 may be expanded, as in FIG. 7b, 9c, 10b, 12c, 13b, or 14e, to inflate or otherwise open the needles protective cover or cap 36. In another variation, an alternative means of actuation of the cap system on the epidural catheter may be a wire or string that pulls the cap into a new shape. For example, FIG. 13 demonstrate a sliding umbrella-like mechanism for actuation of the distal epidural catheter based needle tip cover 36. FIG. 10B shows the epidural "needle cap" or "fiber cap" 36 in the opened position. In certain embodiments, the catheter may next need to be pulled back proximally through the needle 2 until, as in FIG. 10C, until the epidural needle cover 36 is engaged over the distal needle tip, protecting the dura 46, neural and vascular structures from the sharp point of the needle 2, which is no longer exposed. Markings on the catheter will demonstrate to the surgeon that the catheter is in the correct position, allowing the blunted epidural instrument to be safely advanced.

Once the tip of the epidural needle 2 has been blunted or capped, and is no longer sharp, the needle may be move safely advanced within the epidural space, preferably in a direction parallel to the dura 46. In one variation, the epidural needle tip is covered by the catheter based device, then is advanced through the epidural space under image guidance (e.g. fluoroscopy, CT, x-ray, MRI, Ultrasound, etc.), towards the area where tissue resection, ablation or remodeling is to be performed.

In an alternative variation of the method and device, as in FIGS. 9, 10, 12, and 14, the epidural catheter 24, in addition to a needle tip cover, also contains a fiberoptic cable 38, which enables conversion of the epidural needle 2 into an epidural endoscope 38. The fiberoptic component 38 of the catheter provides the surgeon with an ability to directly visualize the epidural space 42. In a further variation of the method, both fiberoptic visualization and image guidance may be used concurrently.

Figure 7A:
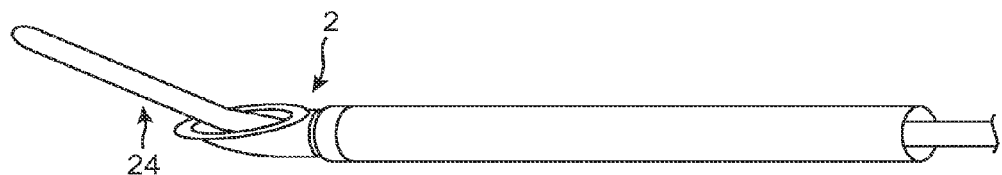
FIG. 7 are schematic side views illustrating a method and apparatus, in accordance with the present invention, for covering with a cap and blunting the sharp tip of the epidural needle post-insertion.
Figure 7B:
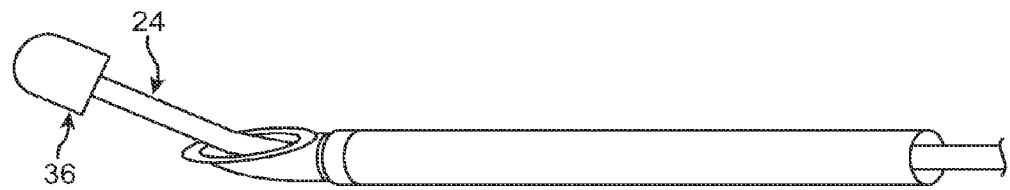
Figure 7C:
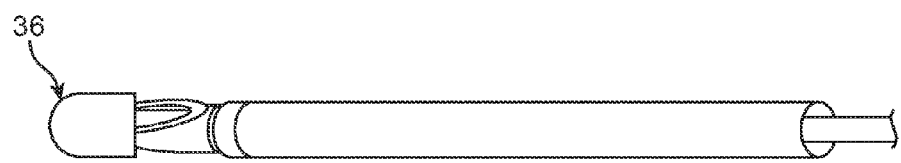
Figure 8A:
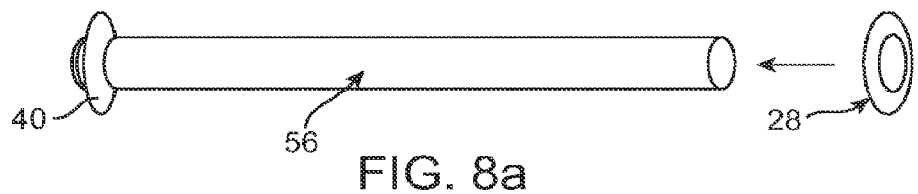
FIG. 8 are also a schematic side view of variations of the apparatus of FIG. 7 with a method for also limiting the depth of insertion of the cannula or needle.
Figure 13A:
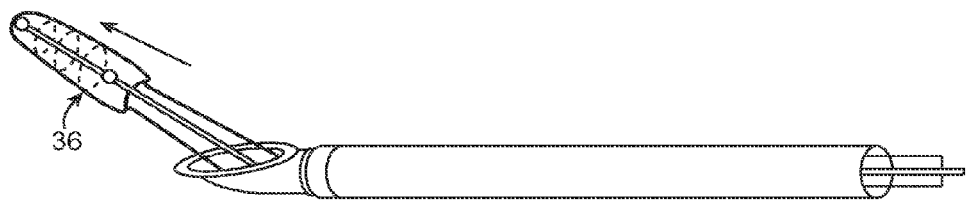
FIGS. 13a, b, c are schematic side views of variations of the apparatus of FIG. 7 or 9.
Figure 13B:
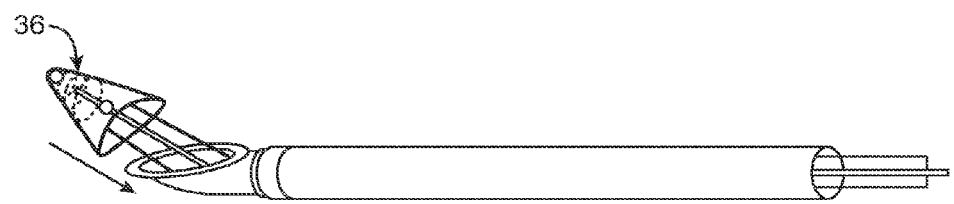
FIGS. 13d, e are schematic side views of an epidural portal over needle apparatus, as shown in FIGS. 13a, b, c; with a distal anchor engaged anterior to the ligamentum flavum, when the portal has been inserted over the needle, into the epidural space.
Figure 13C:
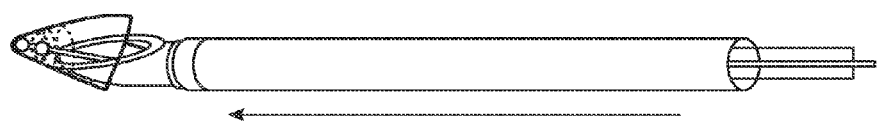
Figure 13D:
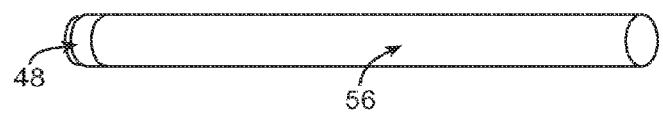
Figure 13E:
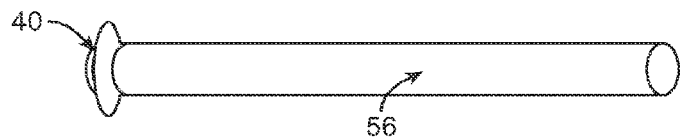
Figure 14A:
FIG. 14 is a schematic side view of variations of the apparatus of FIG. 9.
Figure 14B:
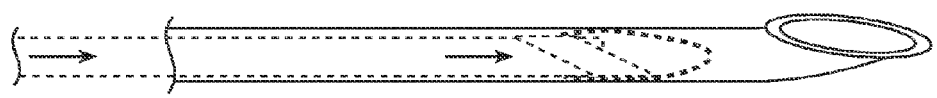
Figure 14C:
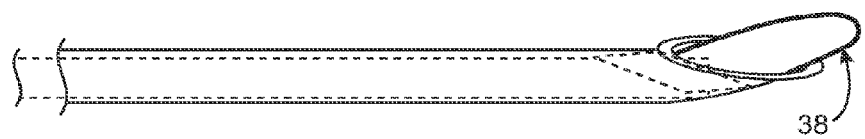
Figure 14D:
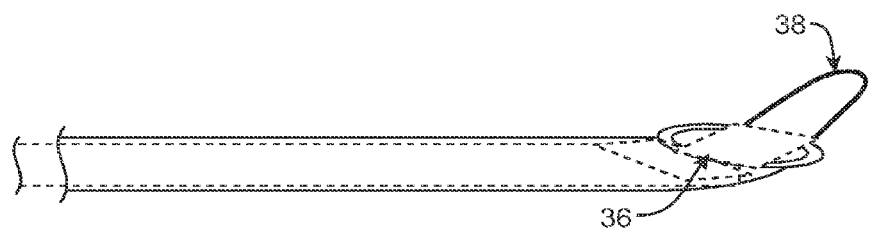
Figure 14E:
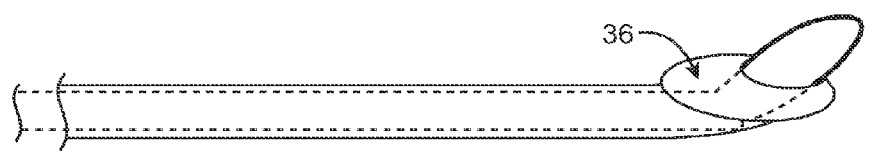

In this apparatus and method for enabling safe manipulation of the apparatus in the epidural space, an epidural needle 2 is first placed in the posterior epidural space 42 in a similar manner to what was described above. With the needle tip in the epidural space 42, an epidural catheter 24 apparatus is used to deliver a cover 36 to the sharp epidural needle tip, converting the needle to a blunt instrument, as shown in FIGS. 7, 10, 12, and 13, for further atraumatic advancement of the apparatus into the epidural space 42. After the catheter 24 is advanced through the epidural needle 2 into the epidural space 42, as in FIGS. 8a and 10a, a distal portion of the catheter is converted to a shape that will be used to cover the sharp epidural needle tip, as illustrated in FIG. 7b. In one variation of the catheter, conversion of the catheter tip to its new shape is triggered via the injection of fluid or air into an actuator within the catheter tip (FIGS. 7b, c). Alternative embodiments of the tip cover 36 are actuated via wire or string that is pulled to bring the tip into its new configuration, e.g. a standard umbrella-like mechanism (FIGS. 13a, b, and c).

Once the cover 36 in the distal catheter 24 is opened, the catheter 24 is gently pulled back until the needle tip is covered and thereby blunted. The capped needle is next carefully advanced within the epidural space 42, between the ligamentum flavum 10 and the dura 46, somewhat parallel to both, towards one of the neural foramen 110, with much less risk of inadvertent dural puncture. In order to further facilitate safe advancement of the capped needle in the epidural space 42, image guidance may be used. Additionally or alternatively, the epidural needle 2 may be converted to an epidural endoscope. Conversion to an endoscope may be performed by either converting the epidural needle 2 to an endoscope directly ("needlescope"), or by utilizing the epidural needle 2 to enable placement of an endoscope cannula or portal 56, which will replace the needle 2. The needle 2 may be converted to an endoscope directly through use of the catheter 24 that is used to cover, blunt, or "safe" the epidural needle tip. The epidural catheter optionally may contain a rigid or flexible fiberoptic element 38, through which the surgeon may view the epidural space 42, thereby converting the epidural needle 2 into an epidural endoscope. The tip of the fiberoptic catheter 38 would, in such a case, be clear.

In a further variation of the apparatus and method, an epidural portal 56 would allow interchangeable epidural endoscopes to be used to view or work within the epidural space. An epidural needle 2 may be used to place an endoscope portal 56, using one of the three following general approaches: (a) In one variation, a portal is an expandable catheter that is delivered as a catheter through the epidural needle 2; (b) In another preferred embodiment, an epidural needle 2 may be inserted into the epidural space, with a thin walled epidural cannula or portal 56 already in place over it, similar to the method and apparatus of standard intravenous cannulation with IV catheters used today. This technique would ideally be used in conjunction with the epidural needle method and apparatus, so that the needle may be advanced far enough to safely also place the neck of the cannula 56 or portal 56, which is a short distance proximal to the distal tip of the epidural needle 2, into the epidural space. In order be able to safely advance the portal 56 into the epidural space, the needle may be covered or blunted, as described above, using a catheter that does not contain a fiberoptic element, as in FIG. 13. With the sharp tip covered, the needle may be subsequently advanced a few millimeters, until the distal tip of the portal has also been advanced into the epidural space 42; (c) In a third embodiment of the method and apparatus, the portal 56 may be inserted over a soft tipped flexible guidewire that has been placed through the epidural needle 2, analogous to the popular "Seldinger Technique" (a standard cannula over needle insertion approach to vascular access).

Figure 15A:
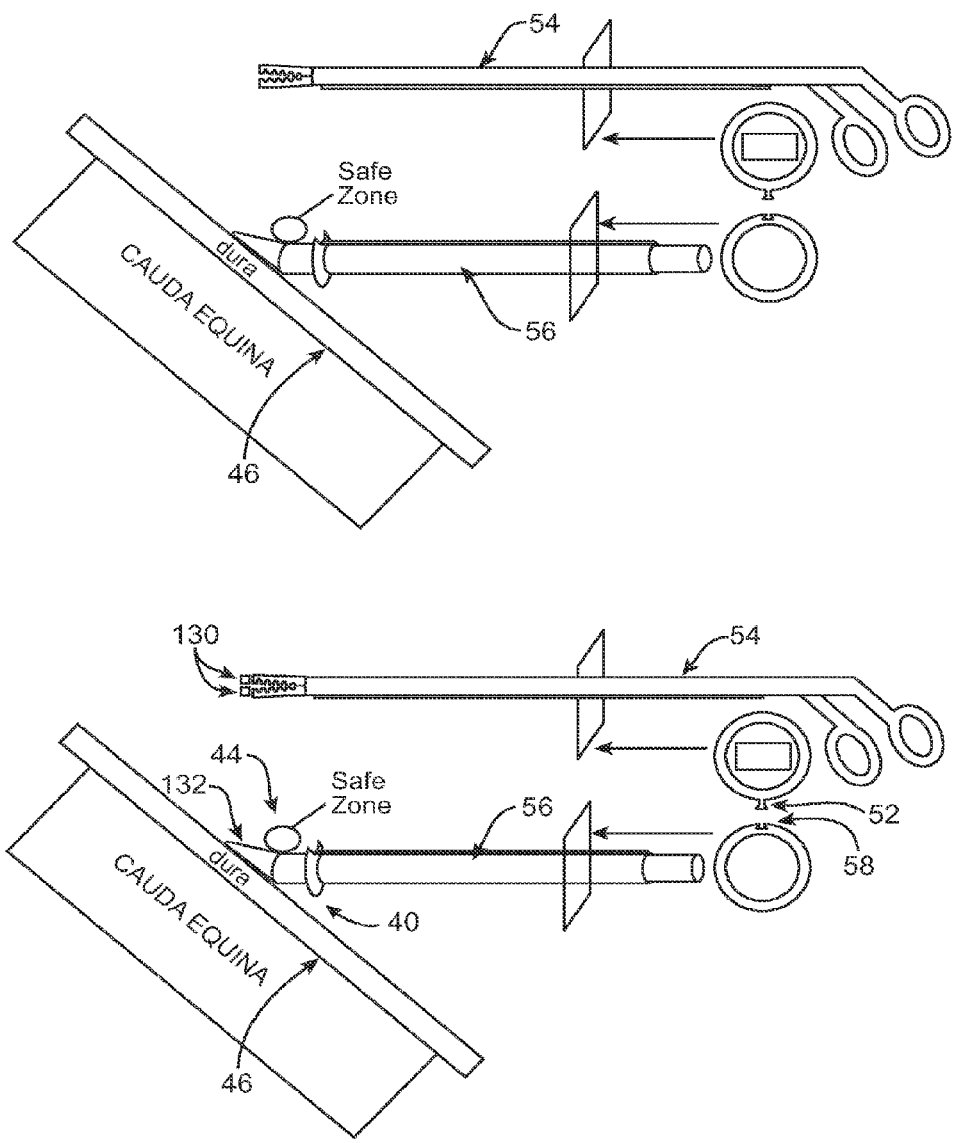
FIG. 15a is a schematic side view, partially in section, of variations of the apparatus, illustrating methods of safely utilizing the apparatus for safe placement and use of surgical tools in or around the epidural space.

With reference to FIG. 15, additional variations of the apparatus of FIG. 10 are described, illustrating methods of safely utilizing the apparatus, in combination with additional surgical tools. Safe tool access, for example, may be facilitated by the inclusion of either a working channel 50 on epidural endoscope 56, or by sliding the tool along a rail 52 and slot 58 interface on the epidural cannula or "needlescope" 56. FIG. 15A shows tool 54 (illustratively a grasper) fitted with rail 52 that mates with a slot 58 of epidural endoscope 56, so that it may be inserted directly into the epidural space 42 and placed in the "safe zone" 44, without the need for a working channel along endoscope/needle 56.

Figure 15B:
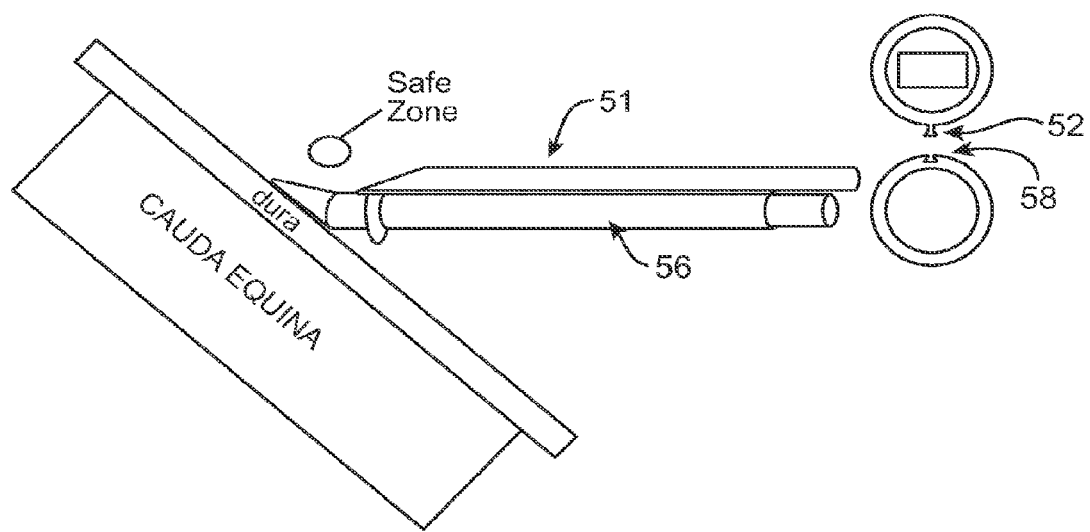
FIG. 15b is a side view, partially in section, illustrating a method and apparatuses for safe placement of a tool or working channel into the epidural space.

In FIG. 15B, working channel 50 is disposed along epidural needle 2, "needlescope", or endoscope 56, e.g., is integrally formed with the endoscope or is positioned via a rail and slot mating, or a similar removable fastening mechanism, with the endoscope. FIG. 15B illustrates an epidural working channel 50 in place, connected to the cannula, needle, or endoscope, with its tool-presenting end adjacent to the "safe zone" 44.

In order to further facilitate working in the epidural space 42, the epidural portal or cannula may have, preferably close to its distal tip, an anchor system 40 to prevent said apparatus from inadvertently slipping out of the epidural space, as illustrated in FIG. 8. The anchor 40 may be engaged towards the distal tip of the cannula or portal 56, anterior to the ligamentum flavum 10. The portal 56 may also be anchored external to the epidural space—e.g., to the patient's skin 70, or within interspinous 78 or supraspinous ligaments, as was illustrated in FIG. 8.

Figure 16:
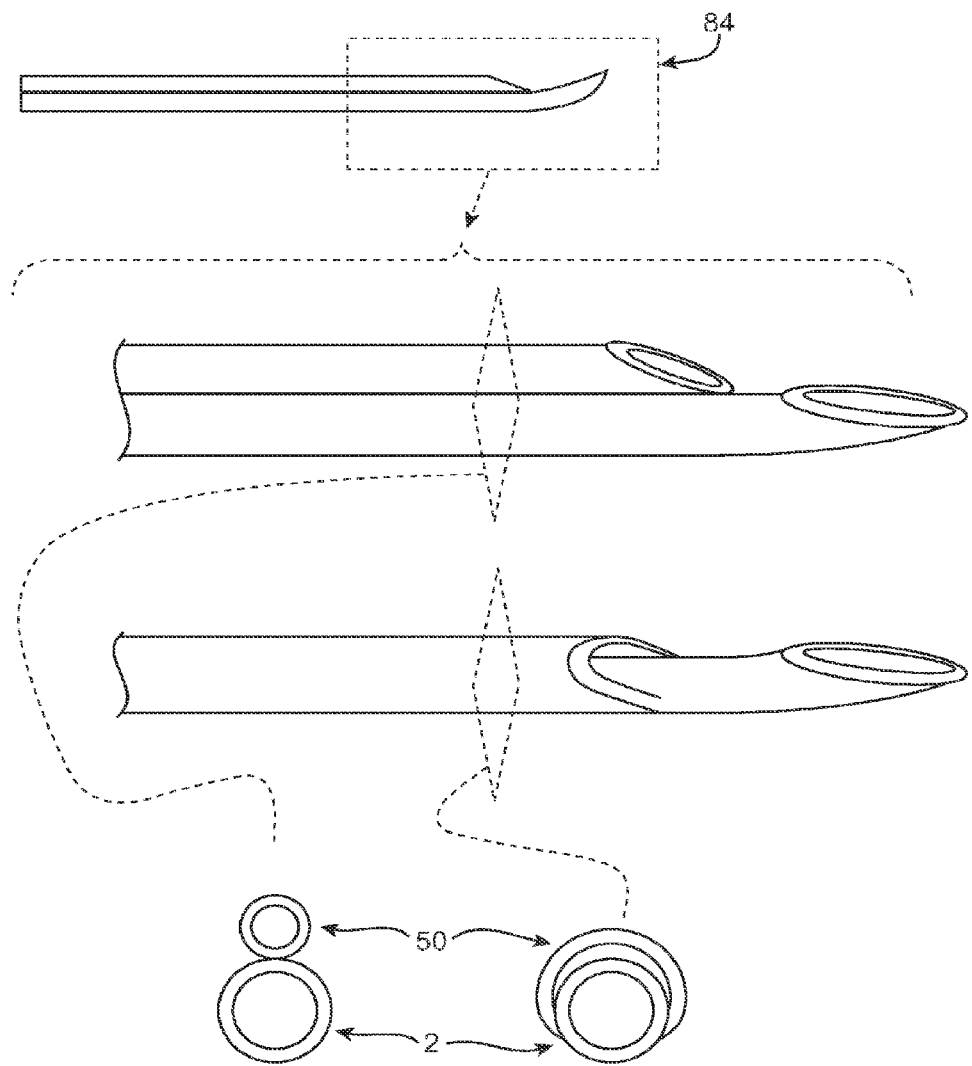
FIG. 16 is a side view illustrating apparatuses that include a double barreled epidural needle, with the epidural needle as the most distal point, and with the working channel the more proximal tip. This system may also be converted to an endoscope and may be used for safe placement of instruments into the epidural space.

Referring now to FIG. 16, an additional method and apparatus for placement of the tissue modification elements is illustrated. A twin lumen epidural needle 84 is illustrated, comprising a working channel 50 adjacent to the epidural needle. The second lumen 50 serves as a working channel, or for the delivery of tools into or adjacent to the epidural space. Note that the distal beveled aperture of the working channel is proximal to the epidural needle tip, and opens onto the side of the epidural needle that the epidural bevel faces.

Figure 17:
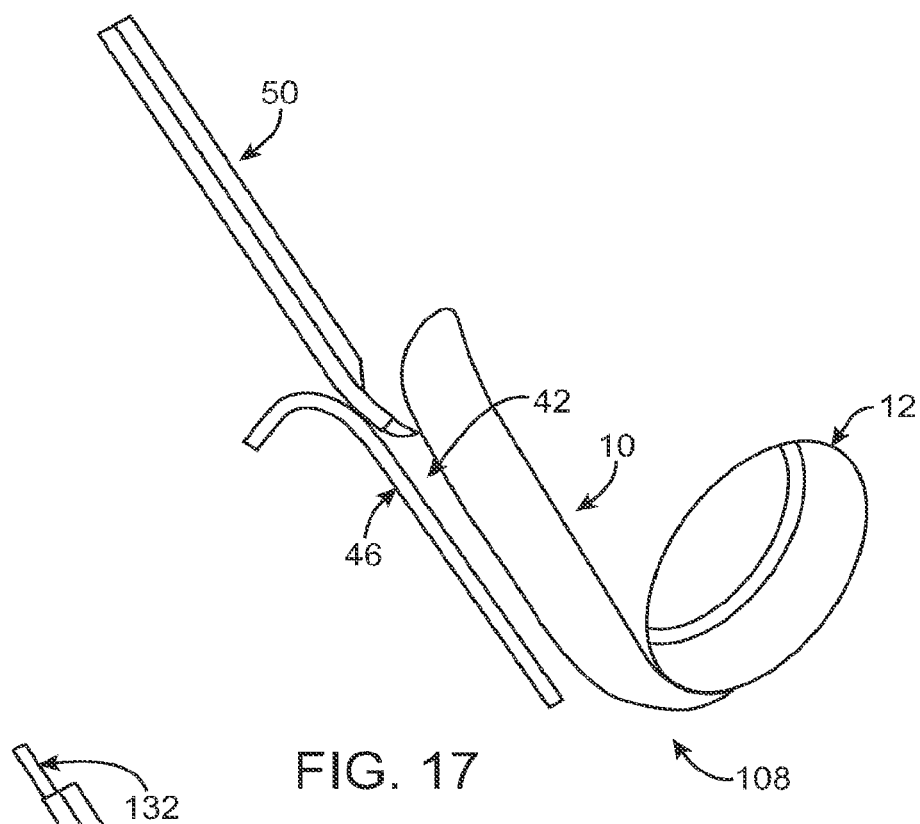
FIGS. 17-19 are cross-sectional views through a patient's spine, illustrating a method and apparatus for placement of a double barreled epidural needle or endoscope, the sharp tip of which has been covered in FIG. 18, and thereby blunted, for safe advancement towards the lateral recess and neural foramina. The blunted epidural needle apparatus may contain a fiberoptic cable for direct visualization, in a preferred embodiment.
Figure 18:
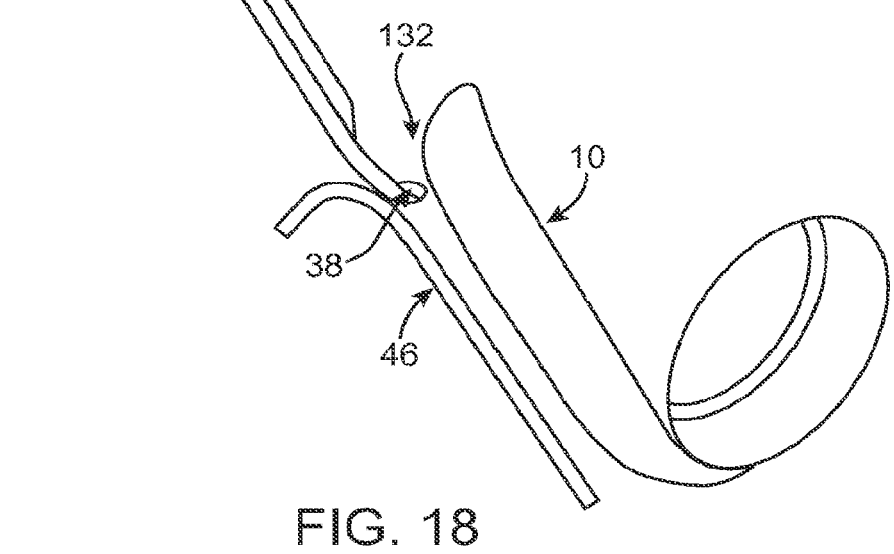
Figure 19:
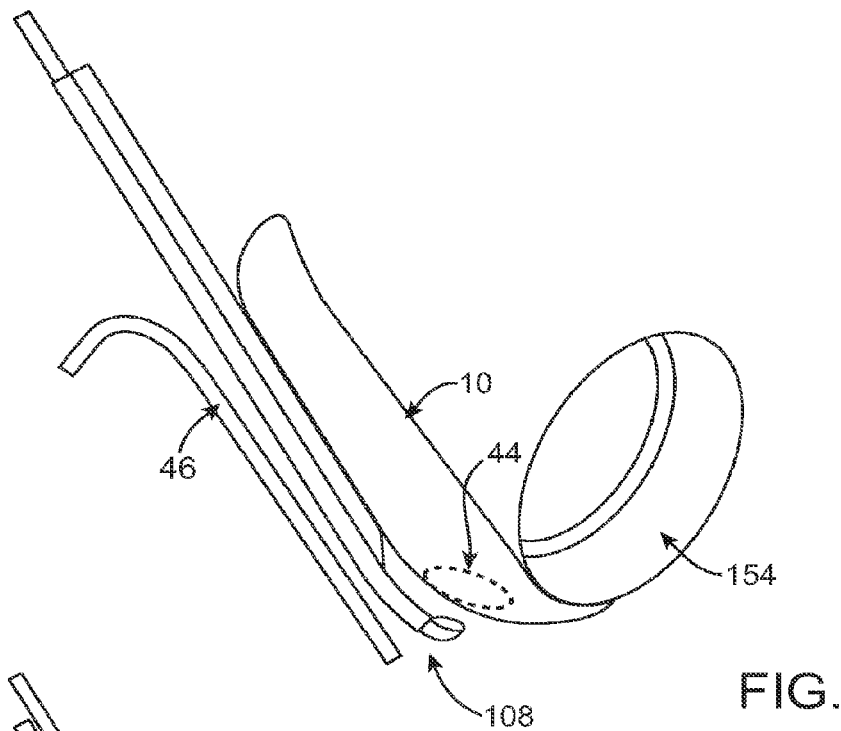
Figure 20:
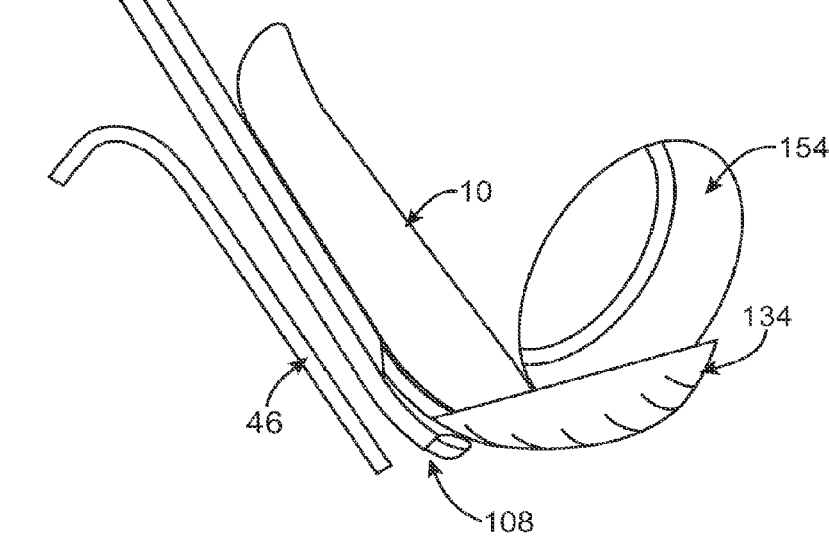
FIG. 20 is a cross-sectional view through a patient's spine that illustrates a method, following FIGS. 17-19, for placement of a working backstop or barrier into the lateral recess and/or neural foramina. The barrier or backstop may contain conductive elements for nerve stimulation and neural localization.
Figure 21A:
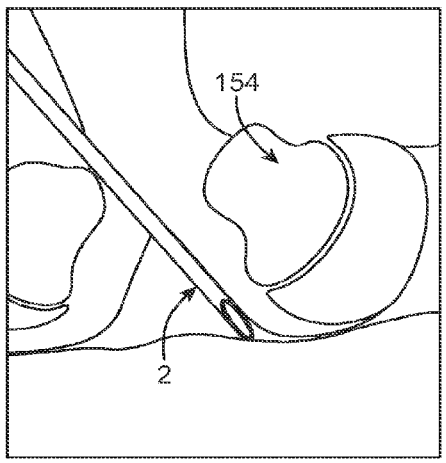
FIGS. 21-22 are cross-sectional views through a patient's spine that illustrate alternative methods and apparatuses for placement of a working backstop or barrier to enable safe tissue resection, ablation, abrasion or remodeling.
Figure 22A:
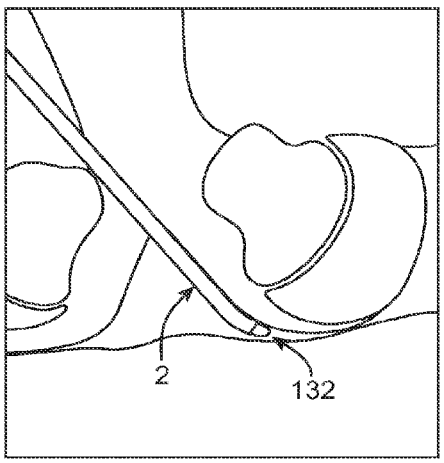
Figure 21B:
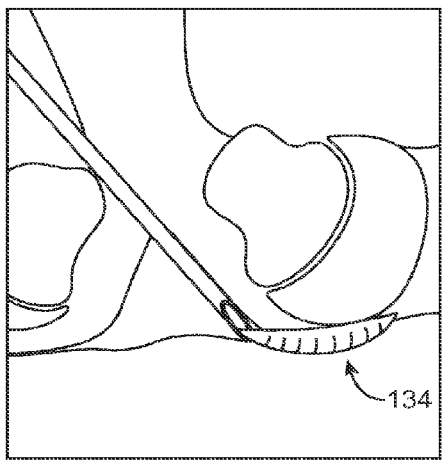
Figure 22B:
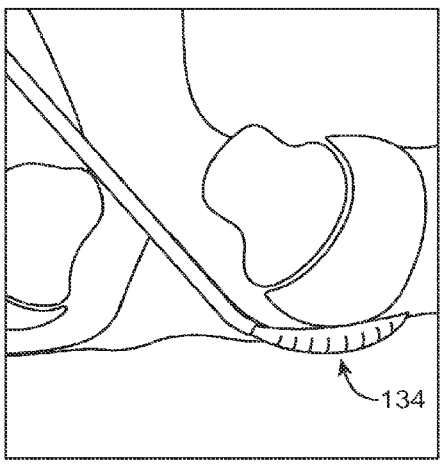
Figure 23:
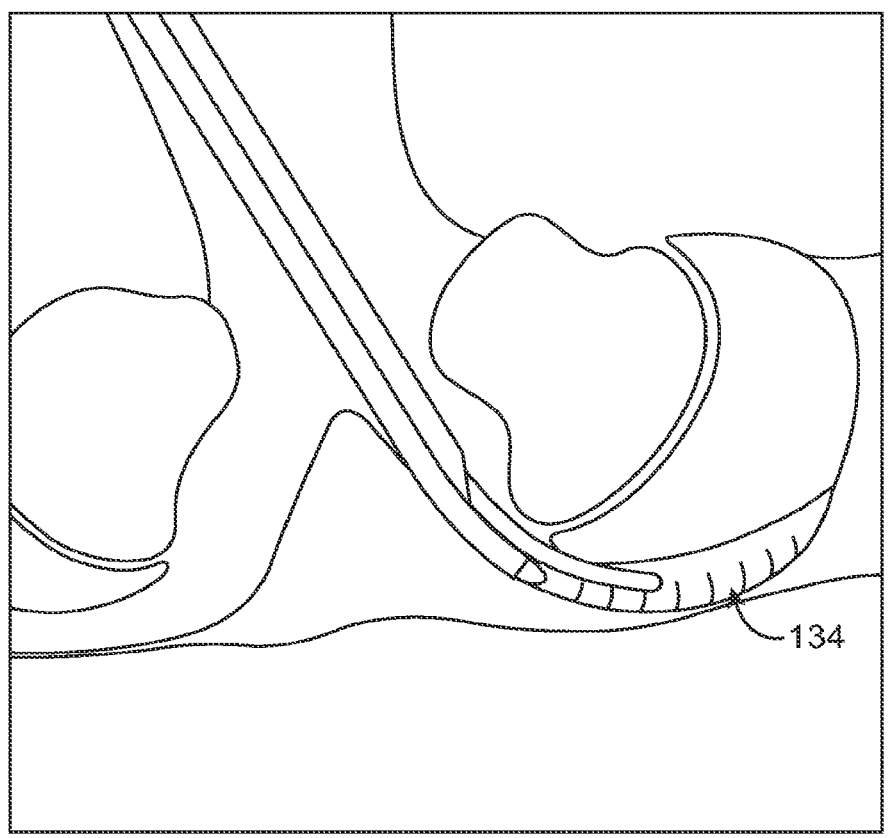
FIG. 23 is a cross-sectional view through a patient's spine that illustrates a tool inserted through the working channel (example shows a shaver or burr), with its tip in position for tissue removal or debridement, adjacent to a protective working backstop or barrier.
Figure 24A:
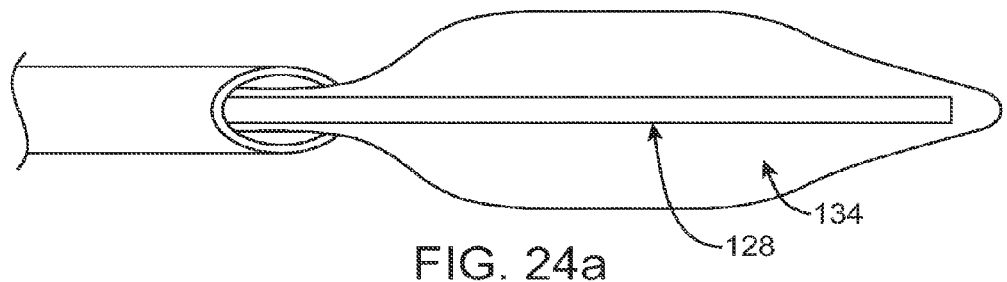
FIGS. 24 are schematic views.
FIG. 24b is a frontal view from above.
FIG. 24c is a front view.
FIG. 24d is a frontal view of the working backstop or barrier apparatus folded for compact delivery.
Figure 24B:
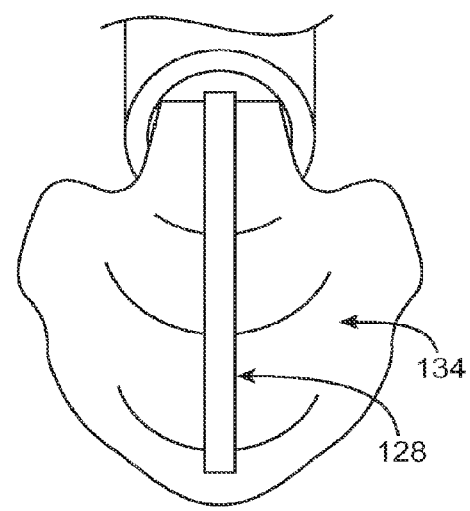
Figure 24C:
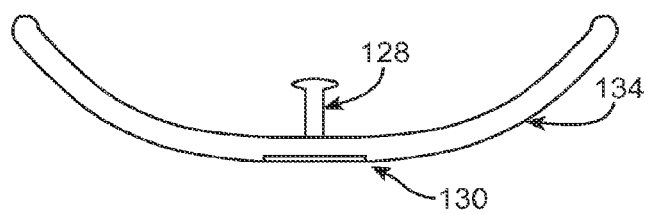
Figure 24D:
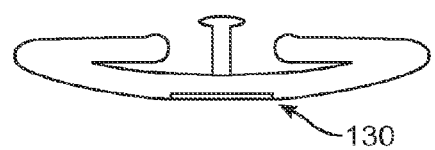

Referring now to FIGS. 17-20 and 45-48, an additional method and apparatus for placement of a tissue abrasion apparatus for selective surgical removal or remodeling of tissue is described. In FIG. 17, the double lumen epidural needle apparatus 84 is positioned for advancement into the epidural space 42. FIGS. 18 and 19 shows how the covered and blunt tip of the epidural needle 2, double lumen epidural needle 84, or the blunt end of the epidural endoscope 38, may be advanced into the ipsilateral or contralateral lateral recess 108, towards the neural foramen 110, in a direction parallel to both the adjacent ligamentum flavum 10 and the dura 46. In the illustrated example of the apparatus and method labeled FIG. 18, a fiberoptic element 38 has been placed within epidural needle 2, providing both a means for fiberoptic visualization of the epidural space 42 and a means to blunt the needle and thereby protect the tip of the needle from damaging the dura 46 or neural or vascular structures. In FIG. 19, the endoscope has been advanced along ligamentum flavum 10 (visually a "yellow ligament") to the lateral recess 108. "Safe zone" 44 designates the area in which a medical practitioner may resect, ablate, or otherwise modify tissue safely, directly visualizing the area of tissue modification through the fiberoptic element. The second lumen 50 of the two lumen needle 84 or endoscope may be used as a working channel, or to dispense the abrasive element 14 and/or its protective sleeve 6 (FIGS. 43-48), or the working barrier 134 (FIG. 20) described in the primary patent referenced herein. After the neural foramen 110 has been cannulated with a non-sharp curved needle 22 or catheter (FIG. 43), and after the flexible, sharp, straight needle or wire 2 has been passed through the curved needle 22 until its tip is advanced through the skin in the patient's back (FIG. 43), the abrasion apparatus 14 and/or its sleeve or cover 36 are pulled through the neural foramen 110, as illustrated in FIGS. 45-48. The curved needle 22 or tube may, for example, be fabricated from spring steel, Nitinol, or other memory material that will allow it to be inserted through a straight needle, but to return to a fixed curve upon exiting the straight epidural needle 2 or working channel 50. The curved needle 16 optionally may be steerable. Preferably, the curved needle tip is not sharp, but is rounded or designed in other fashions less likely to cut tissue, in order to reduce a risk of neural or vascular damage.

In yet an additional embodiment of the invention ("portal over epidural needle" variation), an epidural portal 56 may be inserted into the epidural space as a catheter over the epidural needle 2 (as in FIG. 13), similar to the design for placement of standard intravenous catheters used today. With such an approach, advancing the blunted needle (sharp tip covered) by several millimeters will also bring the distal tip of the portal into the epidural space 42. Subsequently, the needle may be withdrawn from the portal, which is held in place by the surgeons other hand, leaving the epidural portal in the epidural space 42 as a working channel or endoscope guide.

Figure 8B:
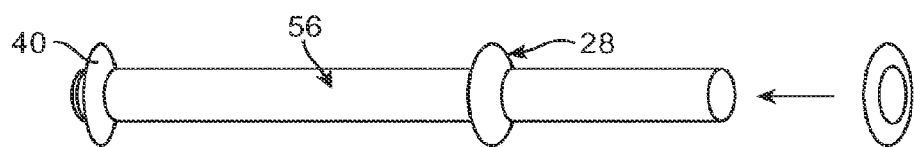
Figure 9A:
FIG. 9 are schematic side views illustrating a method and apparatus in accordance with the present invention for covering with a cap and blunting the tip of the epidural needle post-insertion, and optionally converting the epidural needle to an epidural endoscope, for safe further advancement of the needle into the epidural space.
Figure 9B:
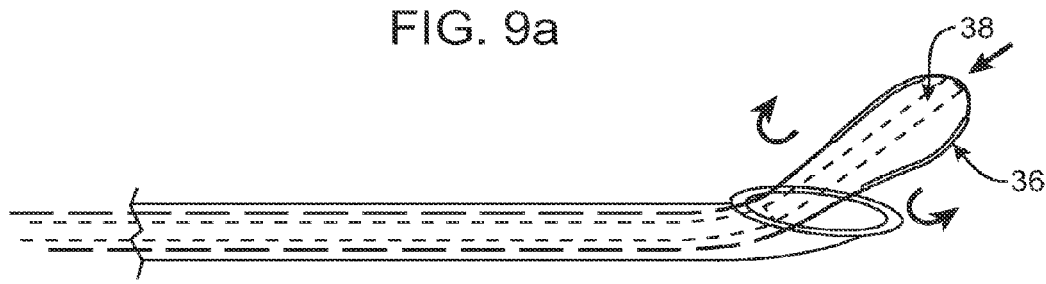
Figure 9C:
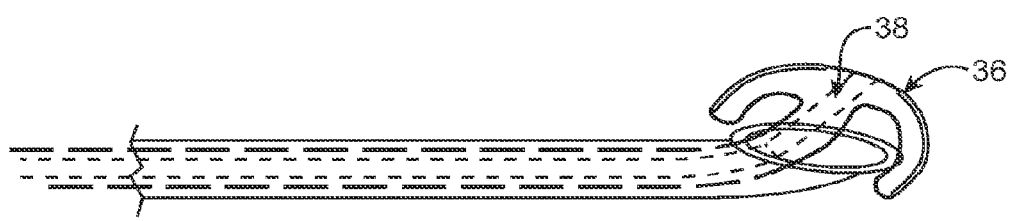

In one variation, the epidural needle 2, needle based endoscope, flexible or rigid endoscope, or portal 56 (for placement over an epidural needle) may have, preferably close to its distal tip, an (e.g., distal) anchor mechanism 40 that may be inflated or otherwise opened (e.g., in the epidural space), to help prevent inadvertent removal of the device from the epidural space 42. It is expected that utilization of an anchor anterior to, or within, the ligamentum flavum 10, will prevent the portal from being pulled inadvertently through the ligamentum flavum 10, and will enhance the reliability and safety of epidural access for minimally invasive endoscopic surgery. FIG. 8 illustrates a distal epidural anchor 40. FIG. 8 also illustrates that the portal, needle, or endoscope may include a proximal anchor or lock 28 (e.g., to anchor on the skin) that may be advanced from the proximal end of the device (skin side), in order to help to prevent the percutaneous device from advancing further into the epidural space than is desired (as in FIG. 8*b*).

FIG. 15 illustrates additional methods of safely utilizing a blunted epidural apparatus in conjunction with additional surgical tools. Safe tool access may, for example, be facilitated with either a fixed working channel 50, as shown in FIG. 16, or by the creation of a rail 52 and slot 58 interface on the tool or epidural endoscope, cannula or "needlescope" 56, as shown in FIG. 15*b*. FIG. 15*a* shows a tool 54 (illustratively a grasper) fitted with a rail 52 that mates with a slot 58 of epidural endoscope 56, so that it may be inserted directly into the epidural space 42 and then advanced until it is placed in the "safe zone" 44 (e.g., for tissue resection or modification, on an opposite side of the epidural tissue), without the need for a working channel along endoscope/needle. The part of the epidural tool that is expected to be in direct contact with the impinging spinal tissues that the surgeon intends to modify provides an ideal location for neural stimulator lead placement 130. In the example illustrated in FIG. 15*a*, an insulated tool shaft is combined with a conductive surface 130 on the tip of the grasping tool 54, to be used for neural stimulation. (note: the use of neural stimulation with sensorimotor monitoring, for neural localization, in conjunction with the current invention, will be discussed later in this document)

In one variation, the epidural needle is curved towards its distal end, e.g., into a hockey stick shape. In a curved configuration, the lumen exits the bevel, distal to, and on the concave side of the bend in the needle's distal shaft. With such a configuration, a "safe zone" 44 is created by inserting the needle so that the side opposite the bevel (convex side of the bend) is in direct contact with the dura 46, and the lumen, on the concave side of the bend, faces the ligamentum flavum 10. This configuration provides a "safe zone" 44, where tools, or a working channel 51, may be reliably placed on the needle side opposite the dura 46.

In FIG. 15*b*, a removable working channel 51 is disposed along epidural needle 2/endoscope 56, e.g., is integrally formed with the endoscope or is positioned via a rail 52 and slot 58 mating with the endoscope 56. FIG. 15*b* illustrates an epidural "needlescope" 56 or endoscope cannula with the working channel 51 in place, with its tool-presenting end adjacent to the "safe zone". In FIG. 16, a double barrel epidural needle 164 is illustrated, comprising a fixed working channel 50 adjacent to the epidural needle. Needle 164 comprises first lumen 2 and second lumen 50. First lumen 2 extends distally of second lumen 50 and terminates at sharpened distal tip. Two variations of the needle are illustrated in FIG. 16.

Referring now to FIGS. 17-20, an additional method and apparatus for selective surgical removal of tissue is described. In FIG. 17, the double lumen epidural needle apparatus is positioned for advancement into the epidural space 42 (e.g., a safe triangle, an area at the most posterior aspect of the epidural space, where epidural needle tip insertion is most consistently safely performed). In FIG. 18, a catheter based fiberoptic element 132 has been placed within epidural needle, providing both a means for fiberoptic visualization of the epidural space 42 and a means to blunt the needle and thereby protect the tip of the needle from damaging the dura 46 or neural or vascular structures. In FIG. 19, the endoscope has been advanced along ligamentum flavum 10 (visually a "yellow ligament") to the lateral recess 108. "Safe zone" 44 designates the area in which a medical practitioner may resect, ablate, or otherwise modify tissue safely, under direct visualization. The second barrel or lumen 50 of the double barreled needle 84 or endoscope may be used as a working channel, or to dispense a tissue modification barrier or working barrier or backstop 134.

In addition to the insertion of tools through the epidural needle, or through an adjacent working channel 50, the same channels may be utilized to insert a barrier 134, or "working backstop" 134 (FIGS. 20, 21*b*, 22*b*, 23, 24, 25), into the spine. In a further variation of the present invention, a flexible, flat, thin mechanical barrier ("working backstop") 134 is placed between the tissue to be resected and adjacent vulnerable neural or vascular structures that are desired to be left intact and uninjured. The barrier provides protection for the dura 46, nerve root 62, dorsal root ganglia, and/or vasculature, by providing insulation and/or preventing direct contact between the tools and these vulnerable structures during tissue manipulation, resection, abrasion, or remodeling. The protective barrier may be placed between the needle based or endoscopically delivered tools and the dura 46 in the central spinal canal; in the lateral recess 108; or between the tools and the neural and neurovascular structures within the neural foramen. The barrier 134 may be placed through the neural foramen anterior to the facet joint 12, either anterior to the ligamentum flavum 10 (epidural space) or within or posterior to the ligamentum flavum 10 (posterior to the epidural space). Tools that may be used in conjunction with this barrier include, but are not limited to, cautery devices (monopolar or bipolar), lasers (erbium, etc.), rasps, rongeurs, graspers, burrs, sanders, drills, shavers, or probes.

The barrier or backstop 134 may be placed percutaneously via a needle 2, endoscope 38, or double barreled needle 84. In addition to epidural endoscopy, image guidance may be combined with the use of straight, curved, or steerable guidewires for the proper placement of the barrier or backstop 134. In an open surgical variation, the barrier or backstop device 134 may be placed through the surgical incision.

The barrier 134 may be synthesized from one of several possible materials, for example, it may be partially fabricated from a spring steel, Nitinol, polymers, or other memory material that will allow a thin, flat barrier to be reconfigured into a more condensed configuration for passage through a straight needle (FIG. 24*d*), after which it returns to its desired shape (FIG. 24*c*) upon exiting the needle 2. The barrier 134, optionally, may be steerable.

Figure 25:
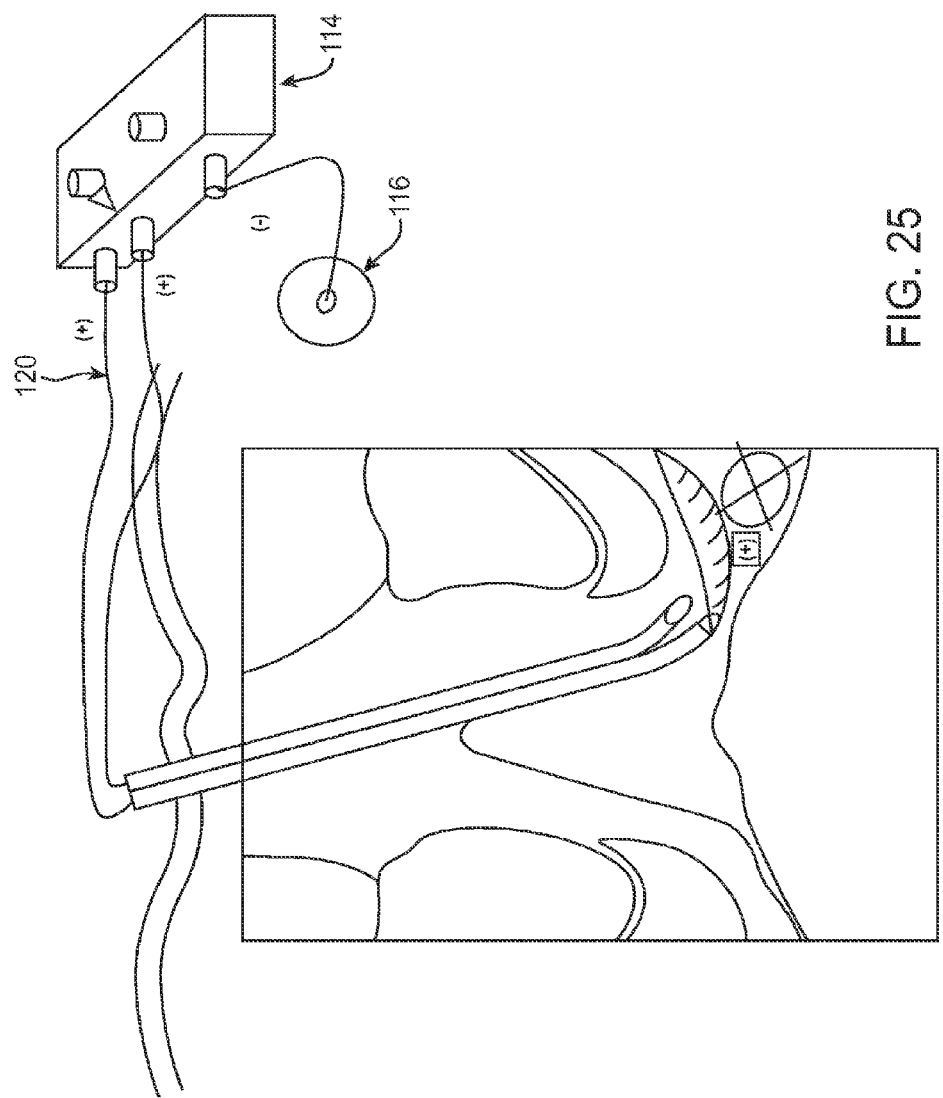
FIG. 25 is a cross-sectional view through a patient's spine that illustrates a methods and apparatuses for providing neural stimulation and neural localization, within a working backstop or barrier, and/or within a tool (a bone burr placed adjacent to a spinal bone spur in the lateral recess, in this illustrative example), for safety in tissue resection, abrasion or remodeling.

As is illustrated in FIG. 25, correct anatomic placement of the backstop device 134 may be validated via monitored electrical neural stimulation through the barrier device 134. Electrical nerve stimulation function may be added to the apparatus via dual conductive elements, the first placed on the working side of the backstop (or the tool used on the working side), where tissue remodeling and resection will occur. In the example illustrated in FIG. 24, the working nerve stimulator on the working side of the barrier may be integrated with the rail 128, through which nerve stimulation may be tested before sliding the tool or sleeve over the rail for tissue modification. A conductive element (e.g., for neural stimulation) may also be placed on the non-working side of the backstop 130. To gain accuracy in neural localization, the stimulation leads on the device are separated by insulation material within the backstop material.

The patient may be kept awake and responsive throughout this procedure, with no neuraxial anesthetics and no systemic analgesia. In this manner, the medical practitioner may, through verbal questioning, elicit responses from the patient in order to ensure that any severe pain that would accompany undue pressure on the nerve root during placement of the tissue modification device and/or during tissue removal or remodeling is immediately recognized prior to nerve injury. Alternatively, for a deeply sedated patient, or one under general anesthesia, nerve stimulation may be monitored via SSEPs or SEPs; visually (motor movement of extremities); via MEPs; and/or via EMG (motor stimulation). In one embodiment of the device, one might use a calibrated sensor, combined with computer analysis, to accurately quantify neural stimulation at different locations, in order to more accurately localize neural structures.

As is illustrated in FIG. 25, there should be no nerve root or dorsal root ganglion stimulation in the exact location where tissue alteration is intended to take place, when one sends appropriate small electrical current through an insulated electrode that is located on the working side of an insulated working barrier, prior to tissue modification tool placement. Correct neural location, relative to the tissue modification tools and barrier may further be ensured by the addition of focused neural stimulation functionality to accompanying surgical instruments. For example, tools used for probing, tissue resection, tissue cauterization, thermal treatment, tissue lasering, tissue manipulation, tissue retraction, and tissue abrasion may contain conductive elements for neural localization. The nerve stimulation capabilities may be used to ensure that the neural elements are not in dangerous proximity, or they may be used to assist with more concise neural localization. For instance, a probe fitted with neural stimulation capabilities in its tip may be used to identify neural structures, through monitoring of sensory or motor stimulation. However, electrical stimulation on the non-working surface of the working barrier, which is in direct or indirect contact with neural structures, should result in motor and/or sensory action potentials, which may be monitored as described above, thereby providing a positive control and assurance of proper barrier placement. For added safety, a surgical device may be designed to automatically stimulate before or during resection, and may even be designed to automatically block resection when nerve stimulation has been sensed.

In a preferred variation, impinging spinal tissue is removed using tissue abrasion apparatus and method. Variations of the apparatus and method may be utilized during an open surgical procedure(s); during an endoscopic surgical procedure(s); or via a percutaneous (needle delivered) surgical approach. Use of a needle-based posterior interlaminar or interspinous approach, a posterior-lateral neuroforaminal approach or a minimally-invasive surgical approach for placement of the neuroforaminal abrasive tissue removal device avoids unnecessary tissue resection and minimizes tissue injury. In addition, further embodiments of the device include nerve stimulation and monitoring capabilities, which, when added to a spinal tissue alteration device, may enable the surgeon to more safely perform the procedure.

Figure 26A:
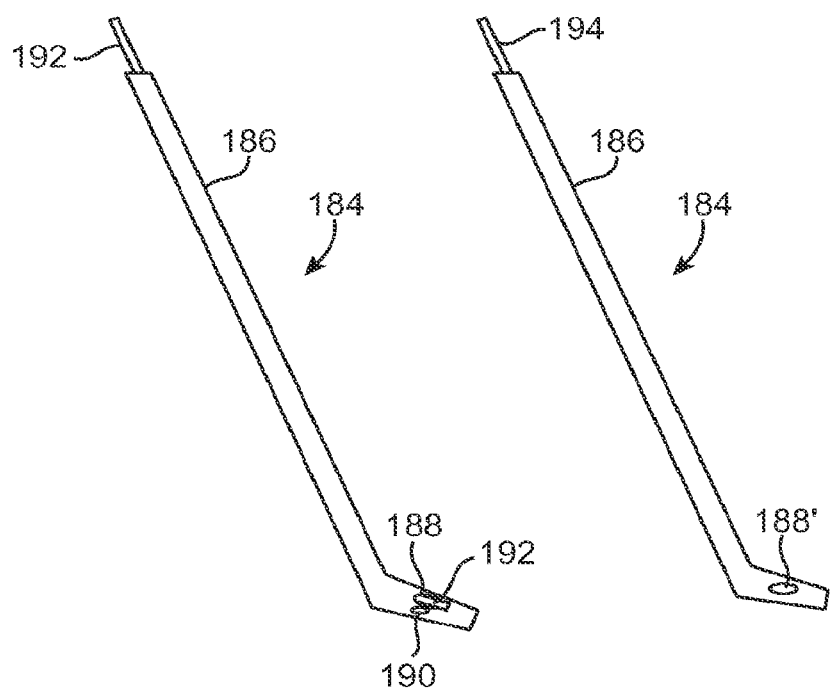
FIG. 26A is a schematic view of apparatus of the present invention for obtaining open surgical access.

As discussed previously, variations of the present invention preferably provide for access, neural protection and/or decompression for treatment of spinal stenosis. With reference to FIGS. 26 and 27, methods and apparatus for obtaining access to the neural foramen utilizing open surgical variations of the present invention are described. FIG. 26A illustrates two variations of access element 184. In the first variation (26A-1), access element 184 comprises cannulated probe 186, illustratively an elevator probe having first and second lumens 188 and 190. Visualization element 192, such as an epidural endoscope, may be advanced through or coupled to lumen 188 to provide visualization at the distal tip of probe 186.

In the second variation (FIG. 26A-2), probe 186 of access element 184 comprises single lumen 188'. Visualization element 192, as well as cannula 194 or curved guide wire 4 described hereinafter, may be advanced through the unitary lumen either in parallel or in sequence. Alternatively, the visualization element may be omitted or may be attached directly to the probe. As will be apparent, access element 184 may comprise any desired number of lumens.

Figure 26B:
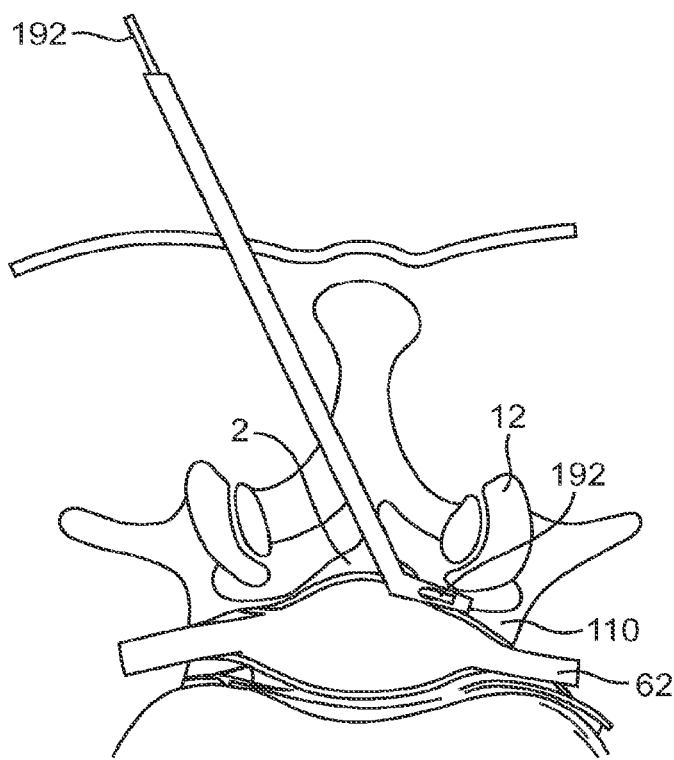
FIGS. 26B-26E are cross-sectional views through a patient's spine, illustrating open surgical methods of using the apparatus of FIG. 26A to obtain access.

In FIG. 26B, the dual lumen variation of access element 184 has been placed through a surgical incision or cut-down in proximity to neural foramen 110 while under optional visualization from element 192. Visualization may facilitate access via a minimally invasive or keyhole surgical cut-down, as opposed to a fully open approach. Direct visualization alternatively or additionally may be utilized.

Figure 26C:
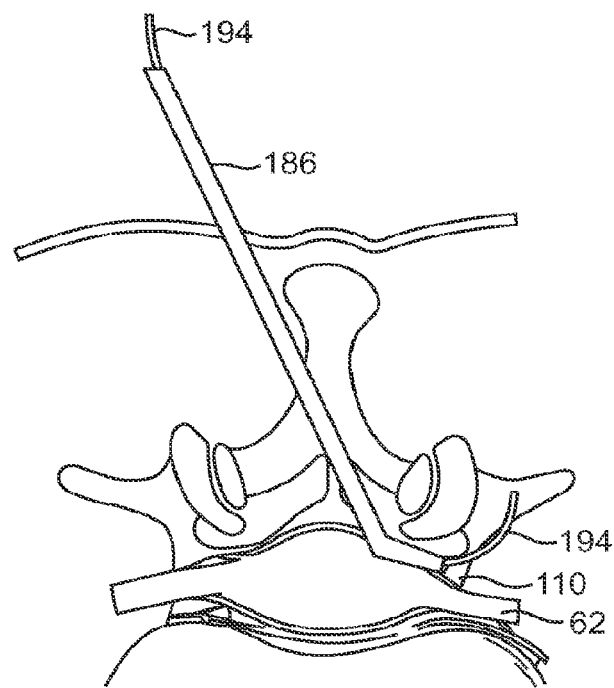
Figure 26D:
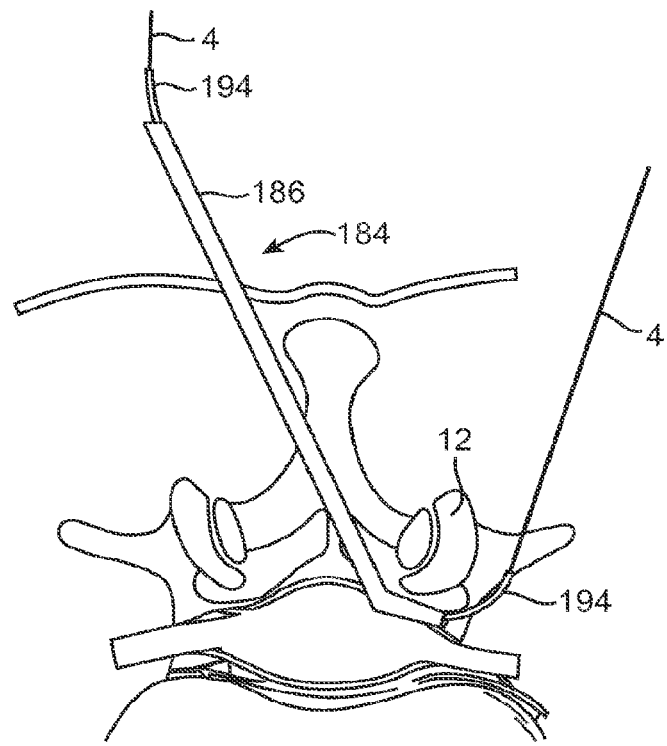
Figure 26E:
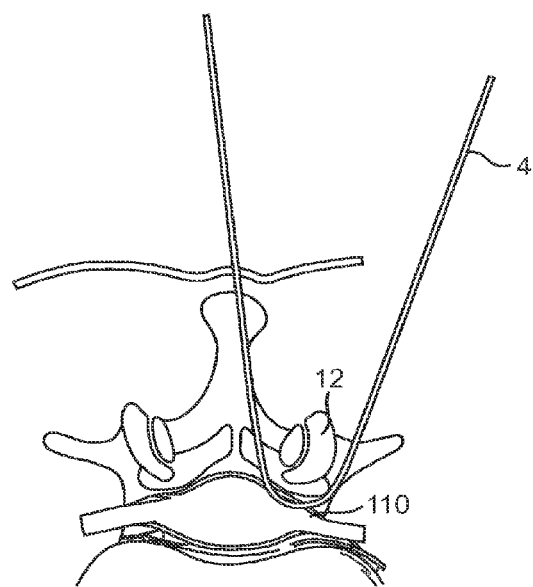

As seen in FIG. 26C, with probe 186 properly positioned, atraumatic curved tube, introducer or cannula 194 may be advanced through lumen 188' of the probe and driven laterally to cannulate the neural foramen 110. Cannula 194 optionally may be configured to deliver a stimulation waveform at or near its distal tip for monitoring proximity to the nerve root during cannulation of the foramina with the cannula. A preferably straight, flexible guide wire 4 or needle, which optionally comprises sharpened tip, then may be advanced through cannula 194 and driven posteriorly through the skin of the patient's back, as in FIG. 26D. Alternatively, a second surgical incision and or cut-down may be formed at or near the exit of the neural foramen for grasping the guide wire and pulling it through. With access guide wire 4 positioned through and across the neural foramen, probe 186 may be removed, as in FIG. 26E. This leaves the guide wire 4 in place to provide access for, e.g., neural protection and tissue removal apparatus, as described hereinbelow.

Figure 27A:
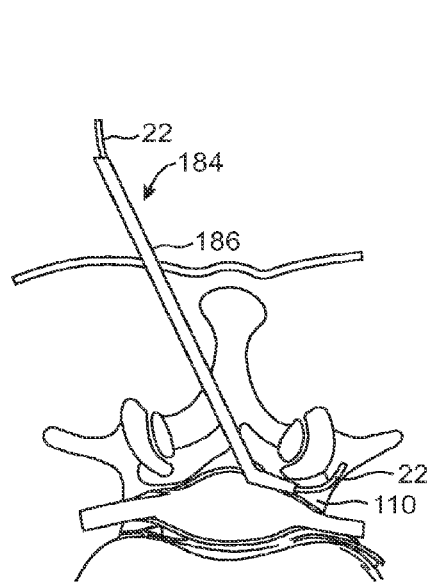
FIGS. 27A and 27B are cross-sectional views through a patient's spine, illustrating a variation of the methods and apparatus of FIG. 26
Figure 27B:
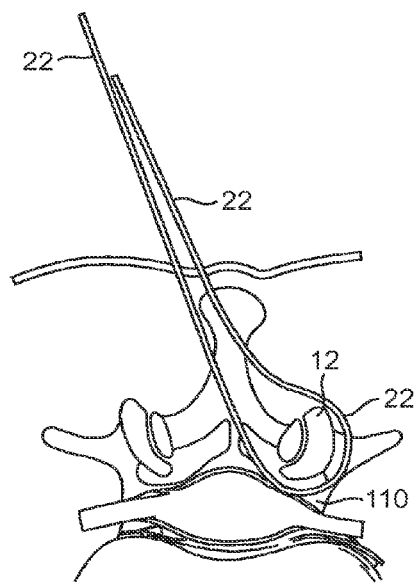

With reference to FIG. 27, an alternative method for obtaining open access is described. As seen in FIG. 27A, curved guide wire 22 may be advanced through lumen 188' of probe 186, such that the guide wire 22 passes through the neural foramen 110, encircles the facet 12 and reemerges in the surgical field. Guide wire 22 optionally may be configured to deliver a stimulation waveform at or near its distal tip for monitoring proximity to the nerve root during passage of the wire through the foramen 110. The needle may, for example, be insulated at regions other than the distal tip. With the wire encircling the facet 12, probe 186 then may be removed, as seen in FIG. 27B, leaving access guide wire 22 in place to provide access for selective removal of impinging tissue.

Access also may be achieved in a percutaneous fashion. For example, access may be achieved via an access element comprising an epidural needle or probe, or via an epidural endoscope having a working channel, that is positioned within the epidural space. In one variation, a curved atraumatic needle or cannula may be advanced through the percutaneous access element and driven laterally to cannulate the neural foramen. A preferably straight, flexible guide wire or needle then may be advanced through the curved needle and driven posteriorly through the skin of the patient's back. In an alternative variation, a curved guide wire may be advanced through the percutaneous access element and passed transforaminally. Percutaneous access optionally may be aided by the use of image guidance, an epidural endoscope or any other visualization technique.

Figure 28:
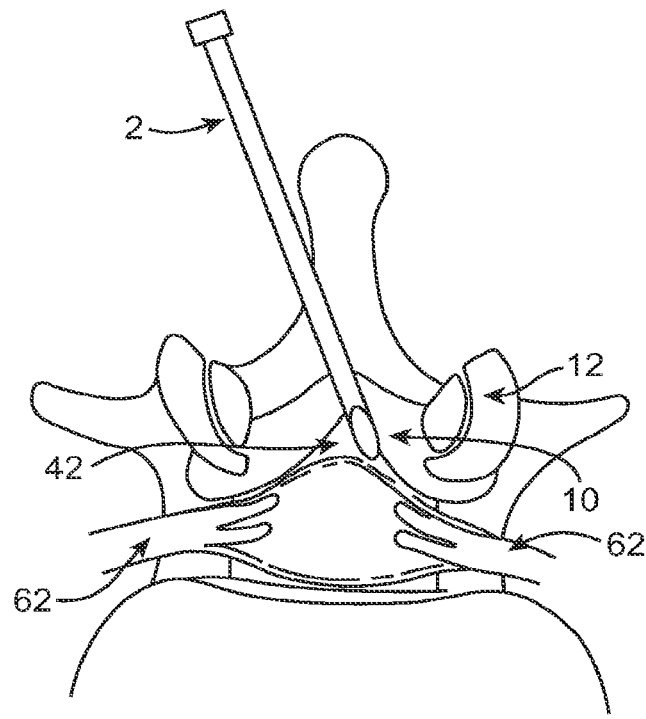
FIGS. 28-35 are cross-sectional views through a patient's spine, illustrating a method and apparatus for selective surgical removal of tissue.

FIG. 28 shows a percutaneous method and apparatus for obtaining access for selective surgical removal of tissue. Access element is disposed within epidural space 42. Access element may comprise, for example, epidural needle 2, an epidural trocar, an epidural endoscope, etc. The needle tip is anterior to the ligamentum flavum 10, but still posterior to the dura 46 in the posterior epidural space 42.

Figure 29:
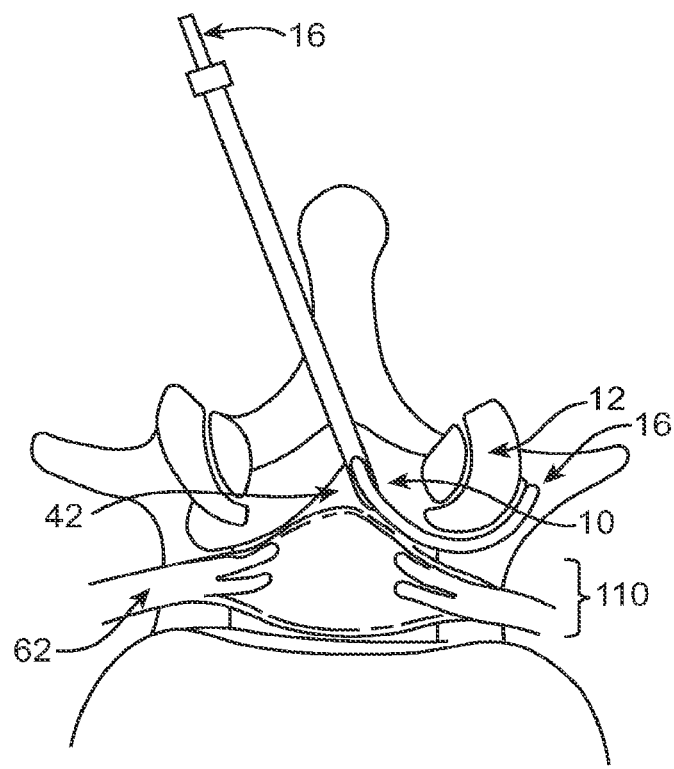

FIG. 29 illustrates a preferred method of cannulating the neural foramina, where an atraumatic curved tube or cannula 16 (e.g., blunt, curved needle composed of memory material) is passed through the straight epidural needle 2 (alternatively, a stiff epidural catheter, or steerable guidewire may be inserted through the needle for this step) to cannulate the neural foramen NF. The curved needle 16 is flexible enough to be passed through the straight epidural needle 2, but is made of a memory material that returns it to its curved configuration upon when it is passed into tissue. The second needle 16 (alternatively, a steerable, stiff catheter or guidewire), is advanced through the epidural space 42, possibly passing through a portion of the ligamentum flavum 10, towards and then through the ipsilateral or contralateral neural foramen 110. The surgeon may use any combination of tactile feel, image guidance, direct visualization, and/or fiberoptic visualization to ensure that the curved element 16 is driven through the neural foramen, anterior to the facet (zygapophysial) joint complex 12, but posterior to the nerve root 62 or ganglion. As discussed previously, the cannulas may be configured to stimulate and monitor response of the nerve root as a safety precaution during cannulation of the foramen.

Figure 30:
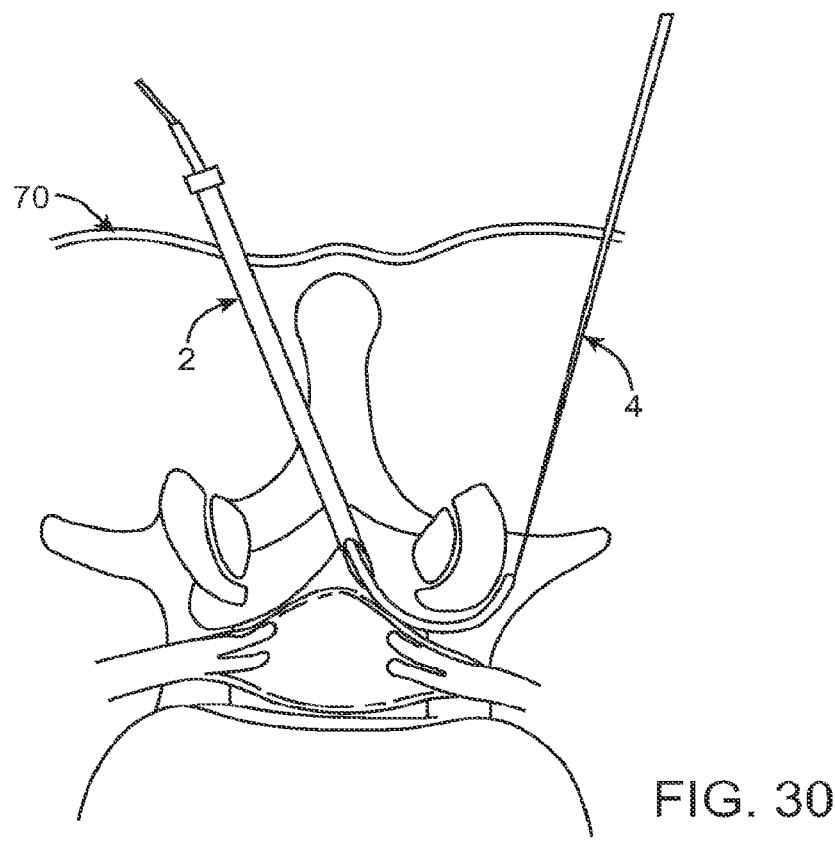

Once the curved element is in position through the neural foramen, the surgeon subsequently passes a smaller gauge straight and sharp flexible guidewire 4 (or needle), as in FIG. 30 through the lumen of the larger curved needle that is in position through the neural foramen 110, until it exits into the tissue lateral to the neural foramen (FIG. 30). This straight wire 4 or straight needle exits the curved element with its tip facing in a posterior or posterior-lateral direction. It is advanced further in this direction, passing to, and then through the skin of the patient's back 70, as in FIG. 30. Access element 2 and cannula 16 then may be removed, as in FIG. 31, leaving access guide wire 4 in place transforaminally to provide access to the lateral recess and neural foramen.

As an alternative to deploying cannula 16 through access element 2, the cannula 16 may be delivered over the access element. As yet another alternative, upon placement of the access element in the epidural space, a stiff rod may be advanced through the lumen of the access element, and the access element may be removed. Cannula 16 then may be deployed over the stiff rod, which then may be removed from the lumen of the cannula and replaced with guide wire 4.

Figure 36:
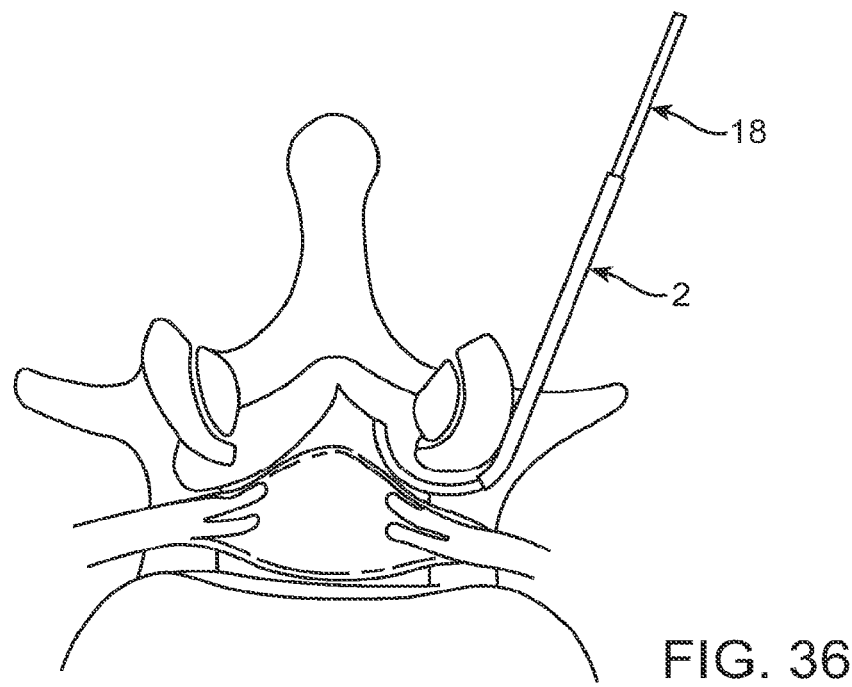
FIGS. 36-39 are cross-sectional views through a patient's spine, illustrating a variation of the method and apparatus of FIGS. 28-35.
Figure 37:
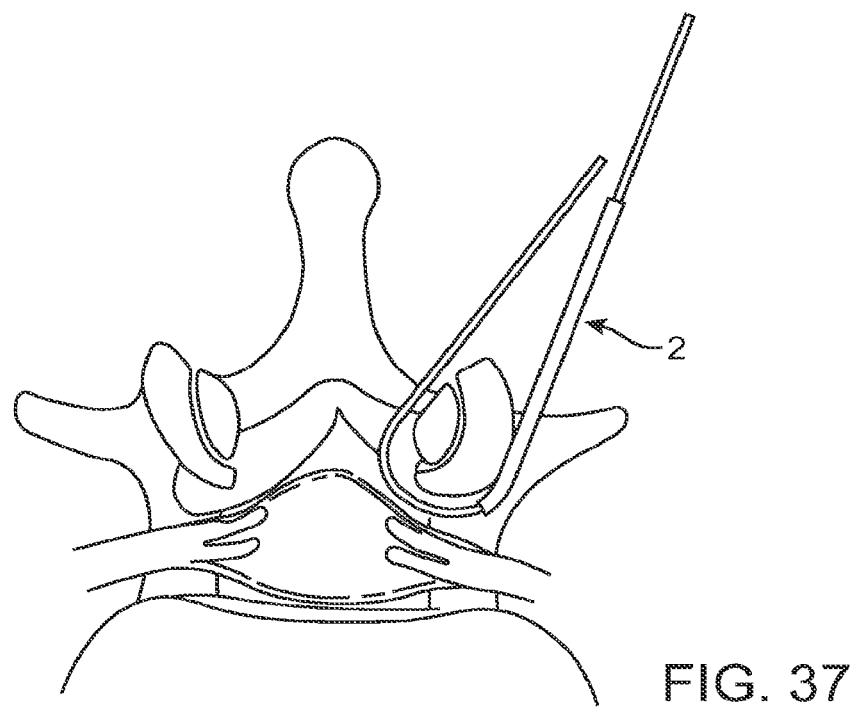
Figure 38:
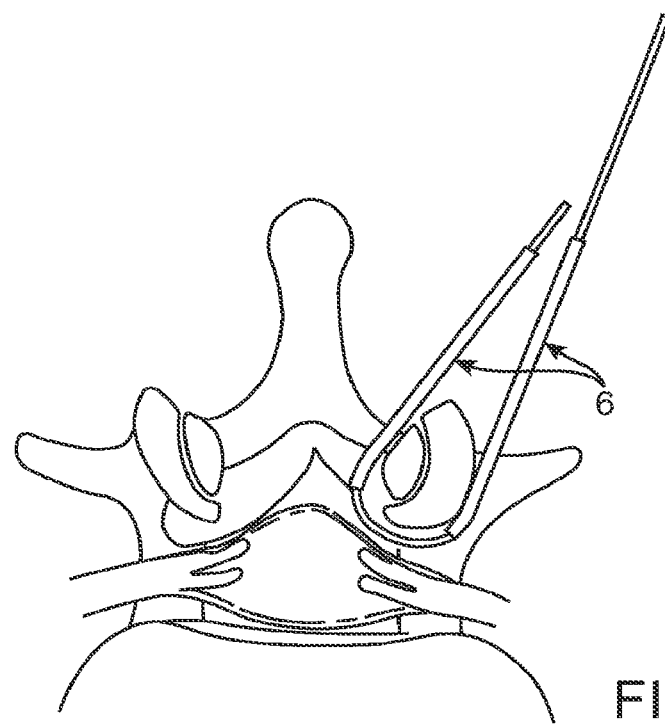
Figure 39:
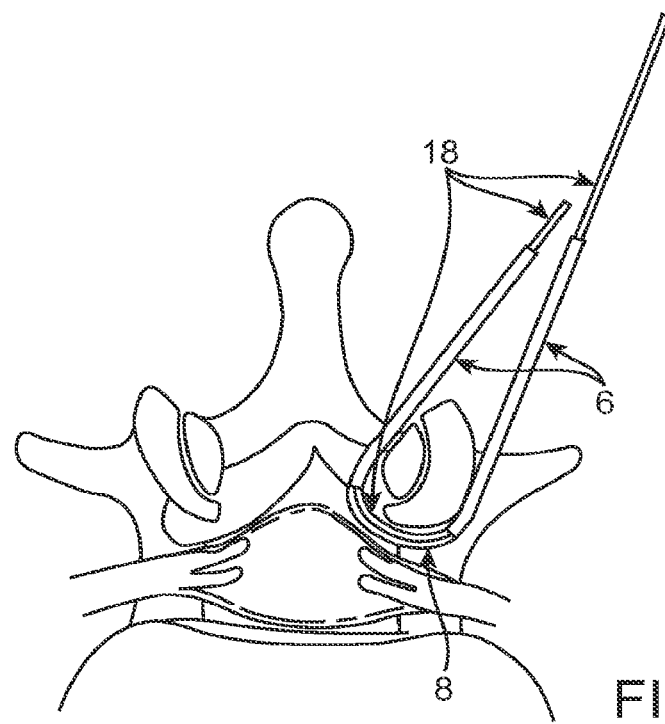

As seen in FIG. 36, a steerable needle or wire 18 is placed through the neural foramina 110 from the lateral towards the medial side of the foramen 110. This lateral to medial neuroforaminal approach may begin with a curved, blunt wire through a straight needle (as described in the previous technique), or using a curved needle technique, a steerable guidewire technique, a needle-through-a-needle technique, or common variations thereof. While a loss of resistance technique is not as helpful with this transforaminal approach to the epidural space 42, as it was in the previously described posterior approach to the epidural space 42, the method is, in many other aspects, otherwise similar to the method illustrated in FIGS. 28-35.

Studies and tests may be performed to ensure that the transforaminally placed apparatus has been properly positioned between the nerve root 62 or ganglia and the facet joint complex 12. For example, imaging of the abrasion element and spinal anatomy (fluoroscopic or other imaging modalities); monitored neural stimulation through the apparatus; or direct (endoscopic or open) visualization may be utilized.

Figure 31:
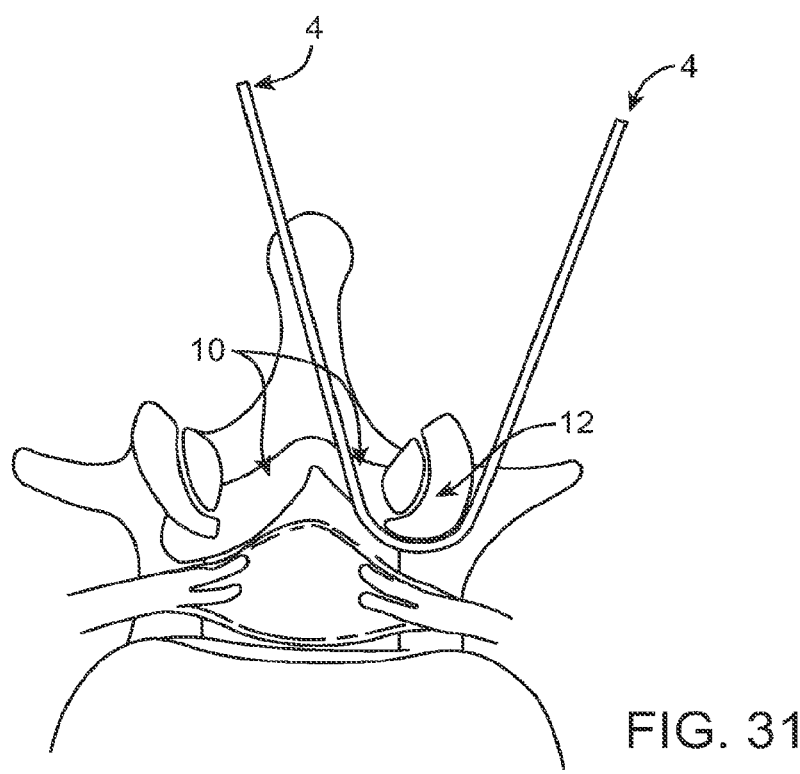

After proper placement has been confirmed, the curved element 16 that was used to initially cannulate the neural foramen is removed, by pulling it back out of the hub of the epidural needle 2, leaving the transforaminal wire 4 in place, as illustrated in FIG. 31. Next the epidural needle 2 may also be removed, if desired, again leaving the wire 4 in its position, through the neural foramen. As shown, both ends of the element 4 remain external to the patient, having exited the skin (percutaneous procedure) or exited the tissue through the surgical wound (open procedure).

Figure 32:
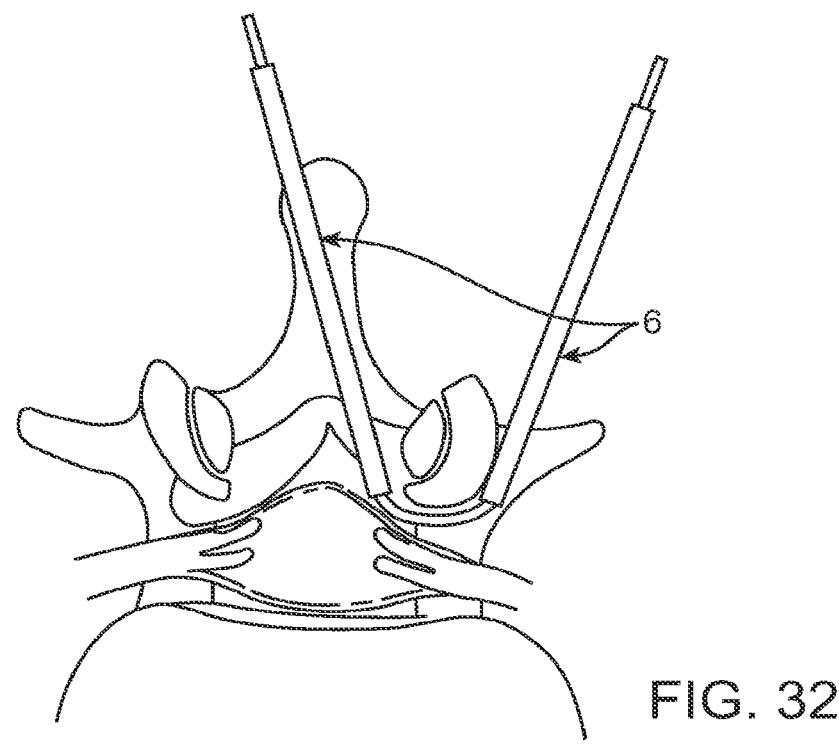
Figure 33:
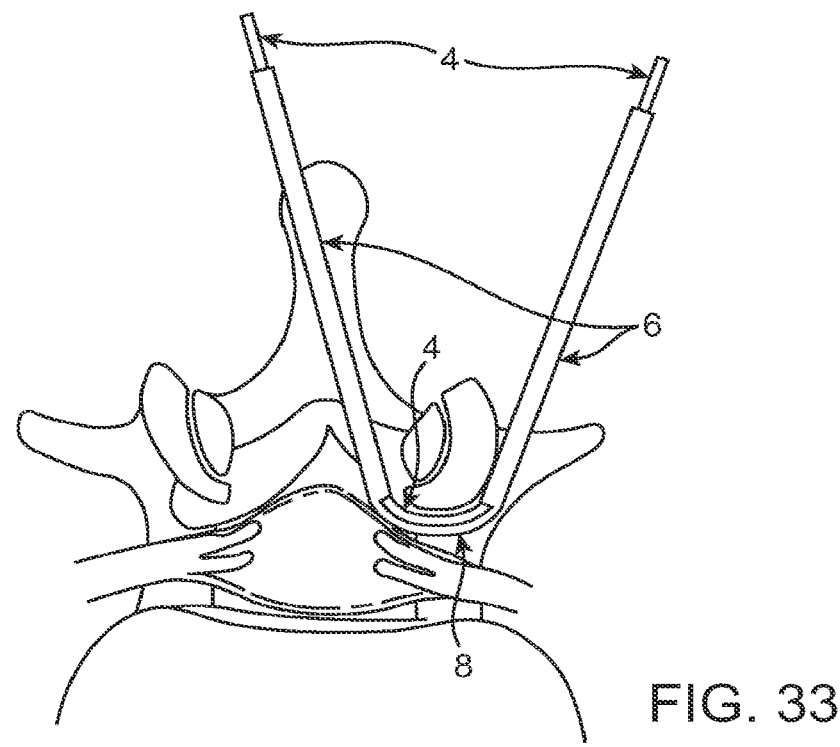
Figure 34:
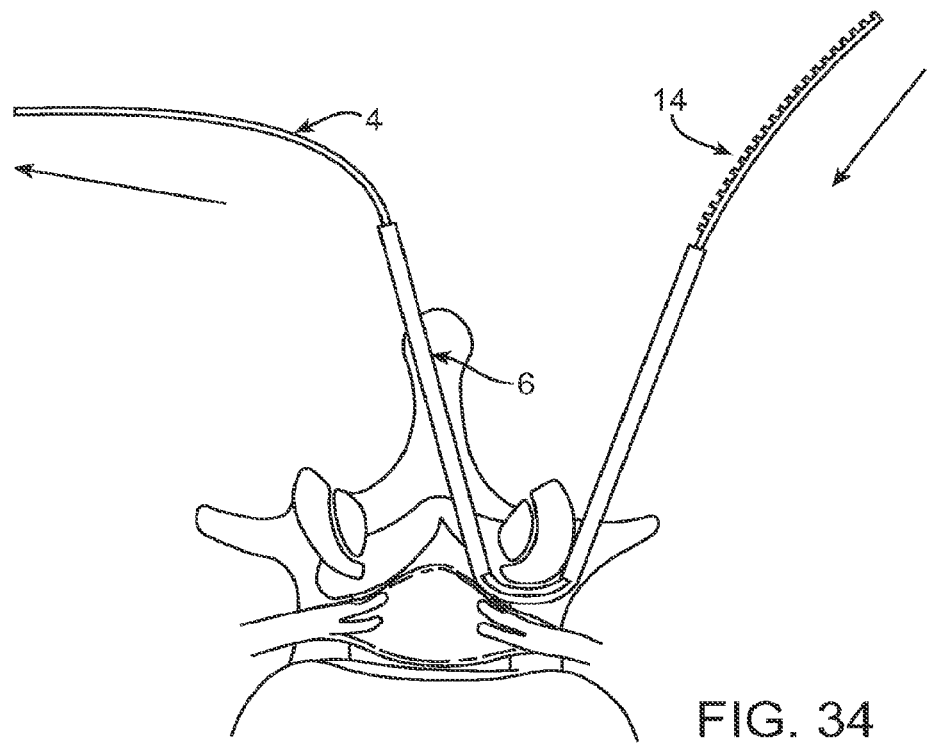
Figure 35:
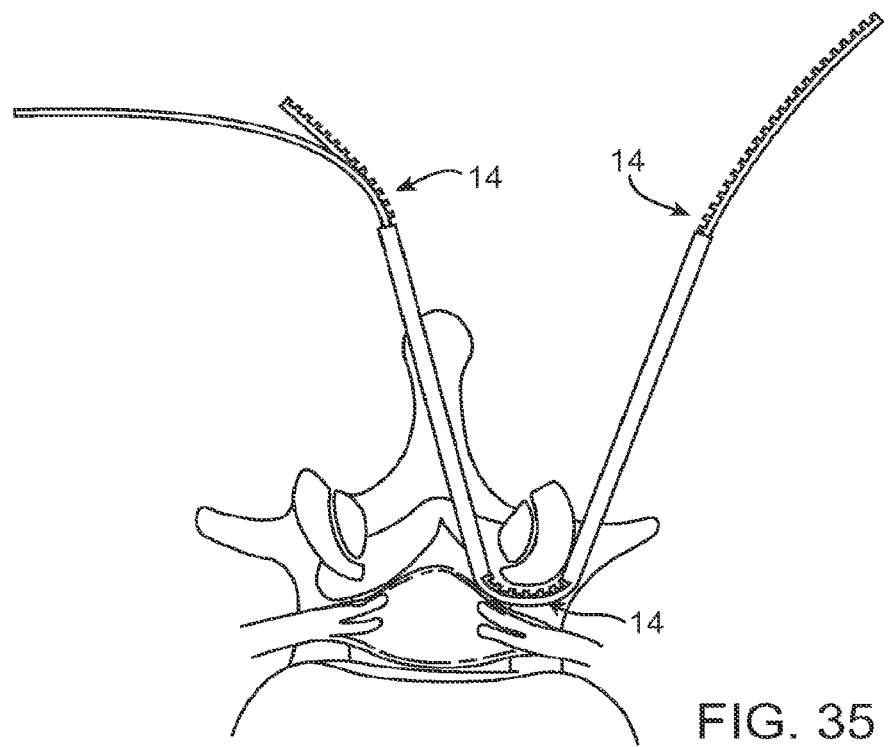

With the wire in position through the neural foramina, there are multiple possible methods for replacing the wire with the abrasion apparatus. One method is illustrated in FIGS. 45-48, where the wire 4 is used to pull into position the abrasion element 14; the abrasion element sleeve or cover 6; or the abrasion element 14 and cover 6 together, as is described in greater detail below. Alternatively, as shown in FIGS. 32 and 33, separate protective sleeves or covers 36 may be passed over both the proximal and distal ends of the transforaminal wire 4. Each sleeve or cover may be advanced to the neural foramen. Next, the neuroforaminally placed wire 4 is connected distally, or proximally, to the abrasive element 14, with an abrasive surface on one side. The abrasive element 14, connected by one end to the transforaminal wire 4, is pulled through the neural foramen, and through the protective sheaths or covers 6, as in FIGS. 34 and 35, until the abrasion element has completely replaced the initially placed wire 4 (or needle). Passage of a tissue dilator over the transforaminal wire 4 or needle, may be helpful, either before or after placement of the sleeve. Protective sleeve(s) 6 illustratively are disposed over both ends of the transforaminal wire 4, in order to protect non-surgical tissues from the abrasive or cutting portion of the device, when it is pulled into place. Alternatively, a protective sleeve, which may be expandable, as illustrated in FIG. 85, may be attached to the end of the wire and pulled through the neural foramina, thereby replacing the initial tranforaminally placed element 4.

Figure 46:
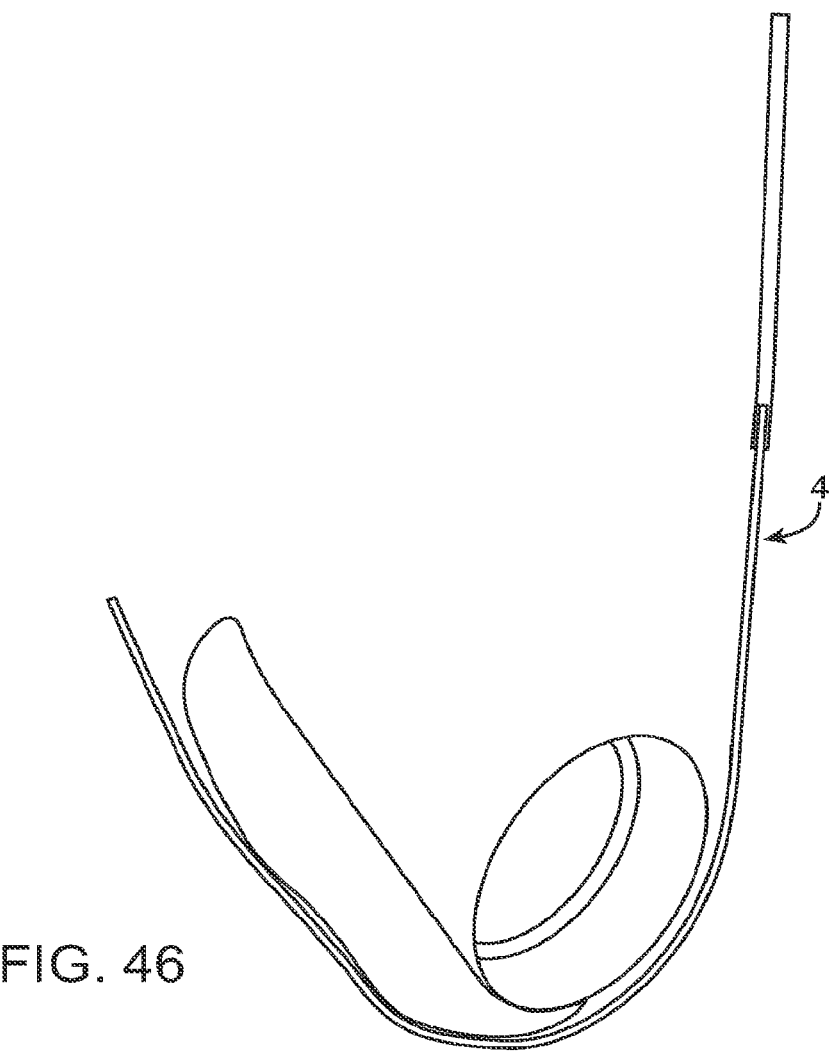
Figure 47:
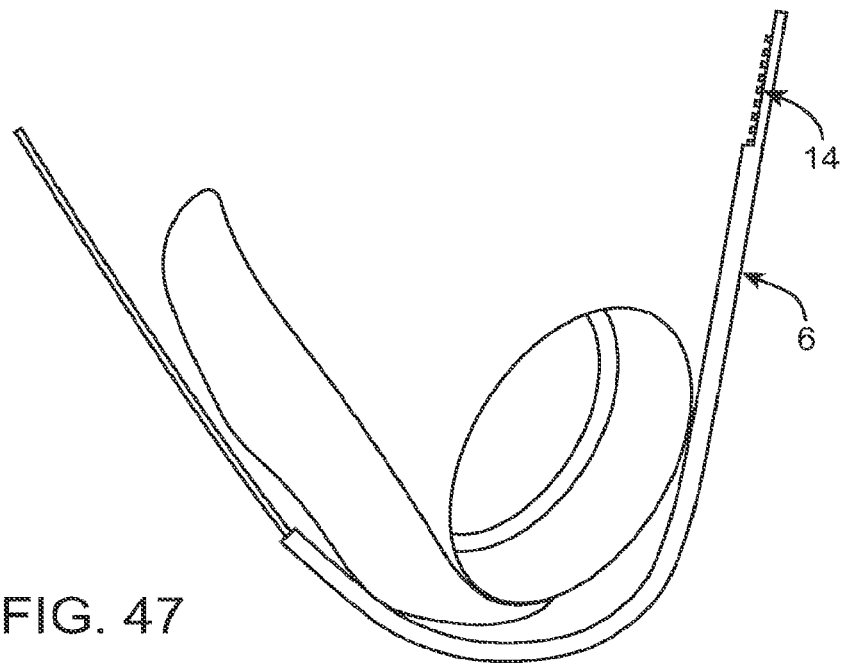
Figure 48:
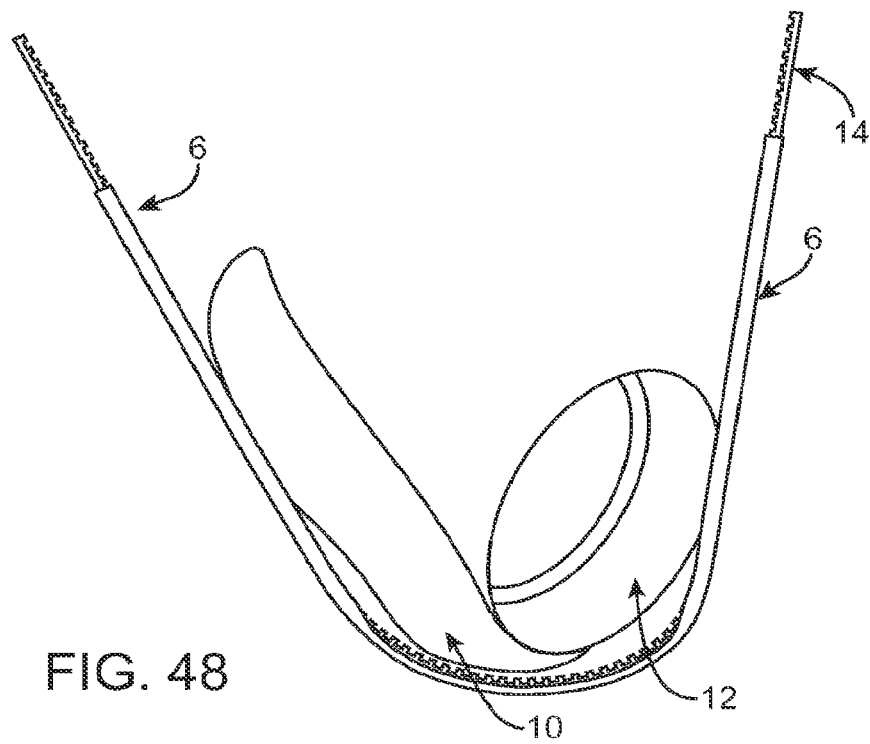

In an alternative preferred embodiment, the abrasive element 14 is positioned within the protective sleeve cover 6, before or after placement of the abrasive element in position through the neural foramina. Please note that the terms "protective sleeve" and "protective cover" are used interchangeably in these descriptions of several examples of the apparatus and methods for protecting vulnerable tissue from the abrasion apparatus. Embodiments of the protective methods and apparatus are illustrated in FIGS. 85-88. With the abrasive element 14 already inside the protective apparatus 94/96, with or without an opening over the abrasive surface where tissue abrasion is to be performed, the protective covering 96, with the abrasive apparatus 14 already inserted within it, may be connected to one end of the needle or guidewire 4 that remains in place through the neural foramen 110. In this preferred method, the combined protective sleeve 6 and the abrasive element 14 are then pulled simultaneously through the neural foramen, by pulling from the opposite end of the preliminarily placed neuroforaminal element 4, while it is removed (FIGS. 46, 47, 48).

Once the abrasion apparatus has been properly positioned through the neural foramina 110, with its protective cover in place 6, it is ready to be tested to ensure it has been properly located. The apparatus may subsequently be utilized for tissue abrasion, tissue removal, and tissue remodeling, as will be described in detail below. Before describing tissue modification in further detail, however, we will describe alternative approaches for placement of the abrasion device into position through the neural foramina. Referring now to FIGS. 36-39, a variation of the method and apparatus of FIGS. 28-35 is described comprising an alternative approach for placement of the tissue modification device, wherein the apparatus 14 is placed from the lateral side of the neural foramen 110. As seen in FIG. 36, steerable cannula 18 is advanced through access element 2 to cannulate the foramen from the lateral towards the medial side of the foramen. (Alternatively, straight guide wire 4 may be advanced through a curved cannula 16 and driven posteriorly out the patient's back along the medial aspect of the facet, similar to above described methods for passing a guidewire through the neural foramina from it's medial side).

Neural protection element 6 illustratively comprises a sheath having opening or window that is placed across the foramen at the position of desired selective tissue removal. The end regions of neural protection element 6 disposed outside the patient optionally may be attached or clipped together to stabilize the element and free up the medical practitioner's hands.

Figures 59, 60:
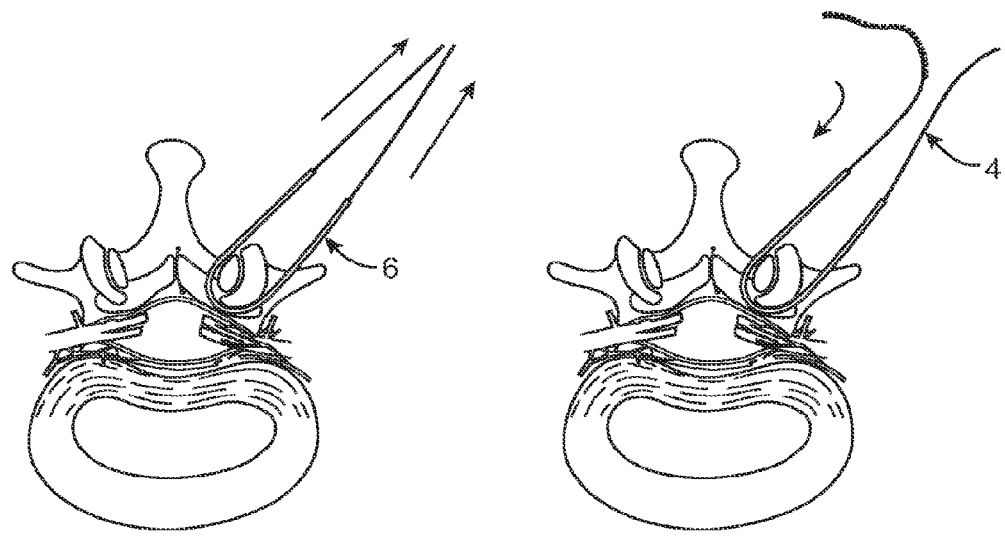
Figures 61, 62:
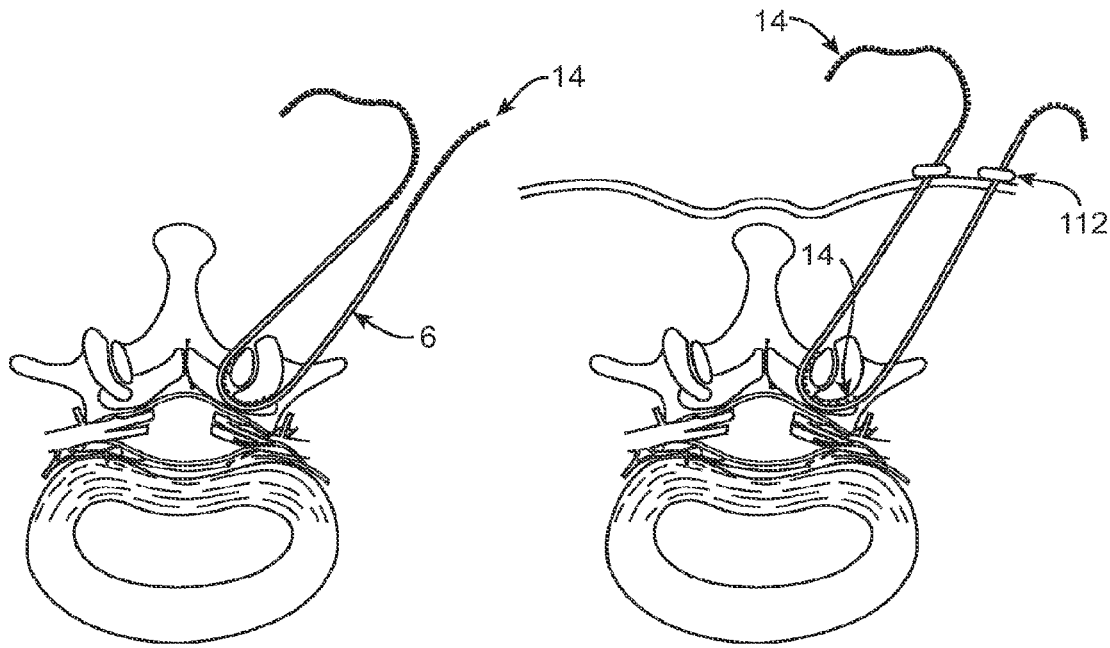
FIG. 62 is a cross-sectional view through a patient's spine, illustrating a methods and apparatus that, under tension, anchors and suspends the working sheath or protective sleeve that covers the neuroforaminal abrasion device.

As illustrated in FIGS. 57-63, a tissue removal device may be positioned between impinging tissue and the neural protection element for safe, selective removal of the impinging tissue. For example, tissue removal device 14 may be delivered through, along or in conjunction with neural protection element 6 to position the tissue removal device across the foramen between the impinging tissue and the neural protection element with tissue removal surface of device locally exposed to the impinging tissue within window of neural protection element 6. In FIG. 60, tissue removal device 14 is coupled to access guide wire 4. In FIG. 61, the tissue removal device is pulled into position by partially or completely removing the guide wire. Tissue removal device 14 alternatively may be positioned across the neural foramen in conjunction with, or at the same time as, neural protection element 6, which optionally may be coupled to guide wire 4 and pulled into position. Furthermore, neural protection element 6 and tissue removal device 14 may be integrated into a single device. As yet another alternative, tissue removal device may be advanced over guide wire 4.

Figure 63:
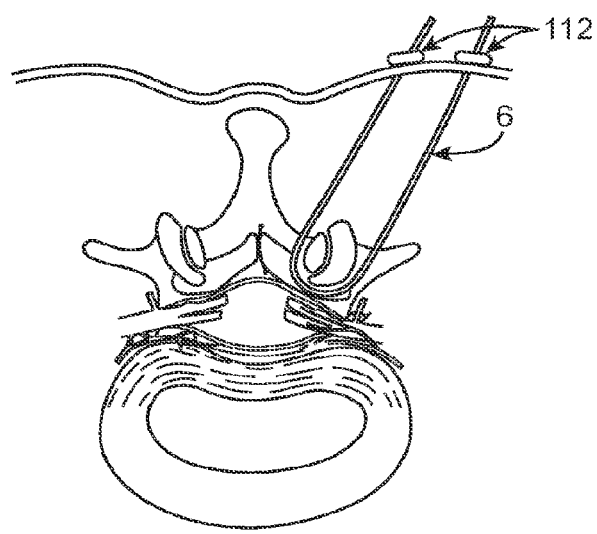
FIG. 63 is a cross-sectional view through a patient's spine, illustrating a method and apparatus that, under tension, provides a percutaneous compression dressing over the abraded area. In this illustration, the compression dressing is the same working sheath or protective sleeve that had covered the neuroforaminal abrasion device.
Figure 66:
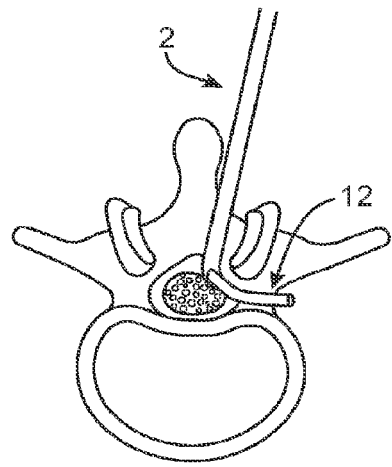
FIGS. 66-73 are schematic cross-sectional views through a patient's spine of a method and apparatus for a posterior midline or paramedian approach to placement of a posterior elements compression, retraction or retention device around the facet complex, through the neural foramina.
Figure 67:
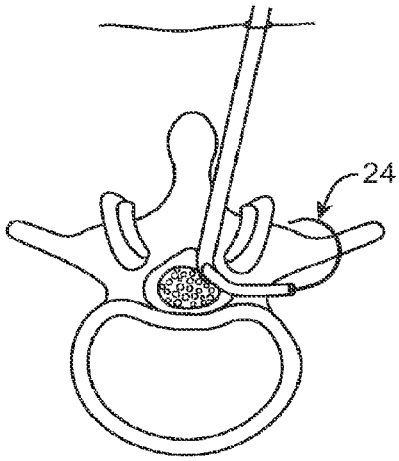
Figure 68:
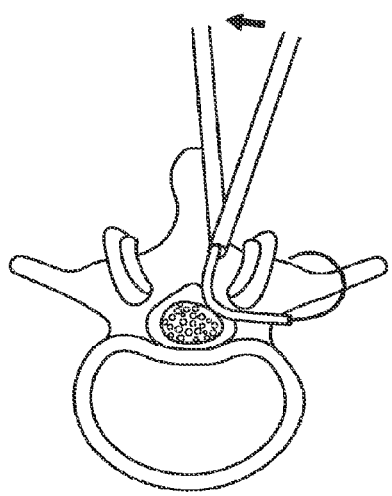
Figure 69:
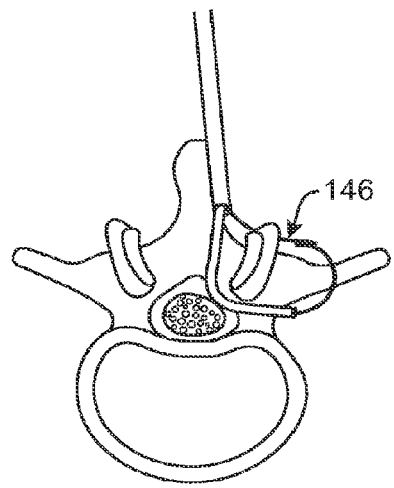
Figure 70:
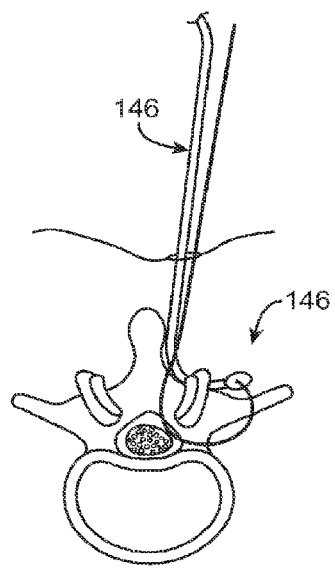
Figure 71:
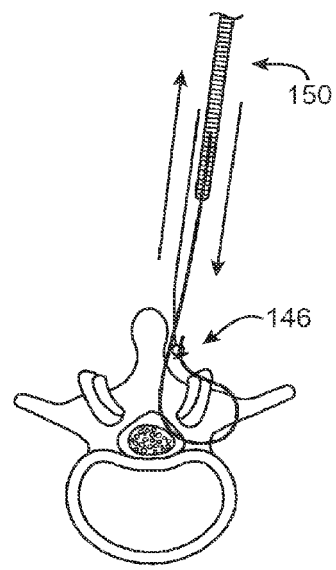
Figure 72:
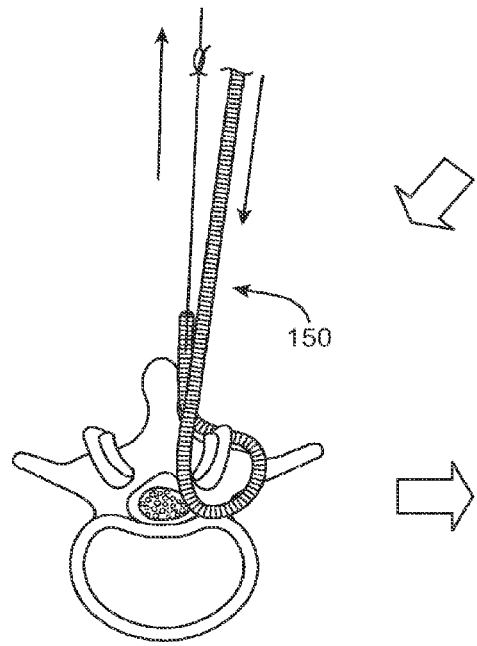

In FIGS. 62 and 63, temporary stops 112 have been attached to neural protection element 6 to maintain the position of the element and free up the medical practitioner's hands, for example, for manipulation of tissue removal device 14. The stops may hold window of sheath 6 of element 14 under tension against the impinging tissue. Stops 112 may be placed or expanded, or removed or collapsed, etc., at any time as desired; for example, the stops may be placed prior to positioning of tissue removal device 14 transforaminally. Stops 112 may comprise any element that temporarily maintains the position of the access element/guide wire, the neural protection element and/or the tissue removal device during a selective tissue removal procedure. As mentioned previously, the end regions of neural protection element 6 alternatively or additionally may be attached or clipped to one another to stabilize the element and free up the medical practitioner's hands.

As an added safety precaution, variations of the present invention optionally may comprise neural localization elements to ensure proper positioning of the access element or guide wire, the neural protection element, and/or the tissue removal device. The neural localization elements may comprise separate elements or may be integrated with the access element, the neural protection element and/or the tissue removal device.

As seen FIG. 64, neural protection element illustratively comprises neural localization element disposed on the backside of the sheath facing nerve root 62. Element comprises a conductive element that is electrically coupled to electrical generator 114 via wires 120. Element illustratively is connected in a monopolar fashion whereby element 120 acts as an active electrode, while ground electrode 116, which is coupled to generator 114 via wire, is attached to the exterior of the patient. However, it should be understood that a bipolar neural localization element alternatively may be provided. Furthermore, neural localization element(s) alternatively or additionally may be disposed on the working side of the neural protection element, or on any other side of the neural protection element or of the tissue removal device.

Neural localization element may be used to ensure that neural structures and adjacent vascular structures are on the non-working or backside of neural protection element 6. Neural localization element on the backside of the sheath (i.e., the side of the sheath that contacts the nerve root when properly positioned) may be activated with a stimulation waveform to stimulate the nerve root, thereby providing a positive control that confirms placement of the backside in proximity to the nerve root. Appropriate low intensity electrical stimulation on the backside surface should result in the stimulation of sensory or motor nerves in the patient's extremity. Likewise, optional neural localization elements on the working side of the sheath (i.e., the side of the sheath that faces impinging tissue slated for removal) may be activated with a stimulation waveform in anticipation of a negative response or no neural stimulation that confirms that the working side is not in contact with the nerve root and that tissue removal may safely proceed. Neural localization elements also may be provided on sides of the sheath 6.

Neural stimulation may be monitored by monitoring somatosensory-evoked potentials (SSEPs), motor-evoked potentials (MEPs), and/or by looking for visual signs of muscular contraction within the extremities. SSEP, SEP, MEP or EMG feedback may be monitored and/or recorded visually, or may be monitored audibly, potentially conveying quantitative feedback related to the volume or frequency of the auditory signal (e.g. a Geiger counter-type of quantitative auditory feedback). Intensity of signal or stimulation may be monitored and used to localize the nerve during placement of neural protection element, as well.

Neural localization may be enabled further by the addition of surgical instruments (e.g. cautery devices, graspers, shavers, burrs, probes, etc.) that are able to selectively stimulate electrically while monitoring nerve stimulation in similar fashions. Quantification of stimulation may enable neural localization. For instance, one might use a calibrated sensor input that recognizes stronger stimulation as the device is moved closer to neural structures. For added safety, tissue removal device 114 may be designed to automatically stimulate before or during tissue removal, and may even be designed to automatically stop tissue removal when nerve stimulation has been sensed.

Figure 40C:
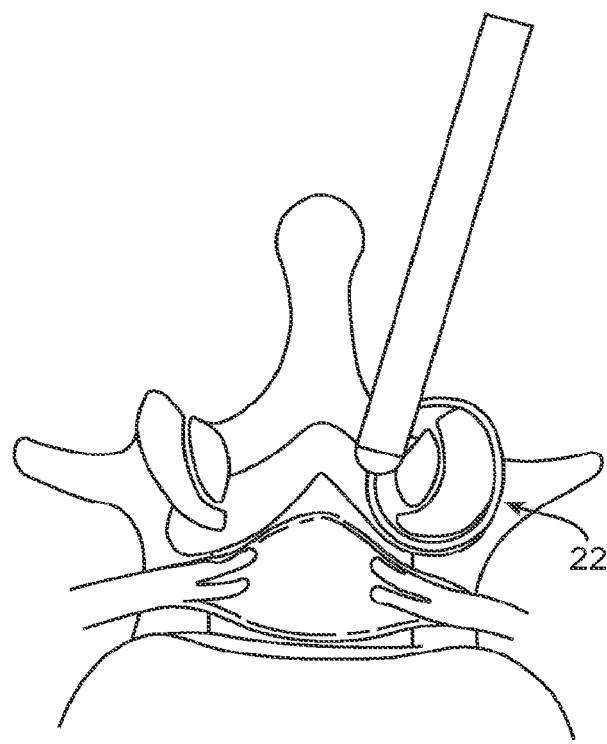

With reference to FIGS. 40a-40e, another variation of the method and apparatus of FIGS. 28-35 is described. In FIG. 40a, the apparatus 20 is placed from an interlaminar; a translaminar, interspinous; or a transforaminal insertion, illustratively via a paramedian, ipsilateral (i.e., medial to lateral) approach. The apparatus can be an epidural probe, which may, for example, comprise an epidural endoscope having a working channel. The apparatus can be advanced in proximity to the medial aspect of the neural foramen. A lateral to medial transforaminal approach with the same type of apparatus may alternatively be used. The blunt or rounded distal tip of apparatus 20 optionally may be somewhat sharper, to facilitate placement. The apparatus 20 may be preceded by a guidewire, a dilator, or a needle introducer (possibly with or followed by an expandable sheath).

Figure 40D:
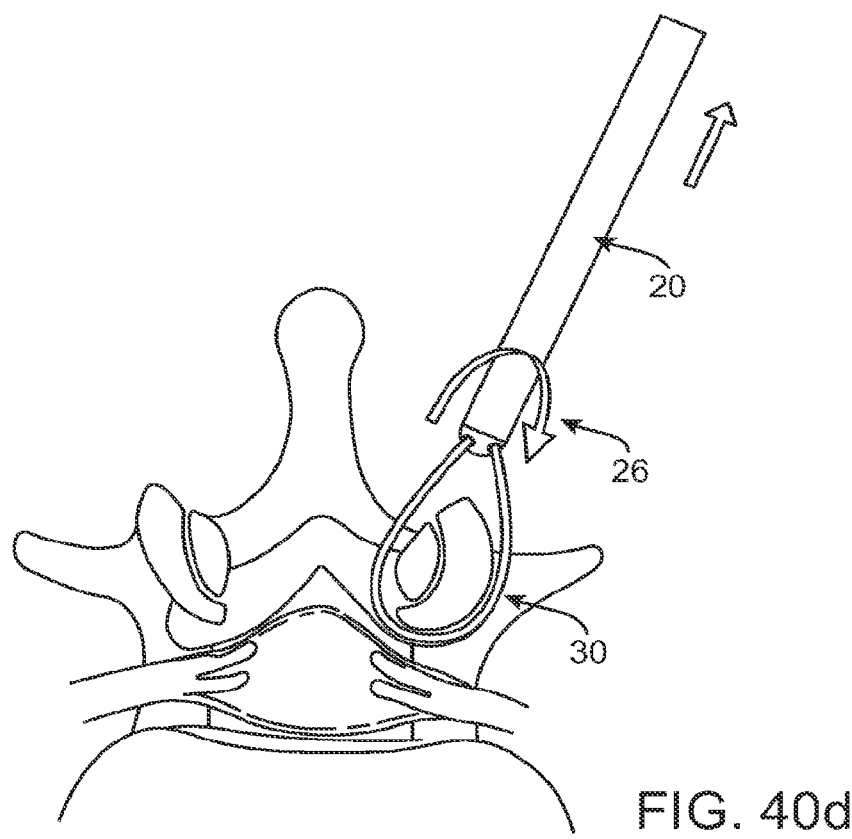

This variation of the apparatus and method, as seen in FIG. 40b, contains a rigid, curved wire or needle 22, which may be steerable, which is driven from the tip of the apparatus 20, laterally through the neural foramen and then posteriorly, around the facet joint complex 12 and back towards apparatus 20, where the needle may be received once again by the apparatus. Curved guide wire 22 can be advanced through the probe such that it passes transforaminally and reengages probe 20 after completely encircling facet 12. As discussed previously, guide wire 22 may be configured to stimulate and monitor the response of the nerve root during transforaminal passage to ensure proper positioning of the wire. As seen in FIG. 40d, probe 200 then is withdrawn from the patient, leaving guide wire 22 in position transforaminally to provide access.

Figure 41:
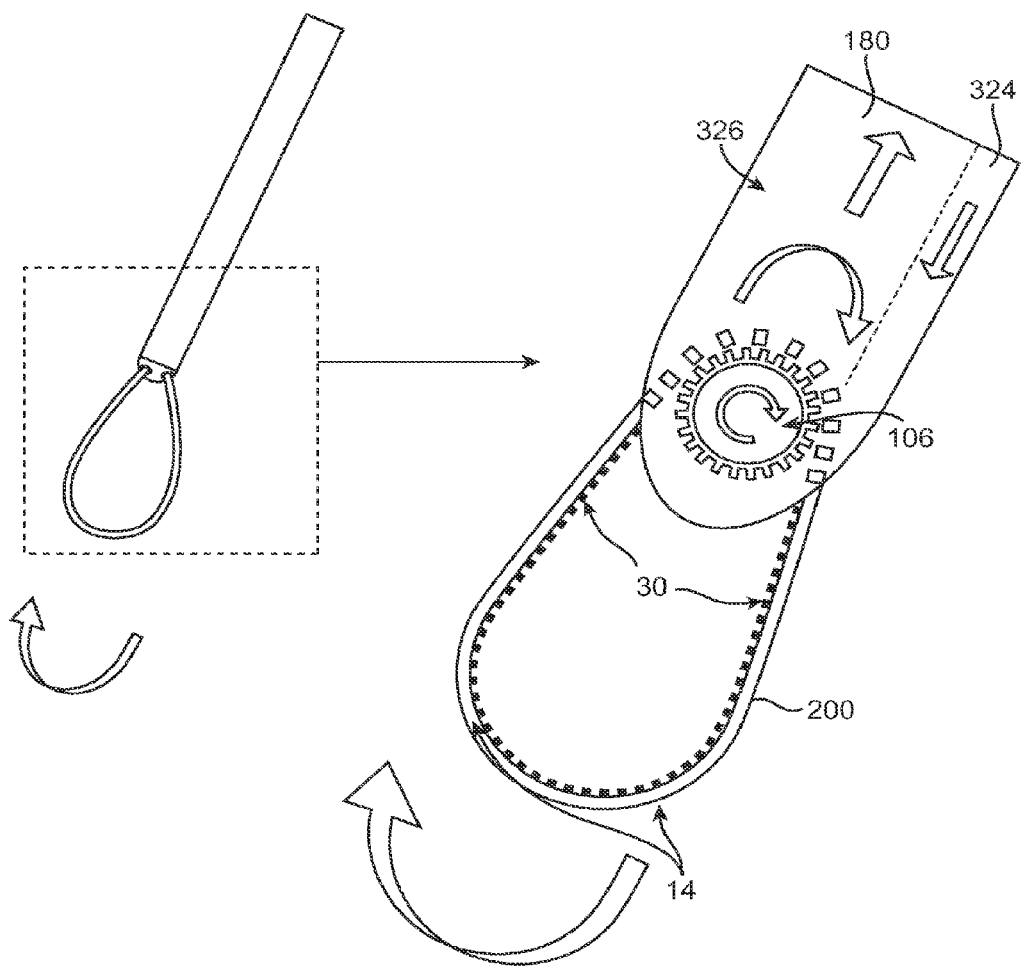
FIG. 41 are a detailed view and a close up of the cross section of the apparatus used in FIG. 40*d*.
Figure 42:
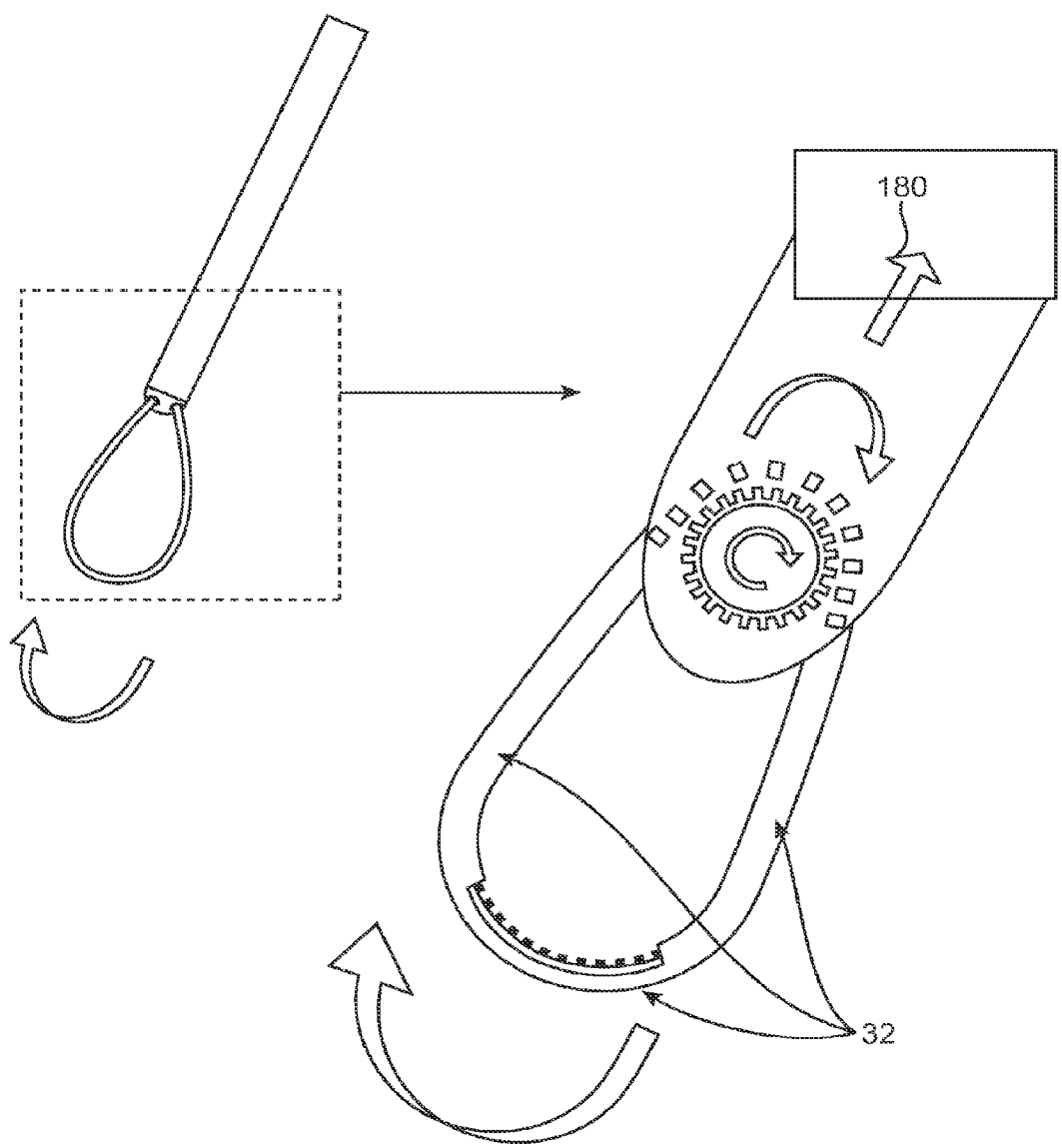
FIG. 42 is an alternative embodiment of the apparatus of FIG. 41.

FIG. 41 provides a cross section through apparatus 20 that illustrates an exemplary geometry for the apparatus comprising a feature that facilitates receiving of the distal end of the needle or rigid guidewire back within the apparatus. Alternative geometries will be apparent. Once received back within apparatus 20, the wire 22 completely encircles the facet joint 12, as in FIG. 40c, d. In FIGS. 41, and 42, guidewire 22 has been replaced by tissue abrasion device 30, e.g., a belt, strap or ribbon, preferably within a protective sheath or cover 32, with the abrasive surface of the device in contact with the anterior-medial facet complex. Apparatus 20 is pulled back, bringing the working surface (exposed abrasive portion) of the instrument into firm contact with operator controlled pressure against the surface from which tissue removal will occur. Neuroforaminal enlargement begins with the movement of the abrasive surface 30 against the anterior and medial portion of the facet complex, in the lateral recess and neural foramen.

With reference to FIG. 41, an enlarged view of the mechanical portion of apparatus 20 is described. An abrasive surface 30 is disposed along the inside side of tissue abrasion element. The abrasion device may be actuated, e.g., via rotation of a gear 106 within the apparatus 20. Debris may be captured within apparatus 20, and stored in the shaft and/or handle, or removed continuously during the procedure. In some variations, tissue removal surface 30 of device 20 comprises one or more powered mechanical tissue removal elements. The powered mechanical tissue removal elements may comprise, for example, band saws, belt shavers, rotary burrs or blades, reciprocating burrs or blades, etc. FIG. 41 illustrates a rotary variation of the tissue removal device that may be powered or operated manually, and that may remove tissue in a single direction, or in a reciprocating fashion. In FIG. 41, tissue removal device 20 comprises a belt coupled to drive wheel 106. The drive wheel may be rotated by hand or via a motor in either direction to advance or retract device 20 relative to neural protection element 32 and window in order to selectively remove tissue.

Irrigation optionally may be provided through element 20 via irrigation lumen 324 of member 20. Suction optionally may be provided through element 20 via suction lumen 326 of member 20. Suction and/or irrigation may be provided intermittently or continuously, as desired by the medical practitioner.

Referring now to FIG. 42, a variation of the apparatus of FIG. 41 is described comprising an additional protective cover 32 that covers one or more sides of the abrasive elements 14 of the device 20 in all regions except for the area covering the tissue where abrasion is to take place. This cover may contain a conductive element in order to enable nerve stimulation and/or to facilitate neural localization. Nerve stimulation capabilities may be present on the internal abrasive surface 30 of device abrasive element, and/or on the external side (non-tissue abrading) of the device, as an added safety measure. For example, the user may send an electric impulse through a conductive element within the back-side (external surface) of the device, expecting to achieve neural stimulation when the device is in place through the neural foramina, while neural stimulation should not be achievable with a similar electrical impulse conducted across a portion of the abrasive side of the device. In this manner, information from monitoring the nerve stimulation may ensure proper placement of the abrasion device and reduce a risk of inadvertent neural or perineural vascular abrasion.

Figure 43:
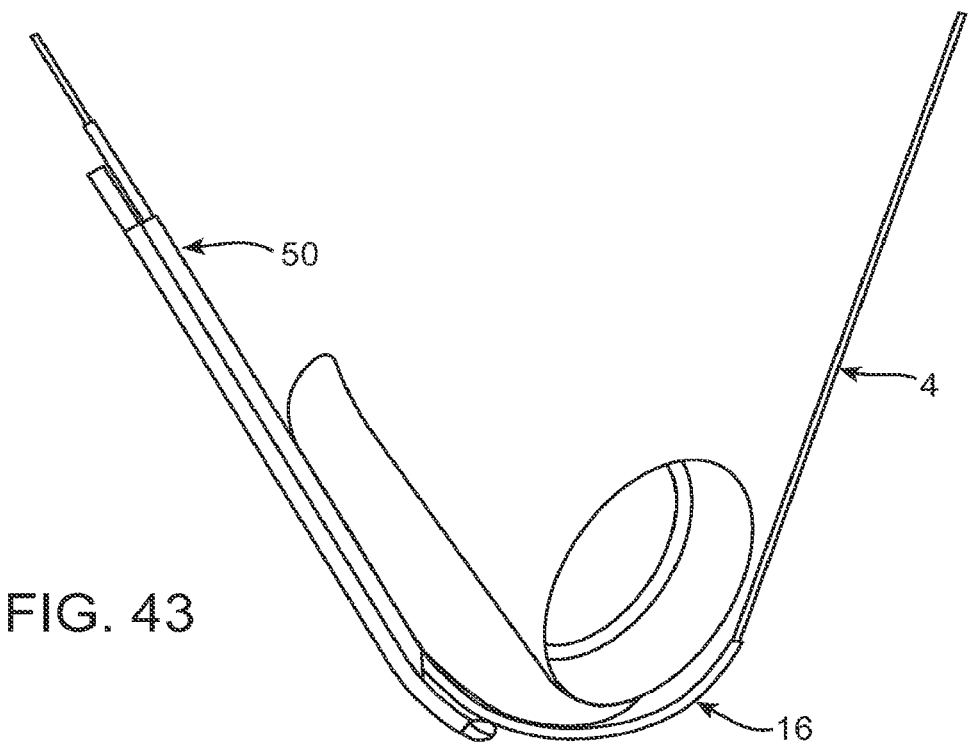
FIGS. 43-48 are partial cross-sectional views through a patient's spine, illustrating a double barrel system used with additional methods and apparatus for placement of an abrasion apparatus through the neural foramina for selective surgical removal of tissue.
Figure 44:
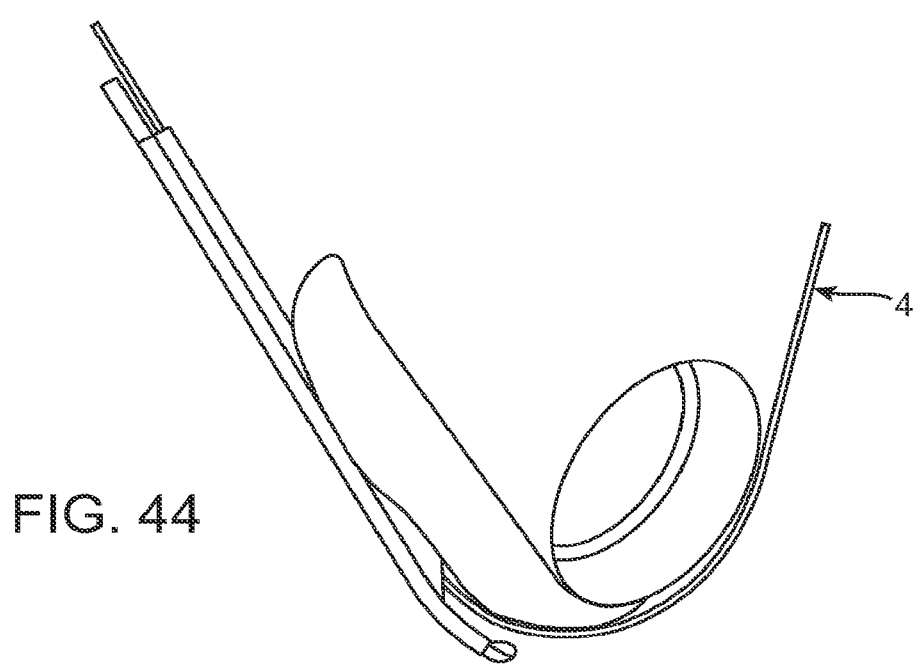
Figure 45:
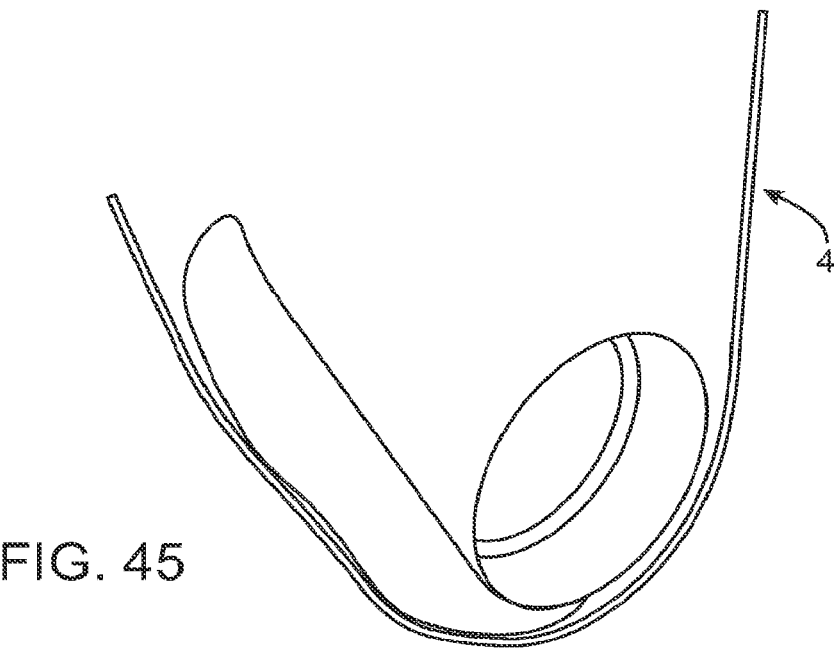

In FIG. 43, straight wire or needle 4 is driven through curved needle 16 disposed in working channel 50 of double barrel epidural needle. This straight wire or needle 4 is advanced until it has penetrated through the skin and out of the patient's body. The straight wire preferably has a sharp tip. In FIG. 44, curved needle 16 is withdrawn from working channel 50, leaving straight wire or needle 4 in place. Then, as seen in FIG. 45, the epidural needle and working channel may be withdrawn from the patient, or, in an alternative embodiment (FIG. 15b), when using a detachable working channel 50, the working channel alone may be withdrawn from the patient, leaving straight wire 4 in place. In FIG. 46, straight wire 4 is hooked to abrasion device 14 and/or the abrasion device's protective sleeve 6. In FIG. 47, the abrasion device 14 and/or the device's protective sleeve are pulled into position by wire 4 as the wire is removed. In FIG. 48, wire 4 has been completely removed, and the abrasion device 14 and its protective sleeve 6 are properly positioned for tissue resection, anterior to the facet 12 and ligamentum flavum 10.

In an open surgical variation, the abrasive element 14 and its cover 6 may be placed through the surgical incision, from a interlaminar, translaminar, or neuroforaminal approach. Visualization and placement may be aided via partial or complete laminectomy, facetectomy, or ligamentectomy. Methods for threading the neural foramina include, but are not limited to the use of a wire, blunt needle, probe, endoscope, or suture. After spinal neuroforaminal placement, the abrasion device 14 is used to selectively remove tissues that impinge on the neurovascular structures within the lateral recess 108 and neural foramen 110, on the anterior side of the facet joint 12. In an open approach, as with a percutaneous approach, the device may be inserted through a needle, optionally under image guidance or with the aid of an epidural endoscope. Once placed through the neural foramina 110 of the spine, around the anterior border of the facet joint 12, and anterior to the ligamentum flavum 10, the medical practitioner may enlarge the lateral recess and neural foramina via frictional abrasion, i.e., by sliding the abrasive surface across the tissue to be resected (e.g., far lateral ligamentum flavum, anterior and medial facet, osteophytes). The abrasion device alternatively or additionally may be placed through the neural foramen 110 anterior to the facet joint 12, but through or posterior to the ligamentum flavum 10. The medical practitioner controls the force and speed of the abrasive surface against the tissue to be removed, while optional protective covers, tubes or sleeves 6 help limit the area exposed to the abrasive element for treatment.

Figure 49:
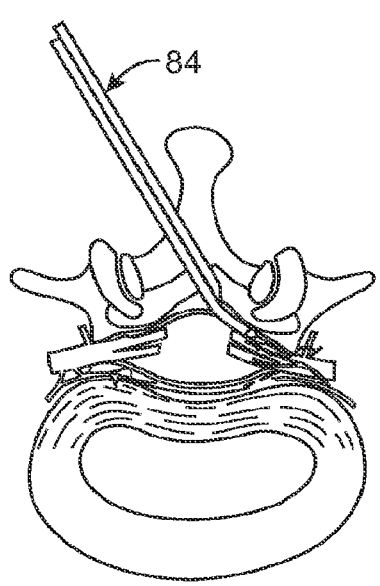
FIGS. 49-61 are cross-sectional views through a patient's spine, illustrating a variation of the methods and apparatus of FIGS. 43-48.
Figure 50:
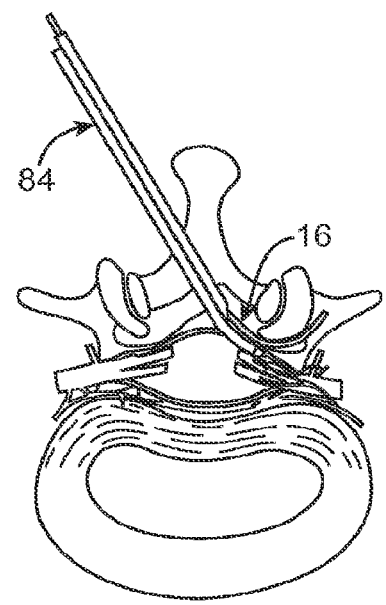
Figure 51:
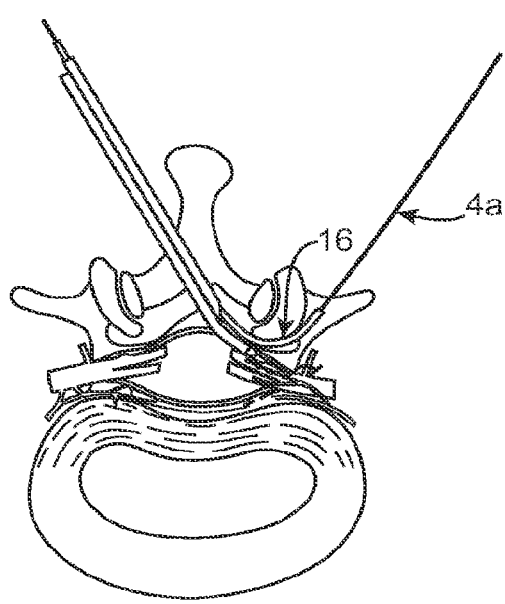
Figure 52:
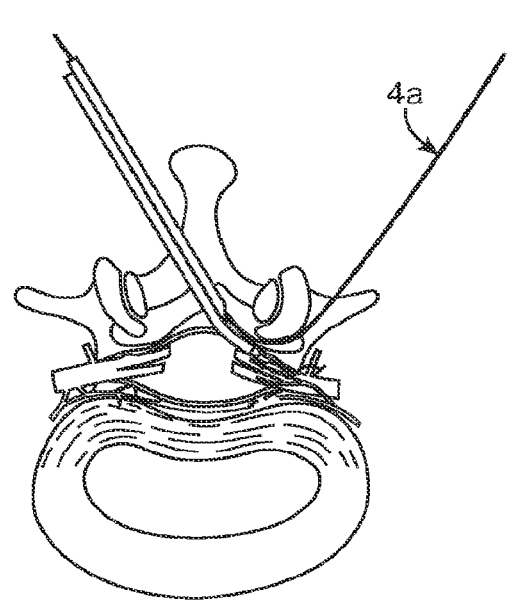
Figure 53:
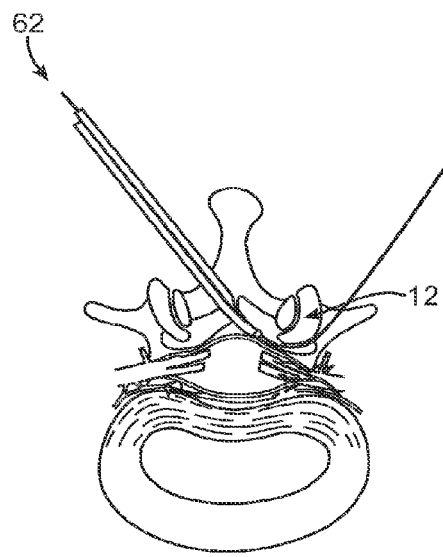
Figure 54:
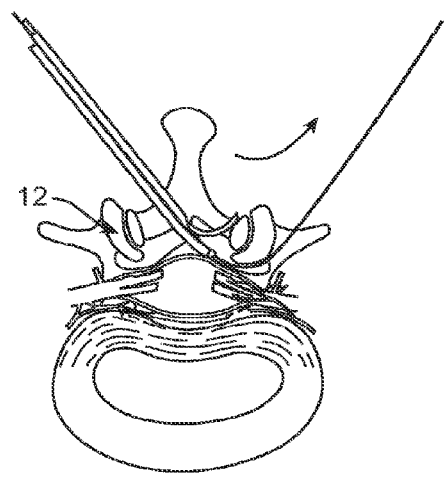
Figure 55:
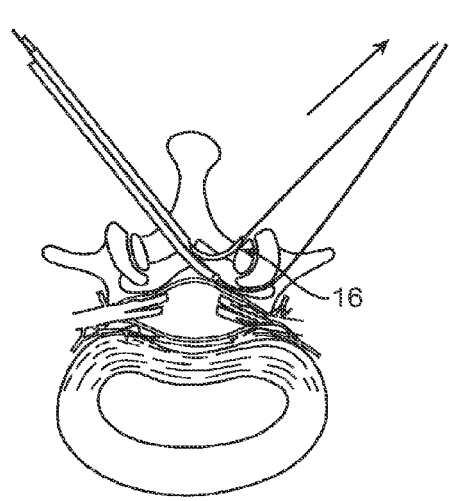
Figure 56:
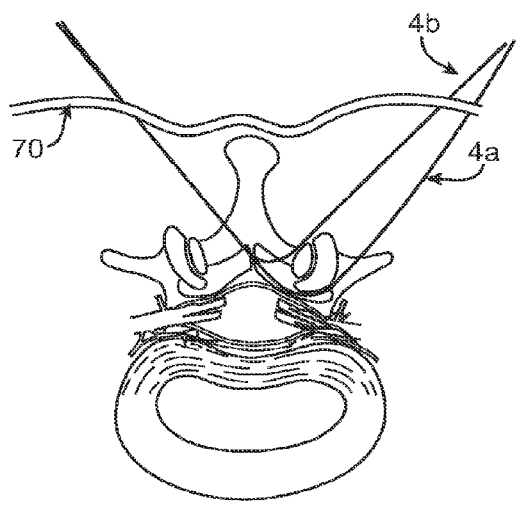

Referring now to FIGS. 49-64, a variation of the method and apparatus of FIGS. 43-48 is described, comprising another preferred approach for placement of the abrasion device. This series begins with FIG. 49, in which a double lumen, blunt tipped, epidural device 84, has already been advanced to the lateral recess 108, using a technique similar to FIG. 19. Next, FIG. 50 shows a curved flexible needle 16, preferably with an atraumatic tip, that has been advanced, via the working channel 50 (FIG. 16), through the neural foramina 110. FIG. 51 illustrates threading of the straight, flexible, sharp tipped wire 4a through the curved needle 22, and advanced posteriorly until it exits the skin of the back. In FIG. 52, the curved needle has been withdrawn, leaving the straight wire 4a in place. In FIG. 53, the double lumen epidural apparatus 84 is slightly withdrawn, from the patient, so that the working channel 50 is directed towards the medial side of the face complex. FIG. 54 shows the curved needle 16 advanced through the working channel again, adjacent to the first wire 4a, this time advancing the same or a different curved, flexible needle 16, towards the opposite side of the facet complex 12. FIG. 55 shows where a second straight flexible wire 4b is advanced through the second placement of a curved needle 16, this time on the medial side of the facet joint. The second sharp, flexible, straight wire 4b is threaded through this second curved needle, and subsequently advanced posteriorly, until the sharp tip of the wire 4b exits the skin 70. FIG. 56 next shows both the curved needles and the double lumen apparatus removed, leaving the wires 4a and 4b in place.

Figures 57, 58:
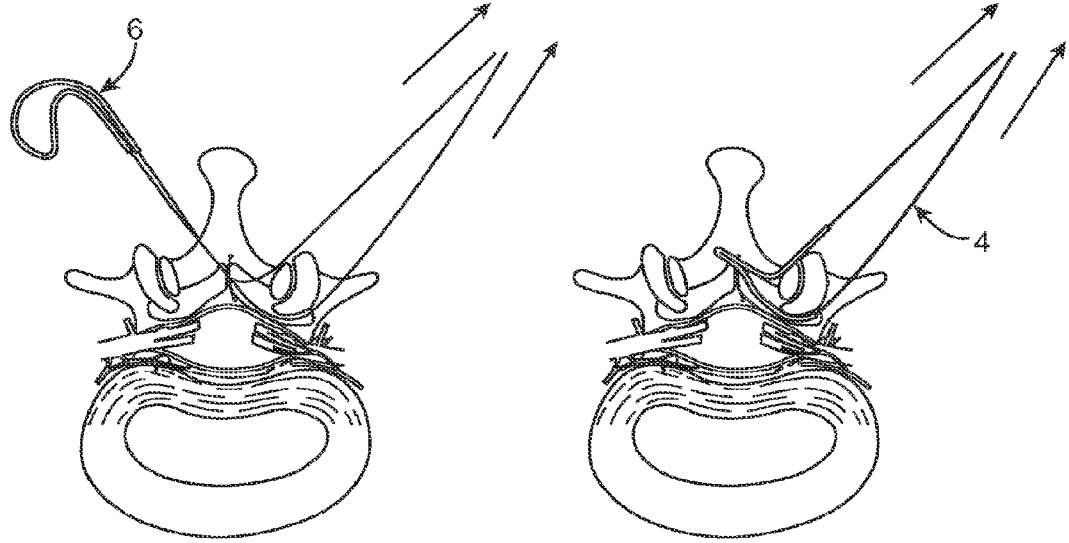

FIG. 57 shows that both wires have been attached to the two ends of the abrasive element 14 and/or the cover 6 of the abrasive element. With access established, via either a percutaneous or an open approach (or a combination thereof), neural protection and/or tissue removal elements may be introduced via the access for safe, selective removal of tissue. It should be understood that the methods and apparatus described hereinafter are equally applicable to both open and percutaneous approaches. For the purpose of clarity, they may be illustrated utilizing only a percutaneous or open access, but this should in no way be construed as limiting.

In order to reduce a risk of neurological damage during selective tissue removal, variations of the present invention optionally may provide neural protection during tissue removal. In one variation, a neural protection element, such as a sheath, shield or backstop, is positioned such that the neural protection element separates impinging tissue in the neural foramen from the underlying nerve root. Tissue removal then may proceed by advancing a tissue removal device into position between the foramen and the neural protection element. When access to the stenosed region is via an open surgical procedure, it may be possible for the medical practitioner to manually place the neural protection element. Alternatively, when using either an open or a percutaneous access, the neural protection element may by advanced over, or pulled into place by, an access guide wire placed as described previously.

Alternatively, the two wires 4a and 4b may be opposite ends of the same continuous wire, with the cover 6 for the abrasive element 14 already placed over the mid-portion of the wire 4. Alternatively, the abrasive element 14 may already have been placed inside said cover 6, and attached at each end to the wires 4a and 4b. FIGS. 58 and 59 show the two wires 4a and 4b pulled and bringing the abrasive element cover, possibly with the abrasive element 14 already placed inside said cover 6, into position through the neural foramina. FIG. 60 illustrates the step that follows placement of the abrasion element cover 6 alone. In FIG. 60, with the wire 4 in place inside the abrasion element cover 6, the abrasive element 14 is now seen to have been attached to the end of the wire. Subsequently, the cover 6 is held open at each end by a grasping device, which also holds the cover 6 under tension against the tissue to be abraded. With the cover anchored thus, the abrasive element 14 is pulled into place by the wire 4a/b, replacing the wire, as has occurred for FIGS. 61 and 62. With the abrasive element in position and the abrasive element cover 6 tightly held open and against the tissue to be abraded, the abrasion element 14 may be pulled back and forth, under tension, against the tissue to be abraded, as in FIG. 62. Alternatively, the abrasive element may be pulled in a single direction across the tissue to be abraded. FIG. 63 illustrates the cover 6 following removal of the abrasive element. Said cover may remain in placed as a compression bandage, under tension against the freshly abraded surface, in order to promote hemostasis, promote tissue remodeling, and trap debris post operatively.

A nerve stimulator may be incorporated into the abrasive surface of the abrasive element, and/or incorporated into the protective cover or sheath for the abrasive element, in order to verify correct placement and enhance safety by allowing the medical practitioner to ensure that neural tissue is not subject to inadvertent abrasion. FIG. 64 illustrates a neural stimulation apparatus. FIG. 64 also illustrates an abrasion element 14, disposed inside of a sheath or cover 6, and held in place by tension retaining elements 112.

The stimulation apparatus 114 delivers a small electrical current through the working surface and/or the non-working surface (backside) of either the tools used in the epidural space, the abrasive element 14, and/or the protective cover 6 of the abrasive element. Preferably, one electrode 120 would be connected to each side (abrasive and non-abrasive) of the entire device and sheath complex, along the full distance where tissue abrasion is planned to occur, in the lateral recess, central canal, or neural foramen. Neural stimulation may be monitored via verbal response to stimulation in an awake or lightly sedated patient, or SSEP, MEP, EMG, or motor evoked muscular movement in an asleep or sedated patient. One possible mechanism for avoiding inadvertent neural damage may be to ensure that there is no neural stimulation when stimulating the working surface of the device. A positive control should be obtainable in the lateral recess and neural foramen, when stimulating the non working surface (back side) of the device or, preferably, the backside of the device cover or sheath 6 (e.g., first portion of locking mechanism).

After the abrasion element, and possibly its protective sheath or cover 6, have been placed through the neural foramina 110 the abrasive surface is brought into firm contact with the tissue to be abraded by pulling tension simultaneously on each end of the abrasion element. When both ends of the abrasive element 14 are pulled simultaneously, the abrasive surface of the device is brought under tension and into firm contact with the impinging spinal tissue on the anterior and medial sides of the facet joint complex. Subsequently, one end of the abrasive element is pulled more forcefully than the other, sliding the abrasive surface is across the target tissue. When one end of the abrasive element is pulled with more force than the other, the ribbon moves in the direction of the stronger pull, while the lesser pull on the opposite end maintains force and creates friction with movement between the abrasive surface and the tissue to be resected. When the optional protective cover 6 or sheath is provided, both of its ends of the are, in one variation, pulled under traction and anchored in place, such that the abrasive element 14 may be pulled in either or both directions through the cover 6 or sheath without significant friction against and/or without causing trauma to adjacent tissues.

Alternatively, the abrasive element 14 may be pulled in a single direction across the tissue. The abrasive belt, strap or ribbon may be a single length, pulled alternately in each direction, or it may be dispensed from a spool, as in FIG. 65*a*, or from a reel to reel configuration, as in FIG. 65*b*, and pulled in both directions or pulled in a single direction, across the tissue to be abraded. An alternative variation of the apparatus and method utilizes an electromechanical, belt driven abrasive tool, an example of which was described previously in FIGS. 41 and 42.

In one variation of the invention, a tissue retention or compression dressing (FIGS. 63, 73, 75) method and apparatus are utilized immediately after the tissue removal, ablation and remodeling procedures described above. For example, following neuroforaminal and lateral recess enlargement, it may be advantageous to leave, as a surgical dressing, a thin flat element 150 pulled tightly against the resected, abraded, or remodeled tissue surface (e.g., around the facet complex). It is expected that a compression dressing of this nature will enhance hemostasis, promote healing and promote subsequent tissue remodeling with the neural foramen widely open. Also, the surgical dressing 150 would provide a barrier to trap tissue debris away from neural or neurovascular structures, while providing an optional technique for delivering medication, possibly as a depot, to the operative site. The dressing 150 would also present a smooth surface towards the nerve root in the immediate postoperative period.

Figure 73:
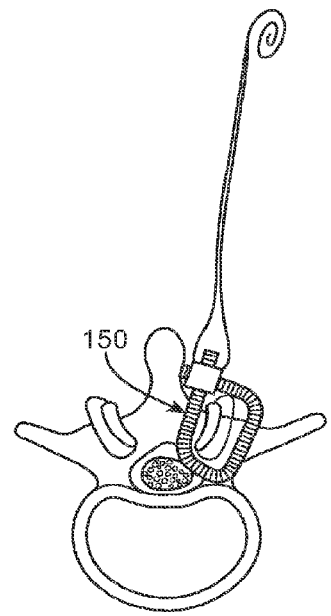
Figure 75A:
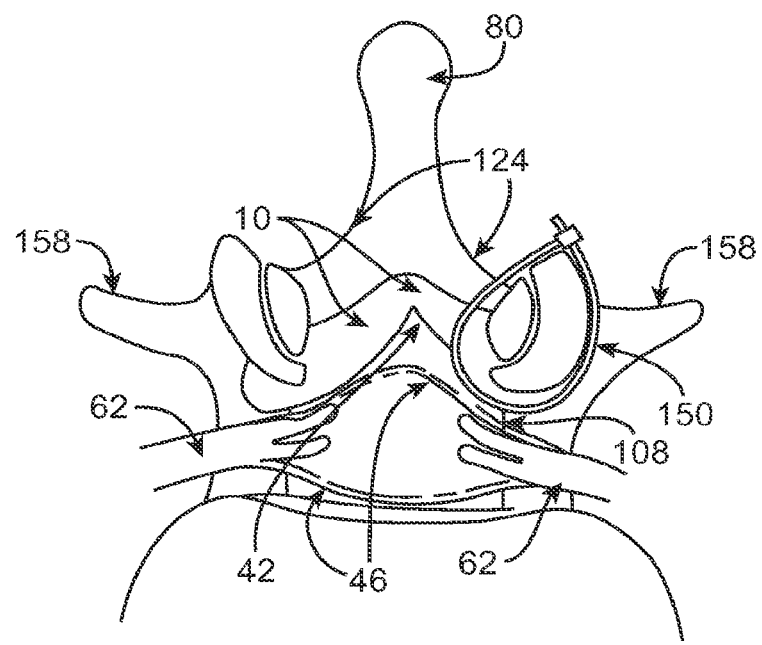
FIG. 75 are schematic cross-sectional views through a patient's spine of a fully implanted compression or retraction remodeling apparatus or compression dressing apparatus.
Figure 75B:
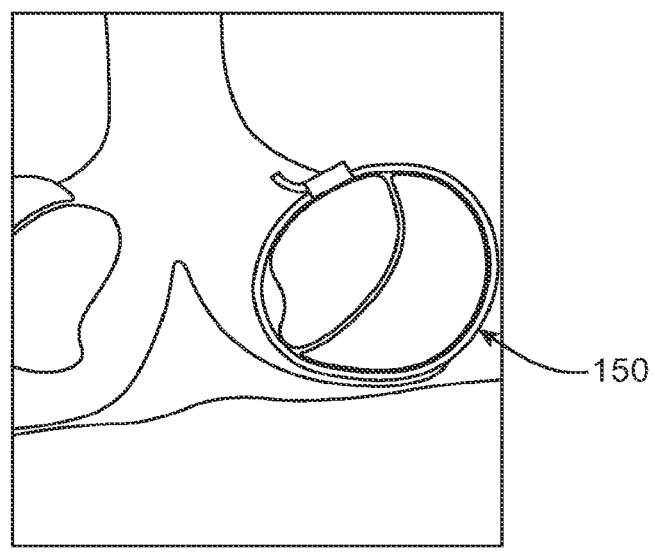

As in FIG. 63, this neuroforaminal compression dressing may be percutaneously held tightly in place against the resected, abraded, or otherwise remodeled surface (e.g., zygapophysial (facet) joint) 12. In certain embodiments, the compression dressing may be either percutaneously removable (as shown in FIGS. 63 and 73), either by pulling the dressing through the neural foramen, or by the inclusion of a biodegradable central component of the dressing, such that the two ends may be removed, with the dressing separating at its biodegradable portion in the middle. In other variations, a compression dressing may include a totally implanted and completely biodegradable dressing, as illustrated in FIGS. 75*a* or *b*.

FIGS. 49-59 and 63, and FIGS. 66-73 illustrate midline or paramedian approaches to percutaneous placement of a neuroforaminal compression device (e.g., percutaneous retention compression dressing or tissue remodeling strap) 150 that is wrapped around the facet complex and retracts the posterior aspect of the neural foramina, effectively dilating the space available for the neural and vascular structures. FIGS. 74*a* and *b* illustrate the first steps in a posterior lateral neuroforaminal approach to placement of a compression element (subsequent steps would share similarities with the approach illustrated in FIGS. 49-59 and 63). A grasper, loop or hook 146 can be for grabbing an end of the guidewire.

Figure 76:
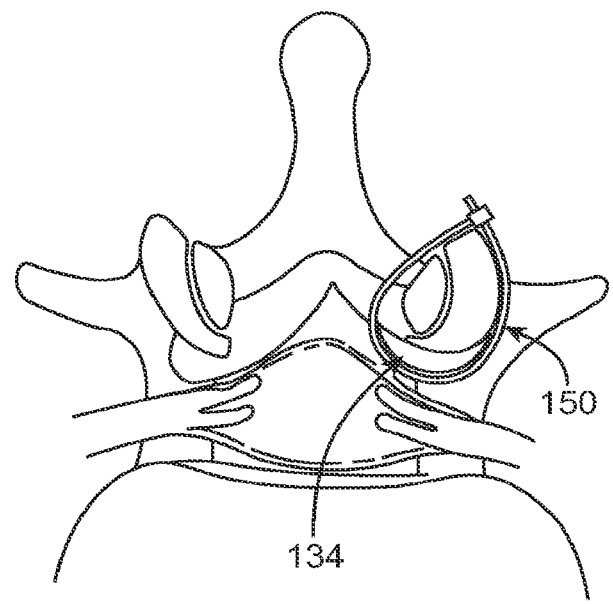
FIG. 76 is a schematic cross-sectional view through a patient's spine of an apparatuses for a compression remodeling strap integrated with a working backstop or barrier.
Figure 77:
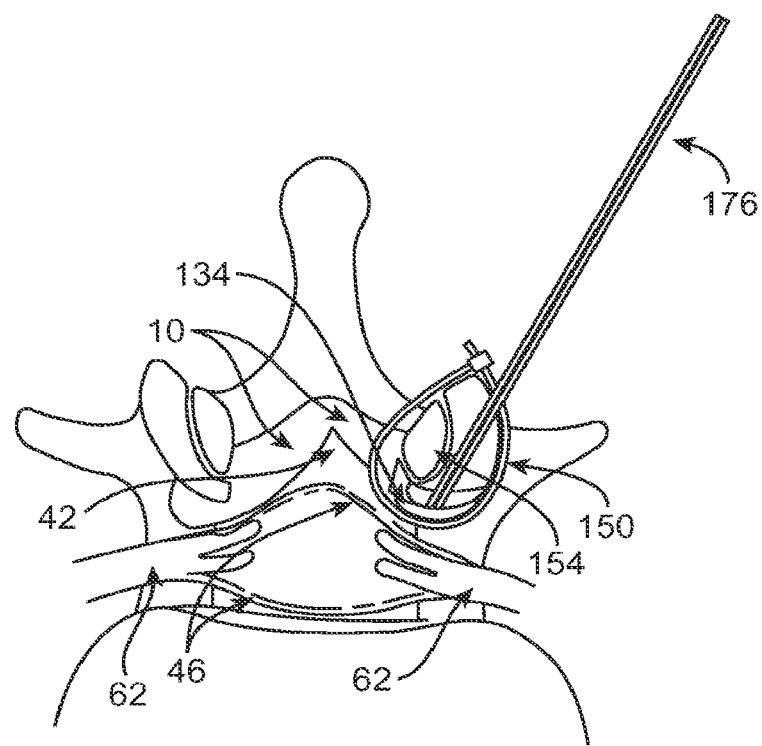
FIG. 77 is a cross-sectional view through a patient's spine that shows a facet drill with a ligament retraction device around a working backstop, and demonstrates a image guided drill used in conjunction with the backstop.
Figure 78:
FIGS. 78-81 are schematic views of cable strap configurations for temporary removable, permanent, or biodegradable compression dressings or remodeling tools.

An additional embodiment of the method and apparatus may combine both the working backstop 134 and the compression element 150, as illustrated in FIGS. 76 and 77.

In these illustrations, the compression element 150 serves to keep the working barrier 134 in proper position. Subsequently, image guidance may be used to guide tools used in open or percutaneous procedural approaches to neuroforaminal and lateral recess enlargement. The example in FIG. 77 illustrates an image guided drill 176 removing a portion of the impinging facet complex. With the barrier in place, possibly further aided by neural stimulation/localization capabilities, selective and safe tissue removal may be more readily performed.

Figure 79:
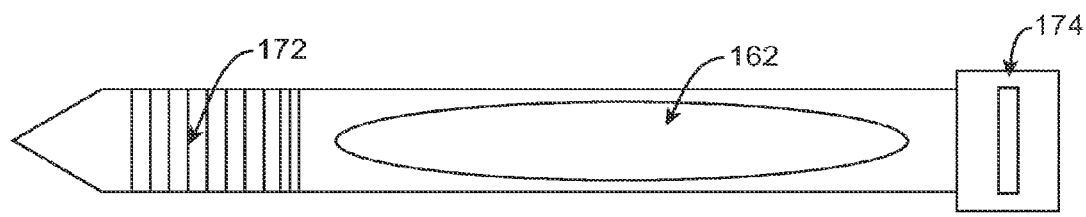

FIGS. 78-81 illustrate some of the compression element embodiments 150. FIG. 79 also contains an area (e.g., a drug depot in a retention strap or compression dressing) 162 for storage of medications for delivery to the tissue retracted by the compression element 150. The compression element can have a locking mechanism that can have a first portion 172 that can insert through a second portion, and can have a locking mechanism that can have a second portion 174 that can receive a first portion 172.

Figure 80:
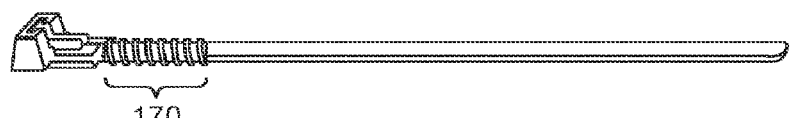
Figure 81:
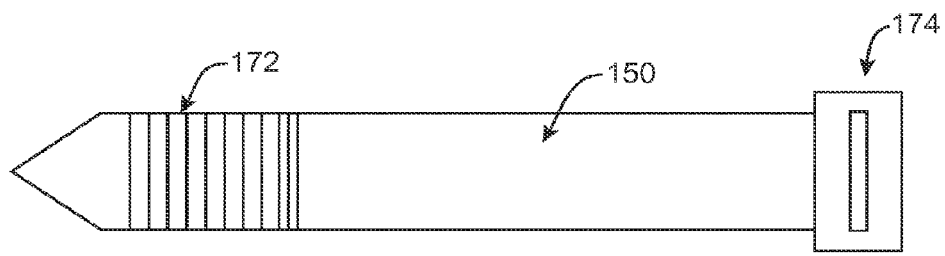
Figure 82:
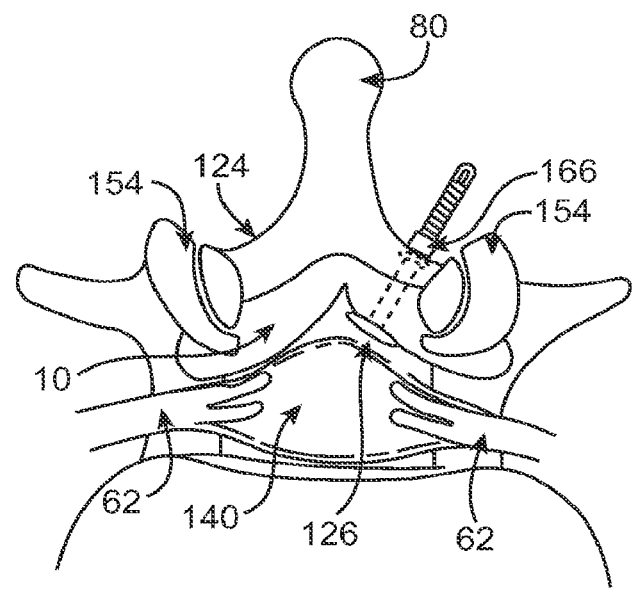
FIGS. 82-83 are schematic cross-sectional and lateral views through a patient's spine of apparatuses for temporary or permanent retraction and retention of the ligamentum flavum.
Figure 83:
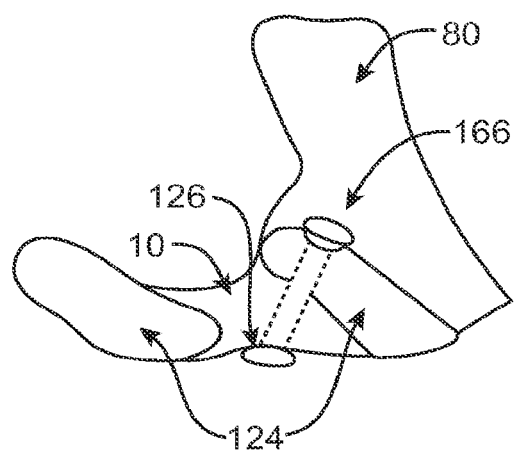

FIGS. 82 and 83 demonstrate additional methods and apparatus for enlargement of the central spinal canal and lateral recess, by retracting the posterior spinal anatomy, in particular the ligamentum flavum 10 (FIGS. 79 and 80 illustrate translaminar ligamentum flavum retraction), in a further posterior direction, away from the dura 46, cauda equina 140, nerve roots 62, and dorsal root ganglia. Such a device would both serve both to retract the spinal tissue posteriorly, and to prevent the posterior elements, particularly the ligamentum flavum 10, from buckling anteriorly into the spinal canal or lateral recess. FIG. 82 illustrates an apparatus with an anchor 126 anterior to or within the ligamentum flavum, a second (e.g., laminar) anchor posterior to the lamina 124 (e.g., for posterior retention) and a mechanism for maintaining tension in order to retract the tissues posteriorly, towards the lamina 22. FIG. 83 illustrates a rivet type device that is placed through a hole that has been drilled through the lamina 124. Such a rivet has an anchor 126 placed anterior to the ligamentum flavum 10, which is retracted posteriorly in order to enlarge the central spinal canal and/or lateral recess. Spinal endoscopy may be used as a tool to place a ligamentum flavum retraction system, or in order to confirm that correct placement and efficacy has been achieved.

Most of the safety issues related to the methods and apparatus described herein are similar to those associated with any surgical procedure, e.g., infection and/or bleeding. Some safety issues are more specific to surgery in and around the spine or spinal cord, and are therefore given special consideration below. These generally relate to spinal nerve injury. Morbidity could result from instruments inadvertently passed through the dura mater, and creating a cerebrospinal fluid leak and/or damaging the cauda equina (caudal to T12-L1) or spinal cord (cephalad to T12-L1) when entering the epidural space. Potentially traumatized structures further include nerve roots, adjacent vasculature, or dorsal root ganglia.

Figure 84A:
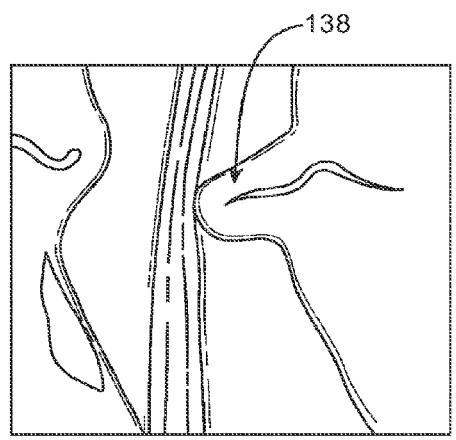
FIG. 84 are sagittal cryosection images through 3 cadaveric spines (courtesy of Wolfgang Rauschning, MD) that illustrate pathological anterior bulging and "buckling" of the ligamentum flavum, encroaching on the spinal canal or lateral recess, a frequent contributing factor in spinal stenosis. In circumstances when similarly protruding ligamentum flavum impinges neural and neurovascular structures in the spinal canal, lateral recess, or neural foramina, then retraction of said ligaments, as in FIGS. 79 and 80 may be beneficial to the patient.
Figure 84B:
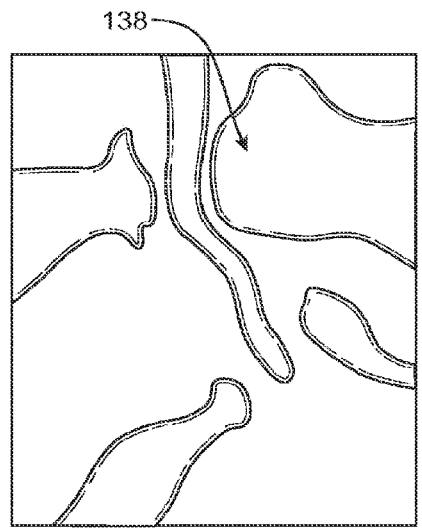
Figure 84C:
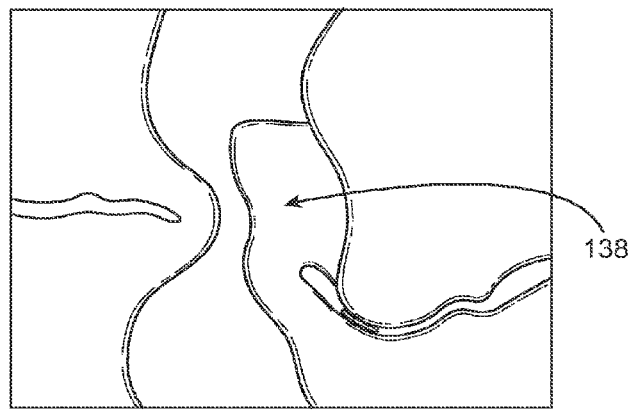
Figure 87A:
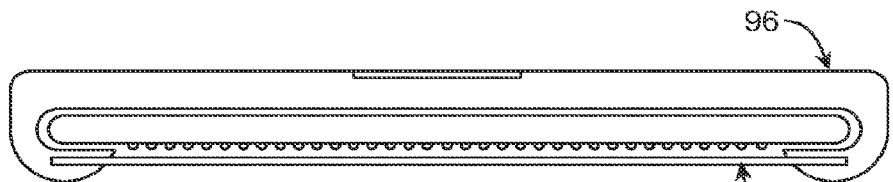
FIG. 87 are schematic views of additional apparatus that may be utilized for selective surgical removal of tissue, and subsequently as a compression dressing, with the ability to act as a therapeutic drug depot.
Figure 87B:
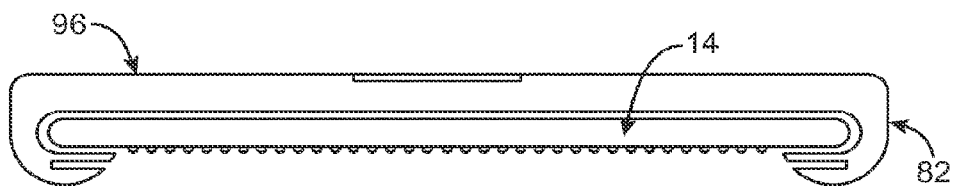
Figure 87C:
Figure 87D:
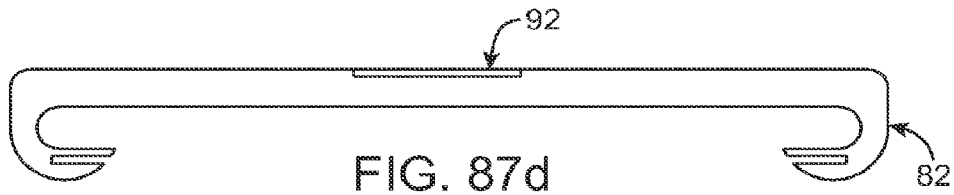
Figure 87E:
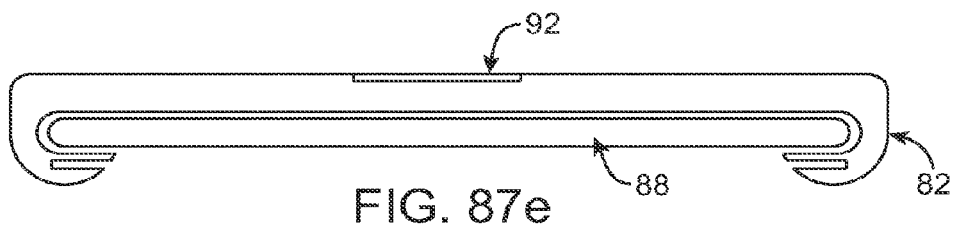
Figure 87F:
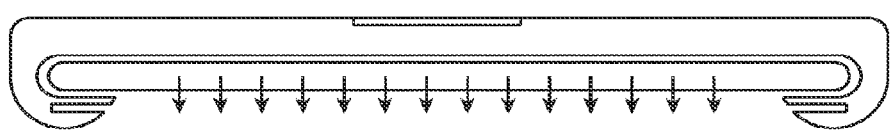

FIG. 84 are sagittal midline cryosections of the lumbar spine (provided courtesy of Wolfgang Rauchning, MD) that demonstrate the ligamentum flavum protruding ("buckling") anteriorly, a potential mechanism for central or lateral recess neural or neurovascular impingement. The ligamentum flavum is a potential target for tissue resection using the herein described methods and apparatus.

FIGS. 85, 86, 87, 88, 90 illustrate preferred embodiments of the protective cover or sheath for the abrasion element, in which the abrasive surface is covered 94 and the backside of the abrasive element may also be shielded 96, to prevent tissue damage in areas where tissue abrasion is not intended. The abrasive element's protective cover is ideally shaped to provide optimal protection of vulnerable tissues, at the same time maintaining both a very small profile, for easy threading of the stenotic neural foramen; and atraumatic edges (e.g. rounded), in order to prevent cutting of or trauma to neural, vascular or other tissue during placement, use or removal of the device. For example, in certain preferred embodiments, the abrasion device may be tubular, with an opening over the tissue to be abraded; or may be flat (FIGS. 86, 87, 88, 90) with atraumatic railings or tracks that facilitate passage of the abrasion element, abrasion surface cover, or other instruments. Side channels, through which the edges of the abrasion element may be maintained but are able to slide freely may be of an atraumatic shape 82. Said side channels may also hold the protective cover 94 for the abrasive side of the abrasion element 14. Note that neural stimulation and localization may be performed through a conductive element in the back cover 96, the front cover 94, or in the abrasive side of the abrasive element itself 14. Both free ends of the device, as well as the ends of the optional protective sheath or cover 6, are positioned external to the patient for manipulation by a medical practitioner.

FIG. 87 show a similar protective cover and abrasive element configuration to that described in FIG. 86, this time with neural stimulation element 92 only illustrated in the non-abrasive side of protective cover. In addition, FIGS. 87*e* and 87*f* show that the abrasive element 14 has been replaced by an alternative element for drug deposition 88, and/or to serve as part of the compression dressing, when the elements are left under tension against the abraded surface, after the operative procedure.

Figure 88A:
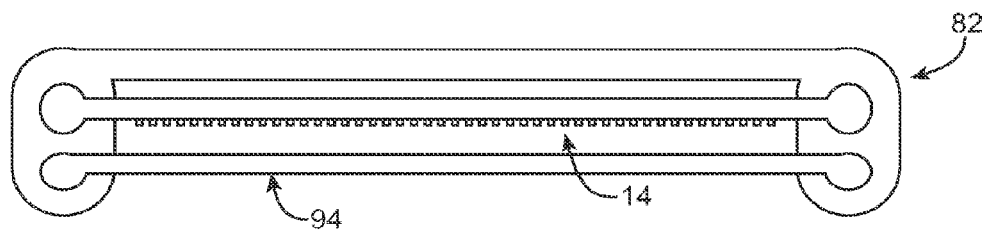
FIG. 88 are schematic views of additional apparatus that may be utilized for selective surgical removal of tissue.
Figure 88B:
Figure 88C:
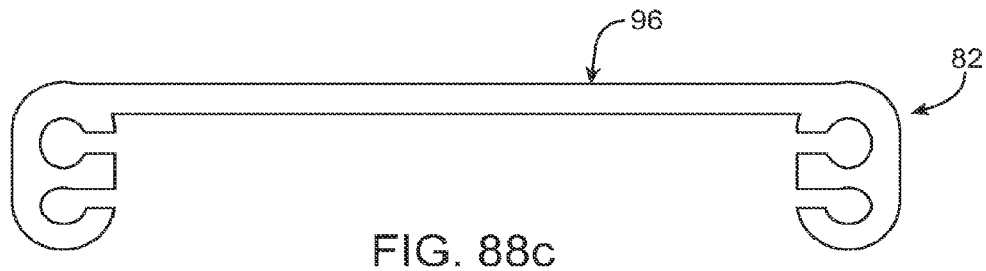

FIG. 88 illustrate an additional similar embodiment of the abrasive element 14 with protective covers 94 and 96. This time, no neural stimulation elements are illustrated.

Figure 89:
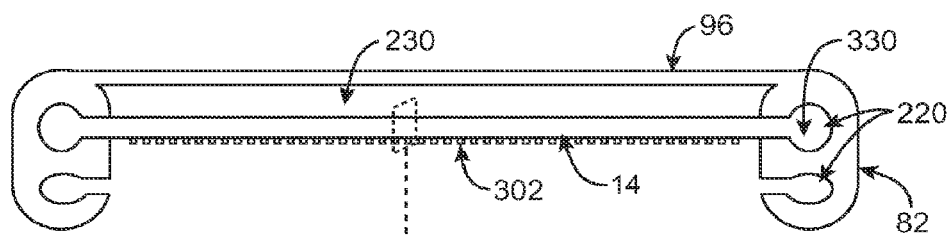
FIG. 89 is a schematic view of an additional apparatus that may be utilized for selective surgical removal of tissue.

Referring now to FIGS. 89 and 90, sections through the abrasive apparatus are illustrated. The abrasive element 14 is seen, housed within the protective covers. In some variations of neural protection element 6 and tissue removal device, the neural protection element 6 and the tissue removal device 14 may comprise mating features to facilitate advancement of the device through the element. In FIG. 89, element 14 comprises track 220 that mates with protrusions 330 of device. In the variation of FIGS. 89 and 90, neural protection element 6 also comprises recessed space 230 disposed between device 14 and the backside of the element. Tissue or debris removal or capture may be accomplished through this space. For example, when tissue removal elements comprise features punched, stamped, cut, etched, etc. through device 14, removed tissue may fall through the punched features and collect within space 230. This space optionally may be emptied of debris during a procedure via irrigation and/or aspiration, but alternatively may be used as a reservoir where debris may collect for removal at the conclusion of a procedure.

As shown, the abrasion element may, for example, be structured as a thin belt or ribbon 14, with an abrasive and/or cutting surface on one of its sides. The abrasive element 14 may exist in a variety of shapes, ranging from flat to curved; from narrow to wide; and from a solid to perforated. The abrasive surface of the abrasive element 14 may, in one variation, contain deep grooves 118 or perforations for the transport of debris away from the operative site. Alternatively, the pattern of abrasive may be designed to control the direction and speed of movement of the surface across the tissue to be abraded (e.g. deep grooves, at a diagonal to the edge of the straps, may be used to facilitate lateral movement of the abrasive element). The width and shape of the abrasive elements may also be varied, in further effort to control the area of tissue to be resected. Finally, in one preferred variation, the surgeon would begin with a coarser grade of abrasive material, in order to gain more aggressive tissue removal. Sequential use of less and less aggressive surfaces would serve to smooth the abraded tissue surface, with the aim of creating an atraumatic surface for contact with neurovascular structures.

Placement of a tissue abrasion device 14 through protective sleeve(s) 6 and into position for selective tissue removal, brings the abrasive surface 14 into contact with the tissue to be removed. A medical practitioner may remove tissue in contact with abrasive surface (FIGS. 90*a, b, c*) by applying a reciprocating or unidirectional motion to the ends of device 14 exterior to the patient. In one variation, a spool or reel to reel configuration may be designed that begins with a coarse grade of abrasive material, and progresses towards less abrasive materials as the spool or reel unwinds.

Figure 90A:
FIG. 90 are schematic views of close-ups of the additional apparatus that may be utilized for selective surgical removal of tissue of FIG. 89.
Figure 90B:
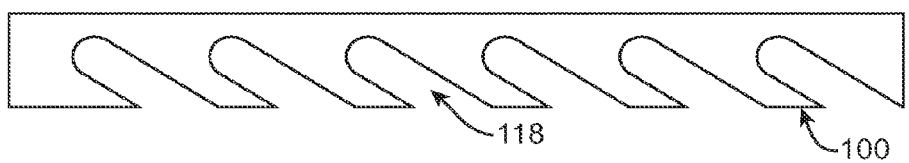
Figure 90C:

FIGS. 90*a*-90*c* illustrate additional mechanical variations of tissue removal elements. FIGS. 90*a* and 90*b* illustrate alternative blade or saw configurations. The blades may comprise various shapes, sizes and configurations, as desired. Furthermore, the blades may be attached to tissue removal device or may be formed by punching or stamping through the device with optional subsequent grinding of the punched edge. Alternatively, the blades may be formed by a chemical etching process. The blades may comprise a 3-dimensional profile to facilitate cutting, for example, a bow or a corrugation or a 'cheese grater' profile. Furthermore, the blades may be placed at one or more angles relative to the direction of tissue removal. Cutting surfaces of the blades may be oriented in a single direction or may be oriented in multiple directions. Additionally, the blades may be serrated. As another alternative, the mechanical elements may comprise fine cutting wires or a Gigli saw. A plurality or cutting wires or Gigli saws may be joined or woven together or flattened to form a substantially planar cutting surface. FIG. 90*c* illustrates an abrasive or rasp variation of element 14.

With reference to FIG. 91, neural protection element 6 and tissue removal device 14 are described in greater detail. As seen in FIG. 91A, window 204 of sheath 6 of neural protection element is disposed on the posterior-facing or working side of the sheath. In some variations, edge 205 of window 200 is sharpened to coact with tissue removal device 14. This may be especially useful when the tissue removal device removes tissue with a blade. In another variation, edge 205 or a portion thereof may be energized, for example, to provide a negative control for neural localization, to ablate or denature impinging tissue and/or to achieve hemostasis. In still further variations, edge 205 is both sharpened and configured to be energized.

Window 204 limits exposure of tissue removal surface of tissue removal device 14 only to the localized region of the patient's tissue where selective tissue removal is desired. As seen in the cross-sectional view of FIG. 91D, neural protection element 14 may completely surround tissue removal device 6 in areas other than window 204. However, as seen in the cross-section of FIG. 91E, tissue removal surface 302 is exposed within the window. Window 204 may be positioned such that it directly underlies and faces the neural foramen and impinging tissue, as in FIGS. 61-64. Irrigation and/or aspiration optionally may be provided through the window 204, e.g., for debris removal. Suction also may be drawn through the window to engage impinging tissue and/or to provide a seal against the tissue. In some variations of neural protection element 6, the window optionally may be opened, closed or re-sized by a medical practitioner as desired. For example, the window may be closed during delivery, opened during selective removal of impinging tissue, then closed during retrieval of the sheath.

Neural protection element 6 preferably comprises an atraumatic profile to reduce tissue injury during placement and retrieval. For example, the element may comprise rounded edges 82, as seen in FIGS. 91D and 91E. The device preferably comprises a low profile having a width that is larger than its height. The width may be any desired width; for example, when used within the neural foramen, width may be up to the distance between adjacent pedicles within the foramen. In one variation, a width of less than about 7 mm may be provided. The height preferably provides for safe placement of element between impinging tissue and nerve root 62. In one variation, a height of less than about 2 mm may be provided. In one variation, element has a length sufficient to allow for transforaminal passage of the element, as well as positioning of ends of the element outside of the patient.

Figure 91A:
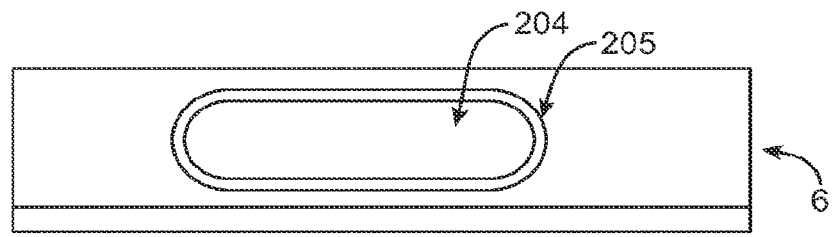
FIGS. 91A-91E are, respectively, a detail view of the working side of a neural protection element, a detail view of the tissue removal surface of a tissue removal device, an assembly view of the neural protection element and the tissue removal device, a cross-sectional view of the element and device along section line A-A of FIG. 91C, and a cross-sectional view of the element and device along section along B-B of FIG. 91D.
Figure 91B:
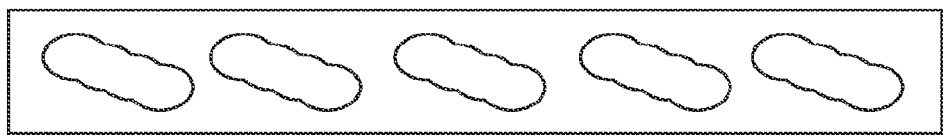

As seen in FIG. 91B, tissue removal device 14 comprises tissue removal surface 302 having tissue removal elements. Tissue removal elements may be chosen, for example, from a wide variety of abrasive elements, cutting elements, electrical ablation elements, or combinations thereof. In FIG. 91, tissue removal elements illustratively comprise sharpened blade edges 118 for cutting through tissue and/or bone. Edges 118 may be formed, for example, by punching through tissue removal device 14 and optionally sharpening the edges of the punch, for example, via a grinding process.

Figure 91C:
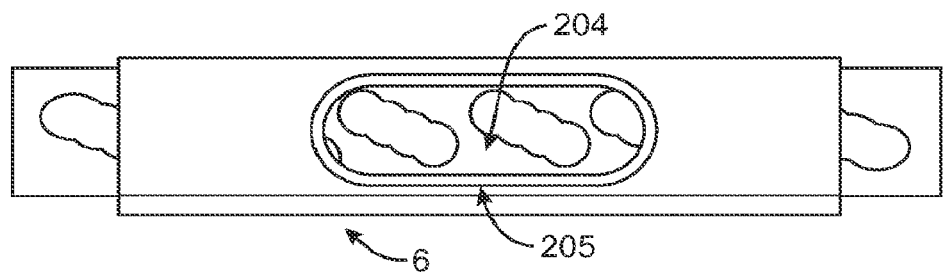
Figure 91D:
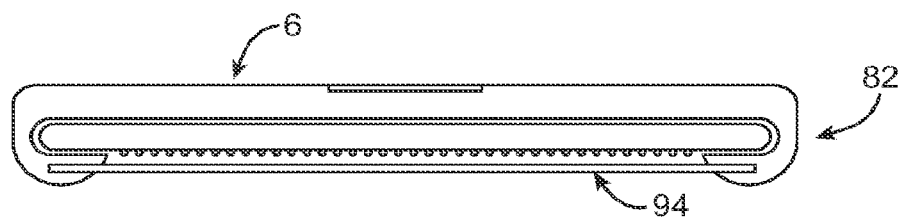
Figure 91E:
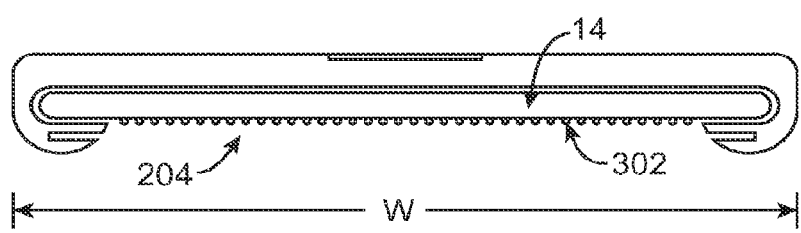
Figure 92A:
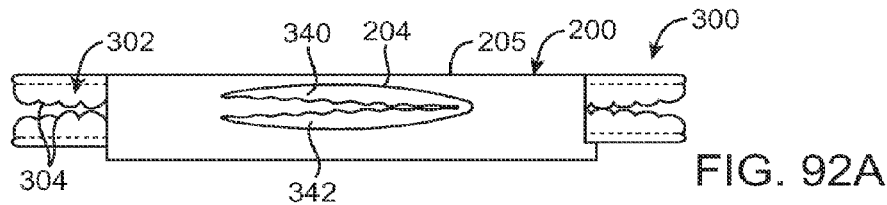
FIGS. 92A-92H are schematic views of additional variations of mechanical tissue removal elements.
Figure 92B:
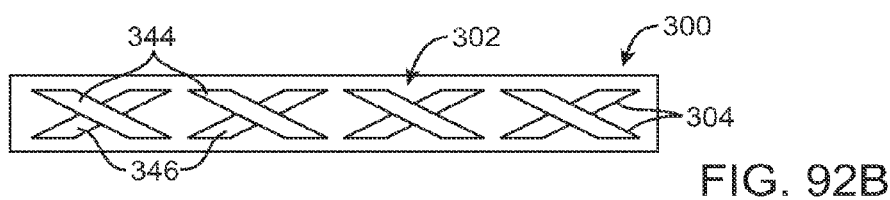
Figure 92C:
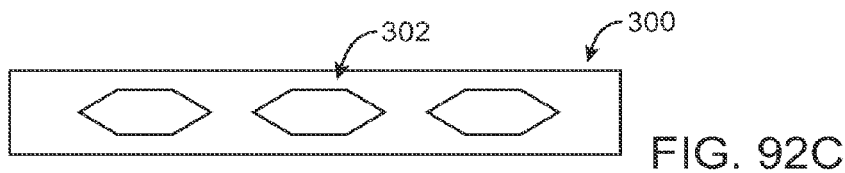
Figure 92D:
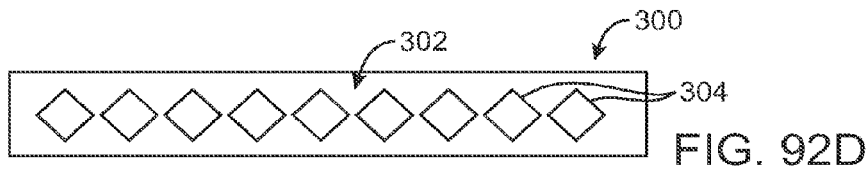
Figure 92E:
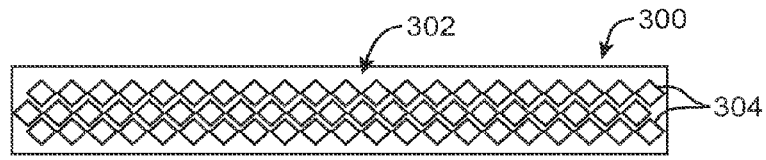
Figure 92F:
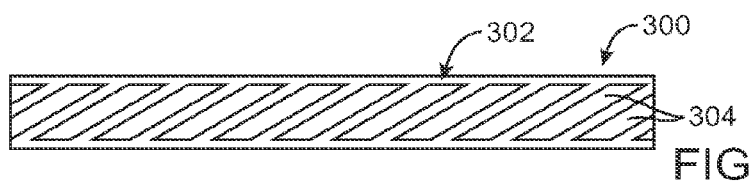
Figure 92G:
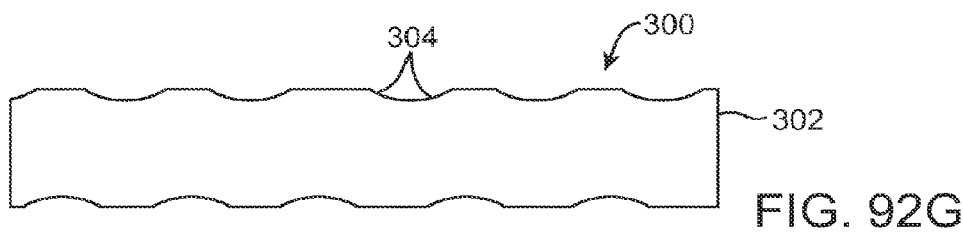
Figure 92H:
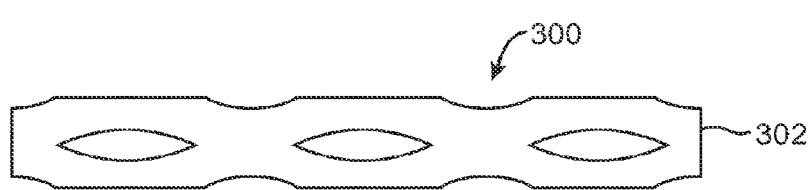

As seen in FIG. 91C, tissue removal device may be positioned within neural protection element 6 such that tissue removal elements on tissue removal surface 302 are locally exposed within window 204 of element. Edge 205 of window 204 may be sharpened to provide for guillotine-type cutting between sharpened edges 100 of the tissue removal device and edge 205 of the window. This may provide enhanced shear forces that may be well adapted to cutting of soft tissue.

With reference again to FIGS. 61-64 in conjunction with FIG. 91, after spinal neuroforaminal placement, tissue removal elements 302 of device may be used to selectively remove tissues that impinge on the neurovascular structures within the lateral recess and neural foramen, anterior to the facet joint, thereby enlarging the lateral recess and neural foramina via selective tissue removal. Impinging tissue to be targeted for removal may include, but is not limited to, lateral Ligamentum Flavum, anterior and medial facet, and osteophytes. Tissue removal may be achieved in a variety of ways.

FIG. 92 illustrate additional variations of mechanical tissue removal elements. In FIG. 92A, tissue removal elements 304 comprise coacting blades 340 and 342 that may be drawn across tissue to achieve a scissor-type cutting action. Edge 205 of window 204 of element 200 may be sharpened to contribute to tissue cutting. In FIG. 92B, a series of blades 344 and 346 cross and are sharpened on both sides for bidirectional or reciprocating scissor-type cutting. FIG. 92C illustrates a v-shaped blade or a scissor-type cutting variation wherein the blades are formed through device coacting with sharp window edge. FIG. 92D illustrates a diamond cutting pattern for tissue removal surface 302. FIG. 92E illustrates a more densely packed diamond cutting pattern. FIG. 92F illustrates a variation wherein the cutting surfaces are angled along a common orientation. FIG. 92G illustrates a variation comprising punched tissue removal elements and scalloped or cut-out edges of device 300, which edges optionally may be sharpened. FIG. 92H illustrates a scissor-type cutting variation with scalloped or cut-out edges. Additional mechanical tissue removal elements will be apparent.

In another variation of tissue removal device, tissue removal elements 304 comprises one or more electrosurgery elements for tissue removal/ablation. The electrosurgery elements additionally or alternatively may be utilized to achieve hemostasis and/or to facilitate neural localization. Monopolar or bipolar RF elements may, for example, be utilized and may be activated with a thermal or substantially non-thermal waveform.

Figure 93A:
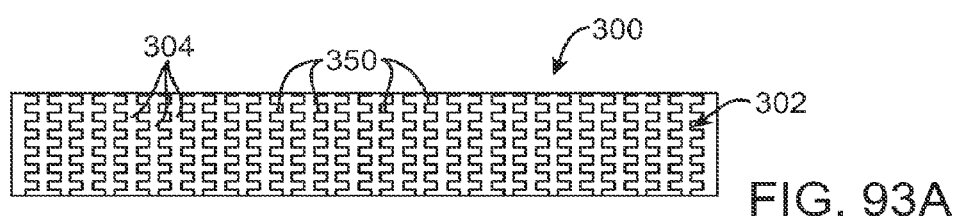
FIGS. 93A-93C are views of a variation of the tissue removal device comprising electrosurgical tissue removal elements.
Figure 93B:
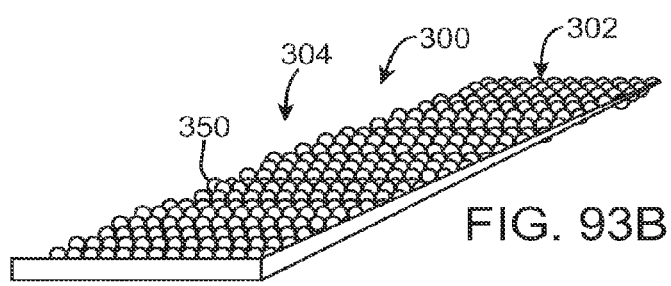
Figure 93C:
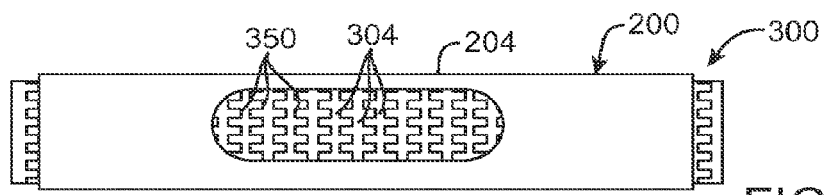

FIG. 93 illustrate an electrosurgical variation comprising a plurality of wire loop electrodes 350 that serve as tissue removal elements 304. Wire loop electrodes 350 are located on tissue removal surface 302 of device 300. Device 300 may, for example, comprise an electric textile or a flexible printed circuit board having wire loop electrodes 350. The electrodes may be brought into contact with impinging tissue, then actuated to remove, singe, denature, or otherwise remodel the tissue. Optionally, tissue that has been treated electrosurgically may be scraped away after electrosurgical treatment in order to remove the tissue. Advantageously, in the variation of FIG. 93, device 300 optionally may remain stationary during tissue removal. The device optionally may be integrated with neural protection element 200 such that the wire loop electrodes are formed on the working side of the protection element. In FIG. 93C, device 300 is shown disposed within neural protection element 200, such that wire loop electrodes 350 are positioned within window 204.

Figure 94:
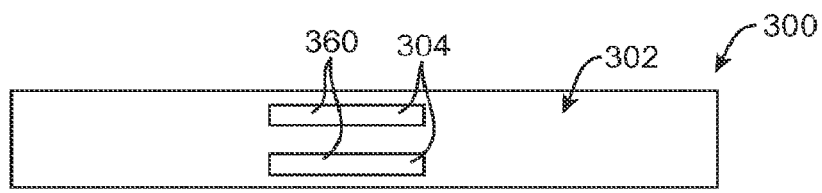
FIG. 94 is a schematic view of another variation of electrosurgical tissue removal elements.

FIG. 94 illustrates an electrosurgical variation comprising bipolar electrode pair 360 that serve as tissue removal elements 304 disposed on tissue removal surface 302 of device 300. Device 300 may, for example, comprise an electric textile or a flexible printed circuit board having electrode pair 360. The electrodes may be brought into contact with impinging tissue, then actuated to remove the tissue. Advantageously, in the variation of FIG. 94, device 300 optionally may remain stationary during tissue removal. The device optionally may be integrated with neural protection element 200 such that the bipolar electrode pair is formed on the working side of the protection element. For example, a bipolar electrode pair may be formed across window 204, and the impinging tissue optionally may be drawn within the window via suction or some other means prior to electrosurgical removal.

Figure 95:
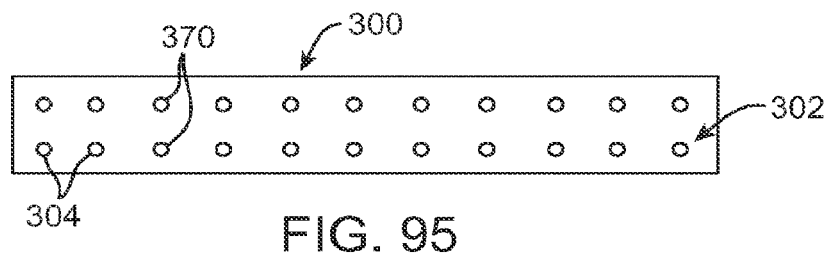
FIG. 95 is a schematic view of another variation of electrosurgical tissue removal elements.

FIG. 95 illustrates another electrosurgery variation of device 300 wherein tissue removal surface 302 comprises a plurality of electrosurgery tissue removal elements 370, illustratively bipolar electrode pairs. The bipolar electrodes may be actuated or energized, either concurrently or in any desired sequence, while surface 302 of device 300 is drawn across impinging tissue to remove the tissue.

Figure 96:
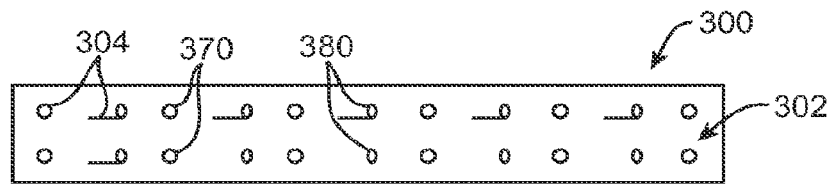
FIG. 96 is a schematic view of a variation of the tissue removal device comprising both mechanical and electrosurgical tissue removal elements.

FIG. 96 illustrates a combined mechanical and electrosurgical tissue removal device 300. Tissue removal surface 302 comprises mechanical tissue removal elements 380, illustratively stamped or raised shaver blades, interspersed with electrosurgery tissue removal elements 370, illustratively bipolar electrode pairs.

Figure 97:
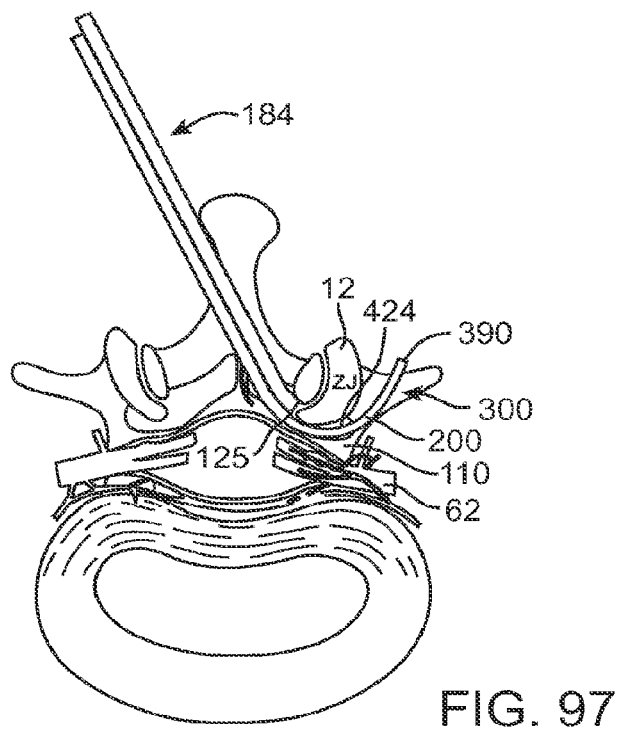
FIG. 97 is a cross-sectional view through a patient's spine, illustrating a variation of methods and apparatus for selective electrosurgical removal of tissue.

FIG. 97 illustrates an exemplary method of using an electrosurgery variation of the tissue removal device. In FIG. 97, neural protection element 200 is delivered, illustratively via previously described access element 180. In this variation, element 200 illustratively comprises a local backstop that does not extend out of the patient. Tissue removal device 300 is positioned between element 200 and the impinging tissue, and optionally may be anchored via temporary tissue anchor 390 to provide leverage for pulling the device into contact with the impinging tissue. Electrosurgery tissue removal elements 304 then may be actuated to remove the impinging tissue and/or provide hemostasis, etc. Although element 200 and device 300 illustratively do not extend out of the patient in the electrosurgery variation of FIG. 97, it should be understood that in other electrosurgery variations the elements may extend outward through the patient's skin as described previously.

Figure 98A:
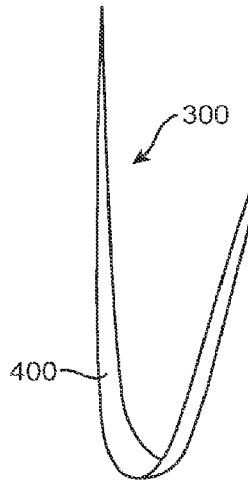
FIGS. 98A-98C are schematic views of a depth-limited variation of the tissue removal device.
Figure 98B:
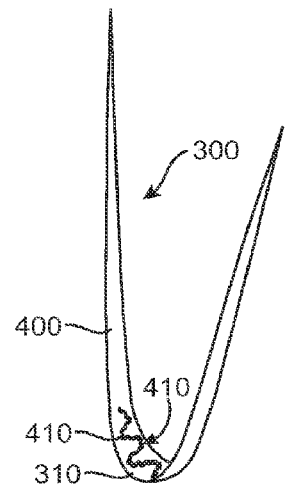

Referring now to FIG. 98, another variation of tissue removal device 300 is described. As seen in FIG. 98A, tissue removal device 300 may comprise flexible support 400 that may be positioned, for example, through or along neural protection element 200, or may be integrated with the neural protection element. As seen in FIG. 98B, at least a portion of support 400 comprises wire saw 410 that is coupled to the support and serves as tissue removal element 304 disposed on the working surface of device 300. The wire saw may be drawn or reciprocated across impinging tissue, such that saw 410 locally removes tissue. Since support 400 is wider than wire saw 410, the support limits a depth of cutting via wire saw 410.

Figure 98C:
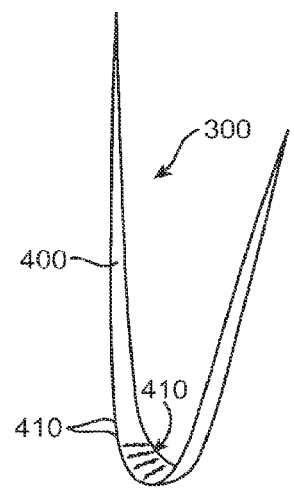

The medical practitioner may move support 400 laterally while drawing or reciprocating the wire saw across tissue in order to enlarge a width of the region in which tissue is removed. Support 400 may limit a depth of cutting during such lateral expansion of the cut area. When the lateral expansion exceeds the width of support 400, cutting to greater depth may be performed as desired. The width of the area of tissue removal alternatively or additionally may be enlarged or expanded by utilizing multiple wire saws 410, as seen in FIG. 98C. The multiple saws may be advanced initially, or may be advanced after creation of an initial cut with a single saw such as that of FIG. 98B. Additional methods of using the variation of FIG. 98 for selective removal of tissue will be apparent.

Figure 99A:
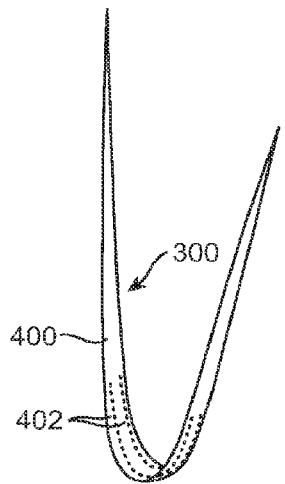
FIGS. 99A and 99B are schematic views of a fenestrated, depth-limited variation of the tissue removal device.
Figure 99B:
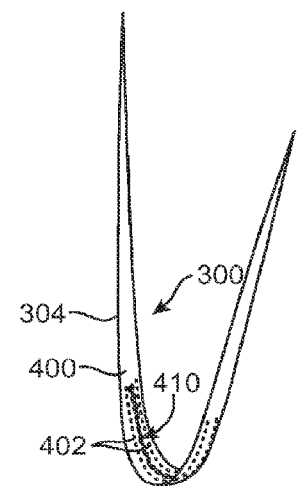

With reference to FIG. 99, a variation of the tissue removal device of FIG. 98 is described. As seen in FIG. 99, support 400 may comprise fenestrations 402 that facilitate passage of removed tissue through the fenestration for removal. FIG. 99A illustrates a segment of support 400 without wire saw(s) 410, while FIG. 99B illustrates a segment with the wire saw. Wire saw(s) 410 may be coupled to the support or optionally may be advanced into position along the support, then reciprocated or moved in conjunction with the support, such that the support limits a depth of cutting via the saw(s). When tissue removal device 300 having fenestrated support 400 is disposed within neural protection element 200, fenestrations 402 may facilitate passage of removed tissue or other debris through the fenestrations, such that they are captured within the neural protection element between the neural protection element and the tissue removal device for removal from the patient.

Referring to FIG. 100, another variation of tissue removal device 300 is shown. In FIG. 100, tissue removal device 300 is integrated within neural protection element 200. The tissue removal device comprises tissue removal elements 304 having blades 420, illustratively cup blades with sharpened edges. Blades 420 are coupled to drive shafts 422 that rotate the blades (either individually or in unison) at high speed for tissue removal. Drive shafts 422 may be utilized (either individually or in unison) to advance and/or retract rotating blades 420 across window 204 of neural protection element 200 for removal of tissue. Although device 300 illustrative comprises a plurality of blades 420 and drive shafts 422, it should be understood that the device alternatively may comprise a single blade and drive shaft, or a single drive shaft for rotating multiple blades Any other tissue removal elements 304 may be utilized with any of the variations of tissue removal device 300, including, but not limited to, lasers, which may comprise one or more optical fibers for delivering a laser beam, high-pressure fluids, thermal elements, radioactive elements, etc. It should be understood that various tissue removal elements may be used in any combination, as desired.

Figure 101:
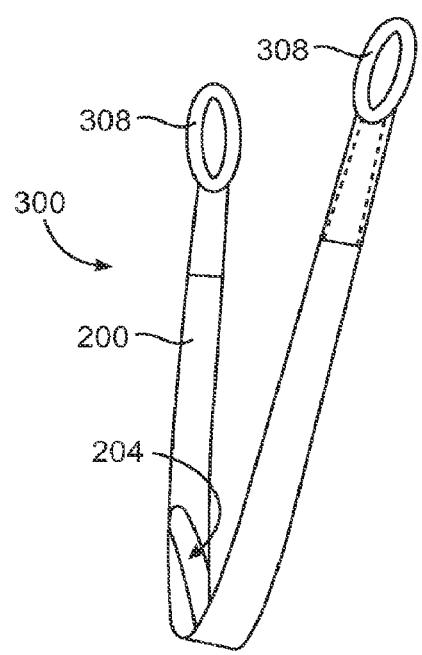
FIG. 101 is a schematic view of a variation of the tissue removal device configured for selective removal of tissue via manual reciprocation.

In one variation, device 300 may be reciprocated, either manually or under power, to cut, abrade or otherwise remove tissue. FIG. 101 illustrates a variation of tissue removal device 300 well-suited for manual reciprocation. In FIG. 101, device 300 illustratively comprises handles 308, one or both of which may be detachable for placement and/or retrieval of the device. The medical practitioner may grasp the handles and reciprocate device 300 to selective remove tissue impinging on window 204 of neural protection element 200.

Figure 102:
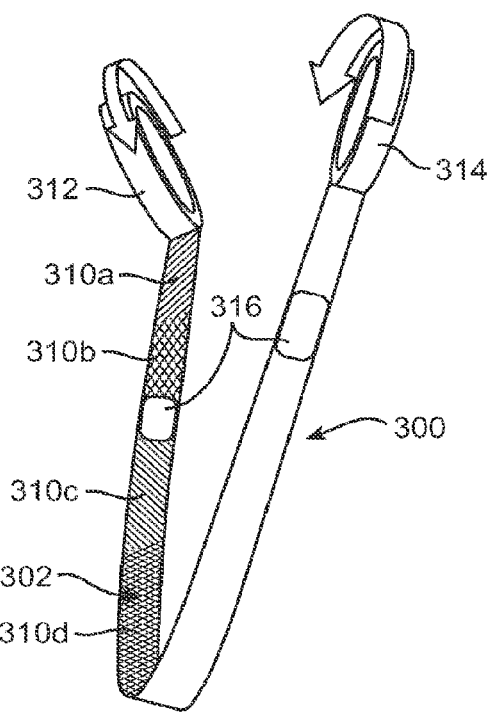
FIG. 102 is a schematic view of a variation of the tissue removal device configured for unidirectional removal of tissue.
Figure 103A:
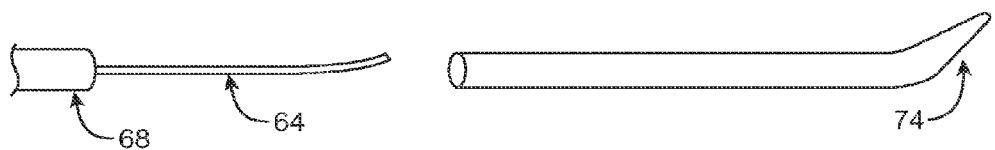
Figure 103B:
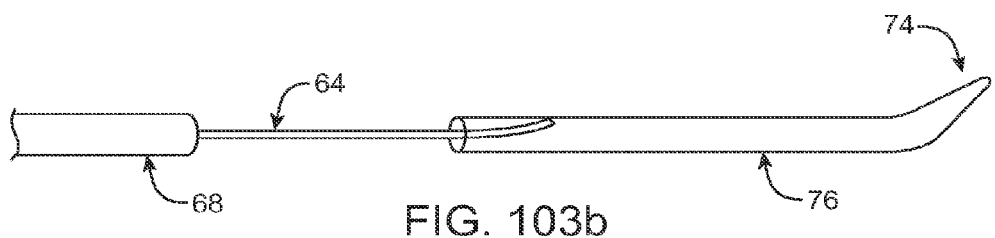
Figure 103C:
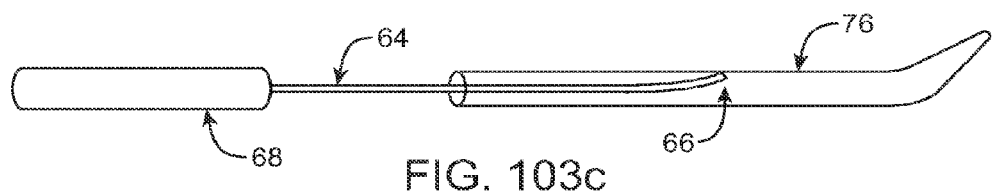
Figure 103D:
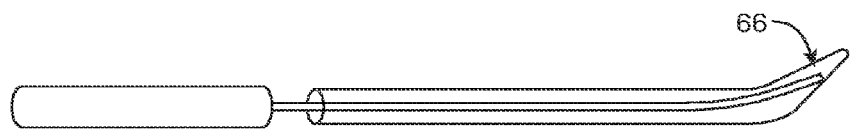

In another variation, device 300 may be pulled in a single direction, either manually or under power, to remove tissue. FIG. 102 illustrates a variation of device 300 well-suited for unidirectional tissue removal, either manual or powered. In FIG. 102, device 300 comprises a reel-to-reel configuration. Tissue removal elements 304 illustratively comprise abrasive regions 310 on tissue removal surface 302 of the device. The abrasive regions may, for example, comprise a diamond or oxide coating on surface 302. Abrasive regions 310a, 310b, 310c, 310d, etc., become progressively less abrasive between reel 312 and reel 314. In this manner, the location where tissue is selectively removed may be smoothed or sanded with a progressively finer 'grit' as surface 302 moves across the tissue in a single direction from reel 314 to reel 312.

Tissue removal device 300 may be tapered, such that the width of the device increases as it is wound between the reels to provide for a gradual decompression. The device optionally may comprise measuring elements 316, such as sensors or progressively larger sounds, for determining the effectiveness of decompression, thereby providing the medical practitioner with an indicator for when the reels may be advanced. Tissue removal surface 302 optionally may comprise section 316 that contacts the tissue surface after selective tissue removal for delivery of bone wax, hemostatic agents such as thrombin, antiproliferative agents, steroids, non-steroidal anti-inflammatory drugs, or any other therapeutic agent.

In one variation, the device includes a compression dressing as illustrated in the percutaneous embodiment described above in FIGS. 63 and 64. Following neuroforaminal and lateral recess enlargement, it may be advantageous to leave, as a surgical dressing, a belt or ribbon pulled tightly against the abraded tissue surface. It is expected that a compression dressing will enhance hemostasis, promote healing and promote subsequent tissue remodeling with the neural foramen widely open. Furthermore, the surgical dressing would provide a barrier to trap tissue debris away from neural or neurovascular structures, while providing an optional technique for delivering medication, possibly as a depot, to the operative site. The dressing would also present a smooth surface towards the nerve root in the immediate post-operative period.

The neuroforaminal compression dressing may, in one preferred embodiment, comprise the optional protective sheath, percutaneously held tightly in place against the abraded surface, after the abrasive apparatus has been removed from its lumen, for a period of time. Alternatively or additionally, a separate percutaneously removable compression dressing may be placed following tissue abrasion. The abrasive material may be followed by a length of compression dressing material on the same reel or spool, or a subsequent reel or spool. Alternatively, a compression dressing may be delivered through the neural foramen as a separate element. The compression element may also be used to deliver medications or other bioactive components (e.g. steroid, biodegradable adhesion barriers, etc.), to the surgical site. The compression dressing material may be, in one variation, partially or completely biodegradable. An entirely biodegradable compression dressing may be placed tightly against the abraded surface, and left completely implanted following the procedure.

Figure 104A:
Figure 104B:
Figure 105A:
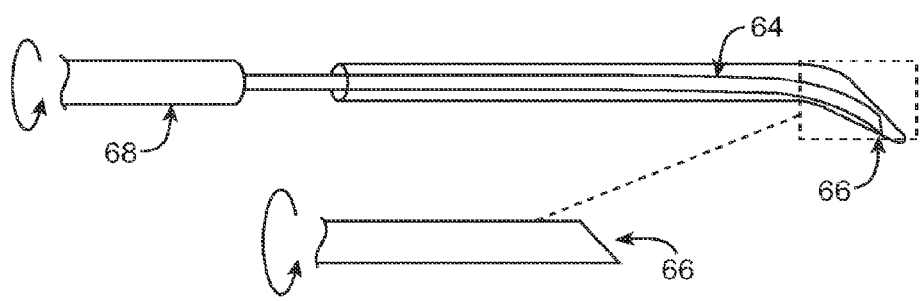
Figure 105B:
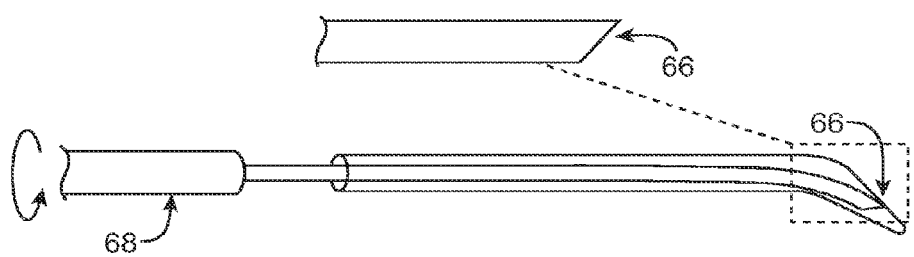
Figure 106A:
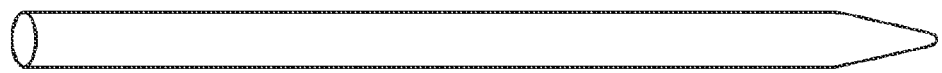
FIGS. 106a-c illustrate various embodiments of a clear tipped cannula with a clear shaft.
Figure 106B:
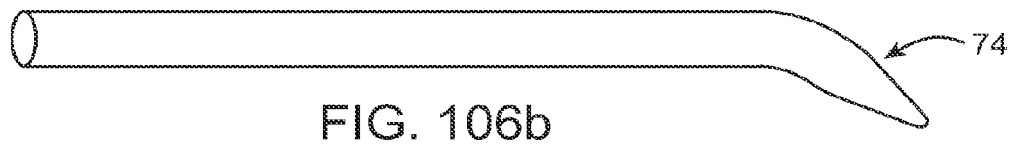
Figure 106C:
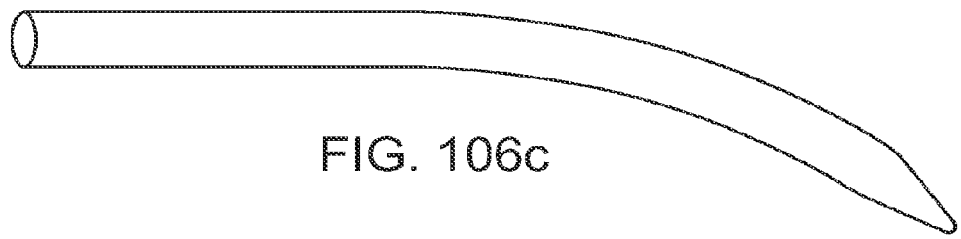
Figure 106D:
FIGS. 106d-f illustrate various embodiments of a clear tipped cannula with an opaque shaft.
Figure 106E:
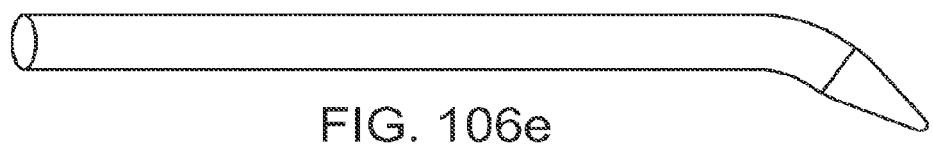
Figure 106F:
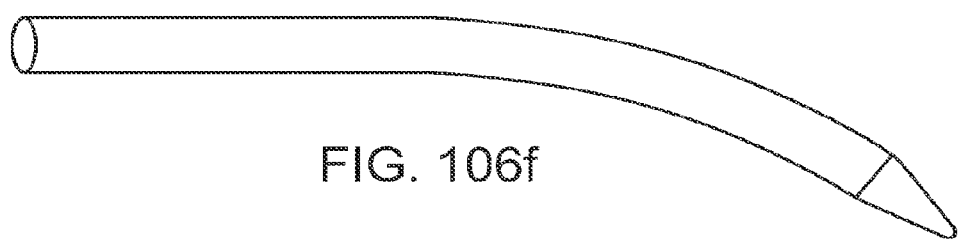
Figure 107A:
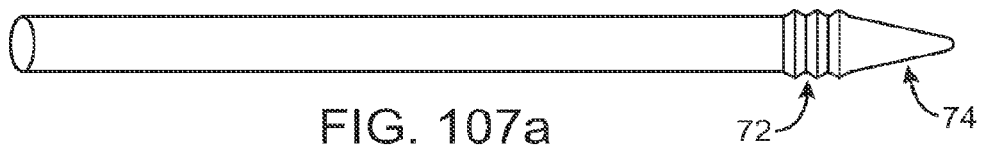
Figure 107B:
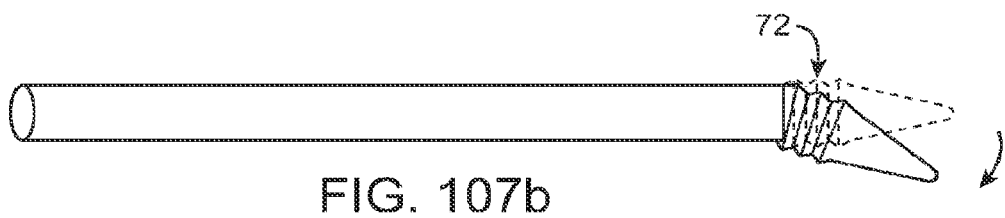
Figure 107C:
Figure 107D:
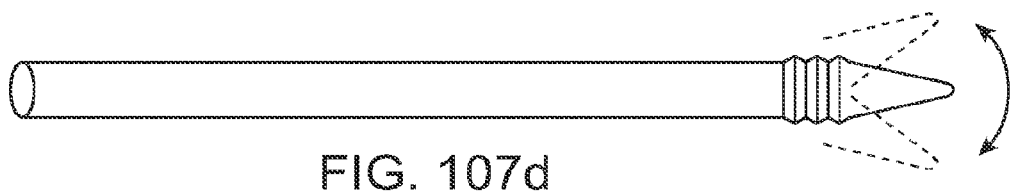
Figure 108:
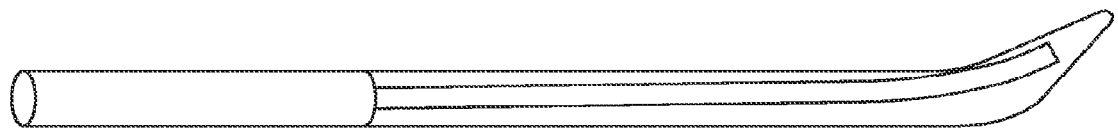
Figure 109A:
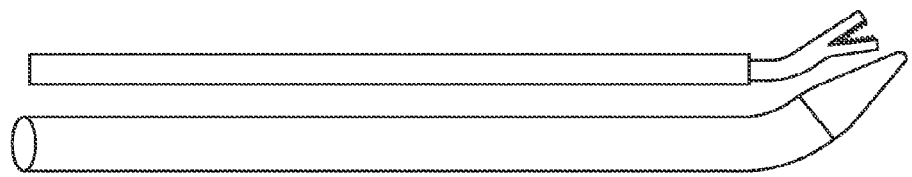
Figure 109B:
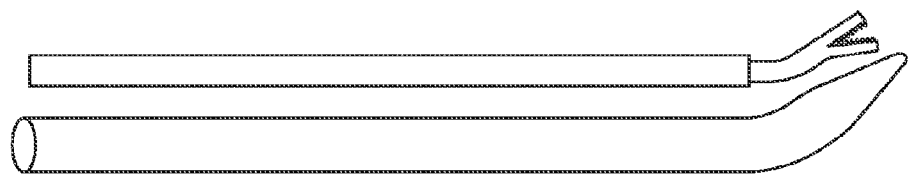
Figure 110A:
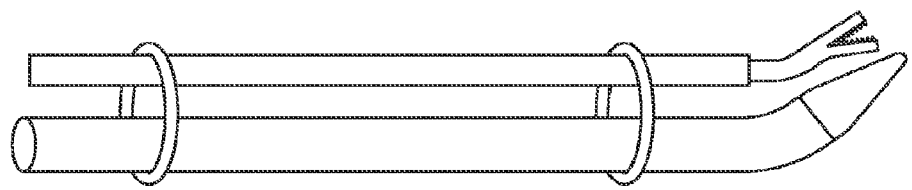
Figure 110B:
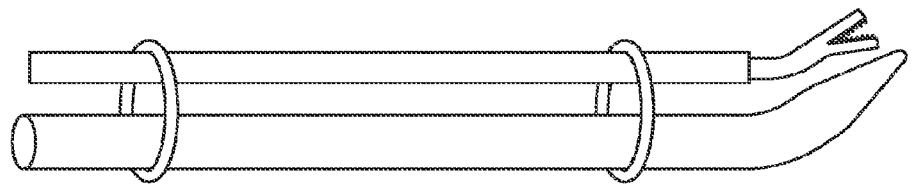
Figure 111A:
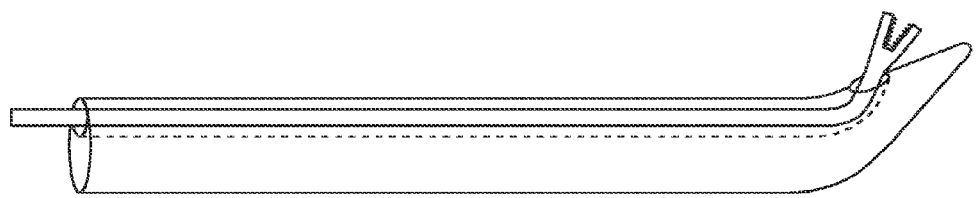
FIG. 111a illustrates an embodiment of a clear tipped cannula with a working channel for a tool.
Figure 111B:
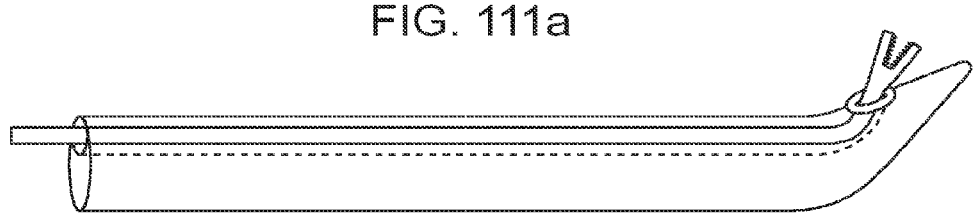
FIG. 111b illustrates an embodiment of a clear tipped cannula with a nerve stimulator at a working channel exit.

Whether placing the apparatus with an epidural needle 2; through the working channel of an epidural needle 50; with an epidural endoscope; or during an open surgical procedure; image guidance may be used to facilitate safe and accurate placement. If the epidural needle 2 has been replaced by, or converted to, an endoscope, direct visualization of the epidural space 42 may be accomplished. In this case, as illustrated in FIGS. 103-104, the clear tip of the fiberoptic scope will facilitate visualization through the fat present in the epidural space 42. The fiberoptic cable may be rigid or flexible, with the flat surface of its distal tip 66 perpendicular (0°, for straight ahead viewing) or at an angle (e.g. 30°, 45°, or 60°). The cannula may be closed at its end, as in FIGS. 103-114, covering and protecting the distal end of the fiberoptic cable with a clear tip 74 which may be solid, fluid, or gas filled, potentially sized and shaped to expand the area of viewing within the fat filled epidural space 42. Additionally the endoscope or "needlescope" may contain an additional channel or space for infusion of fluid into the epidural space, in order to facilitate visualization, to create a space for visualization, and/or to decrease bleeding by increasing pressure, towards or above venous pressure, within the viewing area.

FIGS. 103 through 114 illustrate several embodiments of closed tip portals for epidural fiberoptic visualization. Some description of these portals may be found in the text above. Basically, the portals show several preferred variations of designs that enable visualization through the fat that exists in the epidural space. The clear tips of the portals may be solid and clear, or may contain air or clear liquid. The volume of the tip creates a space for improved perspective during visualization.

Figure 112A:
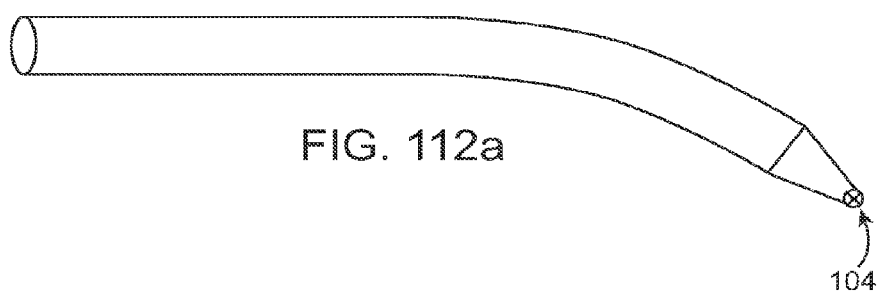
Figure 112B:
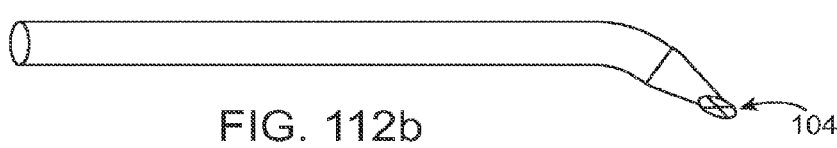
Figure 112C:
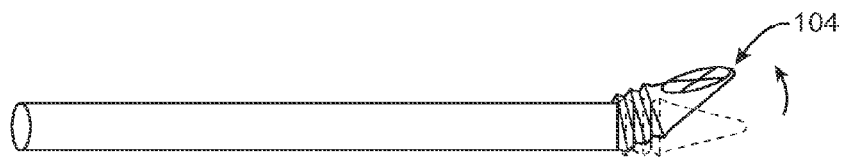
Figure 113A:
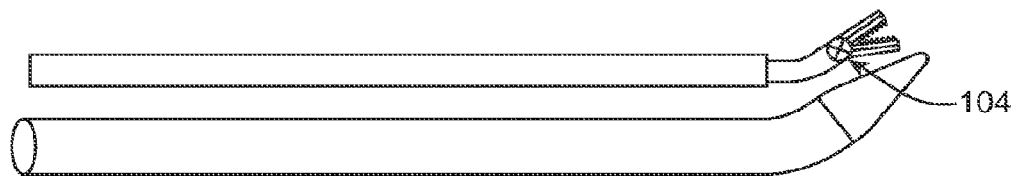
Figure 113B:
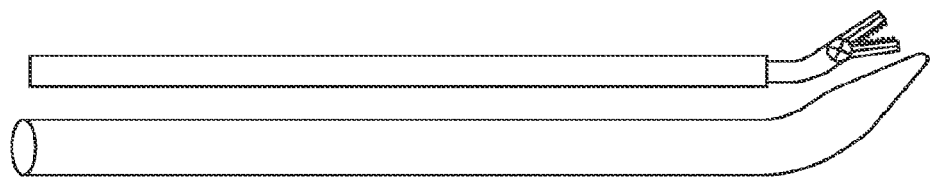
Figure 114A:
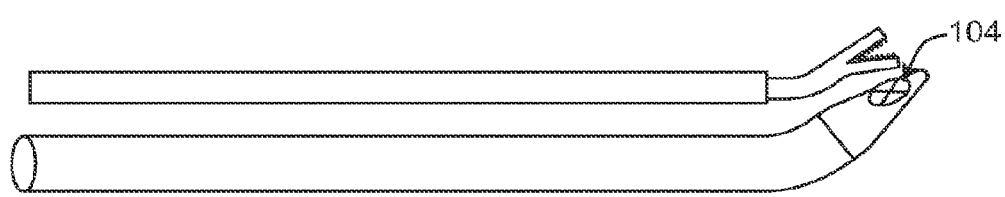
Figure 114B:
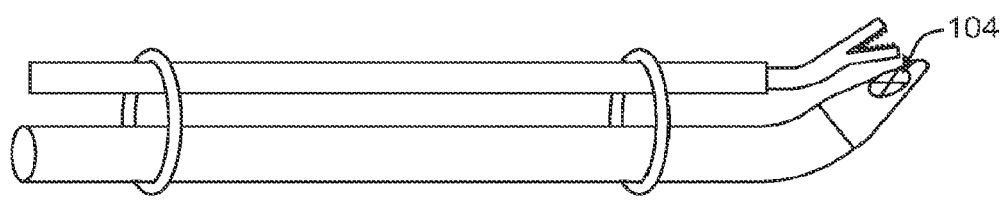

Referring now to FIG. 103, a hockey stick shaped portal facilitates steering of the portal by rotation of the device. Such a design may be used with a flexible, partially flexible, or rigid fiberoptic element 64. Besides steering the portal tip, the fiberoptic element may be rotated separately in order to direct visualization, when angled scope tips are used (e.g. 30°, 45°, 60°). Alternative embodiments, as illustrated in FIG. 107, may allow the tip of the instrument to be steered. FIGS. 109-111, 113, and 114 illustrate means of delivering tools along with the epidural endoscopic portals. Finally, FIG. 112 show a couple of different shapes of the many possible variations that may be helpful in improving visualization and access to the central canal, lateral recesses, neural foramen and posterior annulus of the spine.

Figure 115:
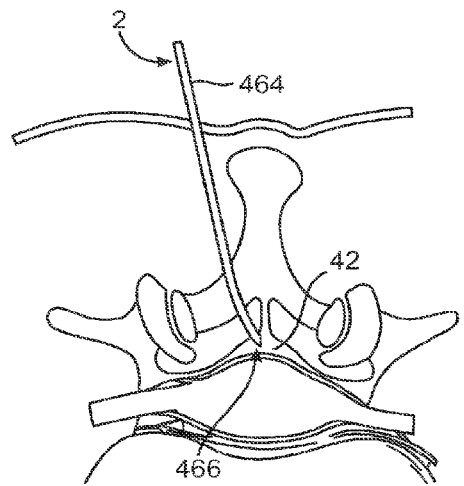
FIGS. 115-116 are cross-sectional views through the lumbar spine, illustrating a standard method for epidural needle and epidural catheter placement.

FIG. 115 illustrates that a percutaneous access element, for example the epidural needle 2, can be deployed in the epidural space 42. The needle 464 can have a sharpened distal needle tip 466. The needle 464 needle 464 can be deployed via percutaneous or open procedures described herein. The needle 464 can be deployed via percutaneous access to the lateral recess and neural foramen 110. The needle 464 can be inserted at or one level below the spinal interspace where tissue removal is desired. The needle 464 can be inserted into the epidural space 42 midline, ipsilateral, or contralateral to the area where the spinal canal, lateral recess and/or neuroforaminal stenosis or impingement is to be treated. Percutaneous access can be aided by image guidance, an epidural endoscope, any other visualization technique, or combinations thereof.

The needle 464 can have multiple barrels or lumen, for example a first lumen and a second lumen (not shown). The first lumen can extend distally of the second lumen. The first lumen and/or the second lumen can terminate in open or closed configurations at the needle tip 466.

Figure 116:
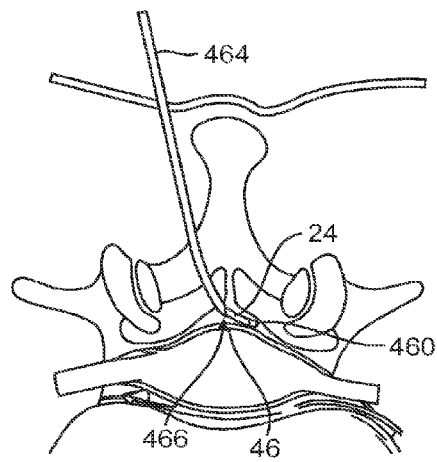

FIG. 116 illustrates that a catheter 24 can then be deployed through the needle 464 and into the epidural space 42, as shown by arrow. The catheter distal tip can have a protective hood 460 or a needle cap, for example, over the needle tip 466.

Figure 117:
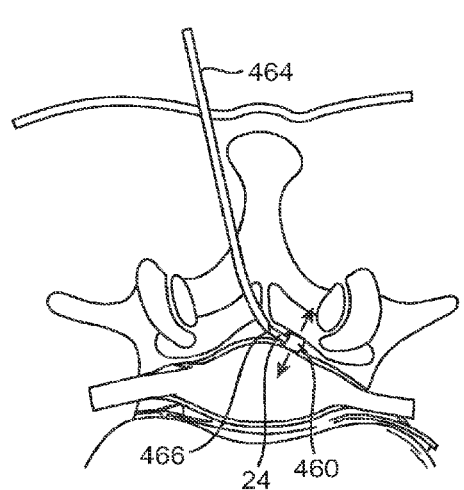
FIGS. 117-118 are cross-sectional views through the lumbar spine, illustrating a method and apparatus that converts a sharp epidural needle into an atraumatic blunt instrument in the epidural space.

FIG. 117 illustrates that when the catheter 24 has been placed in the epidural space 42, the user can open the hood 460, as shown by arrows.

Figure 118:
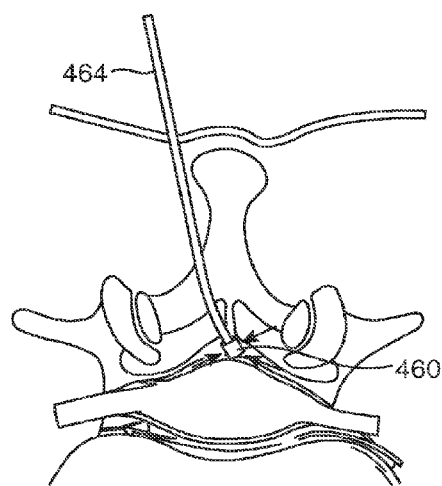

FIG. 118 illustrates that after the hood 460 is opened, the catheter 24 can be slidably retracted through the needle 464 until the hood 460 firmly covers the needle tip 466. When the hood 460 firmly covers the needle tip 466, the catheter 24 can be fixed to the needle 464. The needle 464 with the hood covering the needle tip 466 can be a blunt instrument.

FIG. 119 illustrates that the needle 464 can be advanced, as shown by arrow, until the needle tip 466 is in a lateral recess 108, adjacent to the neural foramina 110. The user can position the needle tip 466 adjacent to the lateral recess 108 using tactile feedback from the needle 464, image guidance (e.g. fluoroscopy), or combinations thereof.

FIG. 120 illustrates that a neural stimulation and localization device 114 can be attached to the catheter 24 and/or needle 464 and or a device within the needle or catheter, for example a tissue protection barrier (not shown). The neural stimulation and localization device 114 can have a controller. The neural stimulation and localization device 114 can be configured to selectively deliver and/or sense electrical current.

The user can visualize the epidural space 42, for example, via a fiber optic element (not shown). The fiber optic element can be covered by a clear distal tip. The fiber optic element can be deployed to the epidural space 42 integral with, or separate from but within, the catheter 24. The fiber optic element can be deployed to the epidural space 42 integral with, or separate from but within, the needle 464. The fiber optic element can be deployed to the epidural space 42 via a working space adjacent the needle 464. The user can deploy an epidural endoscope, for example, to visualize the epidural space 42 including the lateral recess 108 and neural foramen 110.

An access element (not shown) that can have a cannulated probe such as a cannulated ball-tipped probe, Woodson elevator, or Hockey Stick hybrid, can be placed into the epidural space 42. A curved element, such as an atraumatic needle, can then be advanced through the cannula of the probe and into the neural foramen 110. The curved element can cannulate the neural foramen 110.

FIG. 121 illustrates that a tissue protection element or barrier 528 can be deployed through or with the needle 464, and/or the catheter 24, and/or a supplemental curved needle (not shown), and/or a shield (not shown), as shown by arrows. The tissue protection barrier 528 can be part of a tissue removal apparatus. The tissue removal apparatus can be further comprised by the needle, and/or hood.

The tissue protection barrier can be deployed into the lateral recess 108 and/or the neural foramen 110. The tissue protection barrier 528 can be deployed between the tissue to be removed, for example the impinging tissue 424, and the tissue to be protected, for example, the dura mater 46 and associated neural (e.g., spinal cord, nerve roots, dorsal root ganglion) and neurovascular structures. The tissue protection barrier 528 can have contracted and expanded configurations. During deployment, the tissue protection barrier 528 can be in the contracted or expanded configurations. The tissue protection barrier 528 can be separate from, or integral with, the catheter 24 and/or needle 464. The tissue protection barrier 528 in a contracted configuration can be slidably attached to the catheter 24 and/or the needle 464.

The tissue protection barrier 528 can have an atraumatic profile. The tissue protection barrier 528 can have rounded edges. The tissue protection barrier 528 can be a catheter, curved or straight needle, curved or straight shield, sheath, backstop, stent, net, screen, mesh or weave, panel, fan, coil, plate, balloon, accordioning panels, or combinations thereof. The tissue protection barrier 528 can have a tapered configuration.

The tissue protection barrier 528 can have a front side (i.e., working side) and a back side (i.e., neural protection side). The front side 456 can be electrically isolated from the back side 428. The front side 456 can have an electrically conductive surface. The back side 428 can have an electrically conductive surface. The neural stimulation and localization device 114 can be in electrical communication with the front side 456 and/or the back side 428.

Neural stimulation can be monitored via spinal somatosensory-evoked potentials (SSEPs), motor-evoked potentials (MEPs), and/or by looking for visual signs of muscular contraction within the extremities. SSEP, SEP, MEP or electromyogram (EMG) feedback can be monitored and/or recorded visually, and/or can be monitored audibly, potentially conveying quantitative feedback related to the volume or frequency of the auditory signal (e.g. a quantitative auditory feedback). Intensity of signal or stimulation can be monitored and used to localize the nerve during placement.

The neural stimulation and localization device 114 can deliver electrical current to the front side 462. If there is a nervous system response, the tissue protection barrier 528 can be retracted and redeployed with the front side and the back side switched. The neural stimulation and localization device 114 can then deliver electrical current to the front side 456 again and the tissue protection barrier 528 can be readjusted and redeployed until there is no nervous system response from delivering electrical current to the front side 456.

The neural stimulation and localization device 114 can deliver electrical current to the back side 428. If there is no nervous system response, the tissue protection barrier 528 can be retracted and redeployed with the front side and the back side switched. The neural stimulation and localization device 114 can then deliver electrical current to the back side 428 again and the tissue protection barrier 528 can be redeployed and readjusted until there is a nervous system response from delivering electrical current to the back side 428.

The neural stimulation and localization device 114 can deliver electrical current to the back side 428 and the front side 456 and the tissue protection barrier 528 can be readjusted and redeployed until there is a nervous system response from delivering electrical current to the back side 428 and no nervous system response from the front side 456.

The user can deploy to the neural foramen 110 and/or the lateral recess 108 one or more surgical stimulating and monitoring instruments (e.g., cautery devices, graspers, shavers, burrs, probes, combinations thereof) that can selectively stimulate electrically while monitoring nerve stimulation. The surgical can quantify the stimulation to localize the neural tissue (e.g., dura mater, spinal cord, spinal root, dorsal root ganglion). For instance, the user can use a calibrated sensor input that recognizes stronger stimulation as the device is moved closer to neural structures.

FIG. 122 illustrates that the tissue protection barrier 528 can be transformed, as shown by arrows, into the expanded configuration. The hood 460can be retracted toward the needle 464. A balloon (not shown) can be inflated within the tissue protection barrier 528. The tissue protection barrier 528 can be twisted with respect to itself. An electrical current and/or heat can be applied to the tissue protection barrier 528, for example, that can be made from a shape memory alloy. The hood retracting, and/or balloon inflating, and/or tissue protection barrier 528 twisting with respect to itself, and/or heating can expand the tissue protection barrier 528.

A spring can be inside the tissue protection barrier 528. The tissue protection barrier can be the spring, for example when the tissue protection barrier 528 is or has a self-expandable stent or mesh. The spring can be releasably fixed in a compressed state when the tissue protection barrier 528 is in the contracted configuration. When released, the spring can expand the tissue protection barrier 528. The spring can be released by a trigger mechanism.

The expansion of the tissue protection barrier 528 can apply a non-damaging pressure to the nerve branches 62. The tissue protection barrier 528 can have a window 536. The window 536 can be open in the contracted and/or expanded configuration of the tissue protection barrier 528.

Figure 123:
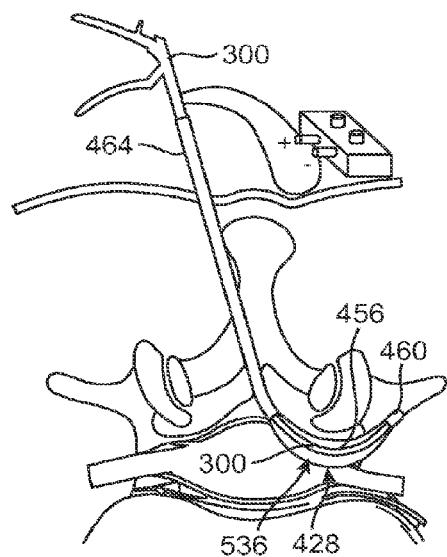
FIG. 123 is a cross-sectional view through a patient's spine, illustrating placement of the energy delivery apparatus into the protected working tissue removal space created by the neural protection element.

FIG. 123 illustrates that a tissue removal device 300 can be attached to, and/or slidably deployed along, through, around or over the needle 464 and/or the catheter 24. The tissue removal device 300 can be deployed between the impinging tissue 424 and the tissue protection barrier 528. The tissue removal device 300 can have a control handle extending from the proximal end of the needle 464. The tissue removal device 300 can be exposed to the impinging tissue through the window 536 (e.g., needlette ports 472).

The tissue removal device 300 can have an energy delivery system (not shown). The energy delivery system can be configured to deliver one or more energies to tissue adjacent to the energy delivery system. The energies can be configured to ablate, vaporize, break up, combinations thereof, or otherwise change the modulus of the tissue. The tissue removal device 300 can be configured to deliver electrical, ultrasound, thermal, microwave, laser, cryo (i.e., removing thermal energy), or combinations thereof.

The tissue removal device 300 can have one or more electrosurgery elements (not shown). The electrosurgery elements can be configured to remove and/or ablate tissue. The electrosurgery elements can achieve hemostasis and/or neural localization in tissue adjacent to the electrosurgery elements. The electrosurgery elements can have monopolar or bipolar RF elements. The RF elements can be activated with a thermal or substantially non-thermal waveform.

The tissue removal device 300 can have or be lasers, high-pressure fluid, thermal elements, radioactive elements, textile electric conductors, conductive wire loops and/or needles configured to be used in tissue contact (e.g., needle ablation), springs, open and/or spring wire weaves, conductive polymers that can have conductive metals chemically deposited thereon, or combinations thereof.

Figure 124:
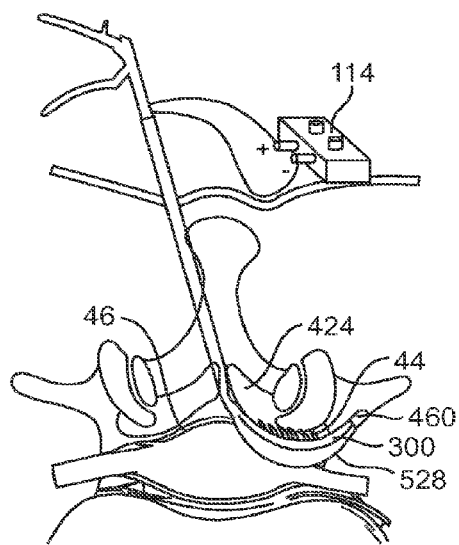
FIG. 124 is a cross-sectional view through a patient's spine, illustrating delivery, to the pathologically impinging tissue, of energy (e.g. electrical, bipolar, monopolar, thermal, laser, cryo, ultrasound, microwave, etc.) in order to vaporize, destroy, break up, liquefy, or otherwise change the impinging tissue modulus for subsequent ease of removal of said pathologically impinging tissue.

FIG. 124 illustrates that the tissue removal device 300, for example the energy delivery system, can transmit energy 44 to the tissue to be removed, for example, the impinging tissue 424. The energy 44 can alter the compression, denaturation, electrosurgical exposure, thermal remodeling (hot or cold), chemical alteration, epoxy or glues or hydrogels, modulus of elasticity, or any combination thereof of the impinging tissue 424. For example, the modulus of elasticity of soft impinging tissue 424 can be increased. An increased modulus of elasticity can improve purchase on the soft impinging tissue 424 with the tissue removal device 300. Remodeling of the tissue during modulus alteration can alleviate impingement and obviate or reduce a need for tissue removal.

The tissue removal device 300 can be designed to automatically stimulate the site of tissue removal, or have the neural stimulation and localization device 114 stimulate the site of tissue removal, before or during tissue removal. The tissue removal device 300 can be configured to automatically stop tissue removal when nerve stimulation is sensed by the front side 456, and/or no nerve stimulation is sensed by the back side 428.

Figure 125:
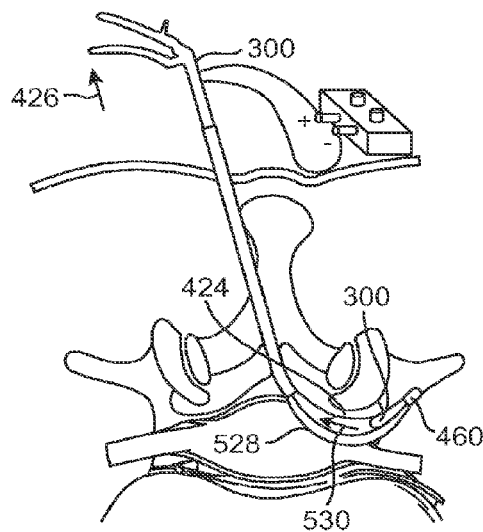
FIGS. 125-126 are cross-sectional views through a patient's spine, illustrating the advancement and retraction of a guillotine blade through the pathologically impinging tissue and/or debris, for removal.

FIG. 125 illustrates that the tissue removal device 300 can have one or more non-powered mechanical tissue removal elements. The non-powered mechanical tissue removal elements can be abrasives such as abrasive belts or ribbons, cutting elements such as blades, knives, scissors or saws, rongeurs, grinders, files, debriders, scrapers, graters, forks, picks, burrs, rasps, shavers, or combinations thereof.

An external activating force, for example as shown by arrow 530 (activating tissue removal) on a handle, can activate the tissue removal device 300, as shown by arrow 530 (tissue removal device operating). The mechanical tissue removal elements can be used in combination or not in combination with the energy delivery device. The mechanical tissue removal elements can be pushed into and/or drawn across the impinging tissue 424 to remove the tissue by cutting, shaving, slicing, scissoring, guillotining, scraping, tearing, abrading, debriding, poking, mutilating, or combinations thereof. The mechanical tissue removal elements (e.g., blades) can be drawn across the impinging tissue 424 in a single direction and/or can be reciprocated. The mechanical tissue removal elements can be manually controlled and/or electronically, pneumatically or hydraulically powered. The mechanical tissue removal elements can be embedded with abrasives and/or have abrasive coatings, such as a diamond or oxide coating.

The blades can have various shapes, sizes and configurations. The blades can coact, for example, in a guillotine-type or scissor-type cutting action. The blades can be attached to or integral with the tissue removal device. The blades can be formed by grinding, punching or stamping through the tissue removal device. The blades can be formed by grinding of a punched or stamped edge of the tissue removal device. The blades can be formed by a chemical etching process. The blades can have a 3-dimensional profile to facilitate cutting, for example, a bow or a corrugation or a 'cheese grater' profile. The blades can be placed at one or more angles relative to the direction of tissue removal. The blades can be configured with the blade cutting across the tissue (i.e., similar to a band saw). The blades can have cutting surfaces. The cutting surfaces can be oriented in a single or multiple directions. The blades can be serrated.

The saw can be a wire saw or saws. The wire saw can be a Gigli saw. Multiple wire saws or Gigli saws can be joined or woven together or flattened to form a substantially planar cutting surface. The wire saw can be mounted on a flat ribbon. The ribbon can be a depth stop, for example, limiting for saw penetration.

The tissue removal device 300 can have one or more powered mechanical tissue removal elements. The powered mechanical tissue removal elements can have, for example, band saws, belt shavers, rotary burrs or blades, reciprocating burrs or blades, or combinations thereof.

Devices and elements known to those having ordinary skill in the art can be used to remove debris from, and/or irrigate, and/or provide suction to, the epidural space 42 including the lateral recess 108 and neural foramen 110 and/or to the tissue removal device itself. The devices and elements for removing debris can be integral with the needle 464 and/or the catheter 24. Debris removal, and/or suction and/or irrigation may be provided intermittently or continuously, as desired by the medical practitioner. Debris removal can include suction and/or irrigation. The tissue removal device 300 can capture debris. Irrigation and/or suction in the tissue removal device 300 can remove the debris from the tissue removal device 300, for example by the debris exiting along the needle 464 and/or catheter 24.

Figure 126:
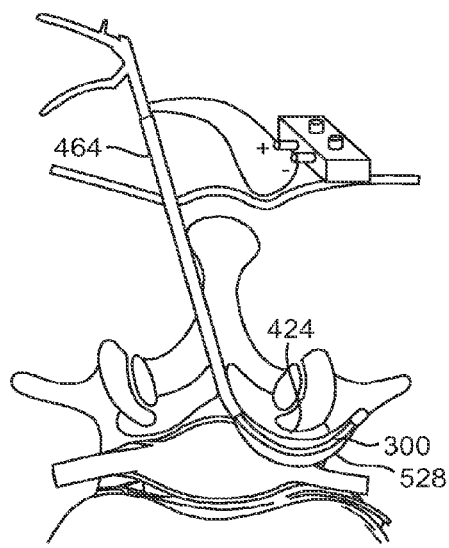
Figure 127:
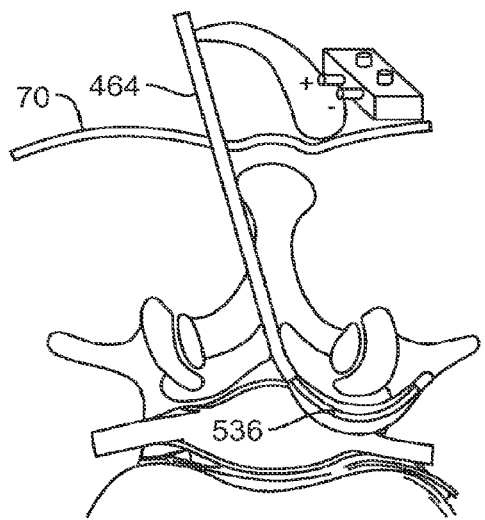
FIGS. 127-130 are cross-sectional views through a patient's spine, illustrating one example of possible steps for the removal of the energy delivery apparatus, neural protection element, epidural catheter and needle.

FIG. 126 illustrates that when tissue removal device 300 removes enough impinging tissue to reduce the pressure on the neural (e.g., nerve roots, spinal cord, dorsal root ganglion) and neurovascular tissue, the tissue removal device 300 can be removed from the tissue protection barrier 528, and/or the needle 464, and/or the catheter 24. The tissue removal device can be withdrawn from the skin 70, as shown in FIG. 127.

Figure 128:
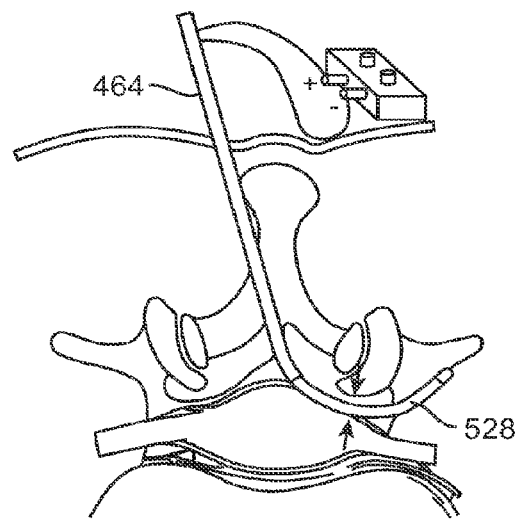
Figure 129:
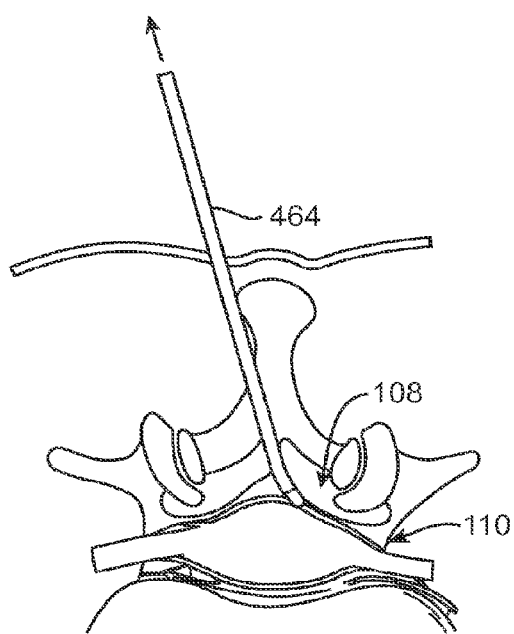
Figure 130:
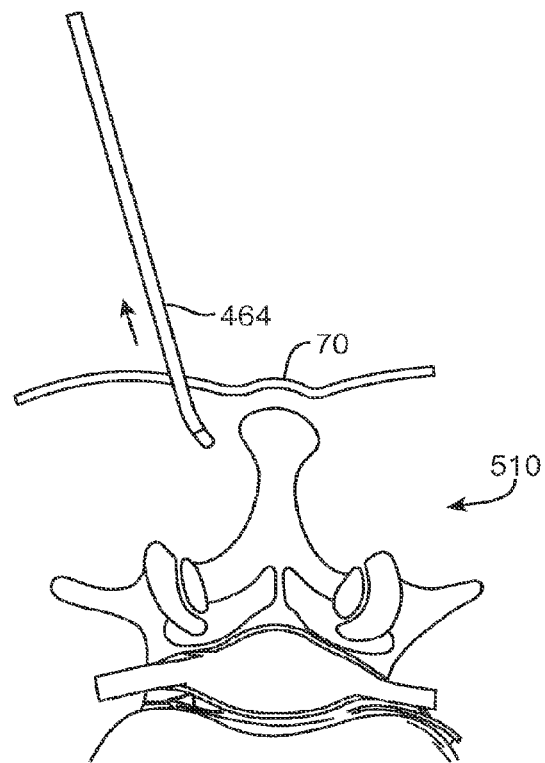

FIG. 128 illustrates that the tissue protection barrier 528 can be transformed into a contracted configuration, as shown by arrows. FIG. 129 illustrates that the needle tip can be translatably retracted, as shown by arrow, from the neural foramen 110 and lateral recess 108. FIG. 130 illustrates that the needle can be translatably withdrawn from the spine 510 and the skin 70.

Figure 131:
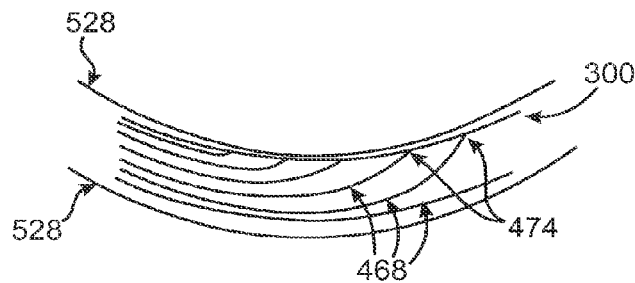
FIG. 131 is a close-up view of an embodiment of section A of FIG. 121.

FIG. 131 illustrates that the tissue protection barrier 528 can be slidably attached to a tissue removal device 300. The tissue removal device 300 can have one or more needlettes 468. The needlettes 468 can be configured to be individually slidable within the tissue removal device 300. The needlettes 468 can each have a needlette tip 474. The needlette tips 474 can be covered, coated or otherwise have a surface and/or by completely made from an electrically conductive material. The needlette 468, for example other than the needlette tip 474, can be covered, coated or otherwise have a surface made from an electrically resistive or insulating material. The surface of the needlette tips 474 can be conductive. The needlette tips 474 can be electrodes. The surface of the non-tip remainder of the needlette 468 can be resistive and/or insulating.

The tissue removal device 300 can have an energy delivery system, such as including the neural stimulation and localization device 114 and the needlette tips. The energy delivery system can be configured to deliver one or more energies to tissue adjacent to the energy delivery system. The energies can be configured to ablate, vaporize, break up, combinations thereof, or otherwise change the modulus of the tissue. The tissue removal device 300, for example via the needlette tips 474, can be configured to deliver electrical, ultrasound, thermal, microwave, laser, cryo (i.e., removing thermal energy), or combinations thereof, energy 44.

The tissue removal device 300 can have one or more electrosurgery elements, for example the needlette tips 474. The electrosurgery elements can be configured to remove and/or ablate tissue. The electrosurgery elements can achieve hemostasis and/or neural localization in tissue adjacent to the electrosurgery elements. The electrosurgery elements can have monopolar or bipolar RF elements. The RF elements can be activated with a thermal or substantially non-thermal waveform.

The tissue removal device 300, for example at the needlette tips 474, can have or be lasers, high-pressure fluid, thermal elements, radioactive elements, textile electric conductors, conductive wire loops and/or needles configured to be used in tissue contact (e.g., needle ablation), springs, open and/or spring wire weaves, conductive polymers that can have conductive metals chemically deposited thereon, or combinations thereof.

Figure 132:
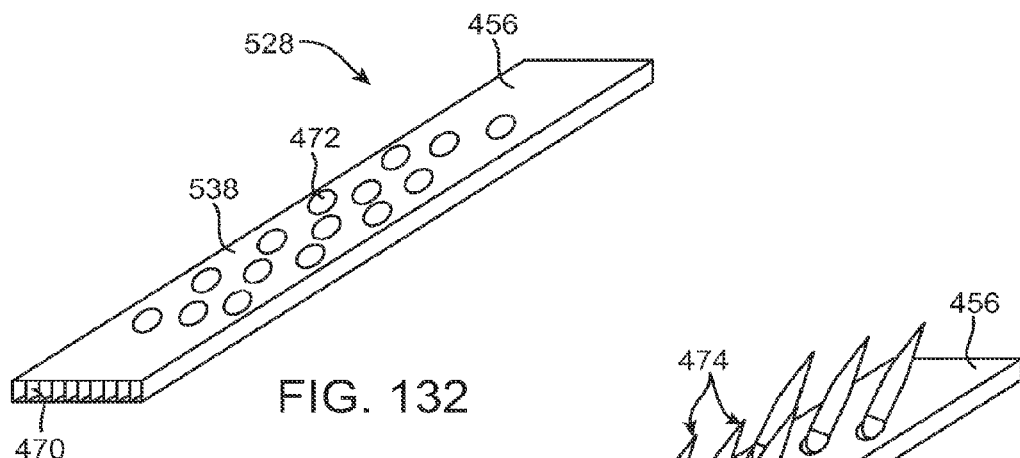
FIGS. 132 and 133 illustrate close-up perspective views of an embodiment of the working surface of the tissue protection barrier.
Figure 133:
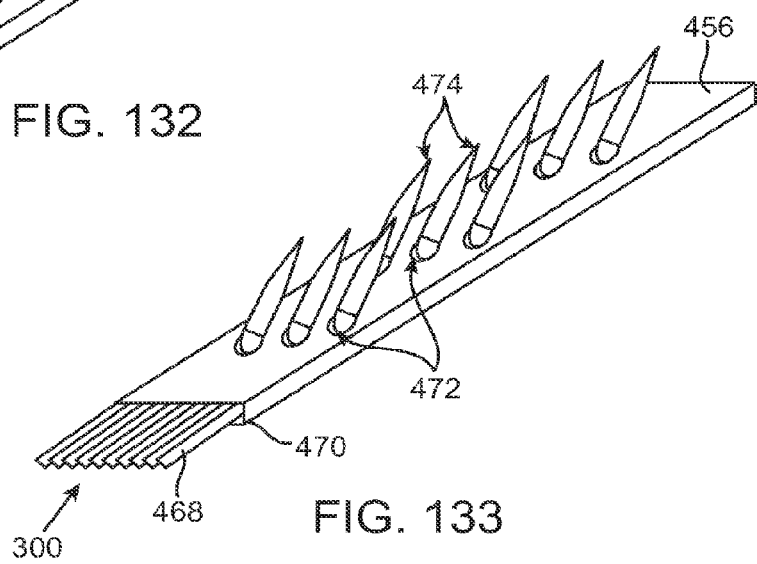

FIGS. 132 and 133 illustrate that the needlettes 468 can be the tissue removal devices 300. The needlettes 468 can be slidably attached directly to the tissue protection barrier 528. The tissue protection barrier 528 (and/or tissue removal device 300) can have one or more windows, for example needlette ports 472. The needlettes 468 can be configured to slidably extend through the needlette ports 472. The needlette ports 472 can be on the front side 456. The needlette ports 472 can be on a working surface 538 of the tissue protection barrier 528 (as shown) or tissue removal device.

The tissue protection barrier 528 (and/or tissue removal device 300) can have needlette conduits 470. The needlettes can be slidably attached to needlette conduits 470. The needlette 468 can be solid. The needlette 468 can be hollow. The needlette 468 can have a conducting wire (not shown) extending therethrough. The needlette tips 474 can be sharp or dull.

Figure 134:
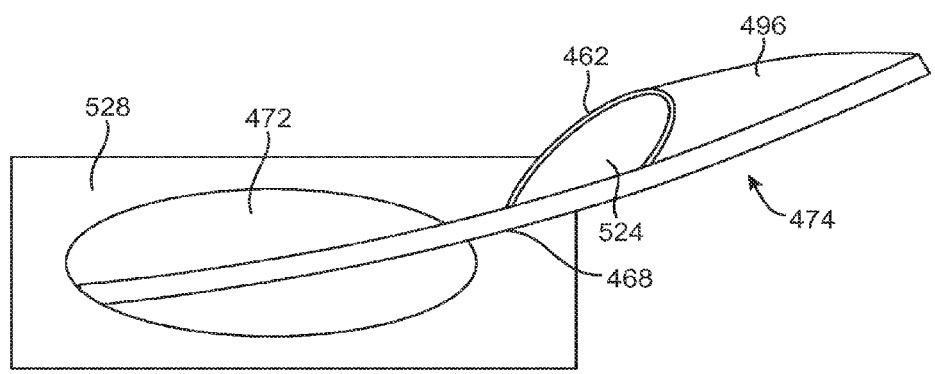
FIGS. 134 and 135 illustrate close-up views of various embodiments of the needlette tip.

FIG. 134 illustrates that the needlette tip 474 can have a shaper or scoop 496, such as a grater or shredder. The scoop 496 can have a tissue entry port 524. The scoop 496 can be open and in fluid communication with a hollow needlette 468. The scoop 496 can have a leading edge 462, for example partially or completely around the perimeter of the tissue entry port 524. The leading edge 462 can be sharpened and/or dulled. The leading edge 462 can be beveled. The leading edge 462 can be electrically conductive. The leading edge 462 can be configured to emit RF energy. The leading edge 462 can be a wire. The needlette tip 474 other than the leading edge can be electrically resistive.

Figure 135:
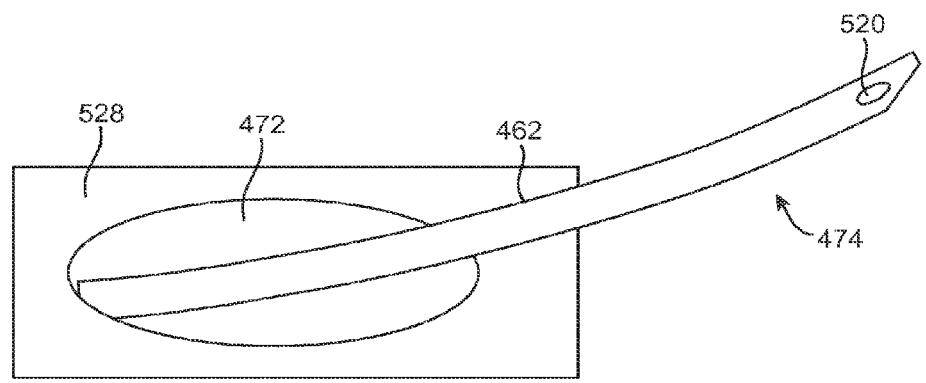

FIG. 135 illustrates that the needlette tip 474 can have a tip hole 520. The tip hole 520 can have a sharpened perimeter. The tip hole 520 can be the tissue entry port 524. The tip hole can be in fluid communication with the hollow needlette 468.

Figure 136:
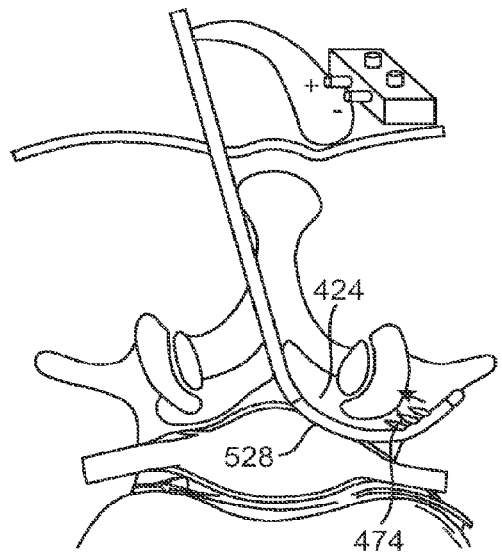
FIGS. 136 and 137 are cross-sectional views through a patient's spine, illustrating placement of the energy delivery apparatus into the protected working tissue removal space created by the neural protection element.

FIG. 136 illustrates that the first needlette tips 474 can deploy, such as by translatably extending, as shown by arrow, from the tissue protection barrier 528 into the impinging tissue 424. The first needlette tips 474 can be configured to deploy in a first deployment direction.

Figure 137:
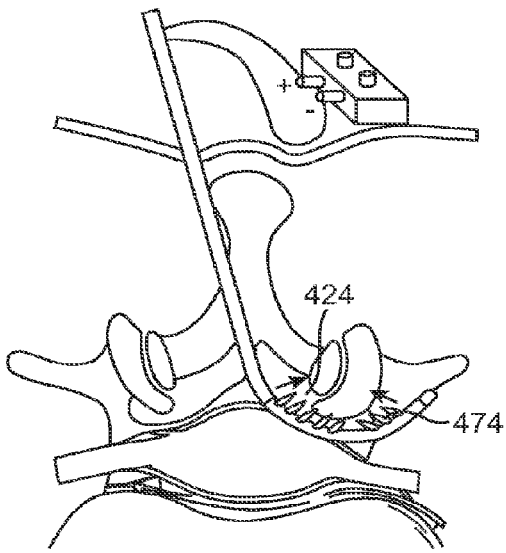
Figure 138:
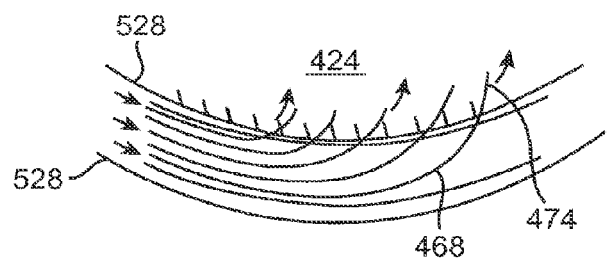
FIG. 138 is a close-up view of an embodiment of section B of FIG. 137.

FIGS. 137 and 138 illustrate that the second needlette tips 474 can deploy, such as by translatably extending, as shown by arrow, from the tissue protection barrier 528 into the impinging tissue 424. The needlette tips 474 can be deployed deeper than the surface of the impinging tissue 424.

The second needlette tips 474 can be configured to deploy in a second deployment direction. The first deployment direction can form a deployment angle with respect to the second deployment direction. The first deployment direction and the second deployment direction can configured to fixedly attach the first and second needlette tips to the impinging tissue 424. The deployment angle can be from about 90 degrees to about 270 degrees, more narrowly from about 90 degrees to about 180 degrees, for example about 120 degrees (as shown in FIG. 137).

Figure 139:
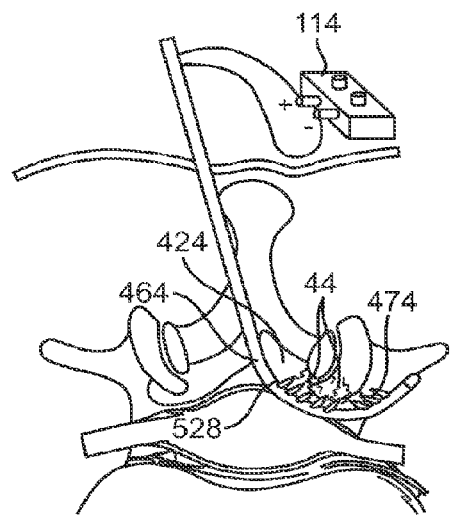
FIG. 139 is a cross-sectional view through a patient's spine, illustrating a method of delivering energy (e.g. electrical, bipolar, monopolar, thermal, laser, cryo, ultrasound, microwave, etc.) to the pathologically impinging tissue.
Figure 143:
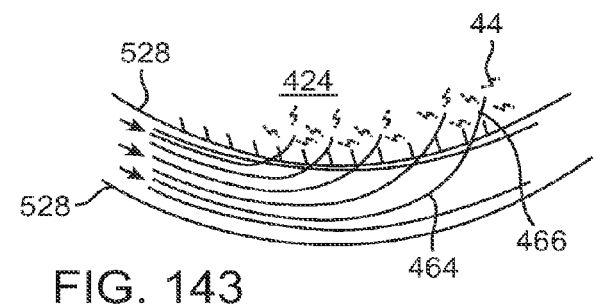
FIG. 143 is a close-up view of an embodiment of section C of FIG. 139.

FIGS. 139 and 143 illustrate that the needlettes 468, for example only through the needlette tips 474, can deliver energy 44 into or onto the impinging tissue. The energy 44 can be acoustic, electrical (e.g., monopolar or bipolar RF), direct heat or cold, or combinations thereof. The energy 44 can ablate and/or evaporate the impinging tissue 424. The energy 44 can be delivered deeper than the surface of the impinging tissue 424. The energy 44 can be created and/or delivered to the needlette tips 474 by the neural stimulation and localization device 114.

The tissue removal device 300, for example the energy delivery system, can transmit an energy 44 to the tissue to be removed, for example, the impinging tissue 424. The energy 44 can alter the compression, denaturation, electrosurgical exposure, thermal remodeling (hot or cold), chemical alteration, epoxy or glues or hydrogels, modulus of elasticity, or any combination thereof of the impinging tissue 424. For example, the modulus of elasticity of soft impinging tissue 424 can be increased. An increased modulus of elasticity can improve purchase on the soft impinging tissue 424 with the tissue removal device 300. Remodeling of the tissue during modulus alteration can alleviate impingement and obviate or reduce a need for tissue removal.

The tissue removal device 300 can be designed to automatically stimulate the site of tissue removal, or have the neural stimulation and localization device 114 stimulate the site of tissue removal, before or during tissue removal. The tissue removal device 300 can be configured to automatically stop tissue removal when nerve stimulation is sensed by the front side 456, and/or no nerve stimulation is sensed by the back side 428.

Figure 140:
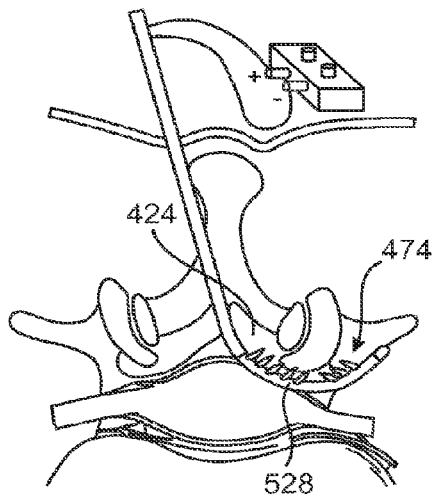
FIGS. 140-142 are cross-sectional views through a patient's spine, illustrating an embodiment of a method of the retraction and removal of the surgical removal apparatus.

FIG. 140 illustrates that the needlettes 468 can remove the impinging tissue 424, for example by suction and/or debridement through holes in or adjacent to the needlette tips 474.

Figure 141:
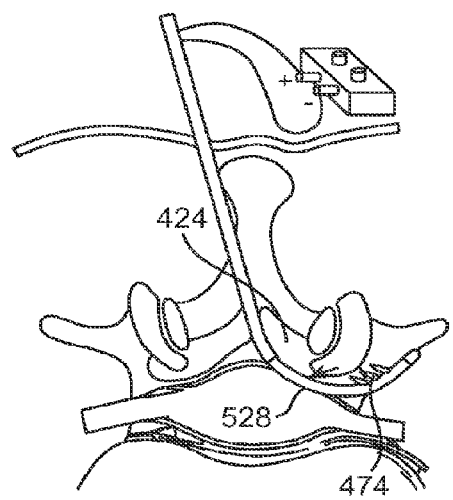

FIG. 141 illustrates that the second needlette tips 474 can be retracted, as shown by arrow, into the tissue protection barrier 528. The first needlette tips 474 can be retracted into the tissue protection barrier 528.

Figure 142:
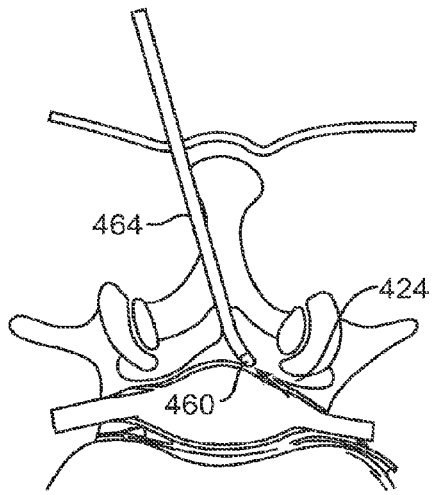

FIG. 142 illustrates that the hood 460 can be retracted, as shown by arrow, onto the needle 464. The needle 464 can be withdrawn from the treatment site.

Figure 144:
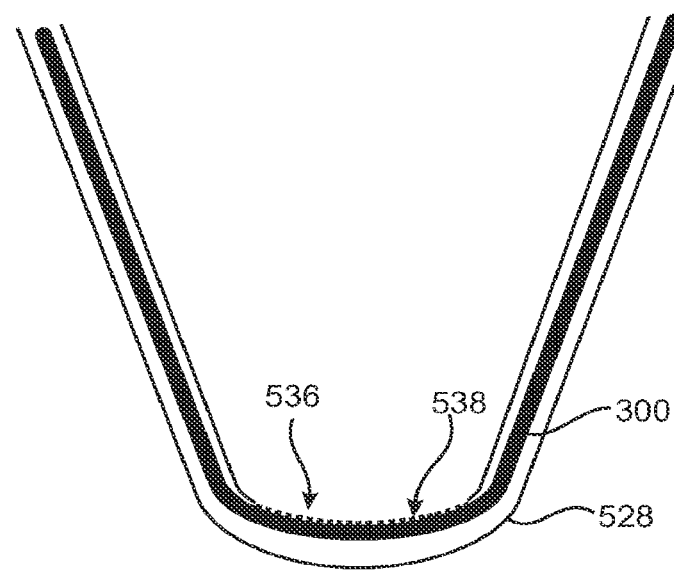
FIG. 144 is a cross-sectional view of an embodiment of the tissue removal apparatus.

FIG. 144 illustrates that the tissue removal apparatus can have the tissue removal device 300 and the tissue protection barrier 528. The tissue removal device 300 can be slidably attached to an inside conduit, channel or hollow of the tissue protection barrier 528. The tissue removal device 300 can have the working surface 538. The working surface 538 can be configured to damage, and/or destroy, and/or remove the impinging tissue. Part or all of the working surface 538 can be exposed through the window 536. The window 536 can be on the front side of the tissue protection barrier 528. The tissue barrier protection 528 can have and/or elute a lubricious coating or material, for example on the surface of the inside conduit, channel or hollow. The tissue removal device 300 can have and/or elute a lubricious coating or material on the entire surface and/or on the surface other than on the working surface 538.

Figure 145:
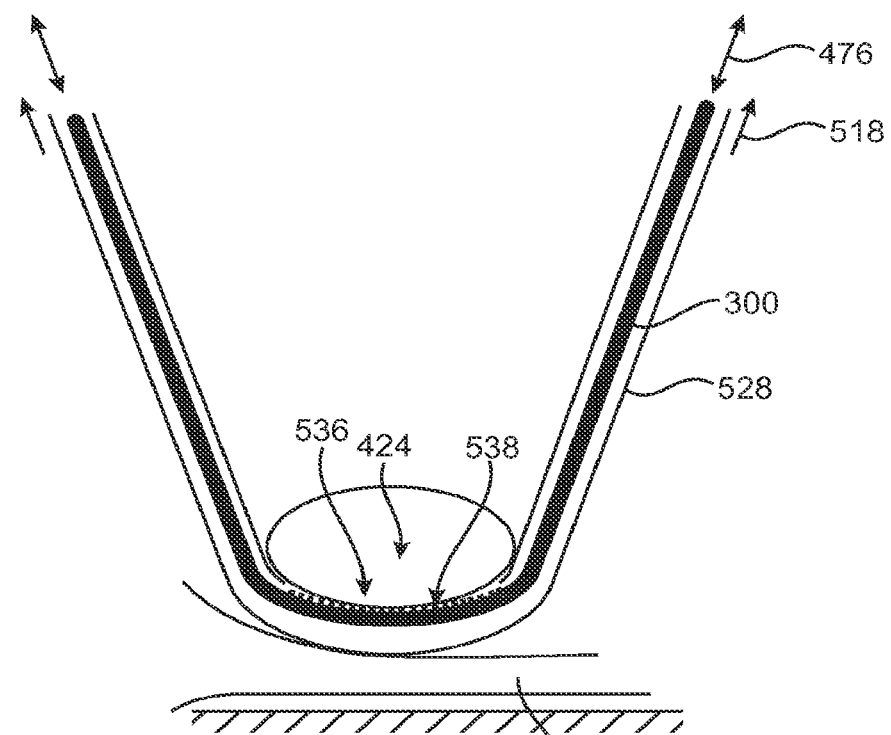
FIG. 145 is a cross-sectional view of an embodiment of a method for using the tissue removal apparatus.

FIG. 145 illustrates that a method of using the tissue removal apparatus 538 can include deploying the window adjacent to the impinging tissue 424. A tension, as shown by arrows 518, can be applied to the tissue protection barrier 528. The tissue removal device 300 can be reciprocated or oscillated, as shown by arrows 476. The oscillation can, for example, result in the working surface 538 to separate impinging tissue 424. The separated impinging tissue 424 can be removed, for example by suction, through the tissue protection barrier 528 and/or the tissue removal device 300. Section D can be equivalent to sections A, B, or C.

The working surface 538 can have one or more non-powered mechanical tissue removal elements. The non-powered mechanical tissue removal elements can be abrasives such as abrasive belts or ribbons, cutting elements such as blades, knives, scissors or saws, rongeurs, grinders, files, debriders, scrapers, graters, forks, picks, burrs, rasps, shavers, or combinations thereof.

The mechanical tissue removal elements can be used in combination or not in combination with the energy delivery device. The mechanical tissue removal elements can be pushed into and/or drawn across the impinging tissue 424 to remove the tissue by cutting, shaving, slicing, scissoring, guillotining, scraping, tearing, abrading, debriding, poking, mutilating, or combinations thereof. The mechanical tissue removal elements (e.g., blades) can be drawn across the impinging tissue 424 in a single direction and/or can be reciprocated. The mechanical tissue removal elements can be manually controlled and/or electronically, pneumatically or hydraulically powered. The mechanical tissue removal elements can be embedded with abrasives and/or have abrasive coatings, such as a diamond or oxide coating.

The blades can have various shapes, sizes and configurations. The blades can coact, for example, in a guillotine-type or scissor-type cutting action. The blades can be attached to or integral with the tissue removal device. The blades can be formed by grinding, punching or stamping through the tissue removal device. The blades can be formed by grinding of a punched or stamped edge of the tissue removal device. The blades can be formed by a chemical etching process. The blades can have a 3-dimensional profile to facilitate cutting, for example, a bow or a corrugation or a 'cheese grater' profile. The blades can be placed at one or more angles relative to the direction of tissue removal. The blades can be configured with the blade cutting across the tissue (i.e., similar to a band saw). The blades can have cutting surfaces. The cutting surfaces can be oriented in a single or multiple directions. The blades can be serrated.

The saw can be a wire saw or saws. The wire saw can be a Gigli saw. Multiple wire saws or Gigli saws can be joined or woven together or flattened to form a substantially planar cutting surface. The wire saw can be mounted on a flat ribbon. The ribbon can be a depth stop, for example, limiting for saw penetration.

The tissue removal device 300 can have one or more powered mechanical tissue removal elements. The powered mechanical tissue removal elements can have, for example, band saws, belt shavers, rotary burrs or blades, reciprocating burrs or blades, or combinations thereof.

Devices and elements known to those having ordinary skill in the art can be used to remove debris from, and/or irrigate, and/or provide suction to, the epidural space 42 including the lateral recess 108 and neural foramen 110 and/or to the tissue removal device itself. The devices and elements for removing debris can be integral with the needle 464 and/or the catheter 24. Debris removal, and/or suction and/or irrigation may be provided intermittently or continuously, as desired by the medical practitioner. Debris removal can include suction and/or irrigation. The tissue removal device 300 can capture debris. Irrigation and/or suction in the tissue removal device 300 can remove the debris from the tissue removal device 300, for example by the debris exiting along the needle 464 and/or catheter 24.

FIG. 146 illustrates that the tissue protection barrier 528 can have a first rail 452 and a second rail 500. The tissue protection barrier 528 can be rigid, flexible or combinations thereof. The tissue protection barrier 528 can be resilient or deformable. The first rail 452 and/or second rail 500 can be rounded to form atraumatic sides of the tissue protection barrier 528. The first rail 452 and/or second rail 500 can be configured to slidably attach to the tissue removal device 300. The first rail 452 and/or second rail 500 can be configured to snap fit and/or interference fit to the tissue removal device 300.

The tissue protection barrier 528 can have a tissue protection barrier test strength. The tissue protection barrier test strength can be equal to or less than about 890 N (200 lbs.), more narrowly equal to or less than about 710 (160 lbs.), yet more narrowly equal to or less than about 350 N (80 lbs.), for example about 180 N (40 lbs.).

The tissue protection barrier 528 can have a taper 516 at a first end. The taper 516 can be configured to dissect tissue, for example, during deployment. The taper 516 can be configured to bluntly dissect tissue, for example, during deployment. The taper 516 can be configured to be atraumatic, for example, not being able to substantially dissect tissue during deployment. The taper 516 can be configured to interference fit the tissue removal device 300.

FIG. 147 illustrates that the tissue protection barrier 528 can have a wire, such as a distal wire 440. The distal wire 440 can be integral with, or fixedly attached to, the taper 516. The distal wire 440 can extend from the taper 516. The distal wire 440 can have a wire test strength. The wire test strength can be equal to or less than about 890 N (200 lbs.), more narrowly equal to or less than about 710 (160 lbs.), yet more narrowly equal to or less than about 350 N (80 lbs.), for example about 180 N (40 lbs.).

During use, the distal wire 440 and/or the taper 516 can be deployed posteriorly exiting the skin. During use, the distal wire 440 and/or the taper 516 can be deployed posteriorly around or through the spine, exiting the spine and deploying substantially to the site at which the needle and/or tissue protection barrier entered. The distal wire 440 and/or the taper 516 can be secured to a substantially fixed location (e.g., the skin, the spine, the user's hand). Additional force can be applied, for example, posteriorly on the tissue protection barrier (e.g., on the first end, and/or a second end). The tissue protection barrier 528 can be forced into the impinging tissue 424.

FIG. 148 illustrates that the distal wire 440 can be attached to a distal wire anchor 442. The distal wire anchor 442 can be fixedly or removably attached to the distal wire 440 after deployment of the distal wire 440 exiting the skin 70 and/or the spine 510. The distal wire anchor 442 can be integral with the distal wire 440. The distal wire anchor 442 can be expandable. The distal wire anchor 442 can be resilient or deformable. The distal wire anchor 442 can have a contracted configuration before deployment. The distal wire anchor 442 can be held in the contracted configuration by a removable sheath.

FIG. 149 illustrates that the shield 528 or distal wire can be slidably and/or fixedly attached to a distal wire sleeve and/or anchor lock 442. The distal wire sleeve and/or anchor lock 442 can fix the distal wire anchor 442 to the distal wire 440, or may provide protection for the tissues while the wire is pulled throught said distal sleeve 438. The distal wire sleeve 438 or anchor lock can interference fit and/or friction fit the distal wire anchor 442. The distal wire sleeve 438 or anchor lock can be fixedly or removably attached to the distal wire 440 after deployment of the distal wire 440 exiting the skin and/or the spine. The distal wire sleeve 438 or anchor lock can be integral with the shield or backstop or distal wire. The distal wire sleeve 438 or anchor lock can be expandable. The distal wire sleeve 438 or anchor lock can be resilient or deformable. The distal wire sleeve 438 or anchor lock can have a contracted configuration before deployment. The distal anchor lock 438 can be held in the contracted configuration by a removable sheath.

The distal anchor lock 438 can be integral with, or fixedly attached to, the taper 516. The distal anchor lock 438 can extend from the taper 516. The distal anchor lock 438 can have a test strength. The test strength can be equal to or less than about 890 N (200 lbs.), more narrowly equal to or less than about 710 (160 lbs.), yet more narrowly equal to or less than about 350 N (80 lbs.), for example about 180 N (40 lbs.).

The distal wire 440 can be integral with, or fixedly attached to, the tissue removal device 300 (not shown in FIG. 149). The distal wire 440 can extend from the tissue removal device 300. The distal wire 440 can be slidably attached to the distal anchor lock 438. The tissue removal device 300 can be slidably attached to the tissue protection barrier 528. During use, the distal wire 440 can be slidably translated within the distal wire anchor 442. Translation of the distal wire 440 can slidably translate the tissue removal device 300. The tissue removal device 300 can be reciprocated, for example, when alternating translations are applied on either end of the tissue removal device 300, such as when applied by a distal wire 440 and/or a proximal wire.

FIG. 150 illustrates that the tissue protection barrier 528 can have a first taper 516 at a first end and a second taper 516 at a second end. The tissue protection barrier 528 can have a proximal wire 484 and a distal wire 440. The proximal wire 484 can be integral with, or fixedly attached to, the first taper 516. The proximal wire 484 can extend from the first taper 516. The distal wire 440 can be integral with, or fixedly attached to, the second taper 516. The distal wire 440 can extend from the second taper 516.

The tissue protection barrier 528 can have one or more wires and no tapers 540. The wires can extend from be integral with, or fixedly attached to, and/or extend from non-tapered ends.

FIG. 151 illustrates that the tissue protection barrier 528 can have a first taper 516 at a first end, a second taper 516 at a second end, a proximal wire 484, a distal wire 440, and a distal wire anchor 442 attached to, or integral with, the distal wire 440. FIG. 152 illustrates that the tissue protection barrier 528 can have a first taper 516 at a first end, a second taper 516 at a second end, a proximal wire 484, a distal wire 440, a proximal wire anchor 482 attached to, or integral with, the proximal wire 484, and a distal wire anchor 442 attached to, or integral with, the distal wire 440. FIG. 153 illustrates that the tissue protection barrier 528 can have a first taper 516 at a first end, a second taper 516 at a second end, a proximal wire 484, a distal wire 440, a proximal wire anchor 482 attached to, or integral with, the proximal wire 484, and a distal wire anchor 442 attached to, or integral with, the distal wire 440. The distal wire 440 can be slidably and/or fixedly attached to a distal wire sleeve and/or anchor lock. The proximal wire 484 can be slidably and/or fixedly attached to a proximal wire sleeve and/or anchor lock 442. The distal wire sleeve 438 may be an extension of the neuroforaminal protection barrier 528, through which the wire 440 is passed in order to prevent damage through abrasion of vulnerable tissues.

Figure 154:
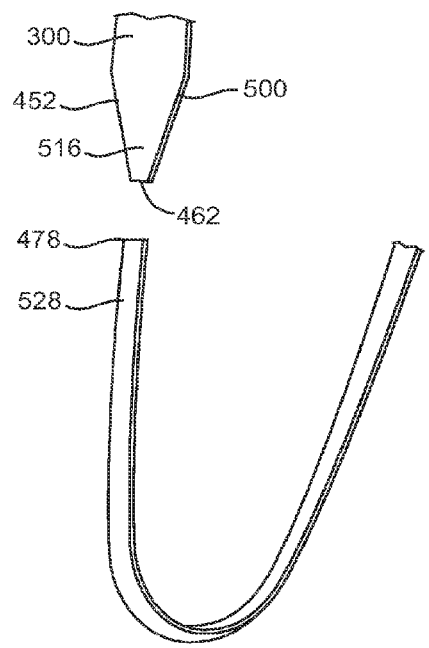
FIGS. 154-157 illustrate an embodiment of a method for using a flexible or spreadable tissue protection barrier, demonstrating dual rails, which are curved for advancement through the neural foramina, and, in this example, are joined by expandable back side protection. This example depicts the tissue removal element serving also as a dilator for the rail and neural barrier system, as it is advanced between the spreadable rails.
Figure 155:
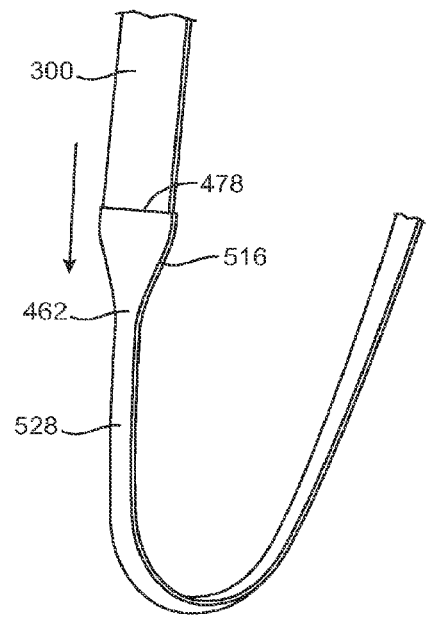

FIG. 154 illustrates that the tissue protection barrier 528 can have a port 478 at a first end. The tissue removal device 300 can have a taper 516 at a first end. The tissue removal device 300 can have a leading end 462 at the first end. The leading edge 462 can be configured to be atraumatic. The tissue removal device 300 can have a first rail 452 and a second rail 500. The first rail 452 and/or the second rail 500 of the tissue removal device 300 can be configured to be atraumatic. The tissue protection barrier 528 can have a first rail and a second rail (not shown in FIGS. 154-157).

FIG. 32 illustrates that the leading edge 462 can be translatably inserted, as shown by arrow, into the port 478. The tissue protection barrier 528 can expand to receive the tissue removal device 300. The tissue protection barrier 528 can expand in a tapered configuration around the taper 516 of the tissue removal device 300. The first rail 452 and/or the second rail 500 of the tissue removal device 300 can slidably attach to the first rail and/or the second rail of the tissue protection barrier 528.

Figure 156:
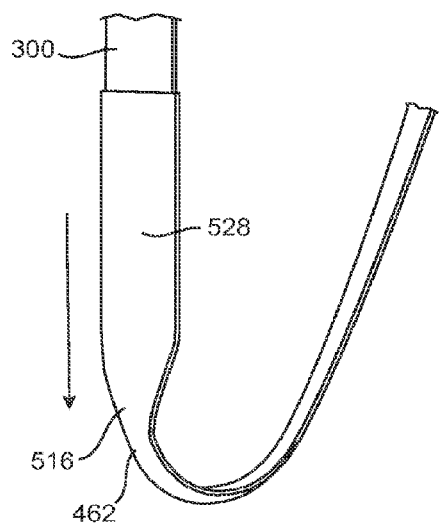

FIG. 156 illustrates that the tissue removal device can be further translatably inserted, as shown by arrow, into the tissue protection barrier 528.

Figure 157:
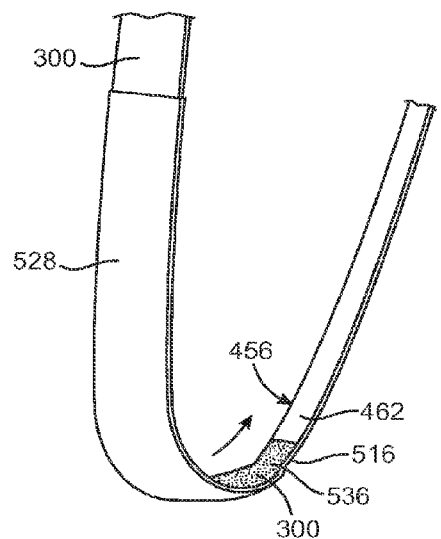

FIG. 157 illustrates that the tissue removal device 300 can be further translatably inserted, as shown by arrow, into the tissue protection barrier 528. The window 536 can expose the tissue removal device 300 on the front side 456 of the tissue protection barrier 528. The tissue removal device 300 can snap fit, interference fit, friction fit, or otherwise fix to the tissue protection barrier 528, for example when the tissue removal device 300 has been inserted to a required length into the tissue protection barrier 528.

Figure 158:
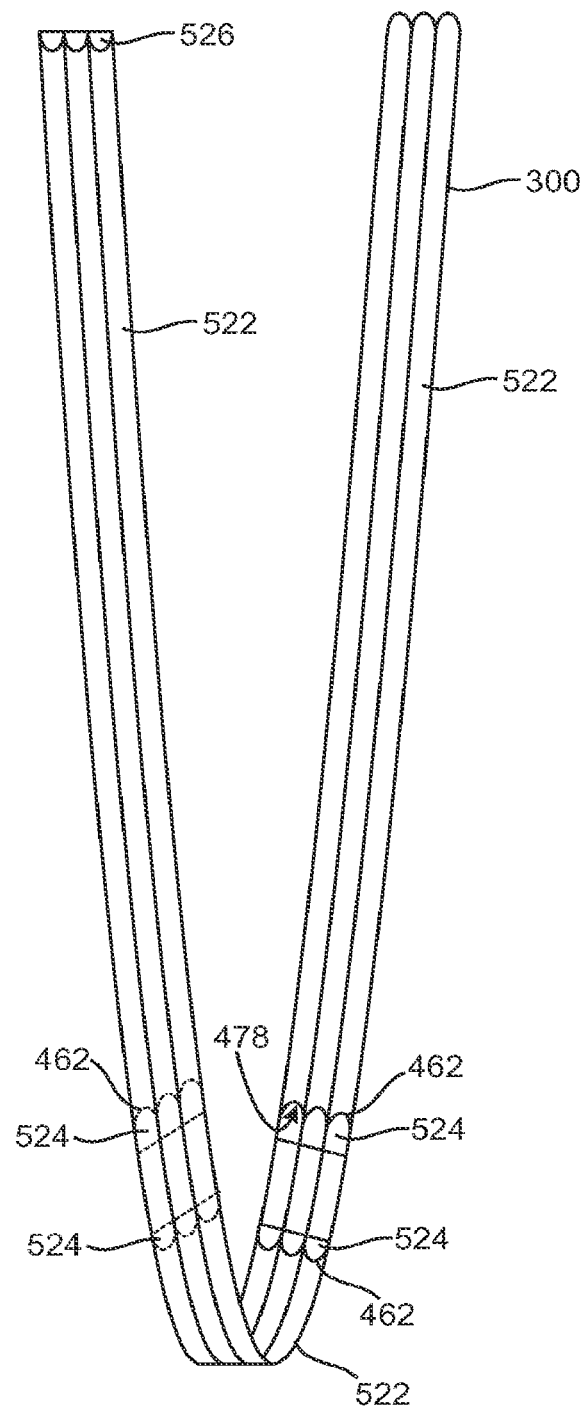
FIG. 158 is a side perspective view with phantom see-through lines of an embodiment of the tissue removal device.

FIG. 158 illustrates that the tissue removal device 300 can have one or more tissue conduits 522. The tissue conduits 522 can be channels or conduits. The tissue conduits 522 can be open at a tissue entry port 478 and/or a tissue exit 526. A leading edge 462 can be around or adjacent to the perimeter of the tissue entry port 478. The leading edge 462 can be a conductor (e.g., and RF device, such as a wire). The leading edge 462 can be sharp and/or dull. The leading edge 462 can be beveled. Pairs of tissue entry ports 524 can oppose each other, as shown, thereby enabling removal of tissue when the tissue removal device is translated in both longitudinal directions. During use, the separated tissue can be removed via the tissue conduits 522.

Figures 159, 160:
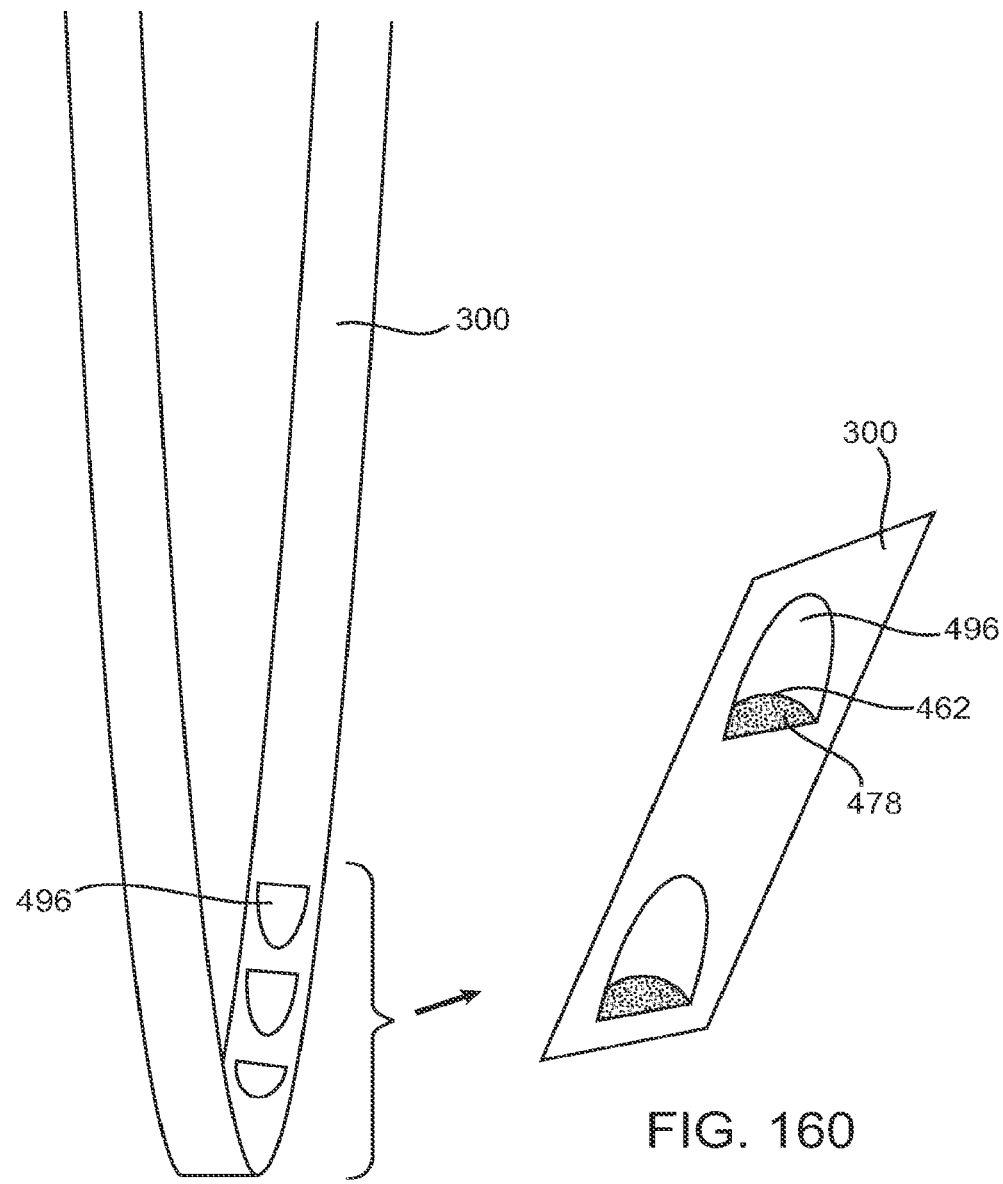
FIG. 159 is a side perspective view an embodiment of the tissue removal device.
FIG. 160 is a reversed close-up view of the bracketed section of the tissue removal device of FIG. 159.

FIGS. 159 and 160 illustrate that the tissue removal device 300 can have shapers or scoops 496, such as graters or shredders. The scoops 496 can have tissue entry port 478. The scoops 496 can be open and in fluid communication with one or more tissue conduits. The scoops 496 can have leading edges 462, for example partially or completely around the perimeter of the tissue entry port 478. The leading edge 462 can be sharpened and/or dulled. The leading edge 462 can be electrically conductive. The leading edge 462 can be configured to emit RF energy. The leading edge 462 can be a wire. The tissue removal device 300 other than the leading edge 462 can be electrically resistive and/or insulating.

Figure 161:
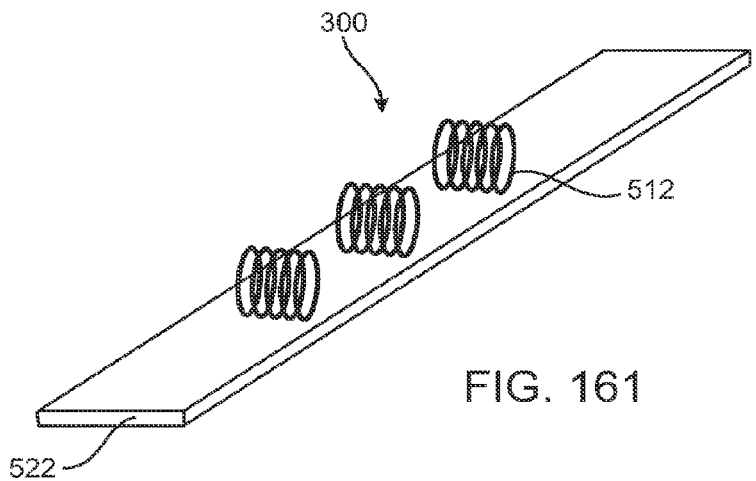
FIGS. 161 and 162 illustrate close up views of an embodiment of a method for using the tissue removal device.

FIG. 161 illustrates that the tissue removal device 300 can have springs 512. The springs 512 can be fixedly or removably attached to the tissue removal device 300. The springs 512 can be attached through the tissue removal device 300, for example into the tissue conduit 522. The tissue removal device 300 can open into the tissue conduit 522 where the springs 512 attach, for example, sufficient to allowing fluid communication through the tissue removal device. The springs can be sharpened and/or dulled. The springs 512 can have flat ribbon coils, and or other coils configured to cut the impinging tissue.

Figure 162:
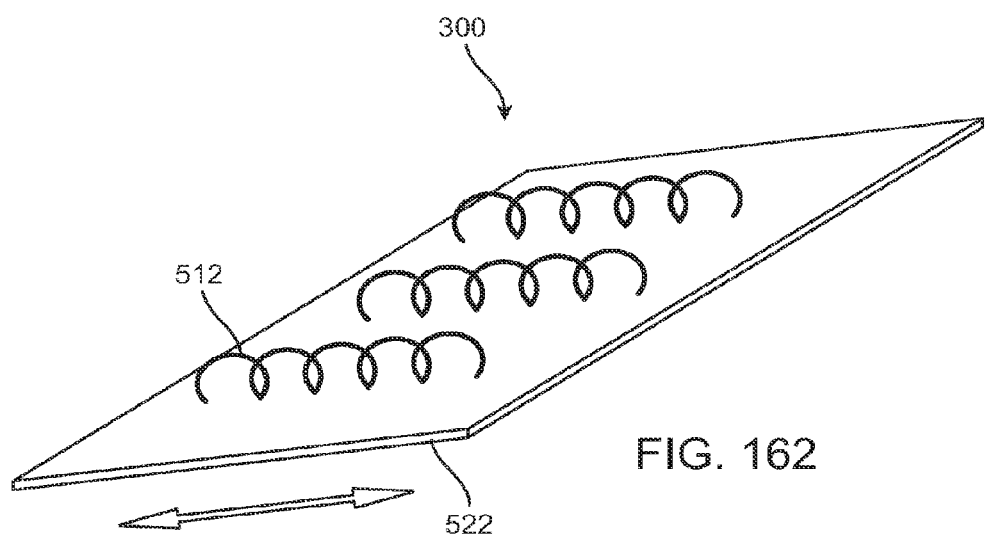

FIG. 162 illustrates that the tissue removal device 300 can be expanded, as shown by arrows. The springs 512 can expand and/or contract with the tissue removal device.

Figure 163:
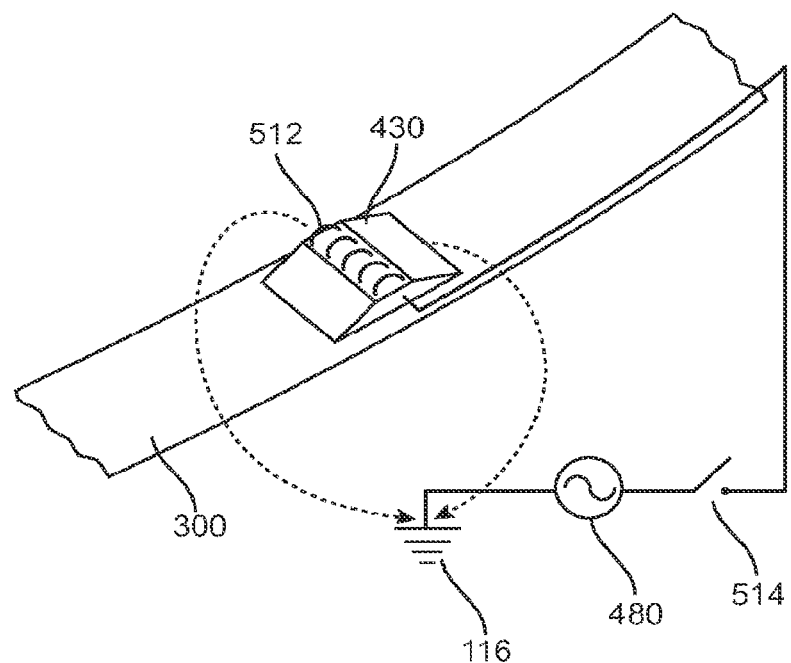
FIGS. 163-165 illustrate close up views of various embodiments the tissue removal device.

FIG. 163 illustrates that the spring 512 can be fixedly or removably attached to, or integral with, a base 430. The base 430 can be made from, for example, a high temperature epoxy (e.g., from Epoxy Technology, Billerica, Mass.), a high temperature plastic, or combinations thereof. High temperature plastics can include, for example, liquid crystal polymer, polysulfones, or polyimide.

The springs 512 can be in electrical communication with a circuit, for example the neural stimulation and localization device. The circuit can have a ground 116, a power source 480, and a switch 514. The power source 480 can have a frequency range from about 100 kHz to about 10 MHz. The springs 512 can be grounded at one or more points. The circuit can create a monopolar spring 512. The base 430 can electrically insulate the spring 512 and the remainder of the tissue removal device 300 (e.g., a ribbon). The circuit can be closed during use.

The spring 512 can have various configurations to alter the cutting performance. For example, the spring can have a circular configuration.

The springs 512 can emit low level voltage prior to tissue removal, for example, to check for nerve stimulation.

Figure 164:
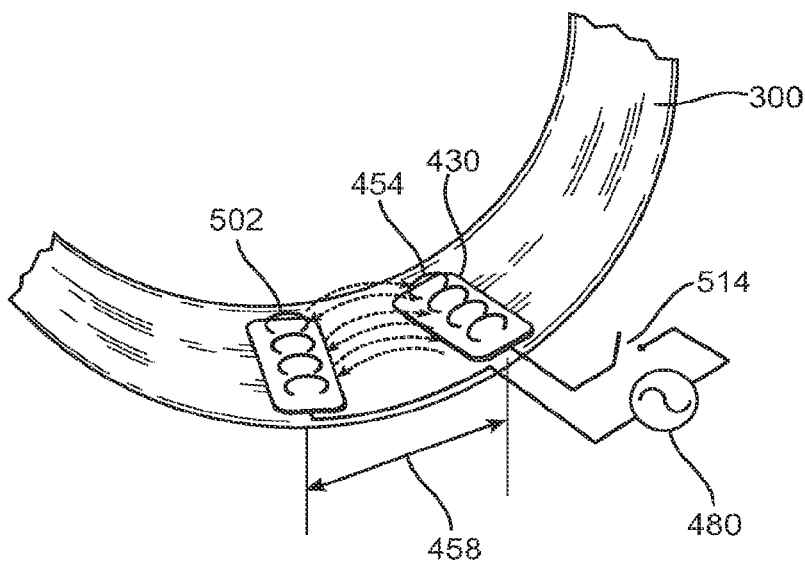

FIG. 164 illustrates that the tissue removal device 300 can have a first spring 512 and a second spring 512. The first spring 512 can be separated from the second spring 512 by a gap distance 458. The gap distance 458 can be from about 100 μm to about 5 cm. The first spring 512 and the second spring 512 can be concurrently attached to the circuit. The first spring 512 can be in direct electrical communication with the second spring 512.

The impedance between the first spring 512 and the second spring 512 can be monitored. For example, if the impedance exceeds threshold values (e.g., the impedance of burning tissue), the circuit can be configured to open.

Figure 165:
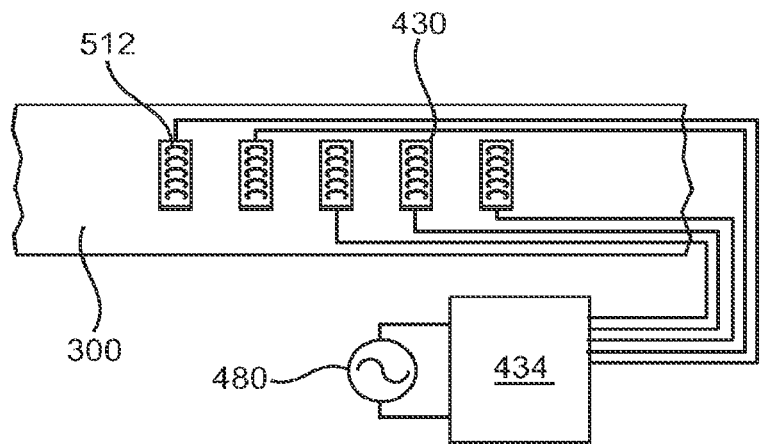

FIG. 165 illustrates that the tissue removal device can have multiple springs 512. The springs 512 can be in electrical communication with a controller 434 in the circuit. The controller 434 can transmit current to any combination of springs 512. The controller 434 can monitor the impedance between springs 512. The controller 434 can open the circuit to a particular spring if the impedance exceeds a threshold.

Figure 166:
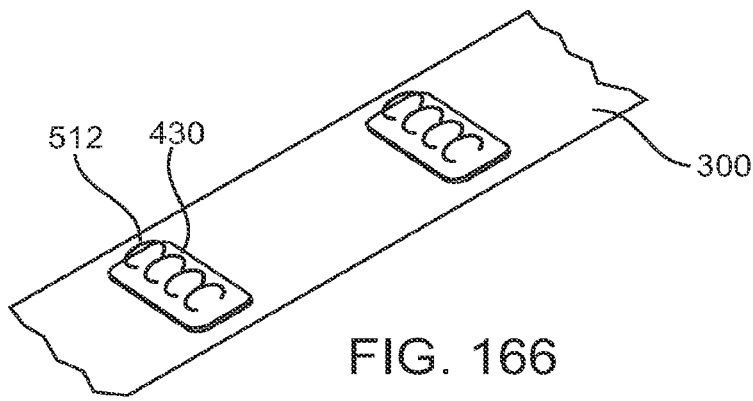
FIGS. 166 and 167 illustrate close up views of an embodiment of a method for using the tissue removal device.
Figure 167:
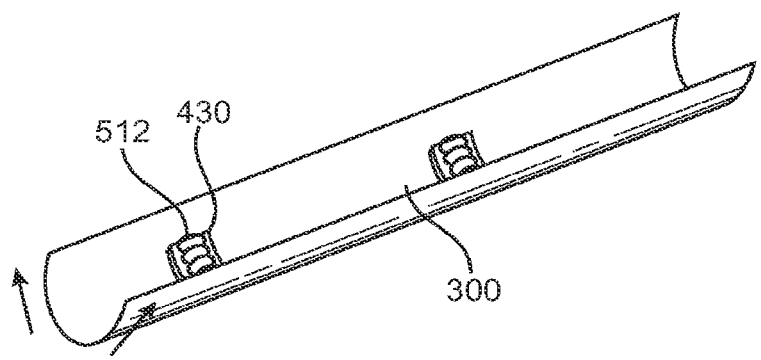

FIG. 166 illustrates the tissue removal device 300 that can have the springs 512 in a non-contracted (e.g., expanded) configuration. FIG. 167 illustrates that the sides of the tissue removal device 300 can be folded, as shown by arrows, to contract the tissue removal device 300, for example for deployment or retraction from a patient's body. The springs 512 can contract and/or expand with the contraction and/or expansion of the tissue removal device 300.

Figure 168:
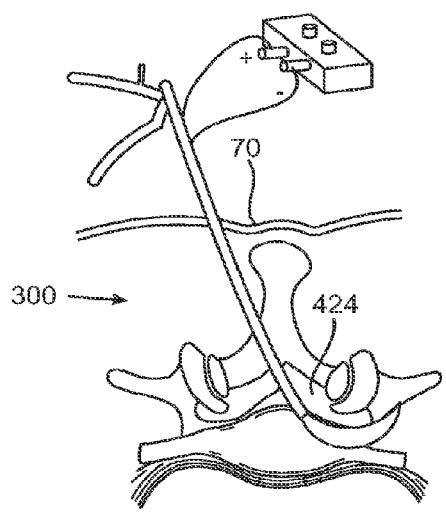
FIGS. 168-171 are cross-sectional views through a patient's spine illustrating a method for deploying the distal wire.
Figure 169:
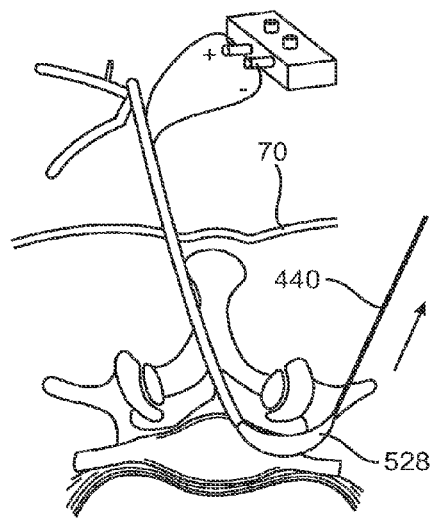
Figure 170:
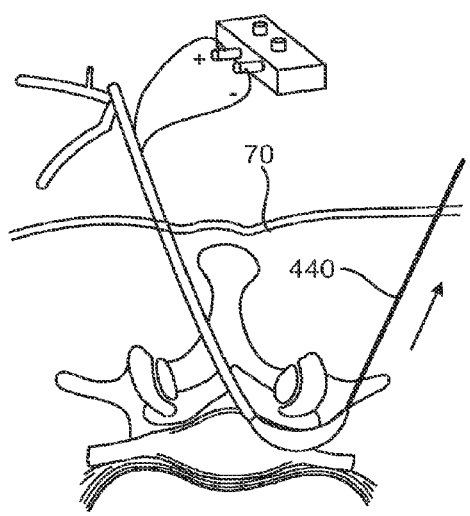
Figure 171:
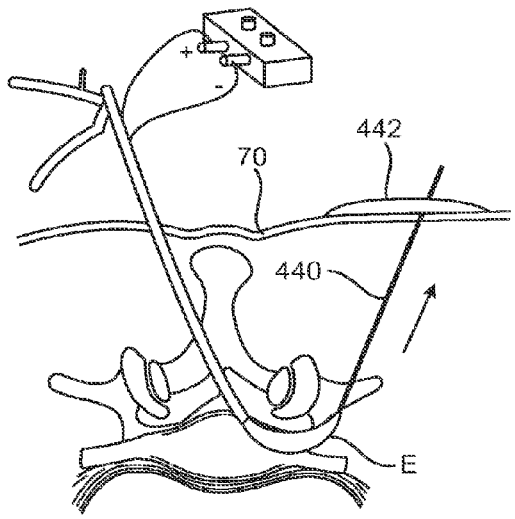

FIG. 168 illustrates the tissue removal apparatus 300 that can be partially deployed percutaneously (i.e., through the skin 70) in the spine. FIG. 169 illustrates that the distal wire 440 can be translatably extended, as shown by arrow, from the distal end of the tissue protection barrier 528. FIG. 170 illustrates that the distal wire 440 can translatably extend, as shown by arrow, through the skin 70. FIG. 171 illustrates that a distal wire anchor 442 can removably attach to the distal wire 440. The distal wire 440 can be fixed, for example, at the surface of the skin 70.

Figure 172:
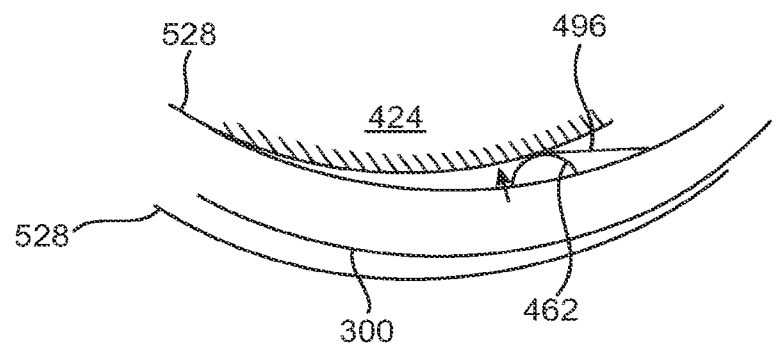
FIGS. 172-174 are close up views of an embodiment of a method for removing the tissue at, for example, section E of FIG. 171.

FIG. 172 illustrates that the leading edge 462 can be pressed into the impinging tissue 424, for example as a result of the tension 518 on the tissue protection barrier 528 and/or tension applied to the tissue removal device 300 during the oscillation 479. The leading edge 462 can purchase the impinging tissue 424. The leading edge 462 can be activated, for example be delivering RF energy to the leading edge.

Figure 173:
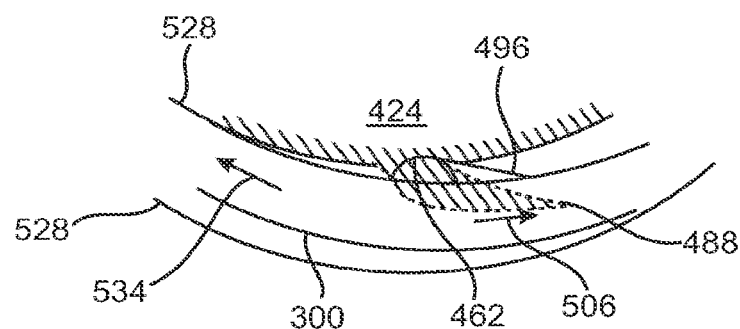

FIG. 173 illustrates that the tissue removal device 300 can be translated, as shown by arrow 534, with respect to the impinging tissue 424. The leading edge 462 can cut into the impinging tissue 424. The scoop 496 can force separation, as shown by arrow 506, of the cut impinging tissue 424 from the remaining impinging tissue 424.

Figure 174:
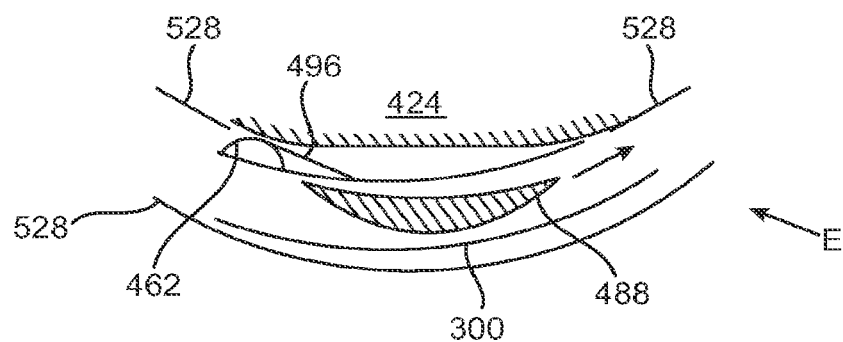

FIG. 174 illustrates that the removed tissue 488 can be removed from the tissue removal device 300 (as shown) or the tissue protection barrier 528, for example by suction.

Figure 175:
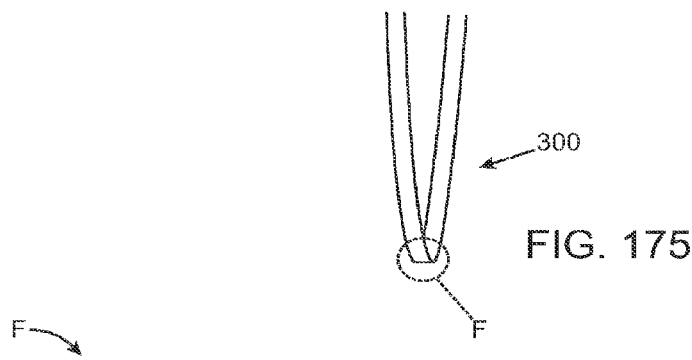
FIGS. 175-178 illustrate a method for deploying the tissue removal device.
Figure 176:
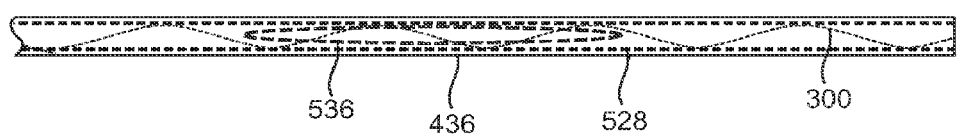

FIGS. 175 and 176 illustrate that the tissue removal apparatus 300 can have a deployment cover 436 over the tissue protection cover 528 prior to, and during, deployment. The deployment cover 436 can be slidably attached to the tissue removal device 300. The tissue removal device 300 can be expandable, for example a self-expandable coil spring. The tissue protection barrier 528 can be expandable, for example a self-expandable coil-reinforced polymer lube (e.g., a stent-graft). The deployment cover 436 can be rigid, for example, to prevent the tissue removal device 300 and/or the tissue protection barrier 528 from expanding. The tissue removal device 300 and/or tissue protection barrier 528 can be manually expandable, for example by having an integrated or attached mechanical expansion device (e.g., an inflation balloon) and/or from being made from shape memory alloy that reconfigures when heated.

Figure 177:
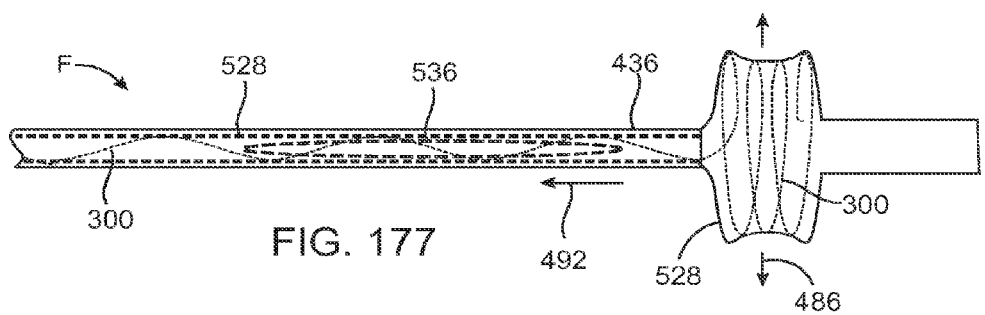

FIG. 177 illustrates that the deployment cover 436 can be retracted, as shown by arrow 492. The tissue protection barrier 528 not covered by the deployment cover 436 can radially expand, as shown by arrows 492. For example, the tissue removal device 300 and/or the tissue protection barrier can self-expand and/or manually expand.

Figure 178:
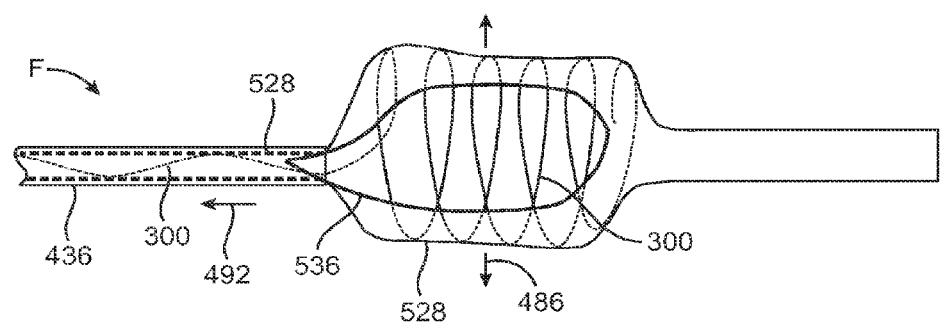

FIG. 178 illustrates that the deployment cover 436 can be retracted, as shown by arrow 492. The window 536 can be exposed. The deployment cover 436 can be completely removed from the tissue protection barrier 528. The tissue protection barrier 528 can be re-covered by the deployment cover 436, for example, immediately before the tissue protection barrier 528 is removed from the treatment site.

FIG. 179 illustrates that the tissue removal device can be the spring 512, for example a coil spring. The spring 512 can be in a flat configuration in the tissue protection barrier 528. The spring 512 can be slidably attached to the tissue protection barrier 528.

FIG. 180 illustrates that the spring 512 can be translated, as shown by arrow 532. The spring can have a first spring section 544 not along the length of the window 536. The spring 512 can have and a second spring section 504 along the length of the window 536. The first spring section 544 can be in the flat configuration. As the spring 512 translates from the first spring section 544 to the second spring section 504, the spring 512 can expand, as shown by arrow 446, into a completely and/or partially expanded configuration. As the spring 512 translates from the second spring section 504 to the first spring section 544, the spring 512 can contract into a flat configuration and retract, as shown by arrow 492, into the tissue protection barrier 528.

Figure 181:
FIGS. 181-187 illustrate methods for deploying the tissue removal device.
Figure 182:
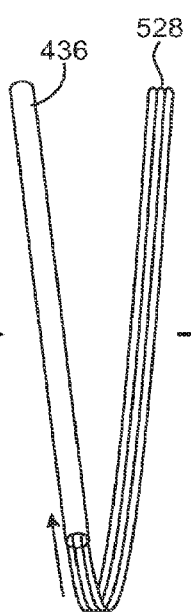
Figure 183:
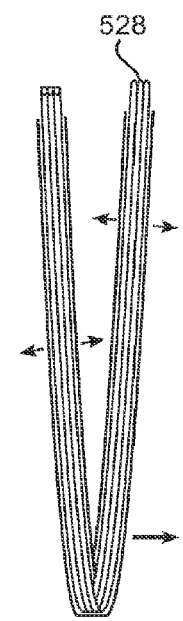
Figure 184:
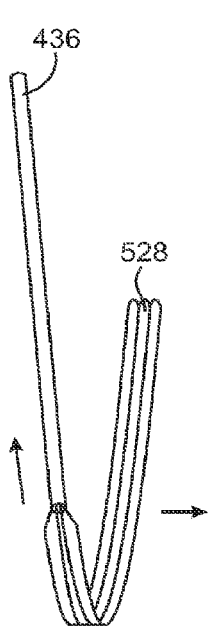
Figure 185:

FIG. 181 illustrates the deployment cover 436 that can have the tissue protection barrier 528 inside the deployment cover 436. FIG. 182 illustrates that the deployment cover 436 can translatably retract, as shown by arrow, from the tissue protection barrier 528. The tissue protection barrier 528 can be in a non-expanded (e.g., contracted) configuration. FIG. 183 illustrates that the tissue protection barrier 528 can then expand after, but not as a direct result of, the retraction of the deployment cover 436. The tissue protection barrier 528 can self-expand or be manually expanded. FIG. 184 illustrates that the deployment cover 436 can be translatably retracted, as shown by arrow, from the entire tissue protection barrier 528. FIG. 185 illustrates the tissue protection barrier 528 in a deployed and expanded configuration.

Figure 186:
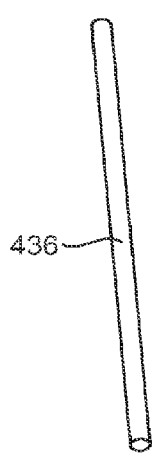
Figure 187:

FIG. 186 illustrates the deployment cover 436 that can have the tissue protection barrier 528 inside the deployment cover 436. FIG. 187 illustrates that the deployment cover can retract, as shown by arrow 492, from the tissue protection barrier 528. The tissue protection barrier 528 can then expand as a direct result of the retraction of the deployment cover 436. The tissue protection barrier 528 can self-expand or be manually expanded. For example, the manual expansion can be driven or triggered by the retraction of the deployment cover 436.

The tissue protection barrier, and/or the access elements, and/or the neural protection element and/or the tissue removal device can have a lubricious coating, for example, a hydrophilic coating, a poly(tetrafluoroethylene) coating. The coating can reduce friction during placement, diagnosis, treatment and/or removal. The tissue removal device, the access elements and/or the neural protection element can by biocompatible and/or non-friable.

Any of the elements and/or entire apparatuses described herein can be made from, for example, a single or multiple stainless steel alloys, nickel titanium alloys (e.g., Nitinol), cobalt-chrome alloys (e.g., ELGILOY® from Elgin Specialty Metals, Elgin, Ill.; CONICHROME® from Carpenter Metals Corp., Wyomissing, Pa.), molybdenum alloys (e.g., molybdenum TZM alloy, for example as disclosed in International Pub. No. WO 03/082363A2, published Oct. 9, 2003, which is herein incorporated by reference in its entirety), tungsten-rhenium alloys, for example, as disclosed in International Pub. No. WO 03/082363, polymers such as polyester (e.g., DACRON® from E. I. Du Pont de Nemours and Company, Wilmington, Del.), carbon fiber composites (e.g., carbon fiber nylon composite, such as carbon fiber reinforced nylon 66), polypropylene, polytetrafluoroethylene (PTFE), expanded PTFE (ePTFE), polyether ether ketone (PEEK), nylon, polyether-block co-polyamide polymers (e.g., PEBAX® from ATOFINA, Paris, France), aliphatic polyether polyurethanes (e.g., TECOFLEX® from Thermedics Polymer Products, Wilmington, Mass.), polyvinyl chloride (PVC), polyurethane, thermoplastic, fluorinated ethylene propylene (FEP), absorbable or resorbable polymers such as polyglycolic acid (PGA), polylactic acid (PLA), polydioxanone, and pseudo-polyamino tyrosine-based acids, extruded collagen, silicone, zinc, echogenic, radioactive, radiopaque materials or combinations thereof. Examples of radiopaque materials are barium sulfate, zinc oxide, titanium, stainless steel, nickel-titanium alloys, tantalum and gold.

Any of the elements and/or entire apparatuses described herein can be or have a matrix for cell ingrowth or used with a fabric, for example a covering (not shown) that acts as a matrix for cell ingrowth. The matrix and/or fabric can be, for example, polyester (e.g., DACRON® from E. I. du Pont de Nemours and Company, Wilmington, Del.), polypropylene, PTFE, ePTFE, nylon, extruded collagen, silicone or combinations thereof.

Any of the elements and/or entire apparatuses described herein can be filled and/or coated with an agent delivery matrix known to one having ordinary skill in the art and/or a therapeutic and/or diagnostic agent. The agents within these matrices can include radioactive materials; radiopaque materials; cytogenic agents; cytotoxic agents; cytostatic agents; thrombogenic agents, for example polyurethane, cellulose acetate polymer mixed with bismuth trioxide, and ethylene vinyl alcohol; lubricious, hydrophilic materials; phosphor cholene; anti-inflammatory agents, for example non-steroidal anti-inflammatories (NSAIDs) such as cyclooxygenase-1 (COX-1) inhibitors (e.g., acetylsalicylic acid, for example ASPIRIN® from Bayer AG, Leverkusen, Germany; ibuprofen, for example ADVIL® from Wyeth, Collegeville, Pa.; indomethacin; mefenamic acid), COX-2 inhibitors (e.g., VIOXX® from Merck & Co., Inc., Whitehouse Station, N.J.; CELEBREX® from Pharmacia Corp., Peapack, N.J.; COX-1 inhibitors); immunosuppressive agents, for example Sirolimus (RAPAMUNE®, from Wyeth, Collegeville, Pa.), or matrix metalloproteinase (MMP) inhibitors (e.g., tetracycline and tetracycline derivatives) that act early within the pathways of an inflammatory response. Examples of other agents are provided in Walton et al, Inhibition of Prostoglandin $E_2$ Synthesis in Abdominal Aortic Aneurysms, *Circulation*, Jul. 6, 1999, 48-54; Tambiah et al, Provocation of Experimental Aortic Inflammation Mediators and Chlamydia Pneumoniae, *Brit. J. Surgery* 88 (7), 935-940; Franklin et al, Uptake of Tetracycline by Aortic Aneurysm Wall and Its Effect on Inflammation and Proteolysis, *Brit. J Surgery* 86 (6), 771-775; Xu et al, Spl Increases Expression of Cyclooxygenase-2 in Hypoxic Vascular Endothelium, *J Biological Chemistry* 275 (32) 24583-24589; and Pyo et al, Targeted Gene Disruption of Matrix Metalloproteinase-9 (Gelatinase B) Suppresses Development of Experimental Abdominal Aortic Aneurysms, *J. Clinical Investigation* 105 (11), 1641-1649 which are all incorporated by reference in their entireties.

Many of the safety issues related to the methods and apparatus described herein are similar to those associated with any surgical procedure, e.g., infection and/or bleeding. Some safety issues are more specific to surgery in and around the spine or spinal cord, and are therefore given special consideration below. These generally relate to spinal neural and neurovascular injury. Central Nervous System injury could result from instruments inadvertently traumatizing the dura mater when entering the epidural space, injuring the nerve root (s), the adjacent vasculature, or the dorsal root ganglion as the apparatus is advanced and utilized towards and through the neural foramen.

Several techniques may be used to reduce a risk of dural, neural or neurovascular injury, including potentially traumatizing structures including nerve roots, adjacent vasculature, or dorsal root ganglia. For example, the tissue alteration (e.g., abrasion) devices may be placed under direct visualization when utilizing an open surgical approach or technique. Likewise, image guidance may be provided during placement or to confirm correct placement. Candidate image guidance techniques include fluoroscopy, fluoroscopy alone, fluoroscopy with additional technology for triangulation and tracking of instruments (e.g. infrared, RF, etc.), MRI, CT, OCT, ultrasound, etc. Catheters or guidewires may include their own image guidance capabilities such as catheter or guidewire-based image guidance, e.g., fiberoptic visualization, catheter-based ultrasound, catheter-based MRI, optical tomography, etc. Alternatively or additionally, endoscopic visualization may be utilized (e.g. flexible fiberoptic endoscope as in Epiduroscope, or via rigid surgical endoscopes), during placement and/or post-placement confirmation of correct placement.

In addition to epidural endoscopy, image guidance may be combined with the use of straight, curved, or steerable guidewires for the proper placement of the neuroforaminal abrasive element. Placement may be achieved percutaneously or through a surgical incision. Such a device may be implanted as an adjunct to an open surgical procedure(s); as an adjunct to an endoscopic surgical procedure(s); or as a separate open, image-guided percutaneous or endoscopic surgical procedure. Percutaneous approaches will enable the surgeon to perform the procedure under local anesthetic in awake or sedated patients, if desired. As discussed, nerve stimulation and localization capabilities may be added to the device in order to enable the surgeon to more safely perform the procedure in an anesthetized, but un-paralyzed patient.

It is expected that the apparatus and methods of the present invention will facilitate a minimally invasive approach to the selective elimination (e.g., alteration, ablation, removal) of pathological spinal tissue, thereby enabling symptomatic relief in patients suffering from spinal stenosis. Spinal neural and neurovascular impingement cause tremendous pain and disability, with symptoms that include back and leg pain, weakness, and decreased sensation. Neural ischemia and injury caused by compression and inflammation may result in a wide range of symptoms or degrees of nerve damage. Symptoms range in severity from mild to severe, and from intermittent to permanent. For example, neurogenic claudication, which is exacerbated by back extension (as occurs when one stands erect and places the spine in extension), may be mild or severe. Symptoms of neurogenic claudication are usually improved by changes in posture that lead to back flexion, such as sitting. The most severe cases of spinal stenosis may lead to permanent neurological damage, including the possibility of the development of cauda equina syndrome.

Spine surgeons lack safe and effective techniques or tools to minimally invasively or percutaneously reduce neural and neurovascular impingement in the spine, while minimizing collateral tissue damage. It is expected that the apparatus and methods of the present invention may be utilized for lateral recess and neuroforaminal enlargement to provide adequate bone and soft tissue resection, while reducing unnecessary destruction of functional bone, ligament or muscle in order to gain access to the tissues to be resected.

Spine surgeons lack safe and effective techniques or tools to minimally invasively or percutaneously reduce neural and neurovascular impingement in the spine, while minimizing collateral tissue damage. It is expected that the apparatus and methods of the present invention may be utilized to provide adequate bone and soft tissue resection to achieve lateral recess, neuroforaminal, and spinal canal enlargement, while reducing unnecessary destruction of functional bone, ligament or muscle in gaining access to the tissues to be modified.

Because critical neural and neurovascular structures are in close proximity to the areas where surgical manipulation, dissection, resection, ablation and remodeling would be therapeutically valuable in the spine, safety at each step in the procedure is of critical importance in order to avoid disabling neurological damage to the patient. For this reason, safety measures, such as working barriers and nerve localization via an integrated nerve stimulator, are described.

It may be desirable to alter an elastic modulus of impinging tissue to facilitate removal of the tissue. For example, it may be desirable to increase the modulus of soft tissue to gain purchase on the soft tissue with the tissue removal elements. Such modulus alteration may be achieved, for example, through compression, denaturation, electrosurgical exposure, thermal remodeling (hot or cold), chemical alteration, epoxy or glues or hydrogels, or any combination thereof, etc. Remodeling of the tissue during modulus alteration may alleviate impingement and obviate or reduce a need for tissue removal.

In order to reduce friction during placement, diagnosis, treatment and/or removal, the open or percutaneous access elements, neural protection element 200 and/or tissue removal device 300 may comprise a lubricious coating, for example, a hydrophilic coating, a poly(tetrafluoroethylene) coating, etc. Furthermore, the tissue removal device, the access elements and/or the neural protection element may by biocompatible and/or non-friable. Integrated or separate debris removal elements also may be provided.

It is expected that the apparatus and methods of the present invention will facilitate selective elimination of pathological spinal tissue, thereby enabling symptomatic relief in patients suffering from spinal stenosis.

Spine surgeons presently lack safe and effective techniques or tools to minimally invasively or percutaneously reduce neural and neurovascular impingement in the spine, while minimizing collateral tissue damage. It is expected that the apparatus and methods of the present invention may be utilized for lateral recess and neuroforaminal enlargement to provide adequate bone and soft tissue resection, while reducing unnecessary destruction of functional bone, ligament or muscle in order to gain access to the tissues to be resected.

Because critical neural and neurovascular structures are in close proximity to the areas where surgical manipulation, dissection and remodeling would be therapeutically valuable in the spine, safety at each step in the procedure is of critical importance in order to avoid disabling neurological damage to the patient. For this reason, safety measures, such as neural protection element 200 and neural localization element 210, may be provided.

It will be apparent to those skilled in the art that various changes and modifications can be made thereto. For example, elements of any of the described variations may be used in any combination, as desired. Furthermore, the apparatus described herein may be used for a variety of selective tissue removal procedures in addition to neural foraminal tissue impingement. For example, the apparatus may be used for treatment of central spinal stenosis. Further, the methods and apparatus described hereinafter are equally applicable to both open and percutaneous approaches. For the purpose of clarity, they have been disclosed utilizing only a percutaneous or open access, but this shall not be construed as limiting.

Although preferred illustrative embodiments of the present invention are described hereinabove, it will be apparent to those skilled in the art that various changes and modifications may be made thereto without departing from the invention. It is intended in the appended claims to cover all such changes and modifications that fall within the true spirit and scope of the invention.

INCORPORATION BY REFERENCE

All publications and patent applications mentioned in this specification are herein incorporated by reference to the same extent as if each individual publication or patent application was specifically and individually indicated to be incorporated by reference.

We claim:

1. A surgical tissue removal device comprising:
   a flexible elongate body that is adapted to conform with a target anatomy, the body having a working surface for separating and removing impinging tissue, the working surface defined by at least one blade edge, where the flexible elongate body is a thin, flat, ribbon shaped flexible body that comprises a profile having a width that is substantially greater than a height;
   a guidewire connector at a distal end region of the flexible elongate body configured to removably connect to an end of a guidewire so that the guidewire and the flexible elongate body can be pulled distally, wherein the at least one blade edge is a v-shaped blade edge; and
   wherein a portion of the flexible elongate body removed from the working surface includes a lubricious layer not on the working surface for removing tissue.

2. The tissue removal device of claim 1, further comprising:
   a distal handle configured to couple to the distal end of the flexible elongate body; and
   a proximal handle configured to couple to a proximal end region of the flexible elongate body, wherein the distal handle and the proximal handle are configured to allow the body to be reciprocated proximally and distally to cut tissue.

3. The tissue removal device of claim 2, wherein the distal handle is configured to connect to the guidewire while a proximal end of the guidewire is connected to the distal end of the flexible elongate body.

4. The tissue removal device of claim 1, wherein a guidewire connector region is configured to hook the flexible elongate body to an end region of the guidewire.

5. The tissue removal device of claim 1, wherein the at least one blade edge comprises a plurality of discrete sharpened blade edges for cutting through tissue and bone.

6. The tissue removal device of claim 1, wherein the at least one blade edge is flush with a surface of the elongate body.

7. A surgical tissue removal device, comprising:
   a flexible elongate body that is adapted to conform with a target anatomy, the body having a working surface for separating and removing impinging tissue, the working surface defined by at least one blade edge extending from one surface of the flexible elongate body, where the flexible elongate body is a thin, flat, ribbon shaped flexible body that further comprises a profile having a width that is substantially greater than a height;
   a guidewire connector on the flexible elongate body configured to connect to an end of a guidewire so that the end of the guidewire connects into the guidewire connector at a distal end region of the flexible elongate body so that the guidewire and the flexible elongate body can be pulled distally to draw the at least one blade edge distally across the target anatomy, wherein the at least one blade edge is a v-shaped blade edge; and
   wherein a portion of the flexible elongate body removed from the working surface includes a lubricious layer not on the working surface for removing tissue.

8. The tissue removal device of claim 7, where the flexible elongate body is configured to pass through a subject's spinal foramen.

9. The tissue removal device of claim 7, where the at least one blade edge comprises a plurality of blade edges located on the surface of the flexible elongate body near an end of the flexible elongate body comprising the guidewire connector so that the end of the flexible elongate body opposite of the guidewire connector does not include a blade edge.

10. The tissue removal device of claim 7, where the at least one blade edge comprises a plurality of blade edges and where the plurality of blade edges comprise a plurality of blade edges located on the surface of the flexible elongate body near a center of the flexible elongate body so that ends of the flexible elongate body do not include any blade edges.

11. The tissue removal device of claim 7, further comprising:
   a distal handle configured to couple to the distal end of the flexible elongate body; and
   a proximal handle configured to couple to the proximal end region of the flexible elongate body, wherein the distal handle and the proximal handle are configured to allow the body to be reciprocated proximally and distally to cut tissue.

12. The tissue removal device of claim 11, wherein the distal handle is configured to connect to the guidewire while a proximal end of the guidewire is connected to the distal end of the flexible elongate body.

13. The tissue removal device of claim 7, wherein a guidewire connector region is configured to hook the flexible elongate body to an end region of the guidewire.

14. The tissue removal device of claim 7, wherein the at least one blade edge comprises a plurality of discrete sharpened blade edges for cutting through tissue and bone.

15. The tissue removal device of claim 7, the body having an axial length and a plurality of blade edges arranged in rows extending from one surface of the flexible elongate body, wherein the rows are disposed transverse to the axial length of the elongate body and the rows are separated by gaps that extend transverse to the axial length of the elongate body.

* * * * *